US012807936B2

(12) United States Patent
Bar-Ziv et al.

(10) Patent No.: US 12,807,936 B2
(45) Date of Patent: Nov. 24, 2026

(54) ASSEMBLY OF PROTEIN COMPLEXES ON A CHIP

(71) Applicant: Yeda Research and Development Co. Ltd., Rehovot (IL)

(72) Inventors: Roy Bar-Ziv, Rehovot (IL); Shirley Shulman Daube, Rehovot (IL); Michael Levy, Rehovot (IL); Reuven Falkovich, Rehovot (IL); Ohad Vonshak, Rehovot (IL); Yiftach Divon, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 1127 days.

(21) Appl. No.: 17/702,880

(22) Filed: Mar. 24, 2022

(65) Prior Publication Data

US 2022/0213467 A1 Jul. 7, 2022

Related U.S. Application Data

(63) Continuation of application No. PCT/IL2020/051037, filed on Sep. 23, 2020.

(60) Provisional application No. 63/053,752, filed on Jul. 20, 2020.

(51) Int. Cl.
*C07K 1/00* (2006.01)
*C12N 15/10* (2006.01)
*G01N 33/543* (2006.01)

(52) U.S. Cl.
CPC ..... *C12N 15/1041* (2013.01); *C12N 15/1062* (2013.01); *G01N 33/54306* (2013.01)

(58) Field of Classification Search
None
See application file for complete search history.

(56) References Cited

U.S. PATENT DOCUMENTS

2012/0171720 A1* 7/2012 Church .................. C12P 19/34 435/68.1
2016/0122749 A1* 5/2016 Nikolay ........... C07K 14/43595 506/10
2017/0306320 A1 10/2017 Jewett et al.

FOREIGN PATENT DOCUMENTS

WO WO 2021/059269 4/2021

OTHER PUBLICATIONS

International Search Report and the Written Opinion Dated Feb. 1, 2021 From the International Searching Authority Re. Application No. PCT/IL2020/051037. (13 Pages).
Search Report Dated May 11, 2020 From the Israel Patent Office Re. Application No. 269674. (6 Pages).
Contreras-Llano et al. "High-Throughput Screening of Biomolecules Using Cell-Free Gene Expression Systems", Synthetic Biology, 3(1): ysy012-1-ysy012-13, Advance Access Publication Jul. 7, 2018.
Daube et al. "Protein Nanomachines Assembly Modes: Cell-Free Expression and Biochip Perspectives: Protein Nanomachines Assembly Modes", Wiley Interdisciplinary Reviews: Wire's Nanomedicine and Nanobiotechnology, XP055763711, 5(6): 613-628, Published Online Jul. 24, 2013.
Heyman et al. "Cell-Free Protein Synthesis and Assembly on a Biochip", Nature Nanotechnology, XP055763559, 7(6): 374-378, Published Online May 27, 2012.
Jewett et al. "In Vitro Integration of Ribosomal RNA Synthesis, Ribosome Assembly, and Translation", Molecular System Biology, 9(Art.678): 1-8, Published Online Jun. 25, 2013.
Karzbrun et al. "Programmable On-Chip DNA Compartments as Artificial Cells", Science, XP055594510, 345(6198): 829-832, Aug. 14, 2014.
Levy et al. "Autonomous Synthesis and Assembly of a Ribosomal Subunit on a Chip", Science Advances, XP055763924, 6(16): eaaz6020-1-eaaz6020-8, Published Online Apr. 15, 2020.

* cited by examiner

*Primary Examiner* — Christopher M Gross

(57) ABSTRACT

A method of assembling and immobilizing proteinaceous complexes is disclosed. In addition, methods of generating functional RNA polymerase and ribosomal subunits are disclosed.

15 Claims, 69 Drawing Sheets
(63 of 69 Drawing Sheet(s) Filed in Color)

Specification includes a Sequence Listing.

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| gp10 | + | + | + | + | + | | + | + | + | | | + | + | + | |
| gp7 | | + | + | + | | | + | + | | + | | + | | + | + |
| gp8 | | | + | + | + | + | + | + | + | + | | + | + | | + |
| gp6 | | | | + | + | | | + | + | + | + | + | + | + | + |
| Band shift | | | | | | | | | | | | | | | |

FIG. 33A
FIG. 33B
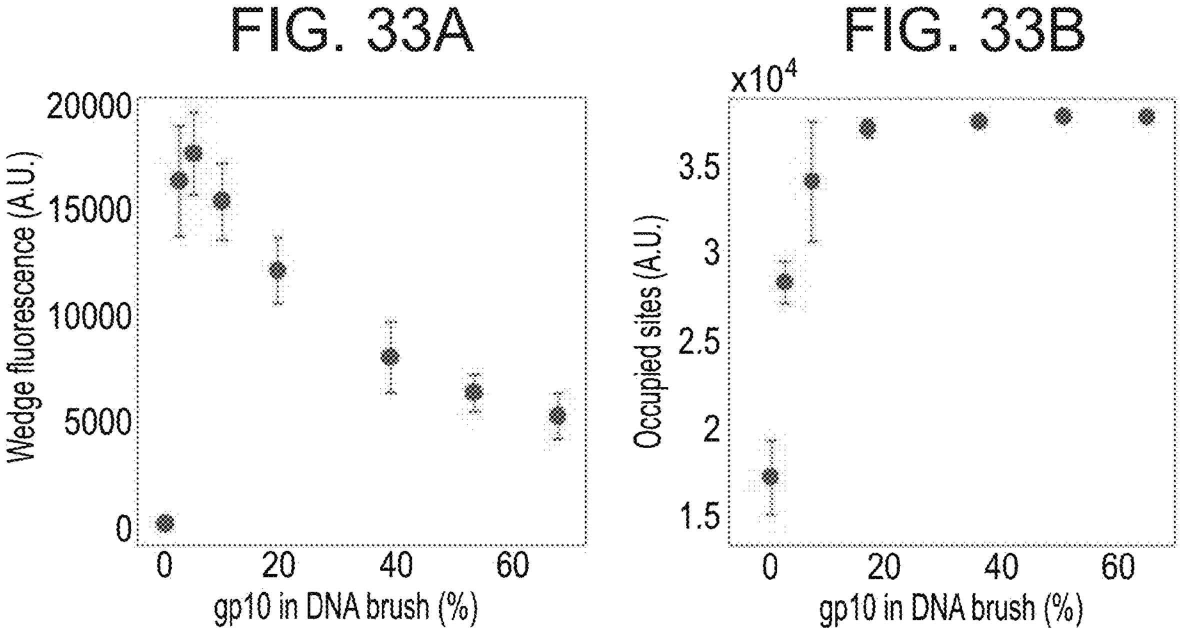
FIG. 33C
FIG. 33D
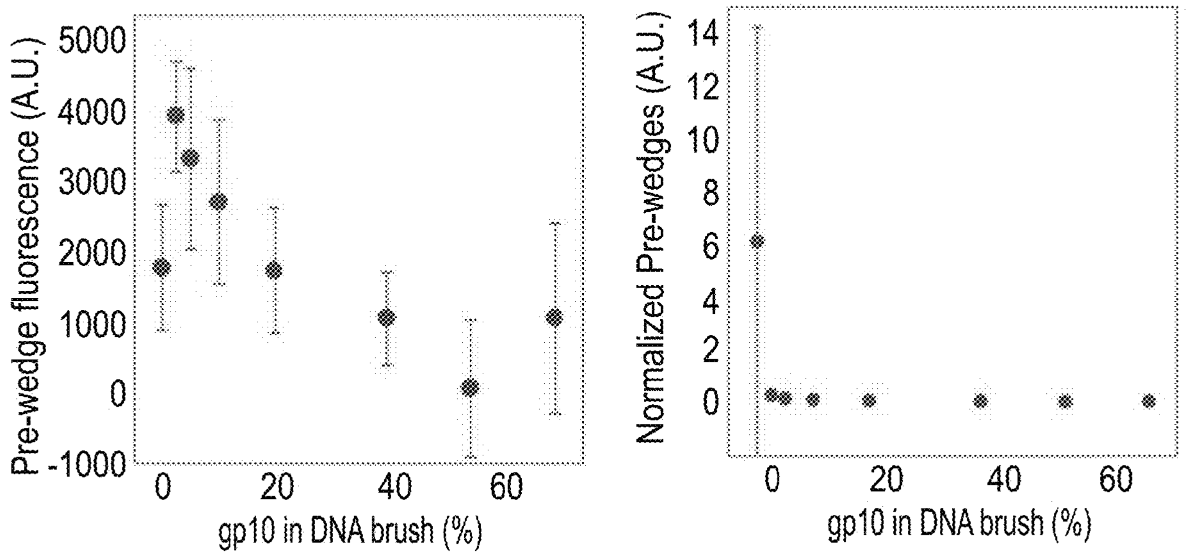

```
                         SEQUENCE LISTING

<160> NUMBER OF SEQ ID NOS: 168

<210> SEQ ID NO 1
<211> LENGTH: 53
<212> TYPE: DNA
<213> ORGANISM: Artificial sequence
<220> FEATURE:
<223> OTHER INFORMATION: Single strand DNA oligonucleotide

<400> SEQUENCE: 1

gcgaaattaa tacgactcac tatagggtaa attgaagagt ttgatcatgg ctc           53


<210> SEQ ID NO 2
<211> LENGTH: 53
<212> TYPE: DNA
<213> ORGANISM: Artificial sequence
<220> FEATURE:
<223> OTHER INFORMATION: Single strand DNA oligonucleotide

<400> SEQUENCE: 2

aaaggcctcc tgcaggttaa ccttactcga gtaaggaggt gatccaaccg cag           53


<210> SEQ ID NO 3
<211> LENGTH: 67
<212> TYPE: DNA
<213> ORGANISM: Artificial sequence
<220> FEATURE:
<223> OTHER INFORMATION: Single strand DNA oligonucleotide
```

<400> SEQUENCE: 3
tggcggctag tgggcaacat gcttcggcat ggcgaatggg acgtaactag cataacccct 60
tggggcc 67

<210> SEQ ID NO 4
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 4
gcgaggaggc tgggaccatg gctagctaag gaggtgatcc aaccgcaggt tcccctac 58

<210> SEQ ID NO 5
<211> LENGTH: 55
<212> TYPE: DNA
<213> ORGANISM: Artificial sequence
<220> FEATURE:
<223> OTHER INFORMATION: Single strand DNA oligonucleotide

<400> SEQUENCE: 5
gtatctgtcg agtagagtgt gggctccgct gcttctttgc tgacgagtgg cggac 55

<210> SEQ ID NO 6
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 6
gaatatctgg acccgaccgt ctccgcagct tcttcctgtt accgttcgac 50

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
atggcaactg tttccatgcg cg 22

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
ctcagcttct acgaagcttt c 21

<210> SEQ ID NO 9
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 9
atgggtcaga aagtacatcc taatg 25

<210> SEQ ID NO 10
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 10
tttacggcct ttacgctgc 19

<210> SEQ ID NO 11
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 11
atggcaagat atttgggtcc taag 24

<210> SEQ ID NO 12
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 12
cttggagtaa agctcgacga tc 22

<210> SEQ ID NO 13
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 13
atggctcaca tcgaaaaaca agc 23

<210> SEQ ID NO 14
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 14
tttccccaga atttcttcaa cgg 23

<210> SEQ ID NO 15
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 15
atgcgtcatt acgaaatcgt ttttatgg 28

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
ctcttcagaa tccccagcat c 21

<210> SEQ ID NO 17
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 17
atgccacgtc gtcgcgtcat t 21

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
ccaacggtag tgtgcgaacg 20

<210> SEQ ID NO 19
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 19
atgagcatgc aagatccgat cgc 23

<210> SEQ ID NO 20
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 20
ggctacgtag cagataattt cgcc 24

<210> SEQ ID NO 21
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 21
atggctgaaa atcaatacta cggc 24

<210> SEQ ID NO 22
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 22
acgtttggag aactgcggac g 21

<210> SEQ ID NO 23

<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 23
atgcagaacc aaagaatccg tatcc 25

<210> SEQ ID NO 24
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 24
acccaggctg atctgcacgt c 21

<210> SEQ ID NO 25
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 25
atggcaaagg caccaattcg tgc 23

<210> SEQ ID NO 26
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 26
tacgcgacgt tttttcggcg g 21

<210> SEQ ID NO 27
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 27
atggcaacag ttaaccagct ggtac 25

<210> SEQ ID NO 28
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 28
agccttagga cgcttcacgc c 21

<210> SEQ ID NO 29
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 29
atggcccgta tagcaggcat taac 24

<210> SEQ ID NO 30
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 30
tttcttgatc ggtttgcgcg g 21

<210> SEQ ID NO 31
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 31
atggctaagc aatcaatgaa agc 23

<210> SEQ ID NO 32
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 32
ccagctagcc tttttcagac cc 22

<210> SEQ ID NO 33
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 33
atgtctctaa gtactgaagc aacag 25

<210> SEQ ID NO 34
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 34
gcgacgcaga cccagg 16

<210> SEQ ID NO 35
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 35
atggtaacta ttcgtttagc acgtc 25

<210> SEQ ID NO 36

<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 36
agctgctttg tttacttctt tgatc 25

<210> SEQ ID NO 37
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 37
atgaccgata aaatccgtac tctgc 25

<210> SEQ ID NO 38
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 38
cagaaccgct ttctctacaa cg 22

<210> SEQ ID NO 39
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 39
atggcacgtt atttccgtcg tcgc 24

<210> SEQ ID NO 40
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 40
ctgatggcga tcagtgtacg gc 22

<210> SEQ ID NO 41
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 41
atgccacgtt ctctcaagaa agg 23

<210> SEQ ID NO 42
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 42
tttcttcttc gctttttttat cagcag 26

<210> SEQ ID NO 43
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 43
atggctaata tcaaatcagc taagaagcg 29

<210> SEQ ID NO 44
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 44
agccagtttg ttgatctgtg c 21

<210> SEQ ID NO 45
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 45
atgccggtaa ttaaagtacg tgaaaac 27

<210> SEQ ID NO 46
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 46
gtacagacga gtgcggcgtg 20

<210> SEQ ID NO 47
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 47
gtttaacttt aagaaggaga tatacat 27

<210> SEQ ID NO 48
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 48
aaaggcctcc tgcaggttaa ccttactta 29

<210> SEQ ID NO 49

<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 49
gtttaacttt aagaaggaga tatacatatg tag 33

<210> SEQ ID NO 50
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 50
gggtagctgg tcccgggagc tcgctt 26

<210> SEQ ID NO 51
<211> LENGTH: 15
<212> TYPE: PRT
<213> ORGANISM: Artificial Sequence
<220> FEATURE:
<223> OTHER INFORMATION: Biotin lygase tag amino acid sequence

<400> SEQUENCE: 51

Leu His His Ile Leu Asp Ala Gln Lys Met Val Trp Asn His Arg
1 5 10 15

<210> SEQ ID NO 52
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 52
atgagtttac ttaataataa agcg 24

<210> SEQ ID NO 53
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 53
tgctgttctc tcaaaatgat aaaatactgt agg 33

<210> SEQ ID NO 54
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 54
atgaaacaaa atattaatat cggtaatgtt g 31

<210> SEQ ID NO 55
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 55
tgcaatcctt atccaacgat aaac 24

<210> SEQ ID NO 56
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 56
atgacagtaa aagcaccttc agtcac 26

<210> SEQ ID NO 57
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 57
ttcatctatt ttaacctgtg ttggattttc agg 33

<210> SEQ ID NO 58
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 58
atgaatgatt caagtgttat ctatcg 26

<210> SEQ ID NO 59
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 59
aaatgtaaac agaatattga tttcttctg 29

<210> SEQ ID NO 60
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 60
atggcaaata cccctgtaaa ttatc 25

<210> SEQ ID NO 61
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 61
ttgtgatata ggctccaaat cgatag 26

<210> SEQ ID NO 62
<211> LENGTH: 28

<212> TYPE: DNA
<213> ORGANISM: Artificial sequence
<220> FEATURE:
<223> OTHER INFORMATION: Single strand DNA oligonucleotide

<400> SEQUENCE: 62
atgctcttta catttttga tccgattg 28

<210> SEQ ID NO 63
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 63
cttatcattt ccataagatt tctcc 25

<210> SEQ ID NO 64
<211> LENGTH: 1674
<212> TYPE: DNA
<213> ORGANISM: Escherichia coli

<400> SEQUENCE: 64
atgactgaat cttttgctca actctttgaa gagtccttaa aagaaatcga aacccgcccg 60
ggttctatcg ttcgtggcgt tgttgttgct atcgacaaag acgtagtact ggttgacgct 120
ggtctgaaat ctgagtccgc catcccggct gagcagttca aaaacgccca gggcgagctg 180
gaaatccagg taggtgacga agttgacgtt gctctggacg cagtagaaga cggcttcggt 240
gaaactctgc tgtcccgtga gaaagctaaa cgtcacgaag cctggatcac gctggaaaaa 300
gcttacgaag atgctgaaac tgttaccggt gttatcaacg gcaaagttaa gggcggcttc 360
actgttgagc tgaacggtat tcgtgcgttc ctgccaggtt ctctggtaga cgttcgtccg 420
gtgcgtgaca ctctgcacct ggaaggcaaa gagcttgaat ttaaagtaat caagctggat 480
cagaagcgca acaacgttgt tgtttctcgt cgtgccgtta tcgaatccga aaacagcgca 540
gagcgcgatc agctgctgga aaacctgcag gaaggcatgg aagttaaagg tatcgttaag 600
aacctcactg actacggtgc attcgttgat ctgggcggcg ttgacggcct gctgcacatc 660
actgacatgg cctggaaacg cgttaagcat ccgagcgaaa tcgtcaacgt gggcgacgaa 720
atcactgtta aagtgctgaa gttcgaccgc gaacgtaccc gtgtatccct gggcctgaaa 780
cagctgggcg aagatccgtg ggtagctatc gctaaacgtt atccggaagg taccaaactg 840
actggtcgcg tgaccaacct gaccgactac ggctgcttcg ttgaaatcga agaaggcgtt 900
gaaggcctgg tacacgtttc cgaaatggat tggaccaaca aaaacatcca cccgtccaaa 960
gttgttaacg ttggcgatgt agtggaagtt atggttctgg atatcgacga agaacgtcgt 1020
cgtatctccc tgggtctgaa acagtgcaaa gctaacccgt ggcagcagtt cgcggaaacc 1080
cacaacaagg gcgaccgtgt tgaaggtaaa atcaagtcta tcactgactt cggtatcttc 1140
atcggcctgg acggcggcat cgacggcctg gttcacctgt ctgacatctc ctggaacgtt 1200
gcaggcgaag aagcagttcg tgaatacaaa aaaggcgacg aaatcgctgc agttgttctg 1260
caggttgacg cagaacgtga acgtatctcc ctgggcgtta aacagctcgc agaagatccg 1320
ttcaacaact gggttgctct gaacaagaaa ggcgctatcg taaccggtaa agtaactgca 1380
gttgacgcta aaggcgcaac cgtagaactg gctgacggcg ttgaaggtta cctgcgtgct 1440
tctgaagcat cccgtgaccg cgttgaagac gctaccctgg ttctgagcgt tggcgacgaa 1500
gttgaagcta aattcaccgg cgttgatcgt aaaaaccgcg caatcagcct gtctgttcgt 1560
gcgaaagacg aagctgacga gaaagatgca atcgcaactg ttaacaaaca ggaagatgca 1620
aacttctcca acaacgcaat ggctgaagct ttcaaagcag ctaaaggcga gtaa 1674

<210> SEQ ID NO 65
<211> LENGTH: 726
<212> TYPE: DNA
<213> ORGANISM: Escherichia coli

<400> SEQUENCE: 65
atggcaactg tttccatgcg cgacatgctc aaggctggtg ttcacttcgg tcaccagacc 60
cgttactgga acccgaaaat gaagccgttc atcttcggtg cgcgtaacaa agttcacatc 120
atcaaccttg agaaaactgt accgatgttc aacgaagctc tggctgaact gaacaagatt 180
gcttctcgca aaggtaaaat ccttttcgtt ggtactaaac gcgctgcaag cgaagcggtg 240
aaagacgctg ctctgagctg cgaccagttc ttcgtgaacc atcgctggct gggcggtatg 300
ctgactaact ggaaaaccgt tcgtcagtcc atcaaacgtc tgaaagacct ggaaactcag 360
tctcaggacg gtactttcga caagctgacc aagaaagaag cgctgatgcg cactcgtgag 420
ctggagaaac tggaaaacag cctgggcggt atcaaagaca tgggcggtct gccggacgct 480
ctgtttgtaa tcgatgctga ccacgaacac attgctatca aagaagcaaa caacctgggt 540
attccggtat ttgctatcgt tgataccaac tctgatccgg acggtgttga cttcgttatc 600
ccgggtaacg acgacgcaat ccgtgctgtg accctgtacc tgggcgctgt tgctgcaacc 660
gtacgtgaag gccgttctca ggatctggct tcccaggcgg aagaaagctt cgtagaagct 720
gagtaa 726

<210> SEQ ID NO 66
<211> LENGTH: 702
<212> TYPE: DNA
<213> ORGANISM: Escherichia coli

<400> SEQUENCE: 66
atgggtcaga aagtacatcc taatggtatt cgcctgggta ttgtaaaacc atggaactct 60
acctggtttg cgaacaccaa agaattcgct gacaacctgg acagcgattt taaagtacgt 120
cagtacctga ctaaggaact ggctaaagcg tccgtatctc gtatcgttat cgagcgtccg 180
gctaagagca tccgtgtaac cattcacact gctcgcccgg gtatcgttat cggtaaaaaa 240
ggtgaagacg tagaaaaact gcgtaaggtc gtagcggaca tcgctggcgt tcctgcacag 300
atcaacatcg ccgaagttcg taagcctgaa ctggacgcaa aactggttgc tgacagcatc 360
acttctcagc tggaacgtcg cgttatgttc cgtcgtgcta tgaagcgtgc tgtacagaac 420
gcaatgcgtc tgggtgctaa aggtattaaa gttgaagtta gcggccgtct gggcggcgcg 480
gaaatcgcac gtaccgaatg gtaccgcgaa ggtcgcgtac cgctgcacac tctgcgtgct 540
gacatcgact acaacacctc tgaagcgcac accacttacg gtgtaatcgg cgttaaagtg 600
tggatcttca aaggcgagat cctgggtggt atggctgctg ttgaacaacc ggaaaaaccg 660
gctgctcagc ctaaaaagca gcagcgtaaa ggccgtaaat aa 702

<210> SEQ ID NO 67
<211> LENGTH: 621
<212> TYPE: DNA
<213> ORGANISM: Escherichia coli

<400> SEQUENCE: 67
atggcaagat atttgggtcc taagctcaag ctgagccgtc gtgagggcac cgacttattc 60
cttaagtctg gcgttcgcgc gatcgatacc aagtgtaaaa ttgaacaagc tcctggccag 120
cacggtgcgc gtaaaccgcg tctgtctgac tatggtgtgc agttgcgtga aaagcaaaaa 180
gttcgccgta tctatggtgt gctggagcgt cagttccgta actactacaa agaagcagca 240
cgtctgaaag gcaacaccgg tgaaaacctg ttggctctgc tggaaggtcg tctggacaac 300
gttgtatacc gtatgggctt cggtgccact cgtgcagaag cacgtcagct ggttagccat 360
aaagcaatta tggtaaacgg tcgtgttgtt aacatcgctt cttatcaggt tagtccgaat 420
gacgttgtaa gcattcgtga gaaagcgaag aagcagtctc gcgtgaaagc cgctctggag 480
ctggctgagc agcgtgaaaa gccaacctgg ctggaagttg atgctggcaa gatggaaggt 540
acgtttaagc gtaagccgga gcgttctgat ctgtctgcgg acattaacga acacctgatc 600
gtcgagcttt actccaagta a 621

<210> SEQ ID NO 68
<211> LENGTH: 504
<212> TYPE: DNA
<213> ORGANISM: Escherichia coli

<400> SEQUENCE: 68
atggctcaca tcgaaaaaca agctggcgaa ctgcaggaaa agctgatcgc ggtaaaccgc 60
gtatctaaaa ccgttaaagg tggtcgtatt ttctccttca cagctctgac tgttgttggc 120
gatggtaacg gtcgcgttgg ttttggttac ggtaaagcgc gtgaagttcc agcagcgatc 180
cagaaagcga tggaaaaagc ccgtcgcaat atgattaacg tcgcgctgaa taacggcact 240
ctgcaacacc ctgttaaagg tgttcacacg ggttctcgcg tattcatgca gccggcttcc 300
gaaggtaccg gtatcatcgc cggtggtgca atgcgcgccg ttctggaagt cgctggggtt 360
cataacgttc tggctaaagc atatggttcc accaacccga tcaacgtggt tcgtgcaact 420
attgatggcc tggaaaatat gaattctcca gcaatggtcg ctgccaagcg tggtaaatcc 480
gttgaagaaa ttctggggaa ataa 504

<210> SEQ ID NO 69
<211> LENGTH: 396
<212> TYPE: DNA
<213> ORGANISM: Escherichia coli

<400> SEQUENCE: 69
atgcgtcatt acgaaatcgt ttttatggtc catcctgacc agagcgaaca ggttccgggc 60
atgatcgagc gctacactgc tgccatcact ggtgcagaag gcaagatcca ccgtctggaa 120
gactggggcc gccgtcagct ggcttacccg atcaacaaac tgcacaaagc acactacgtt 180
ctgatgaacg ttgaagctcc gcaggaagtg atcgatgagc tggaaactac cttccgcttc 240
aacgatgccg ttattcgcag catggttatg cgtaccaagc acgctgttac cgaagcatct 300
ccgatggtta aagcgaaaga cgagcgccgc gagcgtcgcg atgatttcgc aaacgaaacc 360
gcagatgatg cagatgctgg ggattctgaa gagtaa 396

<210> SEQ ID NO 70
<211> LENGTH: 471
<212> TYPE: DNA
<213> ORGANISM: Escherichia coli

<400> SEQUENCE: 70
atgccacgtc gtcgcgtcat tggtcagcgt aaaattctgc cggatccgaa gttcggatca 60
gaactgctgg ctaaatttgt aaatatcctg atggtagatg gtaaaaaatc tactgctgaa 120
tctatcgtat acagcgcgct ggagaccctg gctcagcgct ctggtaaatc tgaactggaa 180
gcattcgaag tagctctcga aaacgtgcgc ccgactgtag aagttaagtc tcgccgcgtt 240
ggtggttcta cttatcaggt accagttgaa gtccgtccgg ttcgtcgtaa tgctctggca 300
atgcgttgga tcgttgaagc tgctcgtaaa cgcggtgata aatccatggc tctgcgcctg 360
gcgaacgaac tttctgatgc tgcagaaaac aaaggtactg cagttaagaa acgtgaagac 420
gttcaccgta tggccgaagc caacaaggcg ttcgcacact accgttggta a 471

<210> SEQ ID NO 71
<211> LENGTH: 393
<212> TYPE: DNA
<213> ORGANISM: Escherichia coli

<400> SEQUENCE: 71
atgagcatgc aagatccgat cgcggatatg ctgacccgta tccgtaacgg tcaggccgcg 60
aacaaagctg cggtcaccat gccttcctcc aagctgaaag tggcaatcgc caacgtgctg 120
aaggaagaag gttttattga agattttaaa gttgaaggcg acaccaagcc tgaactggaa 180
cttactctga agtatttcca gggcaaagct gttgtagaaa gcattcagcg tgtcagccgc 240
ccaggtctgc gcatctataa acgtaaagat gagctgccga aagttatggc gggtctgggt 300
atcgcagttg tttctacctc taaaggtgtt atgactgatc gtgcagcgcg ccaggctggt 360
cttggtggcg aaattatctg ctacgtagcc taa 393

<210> SEQ ID NO 72
<211> LENGTH: 393
<212> TYPE: DNA
<213> ORGANISM: Escherichia coli

<400> SEQUENCE: 72
atggctgaaa atcaatacta cggcactggt cgccgcaaaa gttccgcagc tcgcgttttc 60
atcaaaccgg gcaacggtaa aatcgtaatc aaccaacgtt ctctggaaca gtacttcggt 120
cgtgaaactg cccgcatggt agttcgtcag ccgctggaac tggtcgacat ggttgagaaa 180
ctggacctgt acatcaccgt taaaggtggt ggtatctctg gtcaggctgg tgcgatccgt 240
cacggtatca cccgcgctct gatggaatac gacgagtccc tgcgttctga actgcgtaaa 300
gctggcttcg ttactcgtga cgctcgtcag gttgaacgta agaaagtcgg tctgcgtaaa 360
gcacgtcgtc gtccgcagtt ctccaaacgt taa 393

<210> SEQ ID NO 73
<211> LENGTH: 312
<212> TYPE: DNA
<213> ORGANISM: Escherichia coli

<400> SEQUENCE: 73
atgcagaacc aaagaatccg tatccgcctg aaagcgtttg atcatcgtct gatcgatcaa 60
gcaaccgcgg aaatcgtcga gactgccaag cgcactggtg cgcaggtccg tggtccgatc 120
ccgctgccga cacgcaaaga gcgcttcact gttctgatct ccccgcacgt caacaaagac 180
gcgcgcgatc agtacgaaat ccgtactcac ttgcgtctgg ttgacatcgt tgagccaacc 240
gagaaaaccg ttgatgctct gatgcgtctg gatctggctg ccggtgtaga cgtgcagatc 300
agcctgggtt aa 312

<210> SEQ ID NO 74
<211> LENGTH: 390
<212> TYPE: DNA
<213> ORGANISM: Escherichia coli

<400> SEQUENCE: 74
atggcaaagg caccaattcg tgcacgtaaa cgtgtaagaa aacaagtctc tgacggcgtg 60
gctcatatcc atgcttcttt caacaacacc atcgtgacta tcactgatcg tcagggtaac 120
gcgttgggtt gggcaacagc cggtggttcc ggtttccgtg gttctcgcaa atccactccg 180
tttgcagctc aggttgcagc agagcgttgc gctgacgccg tgaaagaata cggcatcaag 240
aatctggaag ttatggttaa aggtccgggt ccaggccgcg aatctactat tcgtgctctg 300
aacgccgcag gtttccgcat cactaacatt actgatgtga ctccgatccc tcataacggt 360
tgtcgtccgc cgaaaaaacg tcgcgtataa 390

<210> SEQ ID NO 75
<211> LENGTH: 375
<212> TYPE: DNA
<213> ORGANISM: Escherichia coli

<400> SEQUENCE: 75
atggcaacag ttaaccagct ggtacgcaaa ccacgtgctc gcaaagttgc gaaaagcaac 60
gtgcctgcgc tggaagcatg cccgcaaaaa cgtggcgtat gtactcgtgt atatactacc 120
actcctaaaa aaccgaactc cgcgctgcgt aaagtatgcc gtgttcgtct gactaacggt 180
ttcgaagtga cttcctacat cggtggtgaa ggtcacaacc tgcaggagca ctccgtgatc 240
ctgatccgtg gcggtcgtgt taaagacctc ccgggtgttc gttaccacac cgtacgtggt 300
gcgcttgact gctccggcgt taaagaccgt aagcaggctc gttccaagta tggcgtgaag 360
cgtcctaagg cttaa 375

<210> SEQ ID NO 76
<211> LENGTH: 357
<212> TYPE: DNA
<213> ORGANISM: Escherichia coli

<400> SEQUENCE: 76
gtggcccgta tagcaggcat taacattcct gatcataagc atgccgtaat cgcattaact 60
tcgatttatg gcgtcggcaa gacccgttct aaagccatcc tggctgcagc gggtatcgct 120
gaagatgtta agatcagtga gctgtctgaa ggacaaatcg acacgctgcg tgacgaagtt 180
gccaaatttg tcgttgaagg tgatctgcgc cgtgaaatca gcatgagcat caagcgcctg 240
atggatcttg gttgctatcg cggtttgcgt catcgtcgtg gtctcccggt tcgcggtcag 300
cgtaccaaga ccaacgcacg tacccgtaag ggtccgcgca aaccgatcaa gaaataa 357

<210> SEQ ID NO 77
<211> LENGTH: 306
<212> TYPE: DNA
<213> ORGANISM: Escherichia coli

<400> SEQUENCE: 77
atggctaagc aatcaatgaa agcacgcgaa gtaaaacgcg tagctttagc tgataaatac 60
ttcgcgaaac gcgctgaact gaaagcgatc atctctgatg tgaacgcttc cgacgaagat 120
cgttggaacg ctgttctcaa gctgcagact ctgccgcgtg attccagccc gtctcgtcag 180
cgtaaccgct gccgtcaaac aggtcgtccg catggtttcc tgcggaagtt cgggttgagc 240
cgtattaagg tccgtgaagc cgctatgcgc ggtgaaatcc cgggtctgaa aaaggctagc 300
tggtaa 306

<210> SEQ ID NO 78
<211> LENGTH: 270
<212> TYPE: DNA
<213> ORGANISM: Escherichia coli

<400> SEQUENCE: 78
atgtctctaa gtactgaagc aacagctaaa atcgtttctg agtttggtcg tgacgcaaac 60
gacaccggtt ctaccgaagt tcaggtagca ctgctgactg cacagatcaa ccacctgcag 120
ggccactttg cagagcacaa aaaagatcac cacagccgtc gtggtctgct gcgcatggtt 180
tctcagcgtc gtaaactgct cgactacctg aaacgtaaag acgtagcacg ttacacccag 240
ctcatcgagc gcctgggtct gcgtcgctaa 270

<210> SEQ ID NO 79
<211> LENGTH: 249
<212> TYPE: DNA
<213> ORGANISM: Escherichia coli

<400> SEQUENCE: 79
atggtaacta ttcgtttagc acgtcacggc gctaaaaagc gtccgttcta ccaggttgtt 60
gtcgctgaca gccgtaatgc acgcaacggt cgcttcatcg agcgcgttgg tttcttcaac 120
ccaatcgcta gcgaaaaaga agaaggcact cgcctggatc tggatcgcat cgctcactgg 180
gttggccagg gcgcaactat ttctgatcgc gttgctgcgc tgatcaaaga agtaaacaaa 240
gcagcttaa 249

<210> SEQ ID NO 80
<211> LENGTH: 255
<212> TYPE: DNA
<213> ORGANISM: Escherichia coli

<400> SEQUENCE: 80
atgaccgata aaatccgtac tctgcaaggt cgcgttgtta gcgacaaaat ggagaaatcc 60
attgttgttg ctatcgaacg ttttgtgaaa cacccgatct acggtaaatt catcaagcgt 120
acgaccaaac tgcacgtaca tgacgagaac aacgaatgcg gtatcggtga cgtggttgaa 180
atccgcgaat gccgtccgct gtccaagact aaatcctgga cgctggttcg cgttgtagag 240
aaagcggttc tgtaa 255

<210> SEQ ID NO 81
<211> LENGTH: 228
<212> TYPE: DNA
<213> ORGANISM: Escherichia coli

<400> SEQUENCE: 81
atggcacgtt atttccgtcg tcgcaagttc tgccgtttca ccgcggaagg cgttcaagag 60
atcgactata aagatatcgc tacgctgaaa aactacatca ccgaaagcgg taagattgtc 120
ccaagccgta tcaccggtac ccgtgcaaaa taccagcgtc agctggctcg cgctatcaaa 180
cgcgctcgct acctgtccct gctgccgtac actgatcgcc atcagtaa 228

<210> SEQ ID NO 82
<211> LENGTH: 279
<212> TYPE: DNA
<213> ORGANISM: Escherichia coli

<400> SEQUENCE: 82
atgccacgtt ctctcaagaa aggtcctttt attgacctgc acttgctgaa gaaggtagag 60
aaagcggtgg aaagcggaga caagaagccc ctgcgcactt ggtcccgtcg ttcaacgatc 120
tttcctaaca tgatcggttt gaccatcgct gtccataatg gtcgtcagca cgttccggta 180
tttgtaaccg acgaaatggt tggtcacaaa ctgggtgaat tcgcaccgac tcgtacttat 240
cgcggccacg ctgctgataa aaaagcgaag aagaaataa 279

<210> SEQ ID NO 83
<211> LENGTH: 264
<212> TYPE: DNA
<213> ORGANISM: Escherichia coli

<400> SEQUENCE: 83
ttggctaata tcaaatcagc taagaagcgc gccattcagt ctgaaaaggc tcgtaagcac 60
aacgcaagcc gtcgctctat gatgcgtact ttcatcaaga aagtatacgc agctatcgaa 120
gctggcgaca aagctgctgc acagaaagca tttaacgaaa tgcaaccgat cgtggaccgt 180
caggctgcta aaggtctgat ccacaaaaac aaagctgcac gtcataaggc taacctgact 240
gcacagatca acaaactggc ttaa 264

<210> SEQ ID NO 84
<211> LENGTH: 216
<212> TYPE: DNA
<213> ORGANISM: Escherichia coli

<400> SEQUENCE: 84
atgccggtaa ttaaagtacg tgaaaacgag ccgttcgacg tagctctgcg tcgcttcaag 60
cgttcctgcg aaaaagcagg tgttctggcg gaagttcgtc gtcgtgagtt ctatgaaaaa 120
ccgactaccg aacgtaagcg cgctaaagct tctgcagtga aacgtcacgc gaagaaactg 180
gctcgcgaaa acgcacgccg cactcgtctg tactaa 216

<210> SEQ ID NO 85
<211> LENGTH: 1542
<212> TYPE: DNA
<213> ORGANISM: Escherichia coli

<400> SEQUENCE: 85
aaattgaaga gtttgatcat ggctcagatt gaacgctggc ggcaggccta acacatgcaa 60
gtcgaacggt aacaggaaga agcttgcttc tttgctgacg agtggcggac gggtgagtaa 120
tgtctgggaa actgcctgat ggagggggat aactactgga aacggtagct aataccgcat 180
aacgtcgcaa gaccaaagag ggggaccttc gggcctcttg ccatcggatg tgcccagatg 240

```
ggattagcta gtaggtgggg taacggctca cctaggcgac gatccctagc tggtctgaga    300
ggatgaccag ccacactgga actgagacac ggtccagact cctacgggag gcagcagtgg    360
ggaatattgc acaatgggcg caagcctgat gcagccatgc cgcgtgtatg aagaaggcct    420
tcgggttgta aagtactttc agcggggagg aagggagtaa agttaatacc tttgctcatt    480
gacgttaccc gcagaagaag caccggctaa ctccgtgcca gcagccgcgg taatacggag    540
ggtgcaagcg ttaatcggaa ttactgggcg taaagcgcac gcaggcggtt tgttaagtca    600
gatgtgaaat ccccgggctc aacctgggaa ctgcatctga tactggcaag cttgagtctc    660
gtagaggggg gtagaattcc aggtgtagcg gtgaaatgcg tagagatctg gaggaatacc    720
ggtggcgaag gcggccccct ggacgaagac tgacgctcag gtgcgaaagc gtggggagca    780
aacaggatta gataccctgg tagtccacgc cgtaaacgat gtcgacttgg aggttgtgcc    840
cttgaggcgt ggcttccgga gctaacgcgt taagtcgacc gcctggggag tacggccgca    900
aggttaaaac tcaaatgaat tgacgggggc ccgcacaagc ggtggagcat gtggtttaat    960
tcgatgcaac gcgaagaacc ttacctggtc ttgacatcca cggaagtttt cagagatgag   1020
aatgtgcctt cgggaaccgt gagacaggtg ctgcatggct gtcgtcagct cgtgttgtga   1080
aatgttgggt taagtcccgc aacgagcgca acccttatcc tttgttgcca gcggtccggc   1140
cgggaactca aaggagactg ccagtgataa actggaggaa ggtggggatg acgtcaagtc   1200
atcatggccc ttacgaccag ggctacacac gtgctacaat ggcgcataca aagagaagcg   1260
acctcgcgag agcaagcgga cctcataaag tgcgtcgtag tccggattgg agtctgcaac   1320
tcgactccat gaagtcggaa tcgctagtaa tcgtggatca gaatgccacg gtgaatacgt   1380
tcccgggcct tgtacacacc gcccgtcaca ccatgggagt gggttgcaaa agaagtaggt   1440
agcttaacct tcgggagggc gcttaccact ttgtgattca tgactggggt gaagtcgtaa   1500
caaggtaacc gtaggggaac ctgcggttgg atcacctcct ta                      1542
```

<210> SEQ ID NO 86
<211> LENGTH: 906
<212> TYPE: DNA
<213> ORGANISM: Escherichia coli

<400> SEQUENCE: 86

```
atgagcatcg ataaaagtta ctgcggattt attgccatcg tcggacgtcc gaacgttggc     60
aaatccacat tgttgaacaa actgctgggg cagaaaatct ccatcacttc ccgcaaggcg    120
cagacaactc gtcaccgcat tgtggggatc catactgaag gcgcgtatca ggcgatctac    180
gtcgatacac cgggcctgca tatggaagaa aaacgcgcca ttaaccgcct gatgaacaaa    240
gcggcgagca gctctattgg cgatgttgag ctggtgattt ttgtcgttga aggcacccgc    300
tggacgccgg acgacgaaat ggtgctcaac aaactgcgcg aaggcaaagc gccggtaatc    360
ctcgcggtga acaaagtgga caacgtgcag gagaaagccg atctgctgcc gcacctgcag    420
ttcctggcaa gccagatgaa cttcctcgat atcgtgccaa tctctgccga aaccgggctg    480
aatgttgaca ctattgcggc aatcgtgcgt aagcatctac ctgaagcgac tcatcacttc    540
ccggaagatt acatcaccga tcgctcacag cgttttatgg cgtctgaaat catccgcgaa    600
aaactgatgc gtttcctcgg cgctgaactg ccgtactccg tgaccgtgga gatcgaacgt    660
ttcgtctcta acgaacgcgg tggttatgac atcaacggtt tgattctcgt tgagcgtgaa    720
gggcagaaga agatggtcat tggcaacaaa ggggccaaga tcaaaaccat cgggattgaa    780
gcgcgtaaag acatgcagga aatgttcgaa gcgcctgttc accttgaact gtgggtaaaa    840
```

gtgaaatccg gttgggccga cgacgaacgc gcactgcgca gtctcggtta cgttgacgat 900
ctttaa 906

<210> SEQ ID NO 87
<211> LENGTH: 453
<212> TYPE: DNA
<213> ORGANISM: Escherichia coli

<400> SEQUENCE: 87
ttgtccacat tagagcaaaa attaacagag atgattactg cgccagttga ggccctgggt 60
tttgaactgg ttggcatcga atttattcgc ggtcgcacat ccacactgcg catctatatt 120
gatagtgaag atggcatcaa tgttgatgat tgtgctgatg tgagccacca ggtaagtgct 180
gtgctggatg ttgaagatcc catcaccgtt gcttataacc tggaagtctc ctcaccgggt 240
ctcgatcgcc cactgttcac ggctgaacac tacgcccgtt ttgtcggaga agaggtgact 300
ctggttctcc gtatggcggt acaaaaccgt cgtaaatggc agggcgttat caaagcggta 360
gacggtgaaa tgatcacagt taccgtcgaa ggtaaagatg aagtgttcgc gctgagtaat 420
atccagaagg cgaacctggt tccccacttt taa 453

<210> SEQ ID NO 88
<211> LENGTH: 549
<212> TYPE: DNA
<213> ORGANISM: Escherichia coli

<400> SEQUENCE: 88
atgagcaaac aactcaccgc gcaagcacct gttgatccca tcgttttggg gaaaatgggt 60
tcgtcttacg gtattcgtgg gtggctcaga gtgttttctt ccaccgaaga cgccgaaagc 120
atttttgact atcagccctg gtttatccag aaggcgggtc agtggcagca agtccagctg 180
gaaagctgga agcaccacaa tcaggacatg atcatcaagc tgaaaggcgt tgacgatcgt 240
gatgcggcga acctgctgac gaattgtgaa attgtcgtgg attcatcgca gctgcctcag 300
cttgaagagg gtgactacta ctggaaagac ctgatgggct gccaggtagt aaccactgaa 360
ggctacgatc tcggtaaagt cgtcgatatg atggaaaccg gatctaatga cgttctcgtc 420
attaaggcaa acctgaaaga tgcgtttggt atcaaggaac gtctcgtacc gttcctcgat 480
gggcaggtta tcaagaaagt cgatctcact actcgttcaa tcgaagtaga ttgggatcct 540
ggtttttaa 549

<210> SEQ ID NO 89
<211> LENGTH: 402
<212> TYPE: DNA
<213> ORGANISM: Escherichia coli

<400> SEQUENCE: 89
atggcgaaag aatttggtcg cccgcagcgc gtagcgcagg aaatgcaaaa agagatcgct 60
ctcatcctgc agcgtgaaat taaagatcct cgcctgggca tgatgaccac cgtttccggt 120
gtcgaaatgt ctcgcgacct ggcgtatgcc aaagtatatg tgacgttcct caacgacaaa 180
gatgaagacg cggttaaagc gggcatcaaa gcgttgcaag aagcttctgg tttcatccgc 240
agcctgctgg ggaaagcgat gcgcctgcgt atcgtgccgg aactgacctt cttctacgac 300
aactctctgg ttgaagggat gcgcatgtca aacctggtga ccagcgtggt caaacatgac 360
gaagaacgtc gtgttaaccc ggacgacagc aaggaggact aa 402

<210> SEQ ID NO 90
<211> LENGTH: 1053
<212> TYPE: DNA
<213> ORGANISM: Escherichia coli

<400> SEQUENCE: 90
ttgagtaaaa ataaactctc caaaggccag cagcgccgcg tgaacgccaa tcaccagcgt 60
cgtcttaaaa cgtctaagga gaagcccgac tacgacgaca atctgtttgg cgagcctgat 120
gaaggtatcg tcatcagccg ctttggtatg cacgctgatg tggaatccgc cgatggcgac 180
gttcaccgct gcaatattcg ccgtaccatc cgttcgctgg taaccggcga ccgcgtagtc 240
tggcgtccgg gtaaaccggc ggcggaaggc gtaaatgtca aagggatcgt ggaagcggtg 300
catgagcgta cctcggtgtt gacgcgtccg gatttctacg acggcgtaaa acctattgcc 360
gccaacatcg accagattgt cattgtctcc gccattttgc cggagctgtc gctcaatatt 420
atcgaccgtt acctggtggc ctgcgaaacc ttgcagattg agccgattat tgtgctcaac 480
aagatagacc tgctggacga cgaaggcatg gcgttcgtca acgagcagat ggatatctac 540
cgcaatatcg gttatcgcgt attgatggtt tccagccata ctcaggatgg gctaaaaccg 600
ctggaagagg cgttgaccgg gcgcatcagc atttttgccg ggcagtctgg cgtcggcaaa 660
tccagcctgc tgaatgcgtt gctggggctg caaaaagaga tcctgaccaa cgatatctct 720
gacaactcgg ggctcggtca gcacaccacg accgccgctc ggctgtatca cttcccgcac 780
ggcggtgatg tgattgactc cccaggagtg cgtgagttcg gcctctggca cctggagccg 840
gaacaaatca ctcagggctt tgtcgaattc catgactatt taggtctgtg taaatatcgc 900
gattgcaaac acgataccga tccgggctgc gctatccggg aagcggttga ggaagggaaa 960
atcgcggaaa cccgtttcga aaactatcac cgtattctgg aaagcatggc gcaggtaaaa 1020
acgcgtaaaa acttttctga tacggatgac tga 1053

<210> SEQ ID NO 91
<211> LENGTH: 573
<212> TYPE: DNA
<213> ORGANISM: Escherichia coli

<400> SEQUENCE: 91
gtgaataata acctgcaagg agacgctatc gcagctgcga tagatgttct caatgaagaa 60
cgtgtcatcg cctatccaac ggaagccgtt ttcggtgttg ggtgcgatcc tgatagcgaa 120
acagcagtga tgcgactgtt ggagttaaaa cagcgtccgg ttgataaggg gctgatttta 180
atcgcagcaa attacgagca gcttaaaccc tatattgatg acaccatgtt gactgacgtg 240
cagcgtgaaa ccatttttc ccgctggcca ggtcctgtca cctttgtctt tcccgcgcct 300
gcgacaacac cgcgctggtt gacgggccgc tttgattcgc ttgctgtacg agtcaccgac 360
catccgttgg tggttgcttt gtgccaggct tatggtaaac cgctggtttc taccagtgcc 420
aacttgagtg gattgccacc ttgtcgaaca gtagacgaag ttcgcgcaca atttggcgcg 480
gcgttcccgg ttgtgcctgg tgaaacgggg gggcgtttaa atccttcaga aatccgcgat 540
gccctgacgg gtgaactgtt tcgacagggg taa 573

<210> SEQ ID NO 92
<211> LENGTH: 1176
<212> TYPE: DNA
<213> ORGANISM: Staphylococcus aureus

<400> SEQUENCE: 92
atgactgaag aattcaatga atcaatgatt aacgatatta aagaaggtga caaagtcact 60
ggcgaggtac aacaagttga agacaagcaa gttgttgttc atatcaacgg tggtaaattt 120
aatgggatta ttcctattag tcaactatct acgcatcata ttgatagccc aagtgaagtt 180
gtaaaagagg gcgacgaagt tgaagcatat gtcactaaag ttgagtttga tgaagaaaat 240
gaaactggag cttacatctt atctagaaga caacttgaaa ctgagaagtc ttatagttat 300
ttacaagaaa aattagataa taatgaaatc atcgaagcga aagtaacaga agtagttaaa 360
ggtggtttgg ttgttgatgt aggacaaaga ggttttgttc cggcttcact aatttcaaca 420
gacttcattg aggatttctc tgtgtttgat ggacaaacaa ttcgtattaa agttgaagaa 480
ttggatcctg aaaataatag agtcatttta agccgtaaag cagttgaaca agaagaaaac 540
gatgctaaaa aagatcaatt attacaatct ttaaatgaag gcgatgttat tcatggtaaa 600
gtagcgcgtt taactcaatt tggtgcattt atagacattg gtggtgttga tggtttagtg 660
catgtatctg aactttctca cgaacatgtt caaacaccag aagaagtagt ttcaattggt 720
caagatgtta aagttaaaat taaatctatt gatagagata cagaacgtat ttcattatca 780
atcaaagata cgttaccaac acctttcgaa aatattaaag gtcaattcca cgaaaatgat 840
gtcattgaag gtgtcgtagt aagattggca aactttggtg catttgttga aattgcacca 900
ggtgtacaag gacttgtaca tatttctgaa attgcacaca aacacattgg tacgccaggt 960
gaagtgttag aacctggtca acaagtaaat gttaaaatat taggtattga tgaagagaat 1020
gaaagagtat cactatctat taaagcaaca ttaccaaacg aagatgttgt tgaaagtgat 1080
ccttctacga ctaaggcgta cttagaaaac gaagaagaag ataatccaac aattggcgat 1140
atgattggtg ataaacttaa aaatcttaaa ctataa 1176

<210> SEQ ID NO 93
<211> LENGTH: 27
<212> TYPE: DNA
<213> ORGANISM: Artificial sequence
<220> FEATURE:
<223> OTHER INFORMATION: HA tag nucleic acid sequence

<400> SEQUENCE: 93
tacccatacg atgttccaga ttacgct 27

<210> SEQ ID NO 94
<211> LENGTH: 768
<212> TYPE: DNA
<213> ORGANISM: Staphylococcus aureus

<400> SEQUENCE: 94
atggcagtaa tttcaatgaa acaattacta gaagcgggtg ttcacttcgg tcaccaaaca 60
cgtcgttgga acccaaaaat gaaaaaatat atcttcactg agagaaatgg tatttatatc 120
atcgacttac aaaaaacagt gaaaaaagta gacgaggcat acaacttctt gaaacaagtt 180
tcagaagatg gtggacaagt cttattcgta ggaactaaaa aacaagcaca agaatcagtt 240
aaatctgaag cagaacgtgc tggtcaattc tacattaacc aaagatggtt aggtggatta 300
ttaactaact ataaaacaat ctcaaaacga atcaaacgta tttctgaaat tgaaaaaatg 360
gaagaagatg gtttattcga agtattacct aaaaaagaag tagtagaact taaaaaagaa 420
tacgaccgtt taatcaaatt cttaggcgga attcgtgata tgaaatcaat gcctcaagca 480
ttattcgtag ttgacccacg taaagagcgt aatgcaattg ctgaagctcg taaattaaat 540
attcctatcg taggtatcgt tgacactaac tgtgatcctg acgaaattga ctacgttatc 600
ccagcaaacg acgatgctat ccgtgcggtt aaattattaa ctgctaaaat ggcagatgca 660
atcttagaag gtcaacaagg cgtttctaat gaagaagtag ctgcagaaca aaacatcgat 720
ttagatgaaa aagaaaaatc agaagaaaca gaagcaactg aagaataa 768

<210> SEQ ID NO 95
<211> LENGTH: 765
<212> TYPE: DNA
<213> ORGANISM: Artificial sequence
<220> FEATURE:
<223> OTHER INFORMATION: ORF sequences of S. aureus rS2-S21 and assembly
factors from the strain N315 optimized for E. coli codon usage

<400> SEQUENCE: 95
atggccgtta tcagtatgaa acagttgttg gaagccgggg tgcactttgg ccatcagacc 60
cgccgttgga acccaaaaat gaagaagtac attttcacag agcgtaatgg tatttacatt 120
attgatcttc agaaaacggt taaaaaagtc gatgaggcgt ataatttttt aaaacaggtt 180
tcagaggatg gggtcaagt ccttttcgtc ggaacaaaga aacaagcaca agagagcgtt 240
aagagtgaag cggagcgtgc agggcagttt tacattaacc aacgttggct gggcggattg 300
cttacgaatt ataaaaccat ctccaaacgt atcaaacgca tctcggagat tgaaaagatg 360
gaggaggacg gtctgtttga ggtgctgccg aagaaggaag ttgtcgagct gaaaaaagag 420
tacgaccgtt taatcaaatt tttaggcggc attcgtgata tgaagtcgat gccgcaggca 480
ttattcgtag ttgatccccg caaggaacgt aatgcgattg cggaggcccg taaacttaat 540
atccctatcg taggaatcgt cgatactaac tgcgatcccg atgaaatcga ctatgtaatc 600
ccggcaaacg acgacgccat ccgtgcagtc aaactgctga ccgcaaaaat ggctgacgct 660
attctggaag gcaacaaggg cgtcagcaat gaagaggttg ccgctgaaca gaacattgat 720
ttggacgaga aagaaaagag cgaggagacc gaggctactg aggaa 765

<210> SEQ ID NO 96
<211> LENGTH: 654
<212> TYPE: DNA
<213> ORGANISM: Staphylococcus aureus

<400> SEQUENCE: 96
gtgggtcaaa aaattaatcc aatcggactt cgtgttggta ttatccgtga ttgggaagct 60
aaatggtatg ctgaaaaaga cttcgcttca cttttacacg aagatttaaa aatccgtaaa 120
tttattgata atgaattaaa agaagcatca gtttctcacg tagagattga acgtgctgca 180
aaccgtatca acattgcaat tcatactggt aaacctggta tggtaattgg taaaggcggt 240
tcagaaatcg aaaaattacg caacaaatta aatgcgttaa ctgataaaaa agtacacatc 300
aacgtaattg aaatcaaaaa agttgatctt gacgctcgtt tagtagctga aaacatcgca 360
cgtcaattag aaaaccgtgc ttcattccgt cgtgtacaaa aacaagcaat cactagagct 420
atgaaacttg gtgctaaagg tatcaaaact caagtatctg gtcgtttagg cggagctgac 480
atcgctcgtg ctgaacaata ttcagaagga actgttccac ttcatacgtt acgtgctgac 540
atcgattatg cacacgctga agctgacact acttacggta aattaggcgt taaagtatgg 600
atctatcgtg gagaagttct tcctactaag aacactagtg gaggaggaaa ataa 654

<210> SEQ ID NO 97

<211> LENGTH: 651
<212> TYPE: DNA
<213> ORGANISM: Artificial sequence
<220> FEATURE:
<223> OTHER INFORMATION: ORF sequences of S. aureus rS2-S21 and assembly
factors from the strain N315 optimized for E. coli codon usage

<400> SEQUENCE: 97
atgggacaga agatcaaccc cattggactt cgtgttggta tcattcgtga ctgggaagcc 60
aaatggtacg cagagaaaga tttcgcttcg ctgctgcacg aagacttgaa aatccgtaag 120
ttcattgata acgaacttaa ggaggctagc gtctcacacg tggaaattga gcgtgcggca 180
aatcgcatca acatcgccat ccatacgggt aaacctggta tggtaattgg caagggtgga 240
tcggagatcg agaagttgcg taataaactg aacgcattaa ccgataaaaa ggtgcatatc 300
aacgtcattg aaatcaaaaa agtagatctg gatgcgcgct tggttgcgga gaatatcgcc 360
cgtcaattag aaaaccgtgc ttcgttccgt cgcgtgcaga aacaggctat tacgcgcgcc 420
atgaagttag gcgctaaggg catcaagaca caagtatcag ggcgcttagg tggcgctgat 480
attgcacgcg cagagcagta cagcgaagga actgtgccat tacacacctt gcgcgccgat 540
attgattacg cacatgcaga ggcagataca acttatggaa agcttggggt taaggtttgg 600
atttatcgtg gcgaagttct gcccaccaaa aatacctctg gtgggggtaa a 651

<210> SEQ ID NO 98
<211> LENGTH: 603
<212> TYPE: DNA
<213> ORGANISM: Staphylococcus aureus

<400> SEQUENCE: 98
atggctcgat tcagaggttc aaactggaaa aaatctcgtc gtttaggtat ctctttaagc 60
ggtactggta aagaattaga aaaacgtcct tacgcaccag gacaacatgg tccaaaccaa 120
cgtaaaaaat tatcagaata tggtttacaa ttacgtgaaa aacaaaaatt acgttactta 180
tatggaatga ctgaaagaca attccgtaac acatttgaca tcgctggtaa aaaattcggt 240
gtacacggtg aaaacttcat gattttatta gcaagtcgtt tagacgctgt tgtttattca 300
ttaggtttag ctcgtactcg tcgtcaagca cgtcaattag ttaaccacgg tcatatctta 360
gtagatggta aacgtgttga tattccatct tattctgtta aacctggtca aacaatttca 420
gttcgtgaaa aatctcaaaa attaaacatc atcgttgaat cagttgaaat caacaatttc 480
gtacctgagt acttaaactt tgatgctgac agcttaactg gtactttcgt acgtttacca 540
gaacgtagcg aattacctgc tgaaattaac gaacaattaa tcgttgagta ctactcaaga 600
taa 603

<210> SEQ ID NO 99
<211> LENGTH: 600
<212> TYPE: DNA
<213> ORGANISM: Artificial sequence
<220> FEATURE:
<223> OTHER INFORMATION: ORF sequences of S. aureus rS2-S21 and assembly
factors from the strain N315 optimized for E. coli codon usage

<400> SEQUENCE: 99
atggcccgtt ttcgtggaag taattggaaa aagagtcgtc gtcttggaat cagcttgtcc 60
ggcactggaa aggagcttga gaagcgcccg tatgcgcccg gacaacacgg tcctaatcaa 120
cgtaaaaaat taagcgagta tggccttcag ttacgtgaaa agcagaaact tcgctatctt 180
tacggaatga cagaacgtca atttcgcaac acgtttgata tcgcgggcaa aaaatttggc 240

```
gtacacgggg agaattttat gatcttactt gcgtcgcgtc ttgacgccgt cgtttattca    300

cttgggctgg cacgcacccg ccgccaagcg cgtcaattgg tgaaccatgg acacatcttg    360

gtagacggga aacgcgtgga tattccgtct tatagcgtaa agcctgggca gacgatcagt    420

gtacgtgaga aatcgcaaaa acttaatatt atcgtagaat ctgtcgaaat caataatttc    480

gtaccggaat atttgaattt cgacgctgat tctttaaccg gtacttttgt acgtcttcca    540

gagcgcagtg agctgccagc agaaattaac gaacaattga tcgtcgagta ttactcaaga    600


<210> SEQ ID NO 100
<211> LENGTH: 501
<212> TYPE: DNA
<213> ORGANISM: Staphylococcus aureus

<400> SEQUENCE: 100

atggctcgta gagaagaaga gacgaaagaa tttgaagaac gcgttgttac aatcaaccgt     60

gtagcaaaag ttgtaaaagg tggtcgtcgt ttccgtttca ctgcattagt tgtagttgga    120

gacaaaaatg gtcgtgtagg tttcggtact ggtaaagctc aagaggtacc agaagcaatc    180

aaaaaagctg ttgaagcagc taaaaaagat ttagtagttg ttccacgtgt tgaaggtaca    240

actccacaca caattactgg ccgttacggt tcaggaagcg tatttatgaa accggctgca    300

cctggtacag gagttatcgc tggtggtcct gttcgtgccg tacttgaatt agcaggtatc    360

actgatatct taagtaaatc attaggatca aacacaccaa tcaacatggt tcgtgctaca    420

atcgatggtt tacaaaacct taaaaatgct gaagatgttg cgaaattacg tggcaaaaca    480

gtagaagaat tatacaatta a                                              501


<210> SEQ ID NO 101
<211> LENGTH: 498
<212> TYPE: DNA
<213> ORGANISM: Artificial sequence
<220> FEATURE:
<223> OTHER INFORMATION: ORF sequences of S. aureus rS2-S21 and assembly
      factors from the strain N315 optimized for E. coli codon usage

<400> SEQUENCE: 101

atggcgcgtc gtgaagagga gaccaaagag tttgaagagc gtgttgtgac tatcaatcgc     60

gtggcgaaag tcgtgaaagg aggacgccgc ttccgcttta cggctttagt ggtcgtagga    120

gataagaatg gacgtgtggg gttcgggacc gggaaggctc aggaggtgcc cgaagctatt    180

aaaaaagcgg tggaggctgc taaaaaggac ctggtggtag tgccccgcgt cgagggcaca    240

accccacaca ccattacggg tcgctatgga tcagggtctg tctttatgaa gccagcagca    300

cctggaaccg gcgtaatcgc aggaggtccc gtccgcgcgg tacttgagct tgctggaatc    360

actgacatcc ttagtaaatc gttagggagc aacaccccga ttaatatggt ccgtgcgact    420

atcgacgggt tgcagaacct taagaatgca gaagacgtgg cgaaacttcg tggtaaaact    480

gtcgaagagc tgtacaat                                                  498


<210> SEQ ID NO 102
<211> LENGTH: 297
<212> TYPE: DNA
<213> ORGANISM: Staphylococcus aureus

<400> SEQUENCE: 102

atgagaacat atgaagttat gtacatcgta cgcccaaaca ttgaggaaga tgctaaaaaa     60

gcgttagttg aacgtttcaa cggtatctta gctactgaag gtgcagaagt tttagaagca    120
```

```
aaagactggg gtaaacgtcg cctagcttat gaaatcaatg atttcaaaga tggcttctac    180

aacatcgtac gtgttaaatc tgataacaac aaagctactg acgaattcca acgtctagct    240

aaaatcagtg acgatatcat tcgttacatg gttattcgtg aagacgaaga caagtaa       297


<210> SEQ ID NO 103
<211> LENGTH: 294
<212> TYPE: DNA
<213> ORGANISM: Artificial sequence
<220> FEATURE:
<223> OTHER INFORMATION: ORF sequences of S. aureus rS2-S21 and assembly
      factors from the strain N315 optimized for E. coli codon usage

<400> SEQUENCE: 103

atgcgcacat atgaggttat gtatatcgtt cgccccaaca ttgaagagga cgctaaaaag     60

gctttggtag agcgctttaa cggcatcttg gcgaccgaag gtgctgaggt attagaggcc    120

aaagactggg gaaagcgtcg tctggcatat gaaattaatg attttaagga tggtttctac    180

aacatcgttc gtgtgaaaag tgacaacaat aaagcgaccg acgaatttca gcgccttgca    240

aaaatttcag atgatattat tcgttatatg gtgattcgtg aagatgaaga taag          294


<210> SEQ ID NO 104
<211> LENGTH: 471
<212> TYPE: DNA
<213> ORGANISM: Staphylococcus aureus

<400> SEQUENCE: 104

atgcctcgta aaggatcagt acctaaaaga gacgtattac cagatccaat tcataactct     60

aagttagtaa ctaaattaat taacaaaatt atgttagatg gtaaacgtgg aacagcacaa    120

agaattcttt attcagcatt cgacctagtt gaacaacgca gtggtcgtga tgcattagaa    180

gtattcgaag aagcaatcaa caacattatg ccagtattag aagttaaagc tcgtcgtgta    240

ggtggttcta actatcaagt accagtagaa gttcgtccag agcgtcgtac tactttaggt    300

ttacgttggt tagttaacta tgcacgtctt cgtggtgaaa aaacgatgga agatcgttta    360

gctaacgaaa ttttagatgc agcaaataat acaggtggtg ccgttaagaa acgtgaggac    420

actcacaaaa tggctgaagc aaacaaagca tttgctcact accgttggta a             471


<210> SEQ ID NO 105
<211> LENGTH: 468
<212> TYPE: DNA
<213> ORGANISM: Artificial sequence
<220> FEATURE:
<223> OTHER INFORMATION: ORF sequences of S. aureus rS2-S21 and
      assembly factors from the strain N315 optimized for E. coli codon
      usage

<400> SEQUENCE: 105

atgcctcgca aaggttctgt tccaaaacgt gacgtattgc ctgatccgat ccataactcg     60

aaactggtta ctaaactgat taacaagatc atgttggacg gcaaacgtgg aactgcccaa    120

cgcattcttt attcagcatt cgacttggtt gagcagcgtt caggccgcga tgcacttgaa    180

gtttttgagg aggcaattaa caacattatg ccagtattgg aagtaaaggc ccgccgcgtc    240

ggcggaagta actaccaggt ccctgtggag gtccgtcccg aacgccgcac gaccttgggg    300

ttgcgttggt tggtaaatta tgcacgctta cgtggagaaa aaacaatgga ggatcgttta    360

gctaatgaaa ttttagacgc ggccaacaat accggcgggg ccgtgaagaa gcgtgaggat    420

actcataaga tggctgaggc caataaagca tttgcgcatt atcgctgg                 468
```

<210> SEQ ID NO 106
<211> LENGTH: 399
<212> TYPE: DNA
<213> ORGANISM: Staphylococcus aureus

<400> SEQUENCE: 106
atgacaatga cagatccaat cgcagatatg cttactcgtg taagaaacgc aaacatggtg 60
cgtcacgaga agttagaatt acctgcatca aatattaaaa aagaaattgc tgaaatctta 120
aagagtgaag gtttcattaa aaatgttgaa tacgtagaag atgataaaca aggtgtactt 180
cgtttattct taaaatatgg tcaaaacgat gagcgtgtta tcacaggatt aaaacgtatt 240
tcaaaaccag gtttacgtgt ttatgcaaaa gctagcgaaa tgcctaaagt attaaatggt 300
ttaggtattg cattagtatc aacttctgaa ggtgtaatca ctgacaaaga agcaagaaaa 360
cgtaatgttg gtggagaaat tatcgcatac gtttggtaa 399

<210> SEQ ID NO 107
<211> LENGTH: 396
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 107
atgaccatga cagaccctat cgcggacatg ttgacccgcg ttcgcaacgc gaacatggtt 60
cgtcacgaaa agctggagtt accggccagc aacatcaaga aggagatcgc agaaattttg 120
aagagcgaag gtttcattaa gaatgttgaa tacgtcgagg atgataaaca aggtgtattg 180
cgcttattct taaagtacgg ccaaaatgac gagcgtgtta ttacgggatt gaagcgcatc 240
tctaagcccg gcttgcgtgt ttacgccaaa gcttcggaga tgccaaaggt tcttaatggc 300
ctgggtatcg cattagtatc gacctccgaa ggggtgatta ccgacaaaga agcccgtaaa 360
cgcaatgtgg gaggagaaat tattgcttac gtttgg 396

<210> SEQ ID NO 108
<211> LENGTH: 393
<212> TYPE: DNA
<213> ORGANISM: Staphylococcus aureus

<400> SEQUENCE: 108
ttggcacaag ttgaatatag aggcacaggc cgtcgtaaaa actcagtagc acgtgtacgt 60
ttagtaccag gtgaaggtaa catcacagtt aataaccgtg acgtacgcga atacttacca 120
ttcgaatcat taattttaga cttaaaccaa ccatttgatg taactgaaac taaaggtaac 180
tatgatgttt tagttaacgt tcatggtggt ggtttcactg gacaagctca agctatccgt 240
cacggaatcg ctcgtgcatt attagaagca gatcctgaat acagaggttc tttaaaacgc 300
gctggattac ttactcgtga cccacgtatg aaagaacgta aaaaaccagg tcttaaagca 360
gctcgtcgtt cacctcaatt ctcaaaacgt taa 393

<210> SEQ ID NO 109
<211> LENGTH: 390
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 109
atggcgcaag ttgagtatcg tgggaccggg cgtcgcaaaa actcagtcgc acgcgtccgt 60
cttgtacctg gcgaagggaa cattactgtc aacaatcgtg atgtccgcga gtatctgcct 120
tttgagtcgc ttattttaga cttgaaccaa cctttcgatg taacagagac taagggcaat 180
tacgatgtgt tggtaaacgt gcatggtggc ggatttacgg gtcaagctca agcaatccgt 240
catgggattg cgcgcgcgtt actggaagcg gaccccgaat atcgtgggtc tttgaaacgc 300
gcgggactgc ttacccgcga tccccgcatg aaagaacgca aaaagcccgg cctgaaggca 360
gctcgccgtt cgccacaatt ctcgaagcgt 390

<210> SEQ ID NO 110
<211> LENGTH: 309
<212> TYPE: DNA
<213> ORGANISM: Staphylococcus aureus

<400> SEQUENCE: 110
atggcaaaac aaaaaatcag aatcagatta aaagcttatg atcaccgcgt gattgatcaa 60
tcagcagaga agattgtaga aacagcgaaa cgttctggtg cagatgtttc tggaccaatt 120
ccgttaccaa ctgagaaatc agtttacaca atcatccgtg ccgtgcataa gtataaagat 180
tcacgtgaac aattcgaaca acgtacacac aaacgtttaa tcgatattgt aaacccaaca 240
ccaaaaacag ttgacgcttt aatgggctta aacttaccat ctggtgtaga catcgaaatc 300
aaattataa 309

<210> SEQ ID NO 111
<211> LENGTH: 306
<212> TYPE: DNA
<213> ORGANISM: Artificial sequence
<220> FEATURE:
<223> OTHER INFORMATION: ORF sequences of S. aureus rS2-S21 and assembly
factors from the strain N315 optimized for E. coli codon usage

<400> SEQUENCE: 111
atggcgaagc aaaagattcg cattcgctta aaagcatacg atcaccgcgt gatcgatcaa 60
agtgcagaga agatcgtgga gaccgcgaaa cgctcagggg cggatgtatc tggtcctatt 120
cctttgccga cggagaagag cgtgtataca atcatccgtg ctgttcacaa atacaaagat 180
tctcgcgagc agtttgaaca acgtacacac aaacgtttaa tcgatattgt caatccgaca 240
ccgaaaaccg tggatgccct tatgggattg aatctgccgt ccggtgtgga catcgaaatc 300
aagtta 306

<210> SEQ ID NO 112
<211> LENGTH: 390
<212> TYPE: DNA
<213> ORGANISM: Staphylococcus aureus

<400> SEQUENCE: 112
atggcacgta aacaagtatc tcgtaaacgt agagtgaaaa agaatattga aaatggtgta 60
gcacacatcc gttcaacatt caacaacact attgtaacta tcactgatga gttcggtaat 120
gctttatcat ggtcatcagc tggtgcatta ggattcaaag gatctaaaaa atcaacacca 180
tttgcagcac aaatggcttc tgaaactgca tctaaatcag ctatggagca tggtttaaaa 240
acagttgaag taacagttaa aggacctggt ccaggtcgtg aatcagctat tcgtgcatta 300
caatctgcag gtttagaagt aactgcgatc agagacgtta ctccagtacc tcataacggt 360
tgtcgtccac caaaacgtcg tcgtgtataa 390

<210> SEQ ID NO 113
<211> LENGTH: 387
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 113
atggcccgta aacaggtatc ccgcaaacgc cgcgtgaaga aaaacattga gaacggtgtg 60
gcacatatcc gcagcacatt taacaatacc attgttacga ttacggacga gttcggtaat 120
gcgttatcct ggtcgtccgc aggtgctctt gggtttaaag ggtcaaaaaa gtcaacccca 180
ttcgccgcac agatggcaag tgaaaccgca agcaaaagcg caatggaaca tggtcttaaa 240
accgtcgagg taaccgtaaa aggaccaggt cccggtcgtg agagcgcaat ccgcgccttg 300
cagtcggccg gtcttgaggt gactgctatt cgtgatgtca cacctgttcc ccacaacggc 360
tgccgtccac caaagcgtcg ccgcgta 387

<210> SEQ ID NO 114
<211> LENGTH: 414
<212> TYPE: DNA
<213> ORGANISM: Staphylococcus aureus

<400> SEQUENCE: 114
atgccaacta ttaaccaatt agtacgtaaa ccaagacaaa gcaaaatcaa aaaatcagat 60
tctccagctt taaataaagg tttcaacagt aaaaagaaaa aatttactga cttaaactca 120
ccacaaaaac gtggtgtatg tactcgtgta ggtacaatga cacctaaaaa acctaactca 180
gcgttacgta aatatgcacg tgtgcgttta tcaaacaaca tcgaaattaa cgcatacatc 240
cctggtatcg gacataactt acaagaacac agtgttgtac ttgtacgtgg tggacgtgta 300
aaagacttac caggtgtgcg ttaccatatt gtacgtggag cacttgatac ttcaggtgtt 360
gacggacgta gacaaggtcg ttcattatac ggaactaaga aacctaaaaa ctaa 414

<210> SEQ ID NO 115
<211> LENGTH: 411
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 115
atgcccacga tcaaccagtt agttcgcaag ccacgccaaa gcaagatcaa aaaatccgat 60
agtcccgcct tgaacaaggg gttcaattca aagaagaaga agtttacaga tttgaactca 120
cctcagaagc gcggtgtgtg tacccgcgtg ggaacaatga caccgaaaaa gcccaattcg 180
gcgcttcgca agtatgcacg tgtgcgtttg agtaataaca tcgagatcaa cgcgtatatt 240
cccggaattg gacacaatct tcaagaacac tcagttgtac ttgtgcgcgg agggcgtgtc 300
aaggacttac caggagtacg ttatcacatc gtgcgcggag cattagacac aagtggggtt 360
gacgggcgtc gtcagggccg ttcgttatat gggacgaaaa agcctaaaaa c 411

<210> SEQ ID NO 116
<211> LENGTH: 366
<212> TYPE: DNA
<213> ORGANISM: Staphylococcus aureus

<400> SEQUENCE: 116
atggcacgta ttgcaggagt agatattcca cgtgaaaaac gcgtagttat ctcattaact 60
tatatatacg gtatcggtac gtcaactgct caaaaaattc ttgaagaagc taacgtatca 120
gctgatactc gtgtgaaaga tttaactgat gacgaattag gtcgcatccg tgaagttgta 180
gacggttata aagtcgaagg tgacttacgt cgtgaaacta acttaaatat caaacgttta 240
atggaaattt catcataccg tggtatccgt caccgtcgtg gtttaccagt tcgtggtcaa 300
aaaacgaaaa acaacgcgcg tactcgtaaa ggaccagtta aaacggtagc taacaagaaa 360
aaataa 366

<210> SEQ ID NO 117
<211> LENGTH: 363
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 117
atggcgcgta ttgcgggcgt ggatatccca cgcgaaaaac gcgtagtcat cagcttgaca 60
tacatttacg gcatcggaac ttctaccgcg cagaagattc ttgaggaggc taacgtatca 120
gcagataccc gcgtaaaaga cttgaccgac gatgaacttg ggcgcatccg tgaagtcgtt 180
gatggttata aggtggaagg ggacctgcgt cgtgaaacca acttaaacat taaacgcttg 240
atggaaatca gcagctatcg cggaatccgc catcgccgtg gtcttccggt gcgcggccaa 300
aaaacgaaaa acaacgcacg cacacgtaaa ggtccagtaa aaacagttgc taacaagaaa 360
aaa 363

<210> SEQ ID NO 118
<211> LENGTH: 270
<212> TYPE: DNA
<213> ORGANISM: Staphylococcus aureus

<400> SEQUENCE: 118
atggctaaga aatctaaaat agcaaaagag agaaaaagag aagagttagt aaataaatat 60
tacgaattac gtaaagagtt aaaagcaaaa ggtgattacg aagcgttaag aaaattacca 120
agagattcat cacctacacg tttaactaga agatgtaaag taactggaag acctagaggt 180
gtattacgta aatttgaaat gtctcgtatt gcgtttagag aacatgcgca caaaggacaa 240
attccaggtg ttaaaaaatc aagttggtaa 270

<210> SEQ ID NO 119
<211> LENGTH: 267
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 119
atggcgaaga aatcgaaaat tgcgaaggag cgtaagcgcg aggaactggt taacaaatac 60
tacgaactgc gtaaagagtt gaaagcgaaa ggcgactacg aagctcttcg caaacttcca 120
cgcgacagtt ctccaacacg ccttactcgc cgttgtaaag tgactggccg ccctcgtggt 180
gttcttcgca agtttgagat gtcccgtatc gctttccgcg aacacgccca taaaggccag 240
atccccggtg tcaaaaaatc atcttgg 267

<210> SEQ ID NO 120
<211> LENGTH: 270
<212> TYPE: DNA
<213> ORGANISM: Staphylococcus aureus

<400> SEQUENCE: 120
atggcaattt cacaagaacg taaaaacgaa atcattaaag aataccgtgt acacgaaact 60
gatactggtt caccagaagt acaaatcgct gtacttactg cagaaatcaa cgcagtaaac 120
gaacacttac gtacacacaa aaaagaccac cattcacgtc gtggattatt aaaaatggta 180
ggacgtcgta gacatttatt aaactactta cgtagtaaag atattcaacg ttaccgtgaa 240
ttaattaaat cacttggtat ccgtcgttaa 270

<210> SEQ ID NO 121
<211> LENGTH: 267
<212> TYPE: DNA
<213> ORGANISM: Artificial sequence
<220> FEATURE:
<223> OTHER INFORMATION: ORF sequences of S. aureus rS2-S21 and assembly
factors from the strain N315 optimized for E. coli codon usage

<400> SEQUENCE: 121
atggcgattt cacaggagcg caagaacgag attattaaag agtaccgtgt tcacgagact 60
gatacgggct ctcctgaagt acagatcgcg gtcctgacag cggaaatcaa cgccgtaaat 120
gaacacttgc gtacccacaa aaaagaccac catagccgtc gcggattact gaaaatggta 180
gggcgtcgcc gccatttatt gaactatctt cgcagcaagg acatccagcg ttatcgtgag 240
ctgatcaagt ccctgggtat tcgtcgt 267

<210> SEQ ID NO 122
<211> LENGTH: 276
<212> TYPE: DNA
<213> ORGANISM: Staphylococcus aureus

<400> SEQUENCE: 122
atggcagtta aaattcgttt aacacgttta ggttcaaaaa gaaatccatt ctatcgtatc 60
gtagtagcag atgctcgttc tccacgtgac ggacgtatca tcgaacaaat cggtacttat 120
aacccaacga gcgctaatgc tccagaaatt aaagttgacg aagcgttagc tttaaaatgg 180
ttaaatgatg gtgcgaaacc aactgataca gttcacaata tcttatcaaa agaaggtatt 240
atgaaaaaat ttgacgaaca aaagaaagct aagtaa 276

<210> SEQ ID NO 123
<211> LENGTH: 273
<212> TYPE: DNA
<213> ORGANISM: Artificial sequence
<220> FEATURE:
<223> OTHER INFORMATION: ORF sequences of S. aureus rS2-S21 and assembly
factors from the strain N315 optimized for E. coli codon usage

<400> SEQUENCE: 123
atggctgtta agattcgttt aactcgtctg ggtcaaagc gcaatccatt ttaccgcatc 60
gtcgtagccg atgctcgtag tccgcgtgac gggcgtatta tcgaacagat cggcacctat 120

```
aatcctacgt ccgccaacgc cccggagatt aaggttgacg aagcattagc cctgaagtgg    180

ctgaacgatg gggccaaacc gacagatacc gtacataaca tccttagcaa ggaaggaatc    240

atgaaaaaat tcgacgaaca aaagaaagcg aag                                 273


<210> SEQ ID NO 124
<211> LENGTH: 264
<212> TYPE: DNA
<213> ORGANISM: Staphylococcus aureus

<400> SEQUENCE: 124

gtgagcgaaa gaaacgatcg taaagtttat gtaggtaaag ttgtttcaga caaaatggac     60

aagactatta cagtacttgt tgaaacttac aaaacacaca aattatacgg taaacgagta    120

aaatactcta aaaaatacaa aactcatgat gaaaacaatt cagctaaatt aggagacatt    180

gttaaaattc aagaaactcg tcctttatca gcaacaaaac gttttcgtat agtagagatt    240

gttgaagagt cagtaattat ttaa                                           264


<210> SEQ ID NO 125
<211> LENGTH: 261
<212> TYPE: DNA
<213> ORGANISM: Artificial sequence
<220> FEATURE:
<223> OTHER INFORMATION: ORF sequences of S. aureus rS2-S21 and assembly
      factors from the strain N315 optimized for E. coli codon usage

<400> SEQUENCE: 125

atgtccgagc gcaacgaccg taaggtttat gtggggaaag tcgtgtccga caagatggac     60

aaaactatta ccgtactggt ggaaacctac aaaactcaca aactttacgg taaacgtgtc    120

aaatatagca agaaatataa gacgcatgac gaaaacaatt ctgcaaagct tggagatatt    180

gtcaagatcc aagagactcg ccccctttcg gcaactaagc gttttcgcat cgtggaaatc    240

gtggaggaga gcgtgattat t                                              261


<210> SEQ ID NO 126
<211> LENGTH: 243
<212> TYPE: DNA
<213> ORGANISM: Staphylococcus aureus

<400> SEQUENCE: 126

atggcaggtg gaccaagaag aggcggacgt cgtcgtaaaa aagtatgcta tttcacagca     60

aatggtatta cacatatcga ctacaaagac actgaattat taaaacgttt tatctcagaa    120

cgcggtaaaa ttttaccacg tcgtgtaact ggtacttcag ctaaatatca acgtatgttg    180

actacagcta tcaaacgttc tcgtcatatg gcattattac catatgttaa agaagaacaa    240

taa                                                                  243


<210> SEQ ID NO 127
<211> LENGTH: 240
<212> TYPE: DNA
<213> ORGANISM: Artificial sequence
<220> FEATURE:
<223> OTHER INFORMATION: ORF sequences of S. aureus rS2-S21 and assembly
      factors from the strain N315 optimized for E. coli codon usage

<400> SEQUENCE: 127

atggcgggag gtccgcgccg cggtgggcgt cgccgtaaga aggtatgcta ctttactgcg     60

aacggaatca cacacatcga ctataaggat acggagttgt taaaacgttt catcagtgaa    120
```

cgtggcaaga ttttaccccg ccgcgtgaca gggacctcgg ccaaatacca gcgtatgctg 180
actacagcta tcaaacgctc gcgtcacatg gcgcttttgc cttatgtgaa agaggaacaa 240

<210> SEQ ID NO 128
<211> LENGTH: 279
<212> TYPE: DNA
<213> ORGANISM: Staphylococcus aureus

<400> SEQUENCE: 128
atggctcgta gtattaaaaa aggacctttc gtcgatgagc atttaatgaa aaaagttgaa 60
gctcaagaag gaagcgaaaa gaaacaagta atcaaaacat ggtcacgtcg ttctacaatt 120
ttccctaatt tcatcggaca tacttttgca gtatacgacg gacgtaaaca cgtacctgta 180
tatgtaactg aagatatggt aggtcataaa ttaggtgagt ttgctcctac tcgtacattc 240
aaaggacacg ttgcagacga caagaaaaca agaagataa 279

<210> SEQ ID NO 129
<211> LENGTH: 276
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 129
atggcccgca gtattaaaaa gggacctttt gtggatgaac atctgatgaa aaaagtggag 60
gcccaagaag ggagcgagaa aaagcaggtg attaaaactt ggagccgtcg ctctacaatc 120
tttccgaatt tcatcggtca tacatttgcg gtatatgatg ggcgtaaaca cgtccctgtt 180
tacgtaactg aagatatggt aggtcataaa ttgggagaat ttgcacctac acgtacattc 240
aagggtcacg tggcggatga caagaaaaca cgtaga 276

<210> SEQ ID NO 130
<211> LENGTH: 252
<212> TYPE: DNA
<213> ORGANISM: Staphylococcus aureus

<400> SEQUENCE: 130
atggcaaata tcaaatctgc aattaaacgt gtaaaaacaa ctgaaaaagc tgaagcacgc 60
aacatttcac aaaagagtgc aatgcgtaca gcagttaaaa acgctaaaac agctgtttca 120
aataacgctg ataataaaaa tgaattagta agcttagcag ttaagttagt agacaaagct 180
gctcaaagta atttaataca ttcaaacaaa gctgaccgta ttaaatcaca attaatgact 240
gcaaataaat aa 252

<210> SEQ ID NO 131
<211> LENGTH: 249
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 131
atggctaata tcaagtcagc gatcaagcgc gtaaagacca cagaaaaagc tgaggcccgc 60
aatatttccc agaaaagcgc gatgcgtaca gccgttaaga acgctaaaac cgctgtgtct 120
aataatgcgg acaacaaaaa cgagttggtt tctctggcag taaagttggt ggataaggca 180
gcgcaatcta atttgatcca cagcaacaaa gcggatcgta tcaagagcca actgatgaca 240
gcaaataaa 249

<210> SEQ ID NO 132
<211> LENGTH: 177
<212> TYPE: DNA
<213> ORGANISM: Staphylococcus aureus

<400> SEQUENCE: 132
atgtctaaaa cagtagtacg taaaaatgaa tcacttgaag atgcgttacg tagatttaaa 60
cgttcagttt ctaaaagtgg aacaatccaa gaagtacgta aacgtgaatt ttacgaaaaa 120
ccaagcgtaa aacgtaaaaa gaaatcagaa gctgcacgta aacgtaaatt caaataa 177

<210> SEQ ID NO 133
<211> LENGTH: 174
<212> TYPE: DNA
<213> ORGANISM: Artificial sequence
<220> FEATURE:
<223> OTHER INFORMATION: ORF sequences of S. aureus rS2-S21 and assembly
factors from the strain N315 optimized for E. coli codon usage

<400> SEQUENCE: 133
atgtcgaaga cggtggtccg taagaacgag tcattagaag atgcccttcg tcgcttcaaa 60
cgcagtgtat cgaagtctgg gactattcaa gaagtgcgta agcgtgaatt ttacgagaaa 120
ccgtcagtaa agcgcaaaaa gaaaagtgaa gcagcccgta agcgcaagtt taaa 174

<210> SEQ ID NO 134
<211> LENGTH: 1712
<212> TYPE: DNA
<213> ORGANISM: Staphylococcus aureus

<400> SEQUENCE: 134
gttccgcgca catttccccg aaaagtgcta gtggtgctag ccccgcgaaa ttaatacgac 60
tcactatagg gtttttatgg agagtttgat cctggctcag gatgaacgct ggcggcgtgc 120
ctaatacatg caagtcgagc gaacggacga gaagctgcgg agacggtcgg gtccagatat 180
tcgtatctgt cgagtagagt gtgggctccg ctgcttctct gatgttagcg gcggacgggt 240
gagtaacacg tggataacct acctataaga ctgggataac ttcgggaaac cggagctaat 300
accggataat attttgaacc gcatggttca aaagtgaaag acggtcttgc tgtcacttat 360
agatggatcc gcgctgcatt agctagttgg taaggtaacg gcttaccaag gcaacgatgc 420
atagccgacc tgagagggtg atcggccaca ctggaactga gacacggtcc agactcctac 480
gggaggcagc agtagggaat cttccgcaat gggcgaaagc ctgacggagc aacgccgcgt 540
gagtgatgaa ggtcttcgga tcgtaaaact ctgttattag ggaagaacat atgtgtaagt 600
aactgtgcac atcttgacgg tacctaatca gaaagccacg gctaactacg tgccagcagc 660
cgcggtaata cgtaggtggc aagcgttatc cggaattatt gggcgtaaag cgcgcgtagg 720
cggtttttta agtctgatgt gaaagcccac ggctcaaccg tggagggtca ttggaaactg 780
gaaaacttga gtgcagaaga ggaaagtgga attccatgtg tagcggtgaa atgcgcagag 840
atatggagga acaccagtgg cgaaggcgac tttctggtct gtaactgacg ctgatgtgcg 900
aaagcgtggg gatcaaacag gattagatac cctggtagtc cacgccgtaa acgatgagtg 960
ctaagtgtta gggggtttcc gccccttagt gctgcagcta acgcattaag cactccgcct 1020
ggggagtacg accgcaaggt tgaaactcaa aggaattgac ggggacccgc acaagcggtg 1080
gagcatgtgg tttaattcga agcaacgcga agaaccttac caaatcttga catcctttga 1140
caactctaga gatagagcct tccccttcgg gggacaaagt gacaggtggt gcatggttgt 1200
cgtcagctcg tgtcgtgaga tgttgggtta agtcccgcaa cgagcgcaac ccttaagctt 1260
agttgccatc attaagttgg gcactctaag ttgactgccg gtgacaaacc ggaggaaggt 1320
ggggatgacg tcaaatcatc atgcccctta tgatttgggc tacacacgtg ctacaatgga 1380
caatacaaag ggcagcgaaa ccgcgaggtc aagcaaatcc cataaagttg ttctcagttc 1440
ggattgtagt ctgcaactcg actacatgaa gctggaatcg ctagtaatcg tagatcagca 1500
tgctacggtg aatacgttcc cgggtcttgt acacaccgcc cgtcacacca cgagagtttg 1560
taacacccga agccggtgga gtaacctttt aggagctagc cgtcgaaggt gggacaaatg 1620
attggggtga agtcgtaaca aggtagccgt atcggaaggt gcggctggat cacctccttt 1680
ctctctagcc atggtcccag cctcctcgct gg 1712

<210> SEQ ID NO 135
<211> LENGTH: 9
<212> TYPE: PRT
<213> ORGANISM: Artificial sequence
<220> FEATURE:
<223> OTHER INFORMATION: HA tag amino acid sequence

<400> SEQUENCE: 135

Tyr Pro Tyr Asp Val Pro Asp Tyr Ala
1 5

<210> SEQ ID NO 136
<211> LENGTH: 900
<212> TYPE: DNA
<213> ORGANISM: Staphylococcus aureus

<400> SEQUENCE: 136
atgacagaac ataaatcagg atttgtttca attataggta gaccaaatgt agggaagtca 60
acatttgtta atagagtgat tggccataaa atagcaatca tgtccgataa agctcaaaca 120
actagaaata aaattcaagg tgttatgaca agagatgacg cgcaaattat attcattgat 180
acgccaggta ttcataaacc taaacacaaa ttaggtgact atatgatgaa agtcgctaaa 240
aatacattat ctgaaataga tgcaatcatg tttatggtta atgccaatga ggaaattgga 300
cgaggcgatg aatatattat agaaatgttg aaaaatgtta agacaccagt atttttagta 360
ttaaataaaa tagatttagt gcatccagat gaattaatgc caaagattga agaatatcaa 420
agttatatgg actttacaga gattgtacct atttcagcat tagaagggct aaatgtagat 480
cattttattg atgttttaaa gacgtattta cccgaaggac ctaaatatta tccagatgat 540
caaatttcag accatcctga acaatttgta gtgggtgaaa tcattcgtga aaaaatcctt 600
catcttacaa gtgaagaaat ccctcatgcg attggtgtta atgtggaccg tatggttaaa 660
gaaagcgaag atcgtgttca tatcgaagca actatatatg ttgaaagaga ttcgcaaaaa 720
ggaattgtca ttggaaaagg cggtaaaaag ttaaaagaag taggaaaacg tgcgagacgt 780
gatatagaaa tgcttctagg ctctaaagta tacttagaat tatgggtcaa agttcaaaga 840
gactggcgaa acaaagttaa ctttattcgc caaattggtt atgttgaaga ccaagattaa 900

<210> SEQ ID NO 137
<211> LENGTH: 897

<212> TYPE: DNA
<213> ORGANISM: Artificial sequence
<220> FEATURE:
<223> OTHER INFORMATION: ORF sequences of S. aureus rS2-S21 and assembly
      factors from the strain N315 optimized for E. coli codon usage

<400> SEQUENCE: 137
atgacggagc ataaatcagg atttgtctcg attattggtc gtcctaatgt tgggaagagc 60
acctttgtaa atcgtgtcat cggccataaa atcgccatca tgtctgacaa agcacaaacg 120
actcgcaaca aaattcaggg agtaatgacc cgtgatgacg cccaaatcat tttcattgac 180
acacctggaa ttcataagcc aaaacacaag ttgggggact atatgatgaa ggtcgccaaa 240
aacacattat cggaaatcga tgccattatg tttatggtga acgcaaacga ggagatcgga 300
cgtggtgatg aatacatcat tgagatgctg aagaatgtta agactccggt atttcttgta 360
ttaaacaaga tcgacttagt acacccagat gagctgatgc ccaagatcga ggaataccaa 420
agttacatgg atttcacgga gattgtacca atttcggctc tggaaggatt gaacgtcgat 480
cattttattg atgtgcttaa aacttatctt cctgaggggc ctaaatacta ccctgacgat 540
cagatctccg atcatccaga acagttcgta gtgggagaga ttatccgcga gaaaattctg 600
cacttaacat ccgaagagat tccacatgca attggtgtga acgtggatcg tatggttaag 660
gagtccgagg atcgtgtaca catcgaggct acaatttatg tcgaacgtga ctcccaaaaa 720
ggcatcgtta tcgggaaggg tggtaaaaaa ttgaaggagg ttggaaaacg cgcccgccgc 780
gacatcgaga tgcttttggg ctcaaaagtg tacttggagc tttgggtgaa ggtgcaacgt 840
gattggcgta ataaagtgaa tttcattcgc cagattggat acgtcgaaga ccaggat 897

<210> SEQ ID NO 138
<211> LENGTH: 468
<212> TYPE: DNA
<213> ORGANISM: Staphylococcus aureus

<400> SEQUENCE: 138
atgagtaaaa ttacagaaca agtagaagtg attgttcaac caattatgga agacttgaat 60
tttgaacttg tagacgttga atatgtcaaa gagggtagag atcattttct tagaatctct 120
attgataaag aaggtggcgt agatttaaat gattgtacgc tagcttctga aaaaataagt 180
gaagctatgg atgcaaatga tcctattcct gaaatgtatt atttagacgt agcgtcacct 240
ggtgcagaac gtccaattaa aaaagaacaa gatttccaaa atgcaataac taaacctgta 300
tttgtttctt tatatgtacc aattgaaggt gaaaaggaat ggttaggcat tttacaagaa 360
gtcaataatg aaacaattgt agtacaagtt aaaatcaaag caagaacgaa agatatagag 420
ataccgagag acaaaatagc aaaagcacgt cacgcagtta tgatttaa 468

<210> SEQ ID NO 139
<211> LENGTH: 465
<212> TYPE: DNA
<213> ORGANISM: Artificial sequence
<220> FEATURE:
<223> OTHER INFORMATION: ORF sequences of S. aureus rS2-S21 and assembly
      factors from the strain N315 optimized for E. coli codon usage

<400> SEQUENCE: 139
atgtccaaga ttaccgaaca ggtagaagta attgtgcaac ctatcatgga ggaccttaac 60
tttgagcttg tcgacgtaga atacgttaaa gaagggcgcg accacttcct tcgcatctca 120
attgacaagg agggcggggt ggacttaaat gattgtacgc tggcctcaga aaagatcagc 180
gaggcaatgg atgcaaatga ccctattccc gagatgtatt atcttgatgt ggcgagtcca 240
ggggccgaac gtccgatcaa aaaagaacaa gactttcaaa atgcaatcac caagccggtc 300
ttcgtaagtt tatacgtccc aatcgaaggc gaaaaggaat ggctgggaat tcttcaggaa 360
gtgaataacg agaccatcgt cgttcaagtt aaaattaagg ctcgtaccaa ggacatcgaa 420
atcccacgcg ataaaatcgc taaggcacgc catgcggtaa tgatt 465

<210> SEQ ID NO 140
<211> LENGTH: 504
<212> TYPE: DNA
<213> ORGANISM: Staphylococcus aureus

<400> SEQUENCE: 140
atgagagttg aagttggtca aattgttaac acacatggta ttaaaggtga aattaaagta 60
aaatccaatt cagactttac agacgttcgt tttcaacccg gtcaagtgct gacagttgtg 120
cataacaata acgaccttga atatactgtt aagtcacata gagtgcataa agggcttcat 180
atgcttacat ttgaaggtat taataatatt aatgatattg agcatttaaa agggagttct 240
atttatcaag agcgtgatca tgaagatatc gtacttgagg aaaatgaatt ttattattca 300
gatattatag gatgtacagt ttttgatgat caagaaacac caataggtcg tgtaattaat 360
atatttgaaa caggtgcgaa tgatgtgtgg gtgattaaag gatctaaaga atatttgatt 420
ccttatattg ctgatgttgt aaaagaagtg gatgttgaaa ataaaaaaat tatcatcacg 480
ccaatggaag gattgttgga ttaa 504

<210> SEQ ID NO 141
<211> LENGTH: 501
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 141
atgcgcgtag aagtggggca aatcgtaaac acgcacggta tcaaaggcga gatcaaggtg 60
aaatcaaaca gtgattttac agatgtccgc tttcaaccgg gccaagtact gacagtagtc 120
cacaataata atgacttaga atatacagtt aagagtcatc gcgtccacaa gggccttcac 180
atgttgacct ttgaaggtat caacaacatc aatgacatcg aacatttgaa gggtagttct 240
atctaccagg aacgtgacca cgaggacatt gtacttgagg agaatgaatt ttattatagt 300
gacattattg gctgcaccgt ctttgacgac caagagactc cgattggtcg cgtaatcaat 360
atcttcgaga caggggcgaa tgatgtttgg gttattaagg gctcgaagga atatttgatc 420
ccctacattg ctgatgttgt gaaggaggtt gatgtcgaga ataagaagat cattattacg 480
ccgatggagg gcttgttaga t 501

<210> SEQ ID NO 142
<211> LENGTH: 351
<212> TYPE: DNA
<213> ORGANISM: Staphylococcus aureus

<400> SEQUENCE: 142
atgagcagta tgagagcaga gcgtgttggt gaacaaatga agaaggaatt aatggatatc 60
atcaacaata aagtcaaaga tcctcgagtt ggttttatta caattacaga tgttgtttta 120
acaaatgatt tatcgcaggc taaagtattt ttaactgtat taggtaacga taaagaagta 180
gaaaatacat ttaaagcact tgataaagca aaaggcttca ttaagtctga attaggttct 240
agaatgcgat tacgtattat gccggaatta atgtatgaat atgatcaatc aatcgaatat 300
ggtaataaaa ttgaacgaat gattcaagat ttacacaaac aagatagata a 351

<210> SEQ ID NO 143
<211> LENGTH: 348
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 143
atgagtagta tgcgtgctga acgcgttggc gagcagatga agaaggaact tatggatatt 60
atcaataata aggtaaagga cccacgcgtt ggatttatca cgattacgga tgtcgttctt 120
acaaatgatc tgtcgcaggc gaaagtattc ttaactgttc ttgggaacga caaggaggtg 180
gagaatacat tcaaagcctt ggacaaagcg aagggcttca ttaaaagcga gttgggatct 240
cgcatgcgtt tgcgtattat gccagagtta atgtacgaat atgaccagtc cattgagtac 300
ggtaacaaga tcgagcgcat gattcaagac ttacataaac aagacaga 348

<210> SEQ ID NO 144
<211> LENGTH: 876
<212> TYPE: DNA
<213> ORGANISM: Staphylococcus aureus

<400> SEQUENCE: 144
atgaagacag gtcgaatagt gaaatcaatt agtggggtat atcaagtaga cgttaatggc 60
gaacgtttca atacaaaacc acgaggatta tttagaaaga aaaaattttc accggtagtt 120
ggtgatatag tggaatttga agtacaaaac attaacgaag gctatattca tcaagtgttt 180
gagcggaaaa atgagttgaa aagaccacct gtaagtaata tagatacact agtaattgta 240
atgagtgctg tcgagccaaa tttttcaacg caattattag atcgattttt agttattgca 300
cattcgtatc agttaaatgc gagagttttg gtgactaaaa aagataaaac accaattgaa 360
aagcagttcg aaattaatga gttgttgaaa atatatgaaa atattggcta tgagactgaa 420
tttattggaa atgatgatga tcgaaaaaaa attgtagaag cttggccagc tggacttata 480
gtacttagtg gtcaatcagg tgtcggtaag tccactttct taaatcatta tcgtccagaa 540
cttaatcttg agacaaatga tatatcaaaa tcattaaatc gaggaaagca tactacaaga 600
catgtcgaac tattcgaacg tcaaaacggt tatattgcag acacacctgg attcagtgct 660
ttagattttg atcatataga taaagatgaa ataaaagatt attttcttga attaaatcga 720
tatggtgaaa catgtaagtt taggaattgt aatcatatca aagaacctaa ttgtaatgtt 780
aagcatcaat tagagatagg gaatattgcg caatttagat acgaccatta tttacaacta 840
tttaatgaaa tttcaaatag aaaggttaga tattaa 876

<210> SEQ ID NO 145
<211> LENGTH: 873
<212> TYPE: DNA
<213> ORGANISM: Artificial sequence
<220> FEATURE:
<223> OTHER INFORMATION: ORF sequences of S. aureus rS2-S21 and assembly factors from the strain N315 optimized for E. coli codon usage

<400> SEQUENCE: 145

```
atgaagaccg ggcgtattgt taagtccatt agtggggttt accaagtaga tgtaaacggt     60
gagcgtttca atacaaagcc acgtggctta tttcgcaaaa agaaattctc cccagttgtc    120
ggcgatatcg tggaatttga agtccaaaat atcaacgagg ggtacatcca tcaagtattt    180
gagcgtaaga atgagttaaa gcgccctccg gtatcgaaca tcgataccct ggtcattgta    240
atgtccgccg ttgaacctaa tttttcgact cagttacttg atcgtttctt ggtgattgct    300
cattcctatc agttgaatgc tcgtgtattg gttactaaaa aggacaagac gcctattgag    360
aagcagtttg agatcaatga attacttaag atctacgaaa acatcggtta cgagactgag    420
ttcatcggta atgatgacga ccgtaaaaag attgtggaag catggccggc tggtcttatt    480
gttttgtccg gtcaatcagg tgtgggtaaa tccactttct taaaccatta ccgcccagag    540
ttgaatctgg aaaccaacga catctcgaag tctttgaatc gcggtaaaca caccactcgt    600
cacgtagagc tttttgagcg ccaaaatgga tatattgcag acactccagg tttcagcgca    660
ttggacttcg accacattga caaagacgag atcaaggact actttttgga gttaaatcgc    720
tatggcgaga cttgcaaatt ccgcaattgt aatcacatta aagaaccaaa ctgtaatgta    780
aaacaccaat tggaaatcgg aaatatcgct caatttcgtt acgatcatta cctgcagtta    840
tttaatgaga tttcaaatcg taaggtccgt tat                                 873
```

<210> SEQ ID NO 146
<211> LENGTH: 557
<212> TYPE: PRT
<213> ORGANISM: Escherichia coli

<400> SEQUENCE: 146

```
Met Thr Glu Ser Phe Ala Gln Leu Phe Glu Glu Ser Leu Lys Glu Ile
1               5                   10                  15

Glu Thr Arg Pro Gly Ser Ile Val Arg Gly Val Val Val Ala Ile Asp
            20                  25                  30

Lys Asp Val Val Leu Val Asp Ala Gly Leu Lys Ser Glu Ser Ala Ile
        35                  40                  45

Pro Ala Glu Gln Phe Lys Asn Ala Gln Gly Glu Leu Glu Ile Gln Val
    50                  55                  60

Gly Asp Glu Val Asp Val Ala Leu Asp Ala Val Glu Asp Gly Phe Gly
65                  70                  75                  80

Glu Thr Leu Leu Ser Arg Glu Lys Ala Lys Arg His Glu Ala Trp Ile
                85                  90                  95

Thr Leu Glu Lys Ala Tyr Glu Asp Ala Glu Thr Val Thr Gly Val Ile
            100                 105                 110

Asn Gly Lys Val Lys Gly Gly Phe Thr Val Glu Leu Asn Gly Ile Arg
        115                 120                 125

Ala Phe Leu Pro Gly Ser Leu Val Asp Val Arg Pro Val Arg Asp Thr
    130                 135                 140

Leu His Leu Glu Gly Lys Glu Leu Glu Phe Lys Val Ile Lys Leu Asp
145                 150                 155                 160

Gln Lys Arg Asn Asn Val Val Val Ser Arg Arg Ala Val Ile Glu Ser
                165                 170                 175

Glu Asn Ser Ala Glu Arg Asp Gln Leu Leu Glu Asn Leu Gln Glu Gly
            180                 185                 190

Met Glu Val Lys Gly Ile Val Lys Asn Leu Thr Asp Tyr Gly Ala Phe
        195                 200                 205
```

```
Val Asp Leu Gly Gly Val Asp Gly Leu Leu His Ile Thr Asp Met Ala
    210                 215                 220

Trp Lys Arg Val Lys His Pro Ser Glu Ile Val Asn Val Gly Asp Glu
225                 230                 235                 240

Ile Thr Val Lys Val Leu Lys Phe Asp Arg Glu Arg Thr Arg Val Ser
                245                 250                 255

Leu Gly Leu Lys Gln Leu Gly Glu Asp Pro Trp Val Ala Ile Ala Lys
            260                 265                 270

Arg Tyr Pro Glu Gly Thr Lys Leu Thr Gly Arg Val Thr Asn Leu Thr
        275                 280                 285

Asp Tyr Gly Cys Phe Val Glu Ile Glu Glu Gly Val Glu Gly Leu Val
    290                 295                 300

His Val Ser Glu Met Asp Trp Thr Asn Lys Asn Ile His Pro Ser Lys
305                 310                 315                 320

Val Val Asn Val Gly Asp Val Val Glu Val Met Val Leu Asp Ile Asp
                325                 330                 335

Glu Glu Arg Arg Arg Ile Ser Leu Gly Leu Lys Gln Cys Lys Ala Asn
            340                 345                 350

Pro Trp Gln Gln Phe Ala Glu Thr His Asn Lys Gly Asp Arg Val Glu
        355                 360                 365

Gly Lys Ile Lys Ser Ile Thr Asp Phe Gly Ile Phe Ile Gly Leu Asp
    370                 375                 380

Gly Gly Ile Asp Gly Leu Val His Leu Ser Asp Ile Ser Trp Asn Val
385                 390                 395                 400

Ala Gly Glu Glu Ala Val Arg Glu Tyr Lys Lys Gly Asp Glu Ile Ala
                405                 410                 415

Ala Val Val Leu Gln Val Asp Ala Glu Arg Glu Arg Ile Ser Leu Gly
            420                 425                 430

Val Lys Gln Leu Ala Glu Asp Pro Phe Asn Asn Trp Val Ala Leu Asn
        435                 440                 445

Lys Lys Gly Ala Ile Val Thr Gly Lys Val Thr Ala Val Asp Ala Lys
    450                 455                 460

Gly Ala Thr Val Glu Leu Ala Asp Gly Val Glu Gly Tyr Leu Arg Ala
465                 470                 475                 480

Ser Glu Ala Ser Arg Asp Arg Val Glu Asp Ala Thr Leu Val Leu Ser
                485                 490                 495

Val Gly Asp Glu Val Glu Ala Lys Phe Thr Gly Val Asp Arg Lys Asn
            500                 505                 510

Arg Ala Ile Ser Leu Ser Val Arg Ala Lys Asp Glu Ala Asp Glu Lys
        515                 520                 525

Asp Ala Ile Ala Thr Val Asn Lys Gln Glu Asp Ala Asn Phe Ser Asn
    530                 535                 540

Asn Ala Met Ala Glu Ala Phe Lys Ala Ala Lys Gly Glu
545                 550                 555
```

<210> SEQ ID NO 147
<211> LENGTH: 241
<212> TYPE: PRT
<213> ORGANISM: Escherichia coli

<400> SEQUENCE: 147

```
Met Ala Thr Val Ser Met Arg Asp Met Leu Lys Ala Gly Val His Phe
1               5                   10                  15
```

```
Gly His Gln Thr Arg Tyr Trp Asn Pro Lys Met Lys Pro Phe Ile Phe
            20                  25                  30

Gly Ala Arg Asn Lys Val His Ile Ile Asn Leu Glu Lys Thr Val Pro
        35                  40                  45

Met Phe Asn Glu Ala Leu Ala Glu Leu Asn Lys Ile Ala Ser Arg Lys
    50                  55                  60

Gly Lys Ile Leu Phe Val Gly Thr Lys Arg Ala Ala Ser Glu Ala Val
65                  70                  75                  80

Lys Asp Ala Ala Leu Ser Cys Asp Gln Phe Phe Val Asn His Arg Trp
                85                  90                  95

Leu Gly Gly Met Leu Thr Asn Trp Lys Thr Val Arg Gln Ser Ile Lys
            100                 105                 110

Arg Leu Lys Asp Leu Glu Thr Gln Ser Gln Asp Gly Thr Phe Asp Lys
        115                 120                 125

Leu Thr Lys Lys Glu Ala Leu Met Arg Thr Arg Glu Leu Glu Lys Leu
    130                 135                 140

Glu Asn Ser Leu Gly Gly Ile Lys Asp Met Gly Gly Leu Pro Asp Ala
145                 150                 155                 160

Leu Phe Val Ile Asp Ala Asp His Glu His Ile Ala Ile Lys Glu Ala
                165                 170                 175

Asn Asn Leu Gly Ile Pro Val Phe Ala Ile Val Asp Thr Asn Ser Asp
            180                 185                 190

Pro Asp Gly Val Asp Phe Val Ile Pro Gly Asn Asp Asp Ala Ile Arg
        195                 200                 205

Ala Val Thr Leu Tyr Leu Gly Ala Val Ala Ala Thr Val Arg Glu Gly
    210                 215                 220

Arg Ser Gln Asp Leu Ala Ser Gln Ala Glu Glu Ser Phe Val Glu Ala
225                 230                 235                 240

Glu


<210> SEQ ID NO 148
<211> LENGTH: 233
<212> TYPE: PRT
<213> ORGANISM: Escherichia coli

<400> SEQUENCE: 148

Met Gly Gln Lys Val His Pro Asn Gly Ile Arg Leu Gly Ile Val Lys
1               5                   10                  15

Pro Trp Asn Ser Thr Trp Phe Ala Asn Thr Lys Glu Phe Ala Asp Asn
            20                  25                  30

Leu Asp Ser Asp Phe Lys Val Arg Gln Tyr Leu Thr Lys Glu Leu Ala
        35                  40                  45

Lys Ala Ser Val Ser Arg Ile Val Ile Glu Arg Pro Ala Lys Ser Ile
    50                  55                  60

Arg Val Thr Ile His Thr Ala Arg Pro Gly Ile Val Ile Gly Lys Lys
65                  70                  75                  80

Gly Glu Asp Val Glu Lys Leu Arg Lys Val Val Ala Asp Ile Ala Gly
                85                  90                  95

Val Pro Ala Gln Ile Asn Ile Ala Glu Val Arg Lys Pro Glu Leu Asp
            100                 105                 110

Ala Lys Leu Val Ala Asp Ser Ile Thr Ser Gln Leu Glu Arg Arg Val
        115                 120                 125

Met Phe Arg Arg Ala Met Lys Arg Ala Val Gln Asn Ala Met Arg Leu
    130                 135                 140
```

Gly Ala Lys Gly Ile Lys Val Glu Val Ser Gly Arg Leu Gly Gly Ala
145 150 155 160

Glu Ile Ala Arg Thr Glu Trp Tyr Arg Glu Gly Arg Val Pro Leu His
165 170 175

Thr Leu Arg Ala Asp Ile Asp Tyr Asn Thr Ser Glu Ala His Thr Thr
180 185 190

Tyr Gly Val Ile Gly Val Lys Val Trp Ile Phe Lys Gly Glu Ile Leu
195 200 205

Gly Gly Met Ala Ala Val Glu Gln Pro Glu Lys Pro Ala Ala Gln Pro
210 215 220

Lys Lys Gln Gln Arg Lys Gly Arg Lys
225 230

<210> SEQ ID NO 149
<211> LENGTH: 206
<212> TYPE: PRT
<213> ORGANISM: Escherichia coli

<400> SEQUENCE: 149

Met Ala Arg Tyr Leu Gly Pro Lys Leu Lys Leu Ser Arg Arg Glu Gly
1 5 10 15

Thr Asp Leu Phe Leu Lys Ser Gly Val Arg Ala Ile Asp Thr Lys Cys
20 25 30

Lys Ile Glu Gln Ala Pro Gly Gln His Gly Ala Arg Lys Pro Arg Leu
35 40 45

Ser Asp Tyr Gly Val Gln Leu Arg Glu Lys Gln Lys Val Arg Arg Ile
50 55 60

Tyr Gly Val Leu Glu Arg Gln Phe Arg Asn Tyr Tyr Lys Glu Ala Ala
65 70 75 80

Arg Leu Lys Gly Asn Thr Gly Glu Asn Leu Leu Ala Leu Leu Glu Gly
85 90 95

Arg Leu Asp Asn Val Val Tyr Arg Met Gly Phe Gly Ala Thr Arg Ala
100 105 110

Glu Ala Arg Gln Leu Val Ser His Lys Ala Ile Met Val Asn Gly Arg
115 120 125

Val Val Asn Ile Ala Ser Tyr Gln Val Ser Pro Asn Asp Val Val Ser
130 135 140

Ile Arg Glu Lys Ala Lys Lys Gln Ser Arg Val Lys Ala Ala Leu Glu
145 150 155 160

Leu Ala Glu Gln Arg Glu Lys Pro Thr Trp Leu Glu Val Asp Ala Gly
165 170 175

Lys Met Glu Gly Thr Phe Lys Arg Lys Pro Glu Arg Ser Asp Leu Ser
180 185 190

Ala Asp Ile Asn Glu His Leu Ile Val Glu Leu Tyr Ser Lys
195 200 205

<210> SEQ ID NO 150
<211> LENGTH: 167
<212> TYPE: PRT
<213> ORGANISM: Escherichia coli

<400> SEQUENCE: 150

Met Ala His Ile Glu Lys Gln Ala Gly Glu Leu Gln Glu Lys Leu Ile
1 5 10 15

Ala Val Asn Arg Val Ser Lys Thr Val Lys Gly Gly Arg Ile Phe Ser
20 25 30

Phe Thr Ala Leu Thr Val Val Gly Asp Gly Asn Gly Arg Val Gly Phe
35 40 45

Gly Tyr Gly Lys Ala Arg Glu Val Pro Ala Ala Ile Gln Lys Ala Met
50 55 60

Glu Lys Ala Arg Arg Asn Met Ile Asn Val Ala Leu Asn Asn Gly Thr
65 70 75 80

Leu Gln His Pro Val Lys Gly Val His Thr Gly Ser Arg Val Phe Met
85 90 95

Gln Pro Ala Ser Glu Gly Thr Gly Ile Ile Ala Gly Gly Ala Met Arg
100 105 110

Ala Val Leu Glu Val Ala Gly Val His Asn Val Leu Ala Lys Ala Tyr
115 120 125

Gly Ser Thr Asn Pro Ile Asn Val Val Arg Ala Thr Ile Asp Gly Leu
130 135 140

Glu Asn Met Asn Ser Pro Glu Met Val Ala Ala Lys Arg Gly Lys Ser
145 150 155 160

Val Glu Glu Ile Leu Gly Lys
165

<210> SEQ ID NO 151
<211> LENGTH: 135
<212> TYPE: PRT
<213> ORGANISM: Escherichia coli

<400> SEQUENCE: 151

Met Arg His Tyr Glu Ile Val Phe Met Val His Pro Asp Gln Ser Glu
1 5 10 15

Gln Val Pro Gly Met Ile Glu Arg Tyr Thr Ala Ala Ile Thr Gly Ala
20 25 30

Glu Gly Lys Ile His Arg Leu Glu Asp Trp Gly Arg Arg Gln Leu Ala
35 40 45

Tyr Pro Ile Asn Lys Leu His Lys Ala His Tyr Val Leu Met Asn Val
50 55 60

Glu Ala Pro Gln Glu Val Ile Asp Glu Leu Glu Thr Thr Phe Arg Phe
65 70 75 80

Asn Asp Ala Val Ile Arg Ser Met Val Met Arg Thr Lys His Ala Val
85 90 95

Thr Glu Ala Ser Pro Met Val Lys Ala Lys Asp Glu Arg Arg Glu Arg
100 105 110

Arg Asp Asp Phe Ala Asn Glu Thr Ala Asp Asp Ala Glu Ala Gly Asp
115 120 125

Ser Glu Glu Glu Glu Glu Glu
130 135

<210> SEQ ID NO 152
<211> LENGTH: 179
<212> TYPE: PRT
<213> ORGANISM: Escherichia coli

<400> SEQUENCE: 152

Met Pro Arg Arg Arg Val Ile Gly Gln Arg Lys Ile Leu Pro Asp Pro
1 5 10 15

Lys Phe Gly Ser Glu Leu Leu Ala Lys Phe Val Asn Ile Leu Met Val
20 25 30

Asp Gly Lys Lys Ser Thr Ala Glu Ser Ile Val Tyr Ser Ala Leu Glu
35 40 45

```
Thr Leu Ala Gln Arg Ser Gly Lys Ser Glu Leu Glu Ala Phe Glu Val
    50                  55                  60

Ala Leu Glu Asn Val Arg Pro Thr Val Glu Val Lys Ser Arg Arg Val
65                  70                  75                  80

Gly Gly Ser Thr Tyr Gln Val Pro Val Glu Val Arg Pro Val Arg Arg
                85                  90                  95

Asn Ala Leu Ala Met Arg Trp Ile Val Glu Ala Ala Arg Lys Arg Gly
            100                 105                 110

Asp Lys Ser Met Ala Leu Arg Leu Ala Asn Glu Leu Ser Asp Ala Ala
        115                 120                 125

Glu Asn Lys Gly Thr Ala Val Lys Lys Arg Glu Asp Val His Arg Met
    130                 135                 140

Ala Glu Ala Asn Lys Ala Phe Ala His Tyr Arg Trp Leu Ser Leu Arg
145                 150                 155                 160

Ser Phe Ser His Gln Ala Gly Ala Ser Ser Lys Gln Pro Ala Leu Gly
                165                 170                 175

Tyr Leu Asn


<210> SEQ ID NO 153
<211> LENGTH: 130
<212> TYPE: PRT
<213> ORGANISM: Escherichia coli

<400> SEQUENCE: 153

Met Ser Met Gln Asp Pro Ile Ala Asp Met Leu Thr Arg Ile Arg Asn
1               5                   10                  15

Gly Gln Ala Ala Asn Lys Ala Ala Val Thr Met Pro Ser Ser Lys Leu
            20                  25                  30

Lys Val Ala Ile Ala Asn Val Leu Lys Glu Glu Gly Phe Ile Glu Asp
        35                  40                  45

Phe Lys Val Glu Gly Asp Thr Lys Pro Glu Leu Glu Leu Thr Leu Lys
    50                  55                  60

Tyr Phe Gln Gly Lys Ala Val Val Glu Ser Ile Gln Arg Val Ser Arg
65                  70                  75                  80

Pro Gly Leu Arg Ile Tyr Lys Arg Lys Asp Glu Leu Pro Lys Val Met
                85                  90                  95

Ala Gly Leu Gly Ile Ala Val Val Ser Thr Ser Lys Gly Val Met Thr
            100                 105                 110

Asp Arg Ala Ala Arg Gln Ala Gly Leu Gly Gly Glu Ile Ile Cys Tyr
        115                 120                 125

Val Ala
    130


<210> SEQ ID NO 154
<211> LENGTH: 130
<212> TYPE: PRT
<213> ORGANISM: Escherichia coli

<400> SEQUENCE: 154

Met Ala Glu Asn Gln Tyr Tyr Gly Thr Gly Arg Arg Lys Ser Ser Ala
1               5                   10                  15

Ala Arg Val Phe Ile Lys Pro Gly Asn Gly Lys Ile Val Ile Asn Gln
            20                  25                  30

Arg Ser Leu Glu Gln Tyr Phe Gly Arg Glu Thr Ala Arg Met Val Val
        35                  40                  45
```

Arg Gln Pro Leu Glu Leu Val Asp Met Val Glu Lys Leu Asp Leu Tyr
50 55 60

Ile Thr Val Lys Gly Gly Gly Ile Ser Gly Gln Ala Gly Ala Ile Arg
65 70 75 80

His Gly Ile Thr Arg Ala Leu Met Glu Tyr Asp Glu Ser Leu Arg Ser
85 90 95

Glu Leu Arg Lys Ala Gly Phe Val Thr Arg Asp Ala Arg Gln Val Glu
100 105 110

Arg Lys Lys Val Gly Leu Arg Lys Ala Arg Arg Arg Pro Gln Phe Ser
115 120 125

Lys Arg
130

<210> SEQ ID NO 155
<211> LENGTH: 103
<212> TYPE: PRT
<213> ORGANISM: Escherichia coli

<400> SEQUENCE: 155

Met Gln Asn Gln Arg Ile Arg Ile Arg Leu Lys Ala Phe Asp His Arg
1 5 10 15

Leu Ile Asp Gln Ala Thr Ala Glu Ile Val Glu Thr Ala Lys Arg Thr
20 25 30

Gly Ala Gln Val Arg Gly Pro Ile Pro Leu Pro Thr Arg Lys Glu Arg
35 40 45

Phe Thr Val Leu Ile Ser Pro His Val Asn Lys Asp Ala Arg Asp Gln
50 55 60

Tyr Glu Ile Arg Thr His Leu Arg Leu Val Asp Ile Val Glu Pro Thr
65 70 75 80

Glu Lys Thr Val Asp Ala Leu Met Arg Leu Asp Leu Ala Ala Gly Val
85 90 95

Asp Val Gln Ile Ser Leu Gly
100

<210> SEQ ID NO 156
<211> LENGTH: 129
<212> TYPE: PRT
<213> ORGANISM: Escherichia coli

<400> SEQUENCE: 156

Met Ala Lys Ala Pro Ile Arg Ala Arg Lys Arg Val Arg Lys Gln Val
1 5 10 15

Ser Asp Gly Val Ala His Ile His Ala Ser Phe Asn Asn Thr Ile Val
20 25 30

Thr Ile Thr Asp Arg Gln Gly Asn Ala Leu Gly Trp Ala Thr Ala Gly
35 40 45

Gly Ser Gly Phe Arg Gly Ser Arg Lys Ser Thr Pro Phe Ala Ala Gln
50 55 60

Val Ala Ala Glu Arg Cys Ala Asp Ala Val Lys Glu Tyr Gly Ile Lys
65 70 75 80

Asn Leu Glu Val Met Val Lys Gly Pro Gly Pro Gly Arg Glu Ser Thr
85 90 95

Ile Arg Ala Leu Asn Ala Ala Gly Phe Arg Ile Thr Asn Ile Thr Asp
100 105 110

```
Val Thr Pro Ile Pro His Asn Gly Cys Arg Pro Pro Lys Lys Arg Arg
        115                 120                 125

Val


<210> SEQ ID NO 157
<211> LENGTH: 124
<212> TYPE: PRT
<213> ORGANISM: Escherichia coli

<400> SEQUENCE: 157

Met Ala Thr Val Asn Gln Leu Val Arg Lys Pro Arg Ala Arg Lys Val
1               5                   10                  15

Ala Lys Ser Asn Val Pro Ala Leu Glu Ala Cys Pro Gln Lys Arg Gly
            20                  25                  30

Val Cys Thr Arg Val Tyr Thr Thr Thr Pro Lys Lys Pro Asn Ser Ala
        35                  40                  45

Leu Arg Lys Val Cys Arg Val Arg Leu Thr Asn Gly Phe Glu Val Thr
    50                  55                  60

Ser Tyr Ile Gly Gly Glu Gly His Asn Leu Gln Glu His Ser Val Ile
65                  70                  75                  80

Leu Ile Arg Gly Gly Arg Val Lys Asp Leu Pro Gly Val Arg Tyr His
                85                  90                  95

Thr Val Arg Gly Ala Leu Asp Cys Ser Gly Val Lys Asp Arg Lys Gln
            100                 105                 110

Ala Arg Ser Lys Tyr Gly Val Lys Arg Pro Lys Ala
        115                 120


<210> SEQ ID NO 158
<211> LENGTH: 118
<212> TYPE: PRT
<213> ORGANISM: Escherichia coli

<400> SEQUENCE: 158

Met Ala Arg Ile Ala Gly Ile Asn Ile Pro Asp His Lys His Ala Val
1               5                   10                  15

Ile Ala Leu Thr Ser Ile Tyr Gly Val Gly Lys Thr Arg Ser Lys Ala
            20                  25                  30

Ile Leu Ala Ala Ala Gly Ile Ala Glu Asp Val Lys Ile Ser Glu Leu
        35                  40                  45

Ser Glu Gly Gln Ile Asp Thr Leu Arg Asp Glu Val Ala Lys Phe Val
    50                  55                  60

Val Glu Gly Asp Leu Arg Arg Glu Ile Ser Met Ser Ile Lys Arg Leu
65                  70                  75                  80

Met Asp Leu Gly Cys Tyr Arg Gly Leu Arg His Arg Arg Gly Leu Pro
                85                  90                  95

Val Arg Gly Gln Arg Thr Lys Thr Asn Ala Arg Thr Arg Lys Gly Pro
            100                 105                 110

Arg Lys Pro Ile Lys Lys
        115


<210> SEQ ID NO 159
<211> LENGTH: 101
<212> TYPE: PRT
<213> ORGANISM: Escherichia coli
```

<400> SEQUENCE: 159

Met Ala Lys Gln Ser Met Lys Ala Arg Glu Val Lys Arg Val Ala Leu
1 5 10 15

Ala Asp Lys Tyr Phe Ala Lys Arg Ala Glu Leu Lys Ala Ile Ile Ser
20 25 30

Asp Val Asn Ala Ser Asp Glu Asp Arg Trp Asn Ala Val Leu Lys Leu
35 40 45

Gln Thr Leu Pro Arg Asp Ser Ser Pro Ser Arg Gln Arg Asn Arg Cys
50 55 60

Arg Gln Thr Gly Arg Pro His Gly Phe Leu Arg Lys Phe Gly Leu Ser
65 70 75 80

Arg Ile Lys Val Arg Glu Ala Ala Met Arg Gly Glu Ile Pro Gly Leu
85 90 95

Lys Lys Ala Ser Trp
100

<210> SEQ ID NO 160
<211> LENGTH: 89
<212> TYPE: PRT
<213> ORGANISM: Escherichia coli

<400> SEQUENCE: 160

Met Ser Leu Ser Thr Glu Ala Thr Ala Lys Ile Val Ser Glu Phe Gly
1 5 10 15

Arg Asp Ala Asn Asp Thr Gly Ser Thr Glu Val Gln Val Ala Leu Leu
20 25 30

Thr Ala Gln Ile Asn His Leu Gln Gly His Phe Ala Glu His Lys Lys
35 40 45

Asp His His Ser Arg Arg Gly Leu Leu Arg Met Val Ser Gln Arg Arg
50 55 60

Lys Leu Leu Asp Tyr Leu Lys Arg Lys Asp Val Ala Arg Tyr Thr Gln
65 70 75 80

Leu Ile Glu Arg Leu Gly Leu Arg Arg
85

<210> SEQ ID NO 161
<211> LENGTH: 82
<212> TYPE: PRT
<213> ORGANISM: Escherichia coli

<400> SEQUENCE: 161

Met Val Thr Ile Arg Leu Ala Arg His Gly Ala Lys Lys Arg Pro Phe
1 5 10 15

Tyr Gln Val Val Val Ala Asp Ser Arg Asn Ala Arg Asn Gly Arg Phe
20 25 30

Ile Glu Arg Val Gly Phe Phe Asn Pro Ile Ala Ser Glu Lys Glu Glu
35 40 45

Gly Thr Arg Leu Asp Leu Asp Arg Ile Ala His Trp Val Gly Gln Gly
50 55 60

Ala Thr Ile Ser Asp Arg Val Ala Ala Leu Ile Lys Glu Val Asn Lys
65 70 75 80

Ala Ala

<210> SEQ ID NO 162
<211> LENGTH: 84
<212> TYPE: PRT

<213> ORGANISM: Escherichia coli

<400> SEQUENCE: 162

Met Thr Asp Lys Ile Arg Thr Leu Gln Gly Arg Val Val Ser Asp Lys
1 5 10 15

Met Glu Lys Ser Ile Val Val Ala Ile Glu Arg Phe Val Lys His Pro
20 25 30

Ile Tyr Gly Lys Phe Ile Lys Arg Thr Thr Lys Leu His Val His Asp
35 40 45

Glu Asn Asn Glu Cys Gly Ile Gly Asp Val Val Glu Ile Arg Glu Cys
50 55 60

Arg Pro Leu Ser Lys Thr Lys Ser Trp Thr Leu Val Arg Val Val Glu
65 70 75 80

Lys Ala Val Leu

<210> SEQ ID NO 163
<211> LENGTH: 75
<212> TYPE: PRT
<213> ORGANISM: Escherichia coli

<400> SEQUENCE: 163

Met Ala Arg Tyr Phe Arg Arg Arg Lys Phe Cys Arg Phe Thr Ala Glu
1 5 10 15

Gly Val Gln Glu Ile Asp Tyr Lys Asp Ile Ala Thr Leu Lys Asn Tyr
20 25 30

Ile Thr Glu Ser Gly Lys Ile Val Pro Ser Arg Ile Thr Gly Thr Arg
35 40 45

Ala Lys Tyr Gln Arg Gln Leu Ala Arg Ala Ile Lys Arg Ala Arg Tyr
50 55 60

Leu Ser Leu Leu Pro Tyr Thr Asp Arg His Gln
65 70 75

<210> SEQ ID NO 164
<211> LENGTH: 92
<212> TYPE: PRT
<213> ORGANISM: Escherichia coli

<400> SEQUENCE: 164

Met Pro Arg Ser Leu Lys Lys Gly Pro Phe Ile Asp Leu His Leu Leu
1 5 10 15

Lys Lys Val Glu Lys Ala Val Glu Ser Gly Asp Lys Lys Pro Leu Arg
20 25 30

Thr Trp Ser Arg Arg Ser Thr Ile Phe Pro Asn Met Ile Gly Leu Thr
35 40 45

Ile Ala Val His Asn Gly Arg Gln His Val Pro Val Phe Val Thr Asp
50 55 60

Glu Met Val Gly His Lys Leu Gly Glu Phe Ala Pro Thr Arg Thr Tyr
65 70 75 80

Arg Gly His Ala Ala Asp Lys Lys Ala Lys Lys Lys
85 90

<210> SEQ ID NO 165
<211> LENGTH: 87
<212> TYPE: PRT
<213> ORGANISM: Escherichia coli

<400> SEQUENCE: 165

Met Ala Asn Ile Lys Ser Ala Lys Lys Arg Ala Ile Gln Ser Glu Lys
1               5                   10                  15

Ala Arg Lys His Asn Ala Ser Arg Arg Ser Met Met Arg Thr Phe Ile
            20                  25                  30

Lys Lys Val Tyr Ala Ala Ile Glu Ala Gly Asp Lys Ala Ala Ala Gln
        35                  40                  45

Lys Ala Phe Asn Glu Met Gln Pro Ile Val Asp Arg Gln Ala Ala Lys
    50                  55                  60

Gly Leu Ile His Lys Asn Lys Ala Ala Arg His Lys Ala Asn Leu Thr
65                  70                  75                  80

Ala Gln Ile Asn Lys Leu Ala
                85

<210> SEQ ID NO 166
<211> LENGTH: 71
<212> TYPE: PRT
<213> ORGANISM: Escherichia coli

<400> SEQUENCE: 166

Met Pro Val Ile Lys Val Arg Glu Asn Glu Pro Phe Asp Val Ala Leu
1               5                   10                  15

Arg Arg Phe Lys Arg Ser Cys Glu Lys Ala Gly Val Leu Ala Glu Val
            20                  25                  30

Arg Arg Arg Glu Phe Tyr Glu Lys Pro Thr Thr Glu Arg Lys Arg Ala
        35                  40                  45

Lys Ala Ser Ala Val Lys Arg His Ala Lys Lys Leu Ala Arg Glu Asn
    50                  55                  60

Ala Arg Arg Thr Arg Leu Tyr
65                  70

<210> SEQ ID NO 167
<211> LENGTH: 113
<212> TYPE: DNA
<213> ORGANISM: Artificial Sequence
<220> FEATURE:
<223> OTHER INFORMATION: Single strand DNA oligonucleotide

<400> SEQUENCE: 167
gttgtcagaa gtaagttggc cgcagtgtta tcactcatgg ttatggcagc actgcataat     60
tctcttactg tcatgccatc cgtaagatgc ttttctgtga ctggtgagta ctc           113

<210> SEQ ID NO 168
<211> LENGTH: 141
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: biotin conjugated

<400> SEQUENCE: 168
cggatatagt tcctcctttc agcaaaaaac ccctcaagac ccgtttagag gccccaaggg     60
gttatgctag ttacgtccca ttcgccatgc cgaagcatgt tgcccactag ccgccagcga    120
ggaggctggg accatggcta g                                              141

ASSEMBLY OF PROTEIN COMPLEXES ON A CHIP

RELATED APPLICATIONS

This application is a Continuation of PCT Patent Application No. PCT/IL2020/051037 having International filing date of Sep. 23, 2020, which claims the benefit of priority of Israel Patent Application No. 269674 filed on Sep. 25, 2019 and under 35 USC § 119(e) of U.S. Provisional Patent Application No. 63/053,752 filed on Jul. 20, 2020. The contents of the above applications are all incorporated by reference as if fully set forth herein in their entirety.

SEQUENCE LISTING STATEMENT

The ASCII file, entitled 91253SequenceListing.txt, created on Mar. 24, 2022, comprising 106,311 bytes, submitted concurrently with the filing of this application is incorporated herein by reference.

FIELD AND BACKGROUND OF THE INVENTION

The present invention, in some embodiments thereof, relates to cell-free synthesis and immobilization of protein complexes.

The technological drive for miniaturization has been a motivating force for the development of new approaches to manipulate matter down from the micron scale to the nanoscale. Bridging these scales with the macroscopic world comes with an energetic cost, an upper limit for further size reduction. Molecular machines offer new opportunities for bottom-up fabrication, and for the development of soft robots made of compliant materials responsive to the environment and compatible with the human body. Biomolecular assemblies, structures and machines are inspiring by their versatile shape, functionality, efficient modes of operation, and diverse mechanisms of energy conversion. Highly motivating are the unique features of RNA/protein-machines to spontaneously self-assemble into functional complex structures, coupled to their synthesis by gene-expression regulated mechanisms, all occurring out of equilibrium driven by expenditure of chemical energy.

Recent progress in cell-free reconstitution of functional protein machines coupled to protein synthesis has been demonstrated, yet without a means to control the reaction or assess assembly efficiency. A cell-free reaction lacks any trace of cellular architecture, which impacts the abundance, destination, and interaction networks of nascent RNAs and proteins. Cellular transactions are regulated by the spatial organization of genes in operons and clusters, by ribosome and mRNA localization to specific cellular targets and by the crowded cytoplasm.

Ribosomes are the universal decoders of the genetic code that synthesize all cellular proteins in all life forms. Ribosomes are unique biological machines composed of dozens of proteins and scaffolding RNAs, which synthesize their own parts and self-assemble in a sophisticated step-wise process. Ribosome biogenesis has been studied for decades to elucidate the composition of intermediates, assembly order, thermodynamics and kinetics of assembly, yet there is no reconstituted system of ribosomes synthesizing ribosomes to date. Establishing a scenario for the self-assembly of nascent ribosomal proteins (rPs) and RNA (rR) into intact ribosomes is the most crucial step for realizing de novo synthesis of functional ribosomes, which would lead to the bottom-up creation of a minimal self-replicating model of a cell. Previously, non-autonomous ribosome assembly has been demonstrated only from purified ribosomal proteins (rPs), in the absence of intact functional ribosomes.

Additional background art includes Jewett et al., 2013, Molecular Systems Biology 9:678 and Contreras-Llano and Cheemeng, Synthetic Biology, 2018, Vol 3, No. 1, US Patent Application No. 20170306320 and Heyman et al., Nature Nanotechnology, Vol. 7, 2012, pages 374-378.

SUMMARY OF THE INVENTION

According to an aspect of the present invention there is provided a method of assembling and immobilizing a proteinaceous complex comprising:

(a) providing a chamber having at least one surface, wherein a plurality of nucleic acids encoding at least two components of the proteinaceous complex are immobilized onto the at least one surface and wherein a binding agent which binds specifically to one component of the proteinaceous complex is immobilized onto the at least one surface; and (b) contacting the at least one surface of the chamber with agents for performing expression of the components from the plurality of nucleic acids, under conditions that allow expression and immobilization of the proteinaceous complex to the at least one surface, thereby assembling and immobilizing the proteinaceous complex.

According to an aspect of the present invention there is provided a method of generating a ribosomal subunit comprising:

(a) providing a chamber having at least one surface, wherein a plurality of nucleic acids encoding each of the components of the ribosomal subunit are immobilized onto the surface; and (b) contacting the surface of the chamber with agents for expressing the plurality of nucleic acids, under conditions that allow generation of a ribosomal subunit, thereby generating the ribosomal subunit.

According to an aspect of the present invention there is provided a method of analyzing whether a candidate agent disrupts the assembly of a complex comprising:

(a) assembling and immobilizing a complex on a solid surface of a chamber according to the method described herein in the presence of the candidate agent:

(b) analyzing an amount of the assembled complex which is attached to the solid surface, wherein a downregulation in the amount of the assembled complex as compared to the amount of the assembled complex in the absence of the candidate agent, is indicative that the candidate agent disrupts the assembly of the complex.

According to embodiments of the present invention, the proteinaceous complex comprises at least ten proteins.

According to embodiments of the present invention, the complex is functional.

According to embodiments of the present invention, the plurality of nucleic acids encoding each of the components of the proteinaceous complex are immobilized onto the at least one surface.

According to embodiments of the present invention, the components are selected from the group consisting of proteins and RNA.

According to embodiments of the present invention, the proteinaceous complex is selected from the group consisting of a ribosomal subunit, a ribosome, a bacteriophage, a spliceosome, a proteasome, a proteasome subunit, a replisome, a divisome and a virus.

According to embodiments of the present invention, the proteinaceous complex is a ribosomal subunit.

According to embodiments of the present invention, the chamber is comprised in a microfluidic chamber.

According to embodiments of the present invention, the binding agent is an antibody.

According to embodiments of the present invention, the antibody is directed to an affinity tag which is tagged to one component of the proteinaceous complex.

According to embodiments of the present invention, the binding agent is immobilized over the entire area of the at least one surface.

According to embodiments of the present invention, the height of the chamber is between 1-10 μm.

According to embodiments of the present invention, the plurality of nucleic acids encode a promoter operatively linked to a sequence encoding the component.

According to embodiments of the present invention, the affinity tag is selected from the group consisting of hemagglutinin (HA), AviTag, V5, Myc, T7, FLAG, HSV, VSV-G, 6-His, biotin and streptavidin.

According to embodiments of the present invention, the at least one component of the proteinaceous complex comprises a detectable moiety, the at least one component being different to the component which binds to the binding agent.

According to embodiments of the present invention, the binding agent binds the proteinaceous complex with at least ten fold higher affinity when it is in an assembled form over a non-assembled form.

According to embodiments of the present invention, the distance between one of the plurality of nucleic acids to another of the plurality of nucleic acids on the surface is about 30-100 nm.

According to embodiments of the present invention, the agents for performing expression comprise RNA polymerase, ribosomes and aminoacyl tRNA synthetase.

According to embodiments of the present invention, the agents are comprised in a cell-free protein expression system.

According to embodiments of the present invention, the dimension of the chamber are such that at least 50% of the total amount of proteinaceous complex is immobilized to the at least one surface.

According to embodiments of the present invention, the method further comprises detecting the immobilized proteinaceous complex.

According to embodiments of the present invention, the ribosomal subunit is functional.

According to embodiments of the present invention, the ribosomal subunit is a small ribosomal subunit.

According to embodiments of the present invention, the ribosomal subunit is a large ribosomal subunit.

According to embodiments of the present invention, the ribosomal subunit is a bacterial ribosomal subunit.

According to embodiments of the present invention, the ribosomal subunit is a mammalian ribosomal subunit.

According to embodiments of the present invention, the chamber is comprised in a microfluidic chamber.

According to embodiments of the present invention, the sequence of the plurality of the nucleic acids encodes a promoter operatively linked to a nucleic acid sequence encoding the component.

According to embodiments of the present invention, the at least one of the components is tagged with an affinity tag.

According to embodiments of the present invention, the affinity tag is selected from the group consisting of hemagglutinin, AviTag, V5, Myc, T7, FLAG, HSV, VSV-G, 6-His, biotin, and streptavidin.

According to embodiments of the present invention, the pair of the affinity tag is immobilized on the at least one surface of the chamber.

According to embodiments of the present invention, the at least one of the components of the ribosomal subunit is attached to a detectable moiety, wherein the component which is attached to a detectable moiety is different to the component which is tagged with an affinity tag.

According to embodiments of the present invention, the component which is attached to the detectable moiety is the RNA of the ribosomal subunit.

According to embodiments of the present invention, the second ribosomal subunit that binds the ribosomal subunit is immobilized on the surface of the chamber.

According to embodiments of the present invention, the distance between one of the plurality of nucleic acids to another of the plurality of nucleic acids on the surface is about 30-100 nm.

According to embodiments of the present invention, the agents comprise RNA polymerase, ribosome and aminoacyl tRNA synthetase.

According to embodiments of the present invention, the agents are comprised in a cell extract.

According to embodiments of the present invention, the complex is a ribosomal subunit, the candidate agent is an antibiotic.

According to another aspect of the present invention there is provided a method of generating a functional RNA polymerase comprising:

(a) providing a chamber having at least one surface, wherein a plurality of nucleic acids encoding each of the components of the RNA polymerase are immobilized onto the surface; and (b) contacting the surface of the chamber with agents for expressing the plurality of nucleic acids, under conditions that allow generation of the RNA polymerase, thereby generating the RNA polymerase.

According to embodiments of the present invention, at least one of the components is tagged with an affinity tag.

According to embodiments of the present invention, the pair of the affinity tag is immobilized on the at least one surface of the chamber.

According to embodiments of the present invention, the agents comprise an RNA polymerase that is non-identical to the RNA polymerase generated in the chamber.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F. SSU biogenesis on a chip. (A-C) Schemes: (A) rPs and rR (labeled with Broccoli aptamer, green spot) locally expressed from gene brushes and assembled into SSU bound on surface antibodies specific for HA peptide tag (red triangle). (B) Radial brush layouts have rR and rP-HA genes in central brushes, surrounded by brushes of all other rPs, related by color to the assembly map (based on refs. (4, 13)). (C) rPs in the same brush are shaded by a green background, and classified as primary, secondary, or tertiary (P, S, T) binders, respectively, and belong to the 5', central, or 3' structural domains along the rR (Green line). Arrows indicate the dependency order. Each brush layout has a different central rP-HA gene, producing variable rR signal on the surface. (D) rR signal buildup in time for the S15-HA configuration. Scale bar: 100 μm. (E) Top: Signal dynamics of rR binding to primary (left), secondary (center) and tertiary (right) rP-HAs. Bottom: $f_{max}$ of all rP-HAs. Error bars represent the standard deviation over three repeats. (F) SSU to timeline indicating the onset of each rR:rP-HA interaction. Time intervals are averages of three repeats.

Figure 1A:
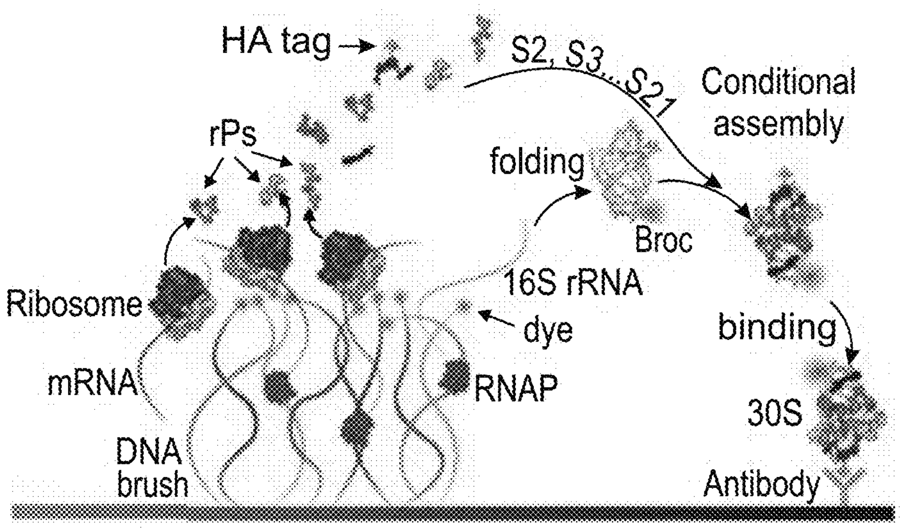
Figure 1B:
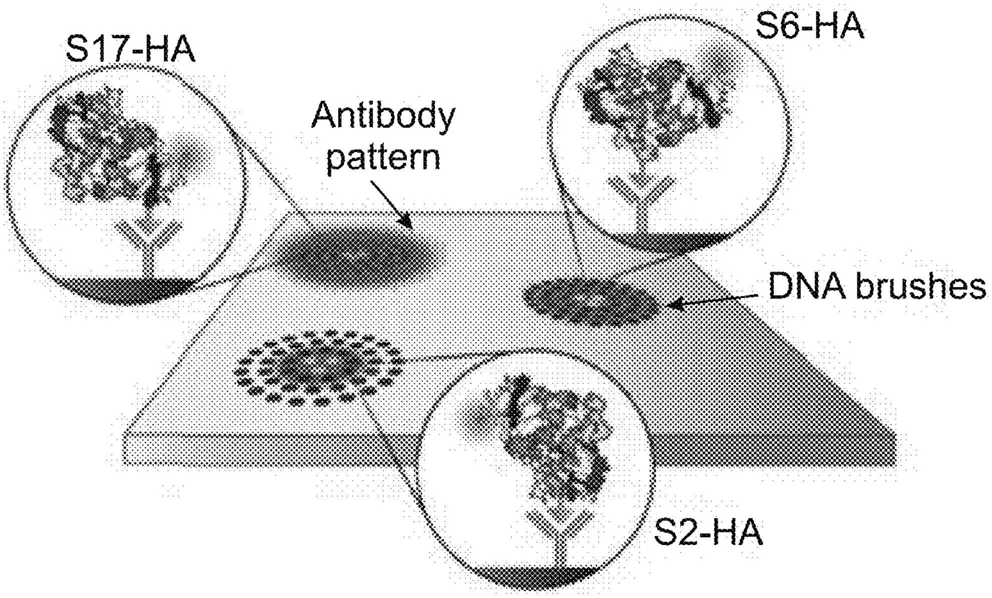
Figure 1C:
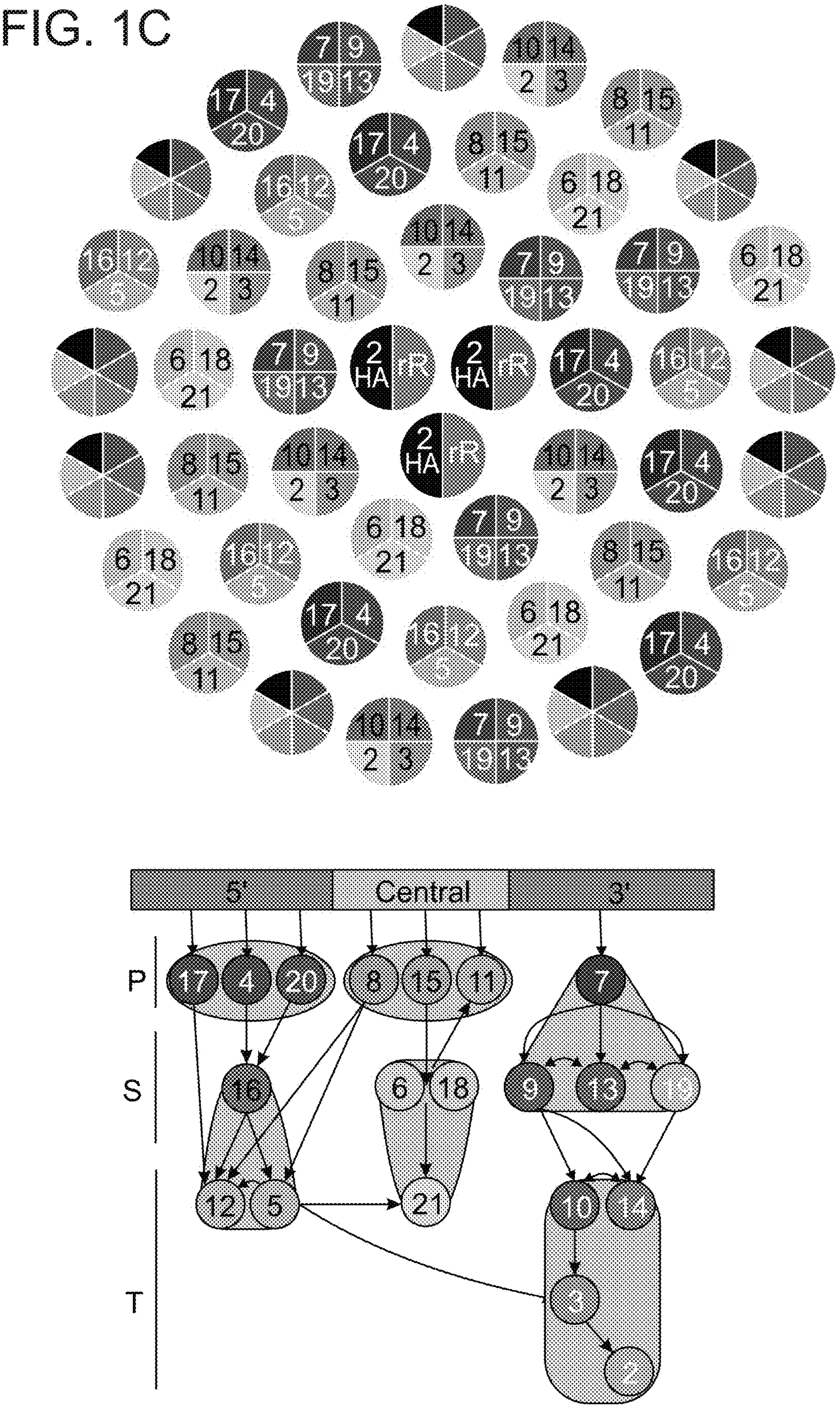
Figures 1D, 1E:
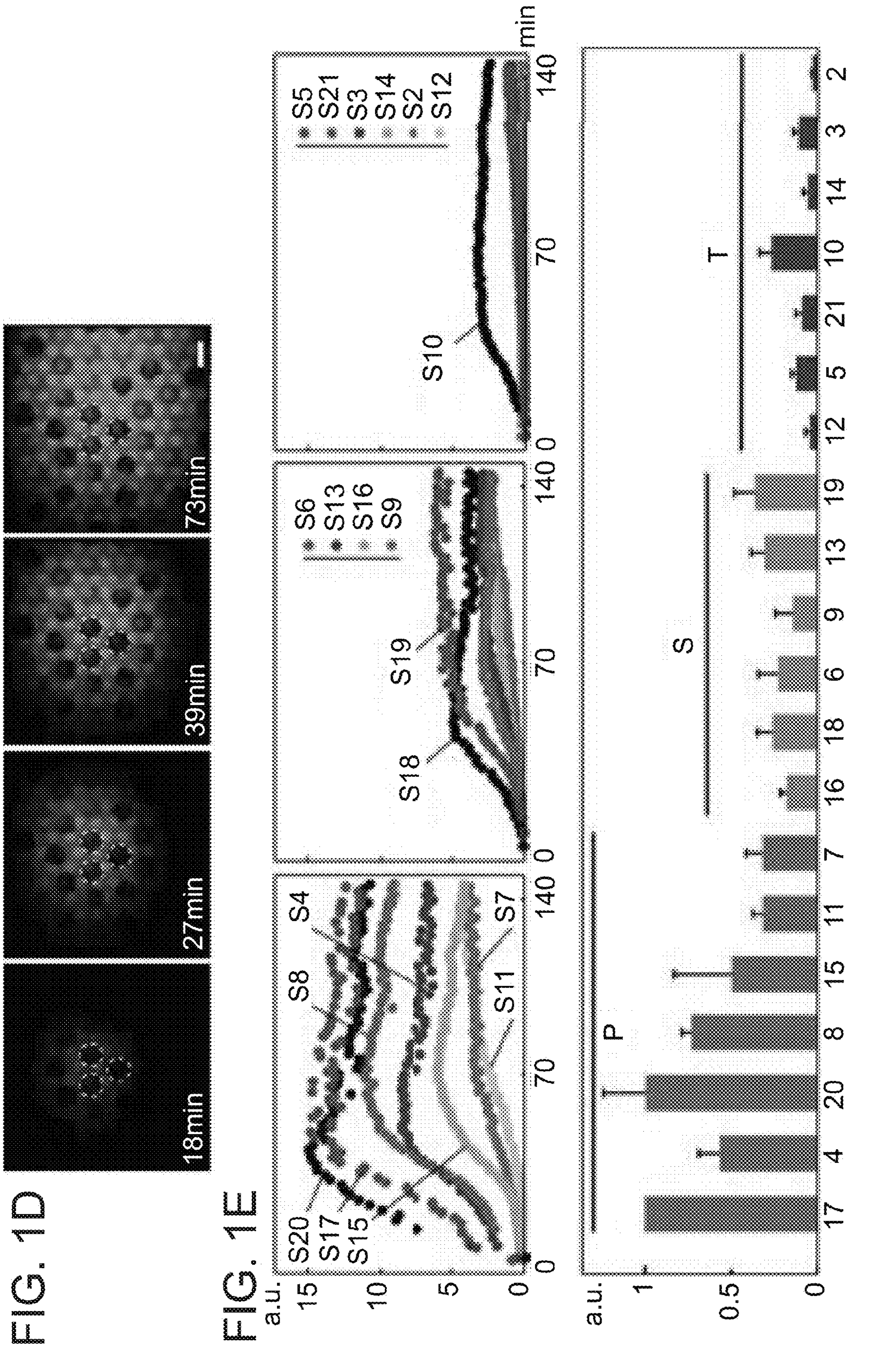
Figure 1F:
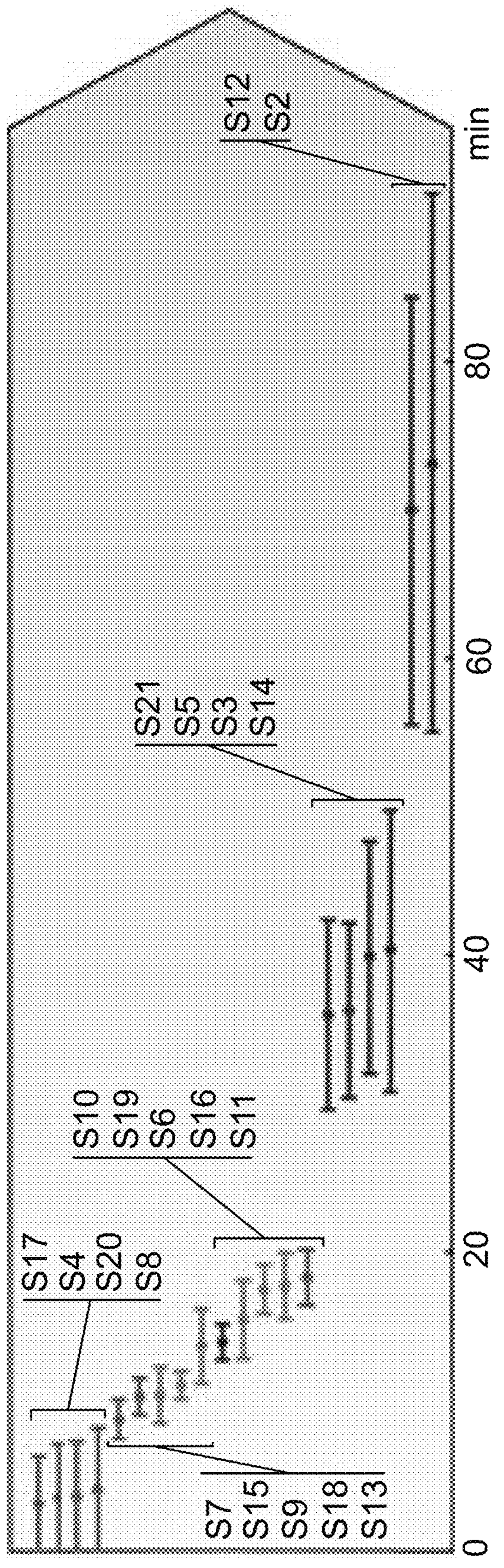
Figure 2A:
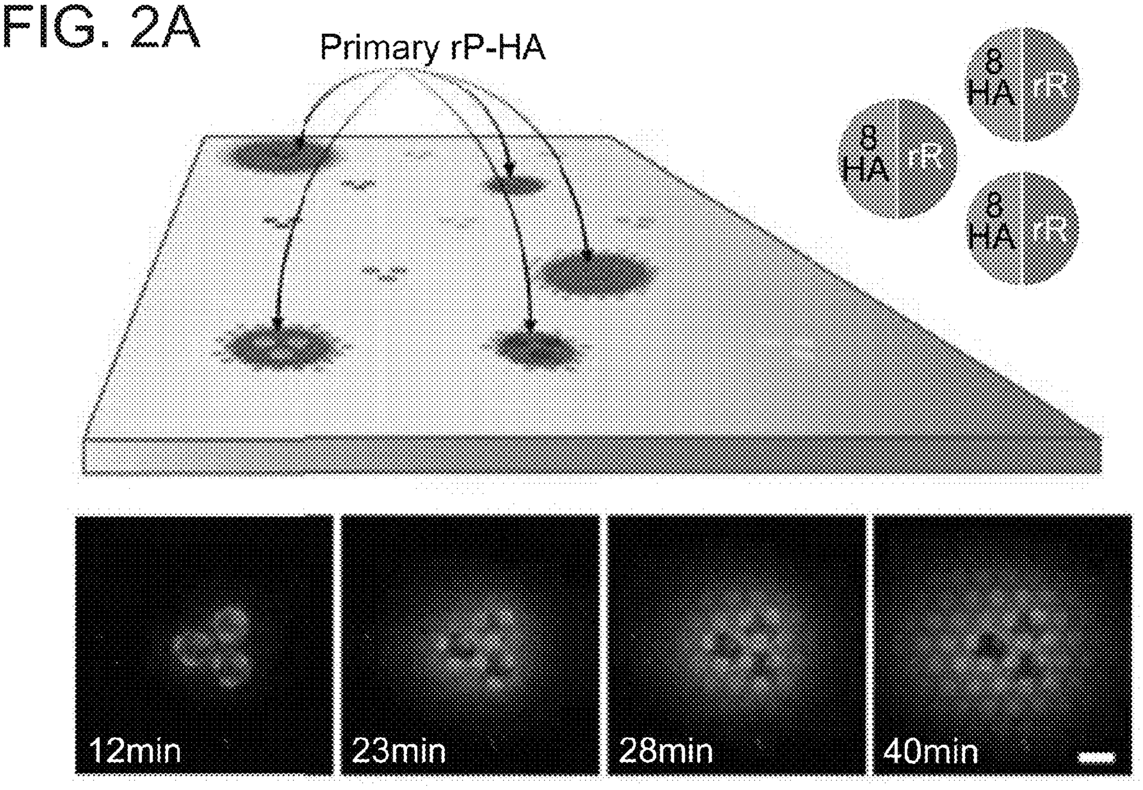
Figure 2B:
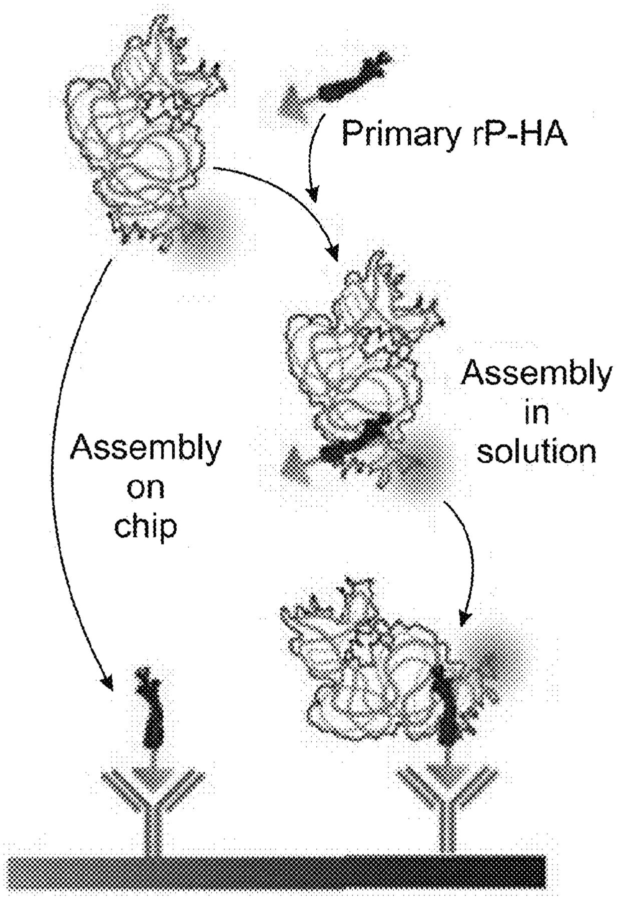
Figure 2C:
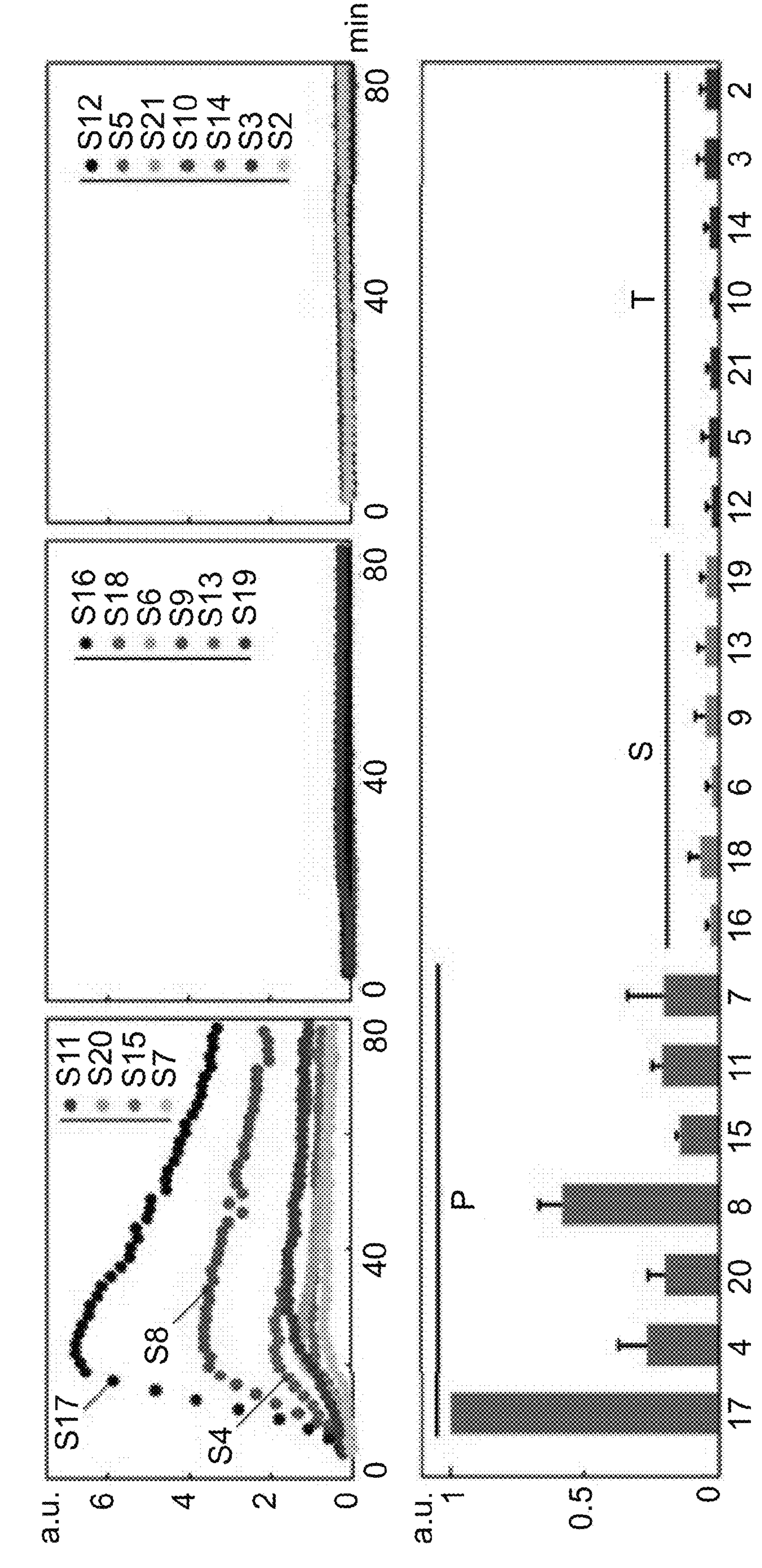

FIGS. 2A-C. rR:rP-HA interactions in the absence of rPs and cofactors. (A) Top: Scheme of brush organization on the chip. Bottom: rR signal buildup in time for the S8-HA layout. Scale bar: 100 μm. (B) Scheme of two possible modes for two-body assembly and binding to the surface: interaction occurring prior or post rP-HA binding to surface antibodies. (C) Top: Signal dynamics of primary (P, left), secondary (S, center) and tertiary (T, right) rP-HAs. Bottom: $f_{max}$ of all P, S, T rP-HAs. Error bars represent the standard deviation over three repeats. Labels as in FIGS. 1A-F.

FIGS. 3A-E. Binding dependencies of secondary rPs. (A) Scheme: two modes of rR binding to rP-HA on the surface, dependent on pre-binding of other rPs to the rR. (B) Brush layouts (a1-a8) of central domain analysis (S6-HA) and the corresponding fluorescent images at t=45 min. Scale bar: 100 μm. (C, D, E) Signal dynamics color maps of brush combinations, central (a1-a15), 5' (b1-b8) and 3' domain (c1-e8). White time intervals represent to. Gene combinations are depicted as grey and white boxes, indicating the presence or absence of an rP gene, respectively. Red frame indicates the rP-HA. Bars are averaged $f_{max}$ values with errors over 3 repeats. Those averaged $f_{max}$ values are presented as Venn diagrams according to the color scale. Partial assembly maps depict in red the dependencies deduced from each experiment. Large arrows represent strong dependencies.

FIGS. 4A-F. Late stages of on-chip SSU assembly. (A) Binding dependencies of rR:S2-HA on SSU domain combinations (a1-a8), depicted as dynamic color maps. Labels are as in FIGS. 3A-E. (B) Averaged $f_{max}$ for different cofactor combinations with and without rPs. Scale bar: 100 μm. (C) Signal dynamics of rR:S2-HA binding in the presence of 4 cofactors and domain combinations. Error bars represent standard deviation over three repeats. (D) Scheme: ribosomes localized on surface antibodies actively engaged in GFP-secM synthesis (SM) with SSU added from the bulk solution. mRNA is produced from nearby DNA brushes. Inset, TIRF dynamic signal of GFP-secM on surface bound ribosomes. (E) Scheme: synthesis and assembly of nascent SSU and binding to surface immobilized LSUs. (F) Signal dynamics color maps of nascent SSU binding onto surface-bound LSU, dependent on different rPs combinations (b1-b4).

FIGS. 5A-E. Experimental setup and data analysis. (A) Experimental setup for TIRF imaging of the chip. (B) Illustration of the organization of different brush configurations and details of the chamber. Each brush is a local source of rPs and/or rR. The proximity between brushes for a specific configuration gives rise to a high local concentration of their products, favoring multi-molecular associations. (C) Background subtraction. At short times, rR signal emerged only at the brushes containing the rR gene, serving as a localized source for rR transcription. Therefore, the first recorded image was subtracted from the rest of the images, leaving only the rR signal localized on surface antibodies. (D) Measurement of the dynamic fluorescent signal. At each time point, the fluorescent signal was the average of 3 to 10 different hexagons close to the three central brushes. The signal between hexagons was subtracted. (E) Evaluation of $t_0$, the signal starting time. The first data points were fitted using a polynomial function. The intersections between this function and two fixed thresholds define the interval containing $t_0$. Scale bar: 100 μm.

Figure 6A:
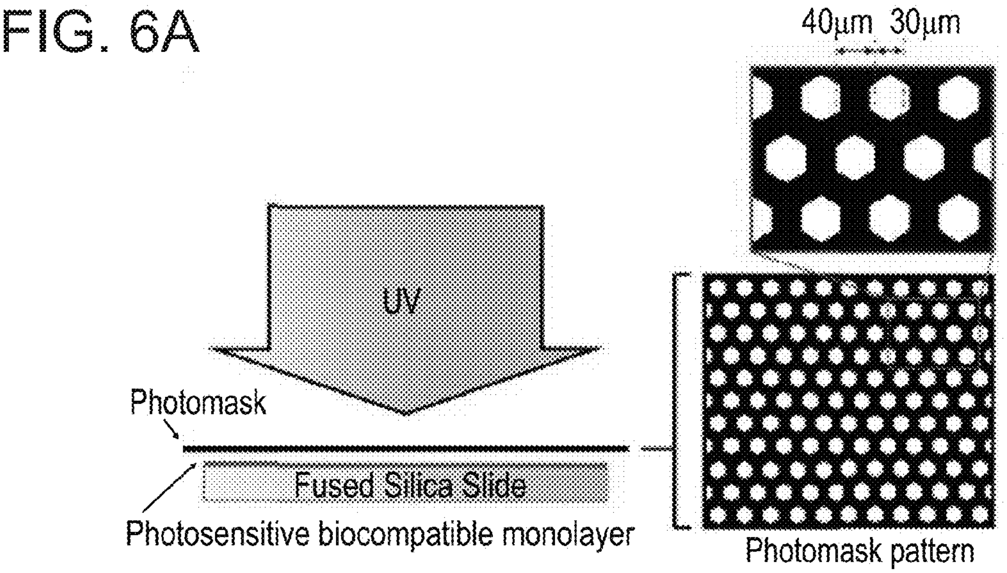
Figure 6B:
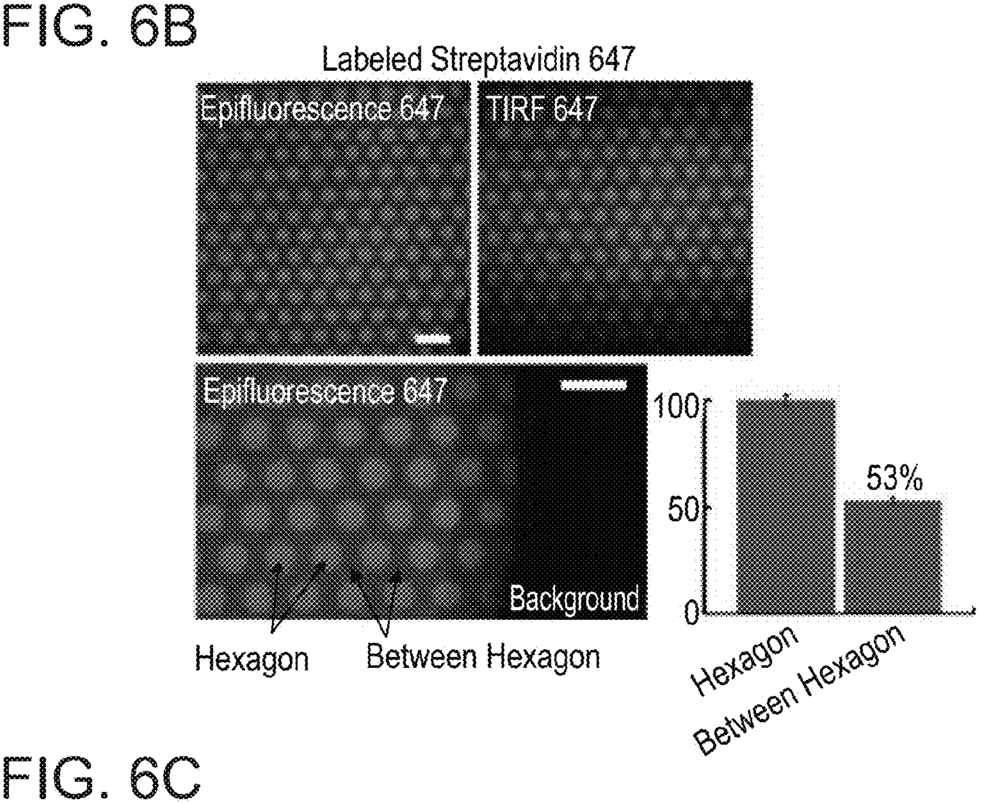
Figure 6C:
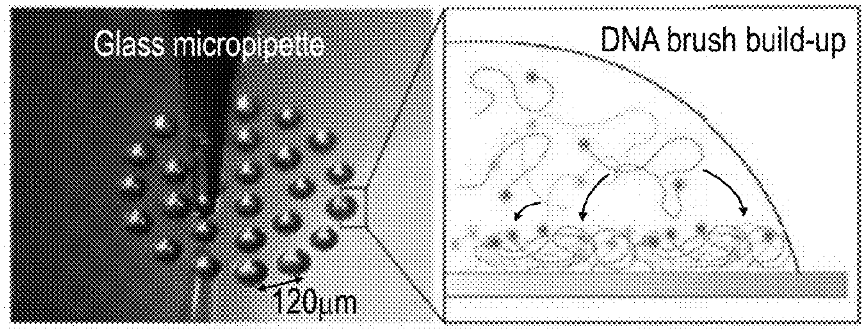

FIGS. 6A-C. Surface-patterning by UV Lithography and DNA deposition. (A) Scheme of the lithography process and details of the photomask. (B) Labeled streptavidin (647 nm) on patterned biotin imaged in epifluorescence and TIRF microscopy. The laser beam illuminates homogeneously a region of 300×300 μm. The streptavidin signal between hexagons reaches 53% of the signal inside hexagons, reflecting the relative level of activation of the photosensitive monolayer. (C) Nano-liter droplets containing SA-DNA conjugates are automatically deposited on the biotin-patterned surface with a 60 μm glass micropipette. The DNA brushes are formed inside the droplets during incubation time. Scale bar: 100 μm.

Figure 7:
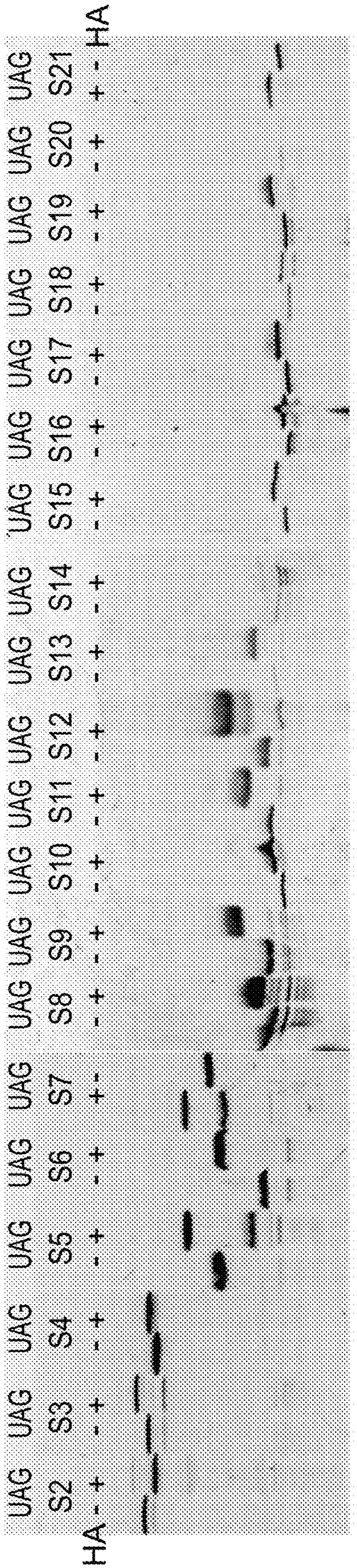

FIG. 7. Cell-free synthesis of SSU rPs. All UAG-rPs (S2-S21) were expressed, each in a separate cell-free reaction, supplemented with a plasmid coding for non-tagged or HA-tagged rP. rPs were in situ labeled by the unnatural amino acid for simple detection in the gel (Methods).

Figure 8A:
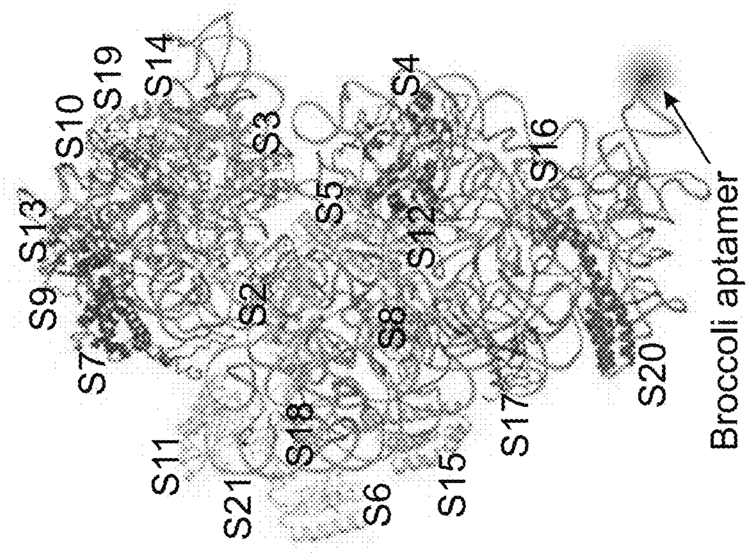
Figure 8B:
Figure 8C:
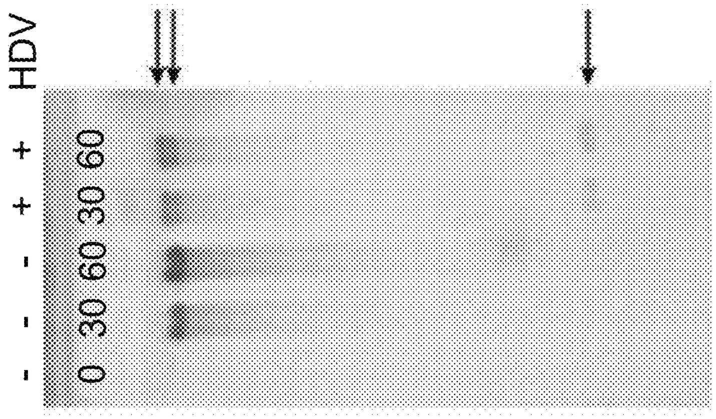

FIGS. 8A-C. rR modifications. (A) A ribbon diagram (PyMol Edu) of 16S rR displaying the position of the rPs and position of Broccoli aptamer insertion into Helix6. Proteins are colored according to the general convention in this work. (B) rR, with and without a Broccoli aptamer, were synthesized in vitro and in situ labeled with a 647-rUTP (647 image). Only the rR-Broccoli band could be visualized by the Broccoli specific DHFBI dye (488 image) (SM methods). (C) rR with and without an HDV ribozyme were in vitro synthesized and resolved by gel electrophoresis after 30 and 60 mins. The position of the RNA fragments resulting from self-cleavage of the HDV ribozyme are marked by arrows.

Figure 9A:
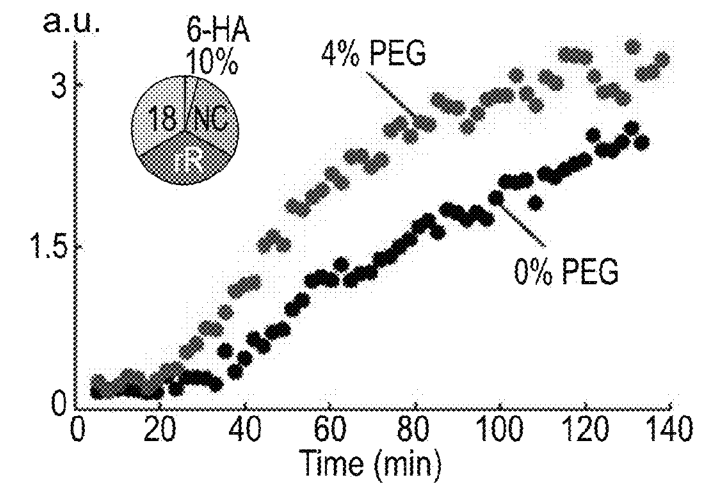
Figure 9B:
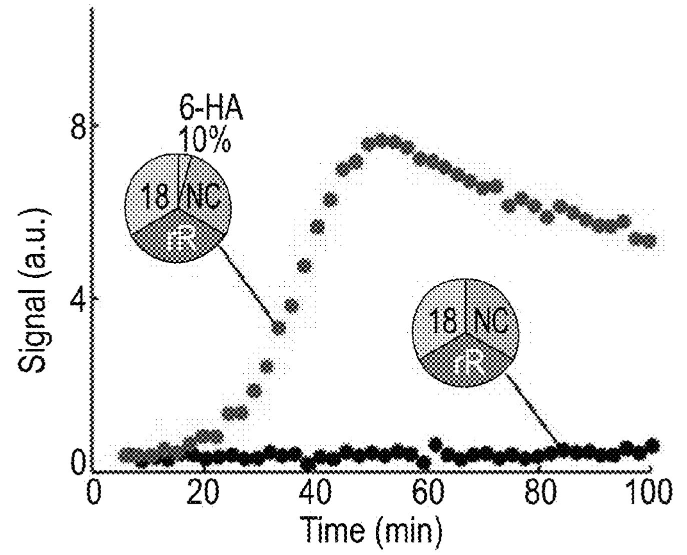
Figure 9C:
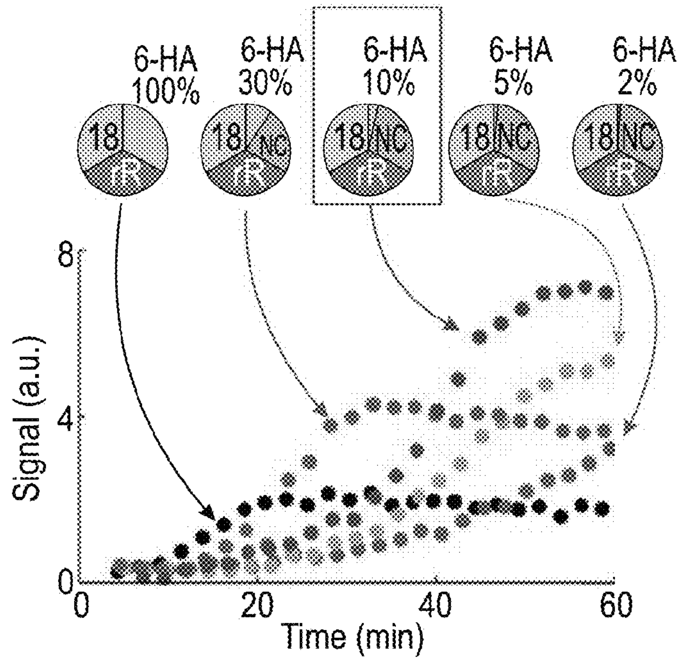

FIGS. 9A-C. Addition of PEG and effect of the rR:rP-HA ratio looking at the rR:S6-HA:S18 interaction. (A) Addition of PEG to on-chip expression reaction of rR:S6-HA:S18 enhances the rate of signal appearance and overall intensity. (B) The rR signal on surface antibodies with and without rP-HA genes. No non-specific pattern was observed without rP-HA. (C) The ratio between S6-HA to rR and S18 affected the rate of signal build-up on surface antibodies and overall intensity. A ratio of 9:1 S6-HA:rR was found to have the highest signal intensity suggesting that the maximal number of rR could be captured albeit with delayed kinetics. Non-coding DNA (NC) was introduced to dilute the rP-HA gene.

Figure 10:
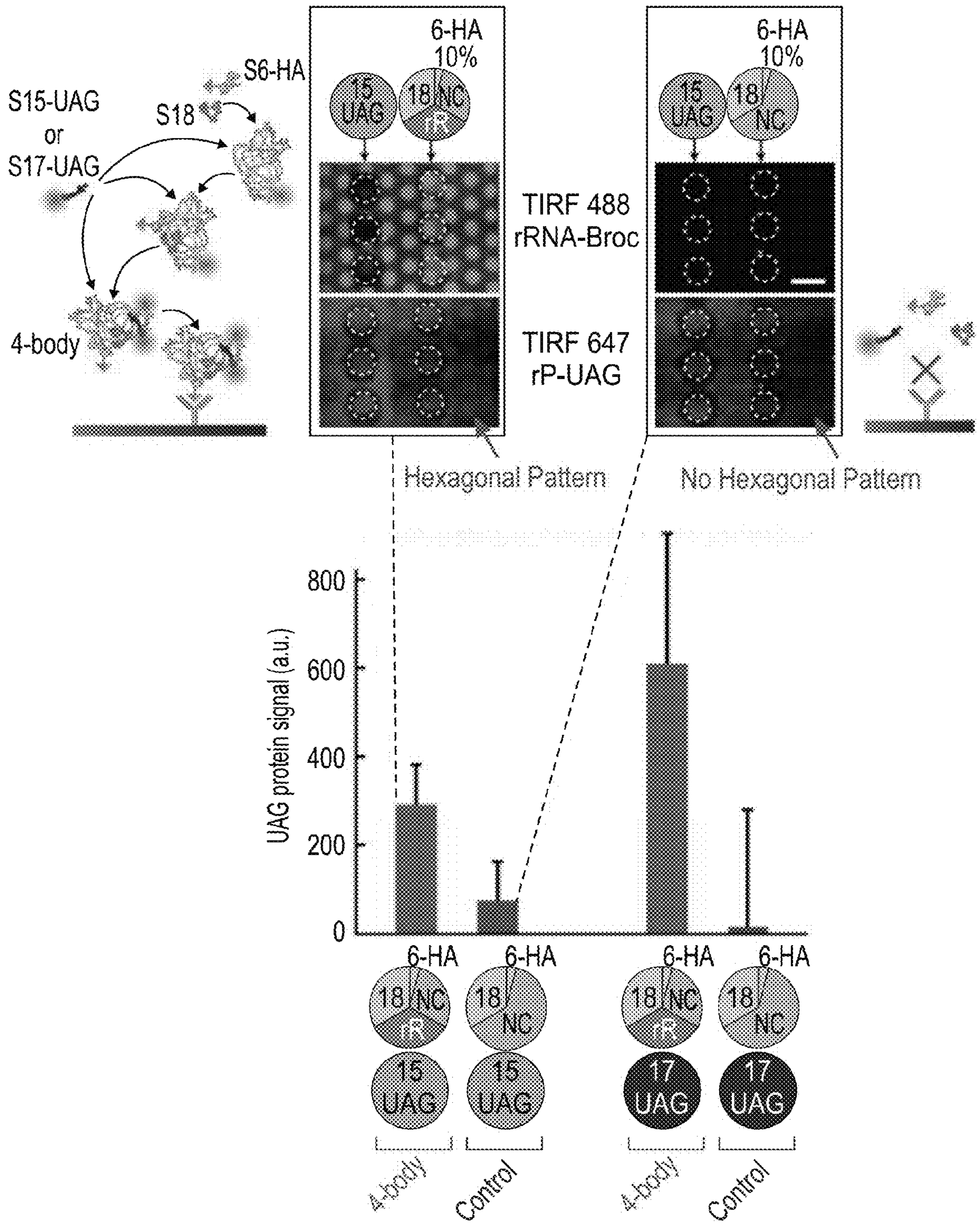

FIG. 10. Direct co-localization of rR and rPs using fluorescent amino acid labeling. A line of brushes composed of genes coding for the primary rP UAG-S15 or UAG-S17 (coding for the incorporation of an unnatural fluorescent amino acid, SM) was positioned next to a line of brushes coding either for the three components S6-HA, S18 and rR, or for only S6-HA and S18. A rR Broccoli signal (TIRF excitation at 488 nm) was observed next to the 3-body brushes, indicating the 3-body assembly on the patterned antibodies (top left picture). No pattern was observed in absence of rR (top right picture). A rP-UAG signal (TIRF excitation at 647 nm) was observed only in presence of the rR, demonstrating the direct binding of the primary rP-UAG as a 4-body complex (bottom left and right pictures). Fluorescent signals of labeled rPs were recorded at t=135 min and t=85 min for S15-UAG and S17-UAG, respectively, with (green bars) and without (grey bars) rR. NC: non-coding DNA. Scale bar: 100 μm.

Figure 11:
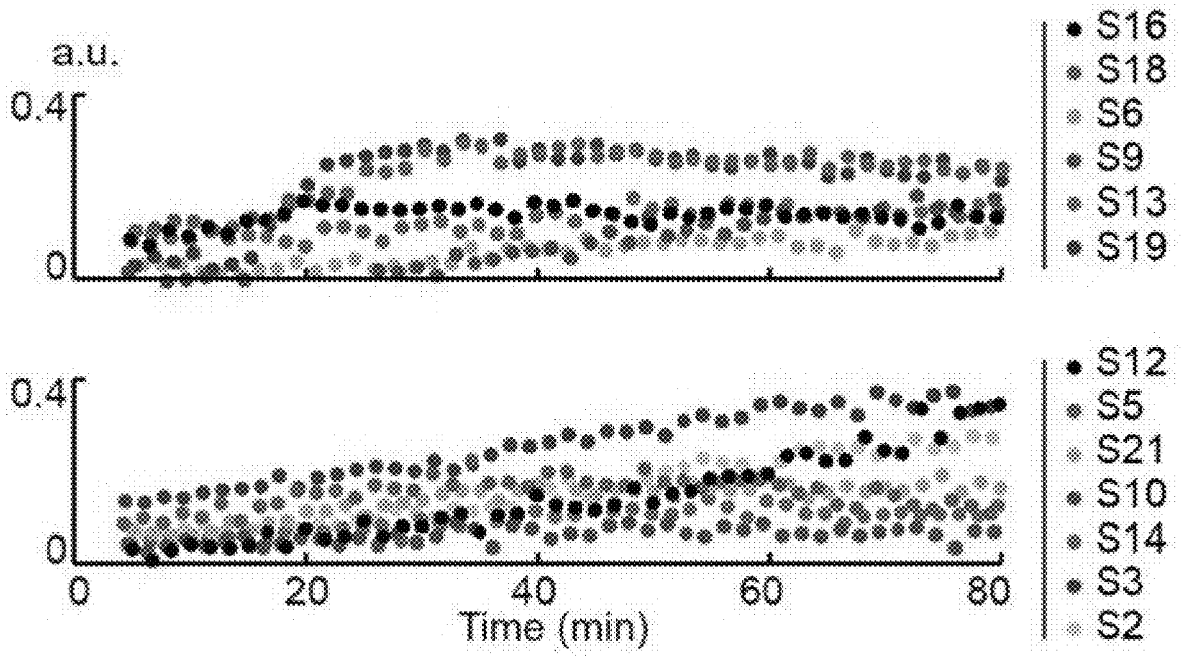

FIG. 11. Interaction of secondary and tertiary rPs with rR in the absence of other rPs. A zoom of the two top right panels of FIG. 2C.

Figure 12B:
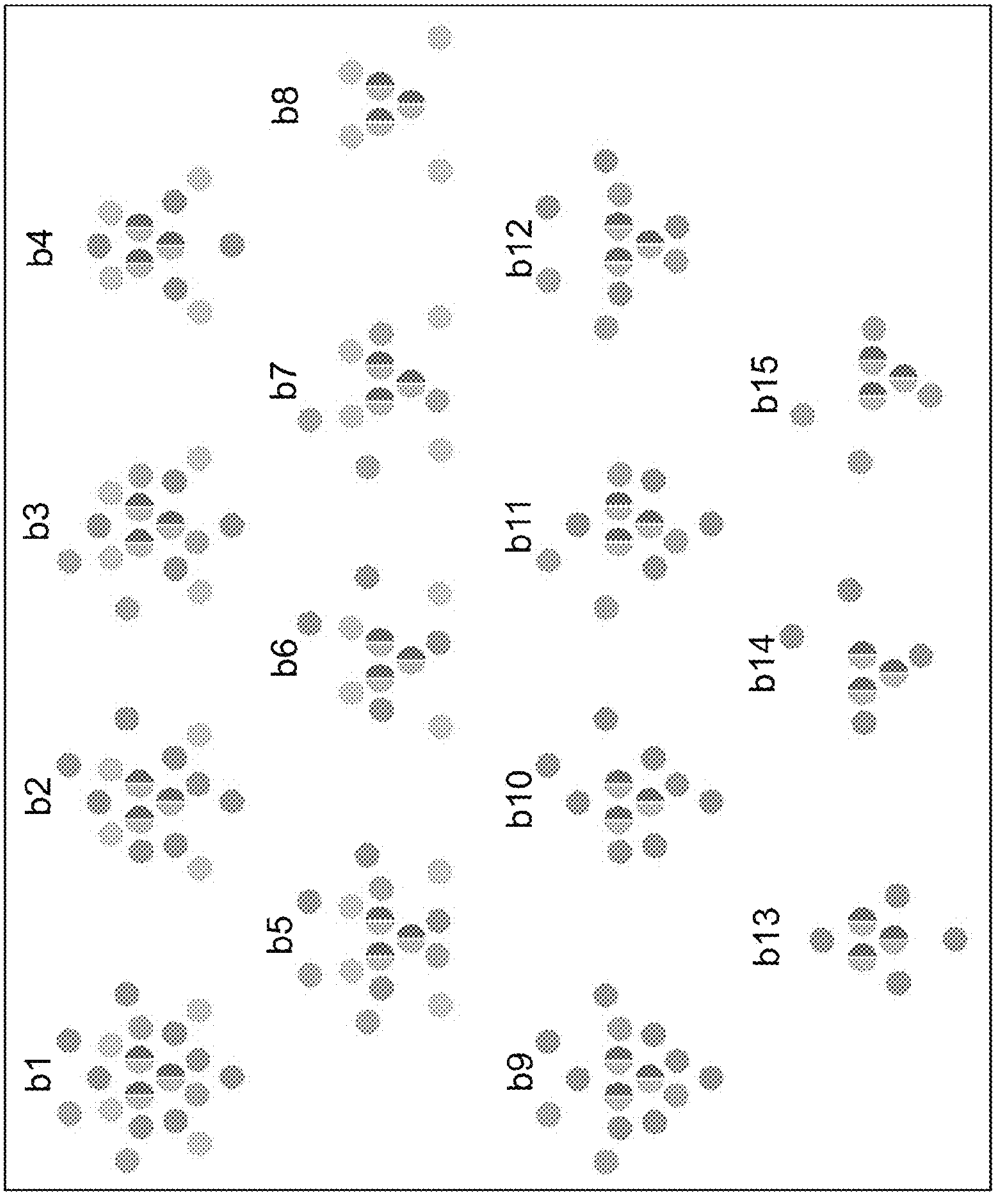
Figure 12A:
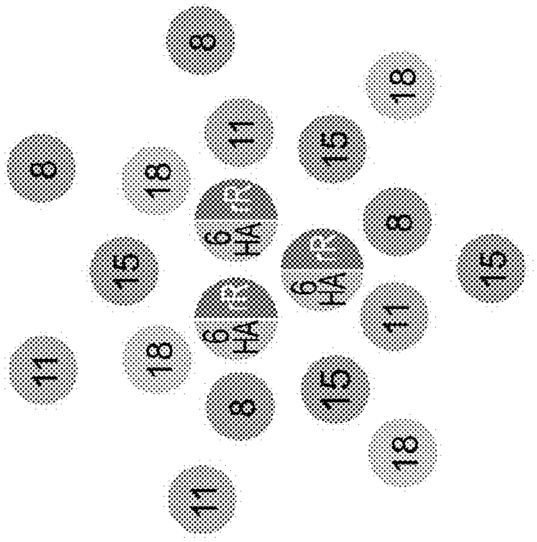
Figure 12C:
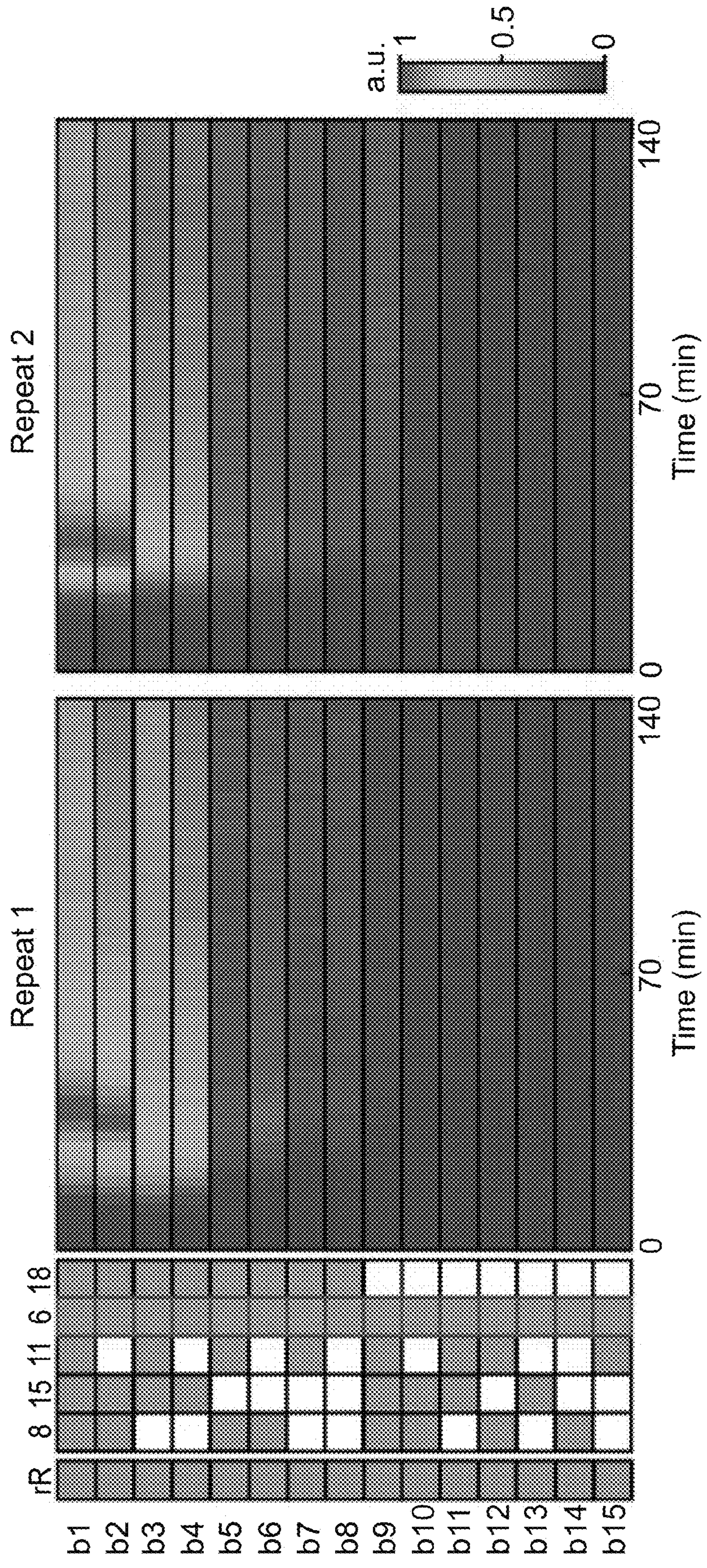
Figure 13A:
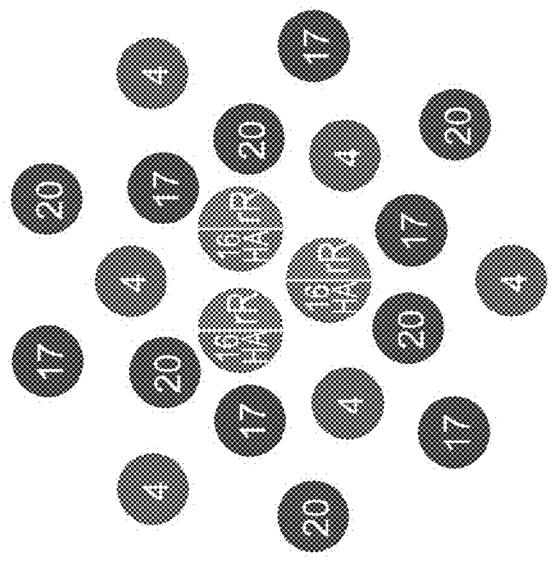
Figure 13B:
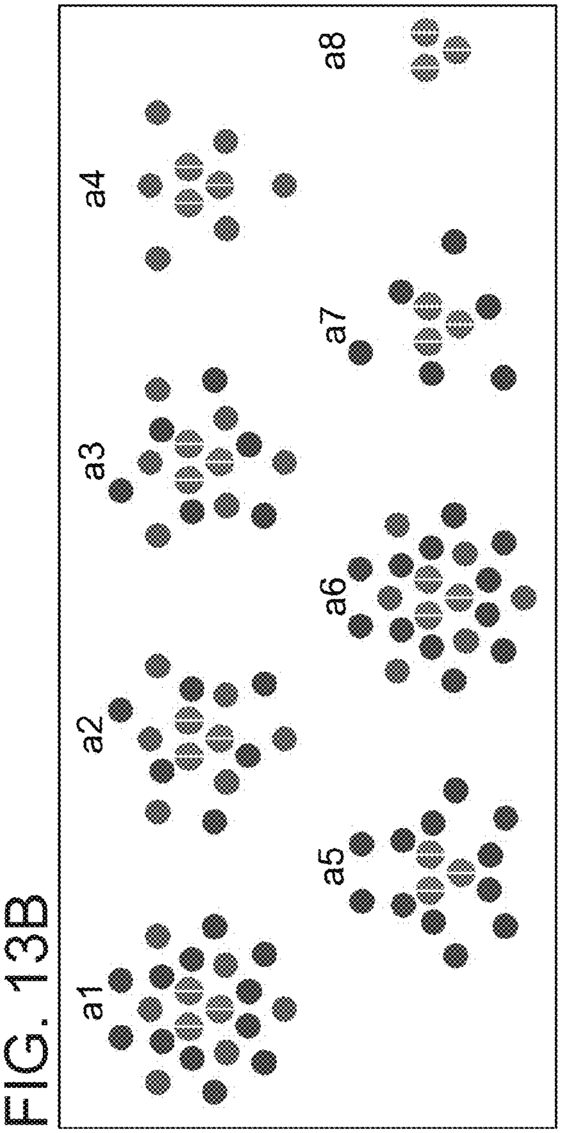
Figure 13C:
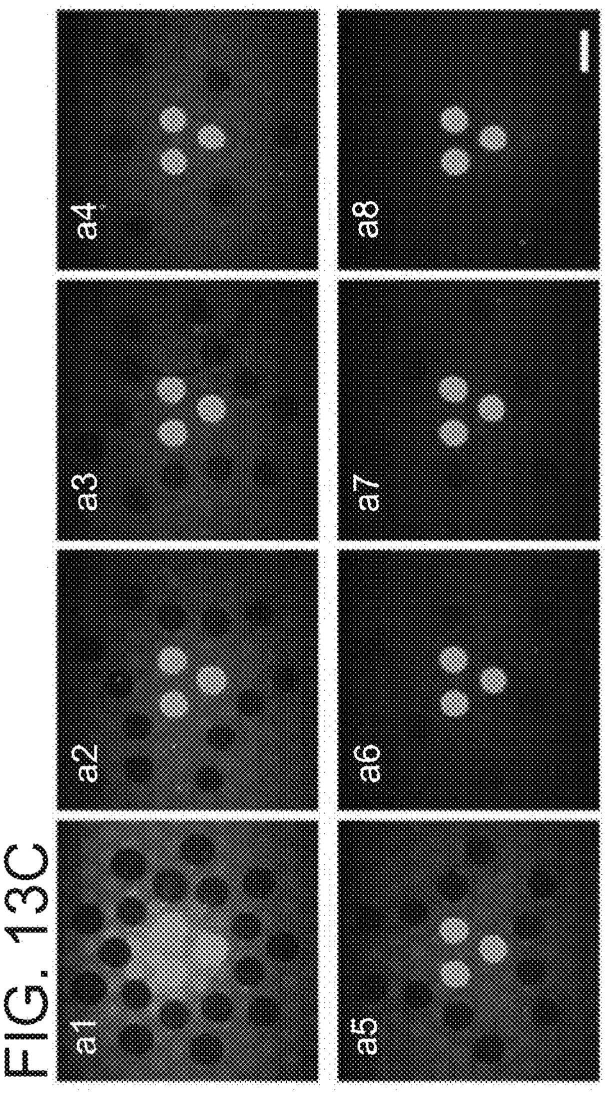
Figure 13D:
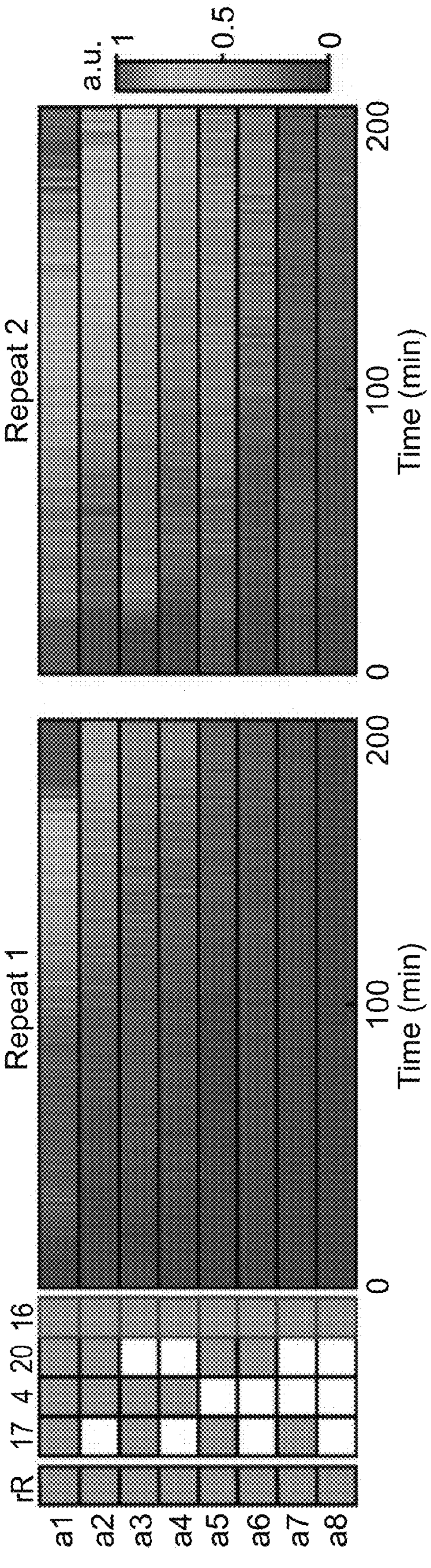
Figure 14A:
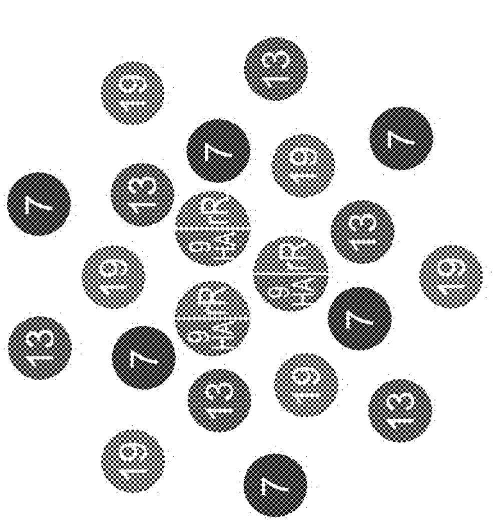
Figure 14B:
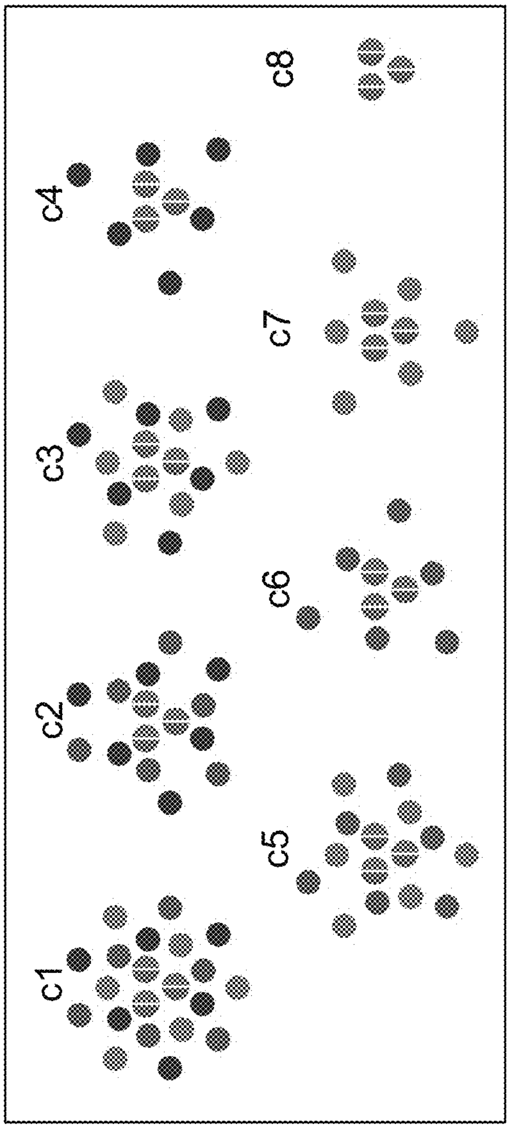
Figure 14C:
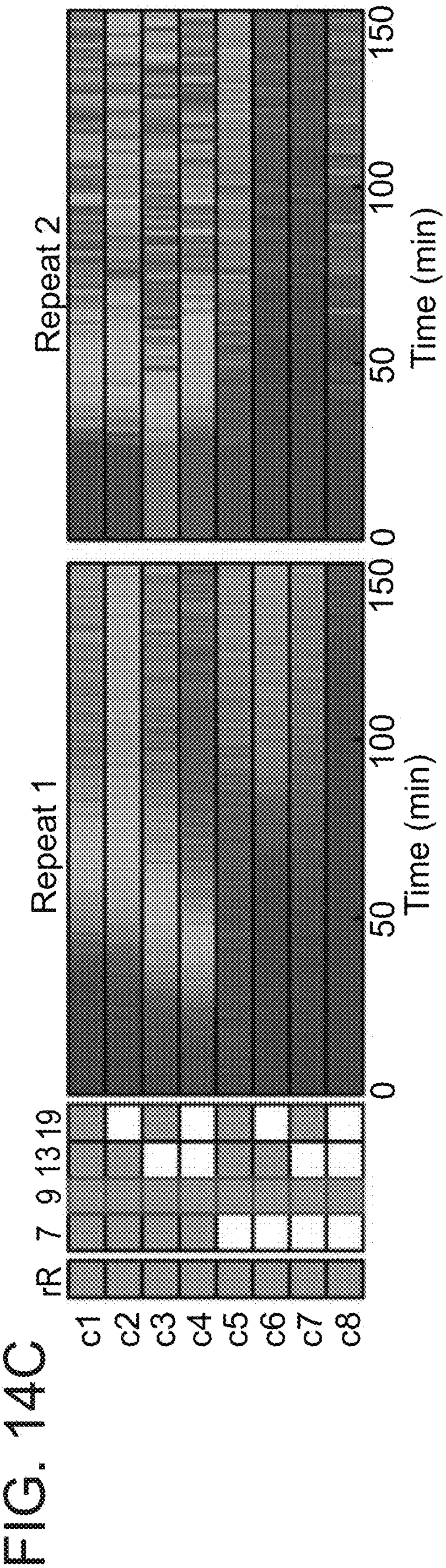
Figure 14D:
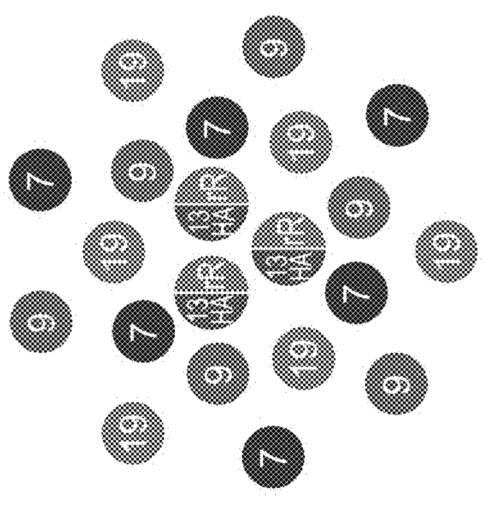
Figure 14E:
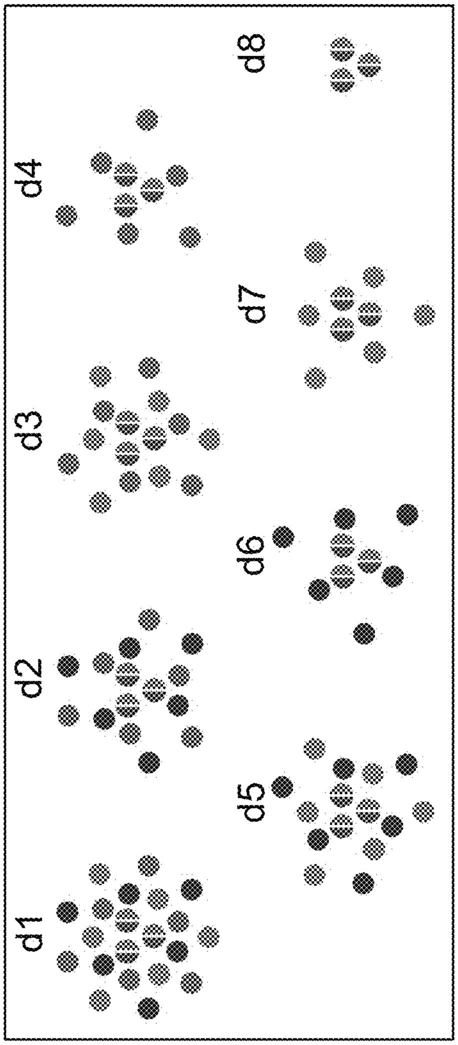
Figure 14F:
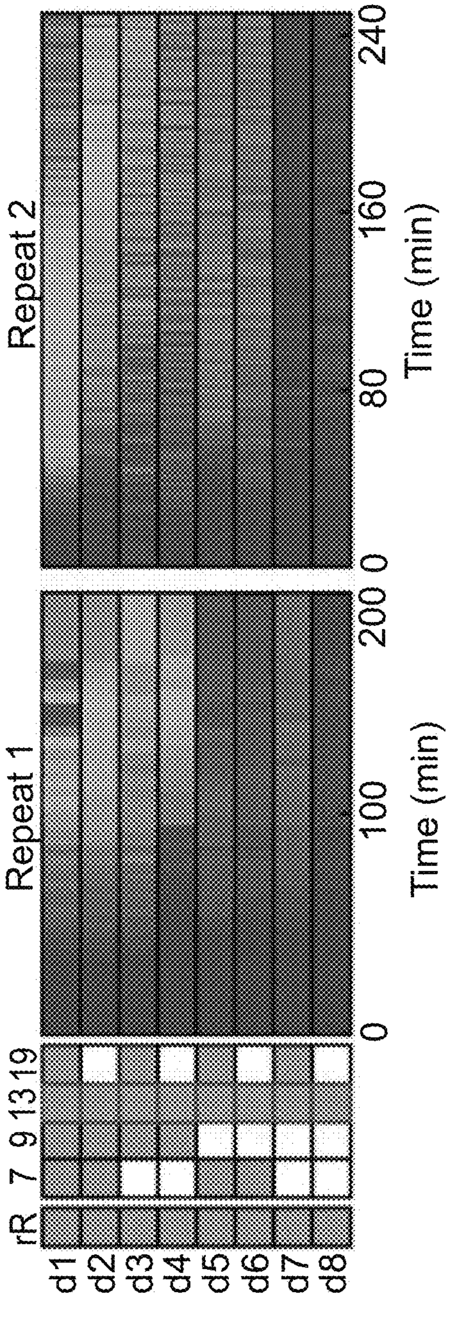
Figure 14G:
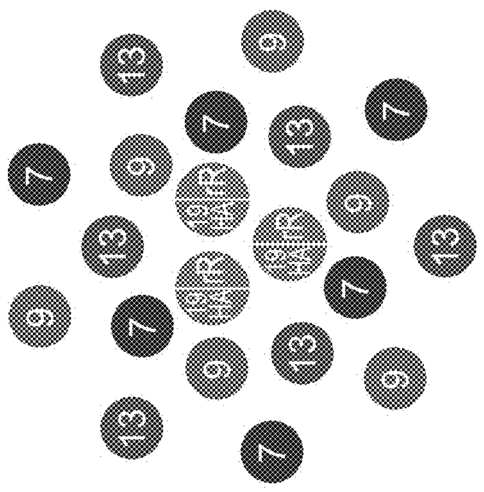
Figure 14H:
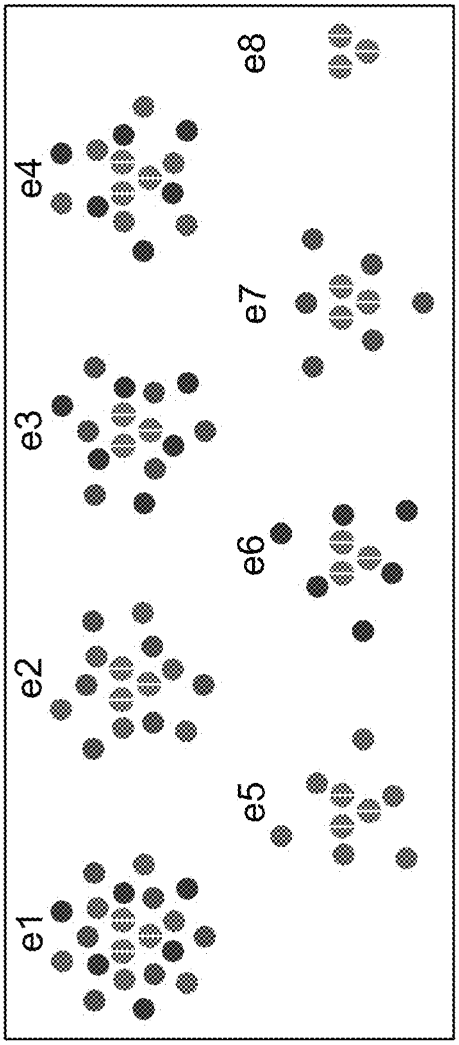
Figure 14I:
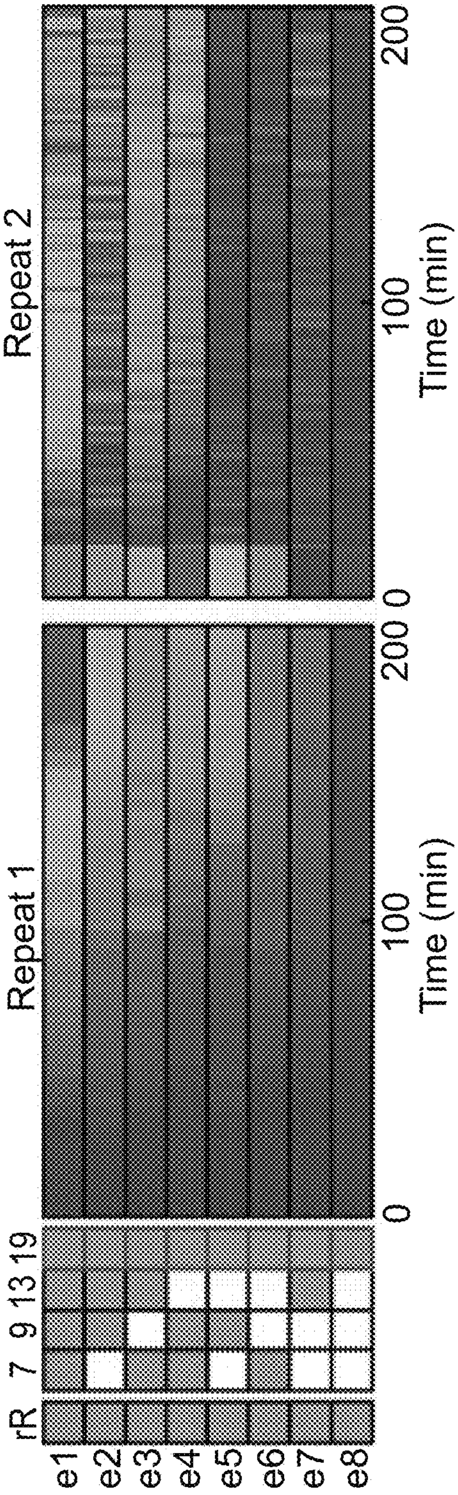

FIGS. 12A-C. rR: S6-HA interaction with different configurations of central domain rPs. (A) Spatial arrangement of the DNA brushes when all the six genes involved are present. (B) The different configurations of the study. (C) Repeats of the experiment presented FIG. 3C.

FIGS. 13A-D. rR:S16-HA interactions with different configurations of 5' domain rPs. (A) Spatial arrangement of the DNA brushes when all the five genes involved are present. (B) The different configurations of the study. (C) TIRF images of the configurations at t=150 min. Scale bar: 100 μm. (D) Repeats of the experiment presented FIG. 3D.

FIGS. 14A-I. rR interactions with S9-HA, S13-HA and S19-HA. (A, D, G) Spatial arrangement of the DNA brushes when all the five genes involved are present. (B, E, H) The different configurations of the studies. (C, F, I) Repeats of the experiments presented FIG. 3E.

Figure 15A:
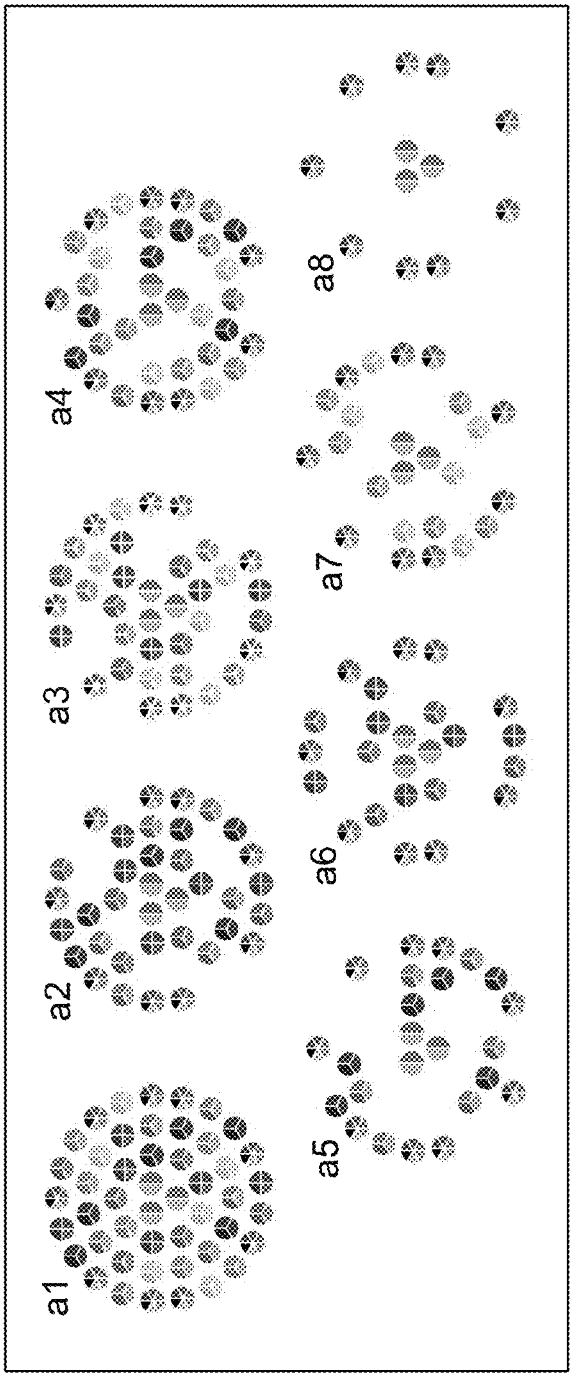
Figure 15B:
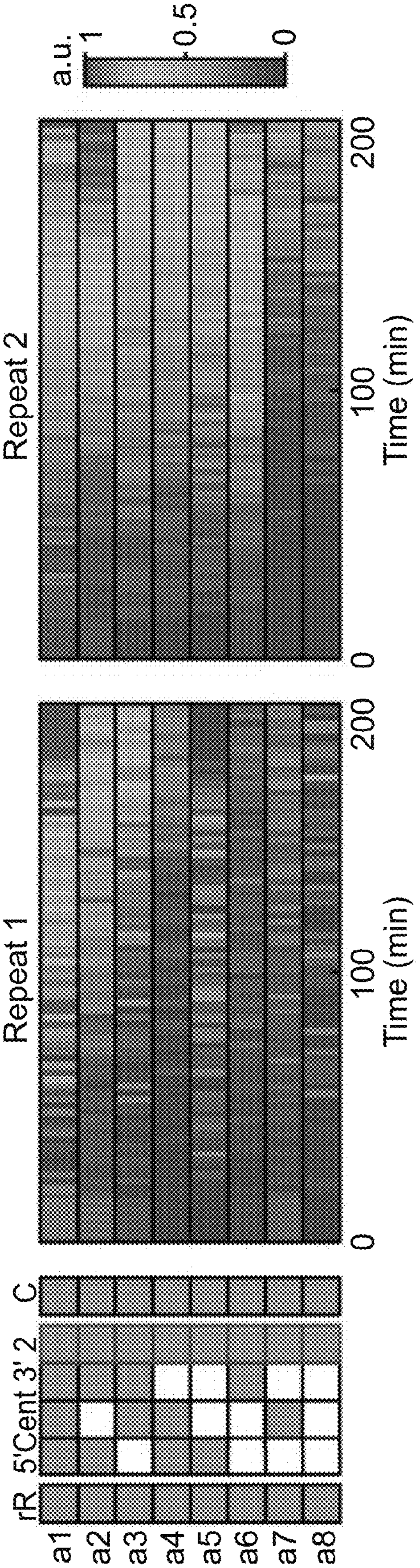

FIGS. 15A-B. rR:S2-HA interactions with 6 cofactors and different domain deletions. (A) The different configurations of the study. (B) Repeats of the experiment presented FIG. 4A.

Figure 16A:
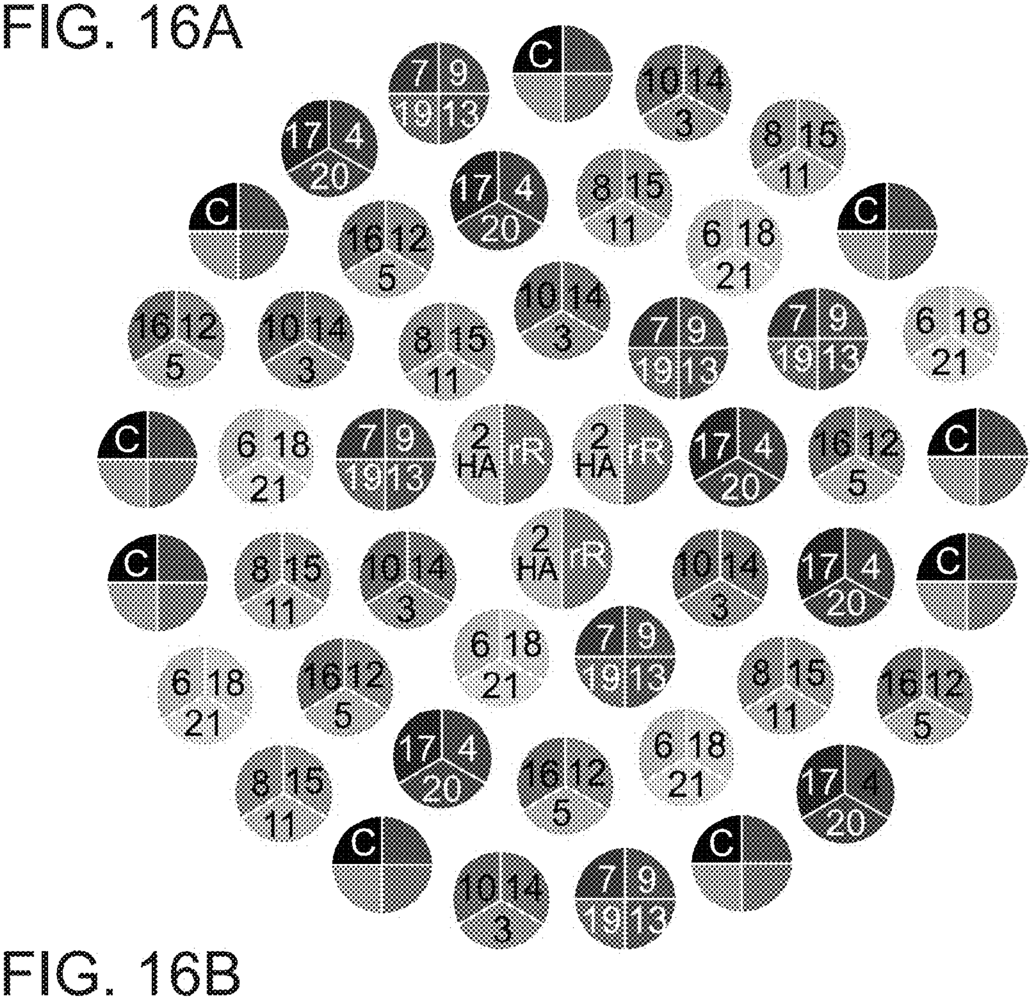
Figure 16B:
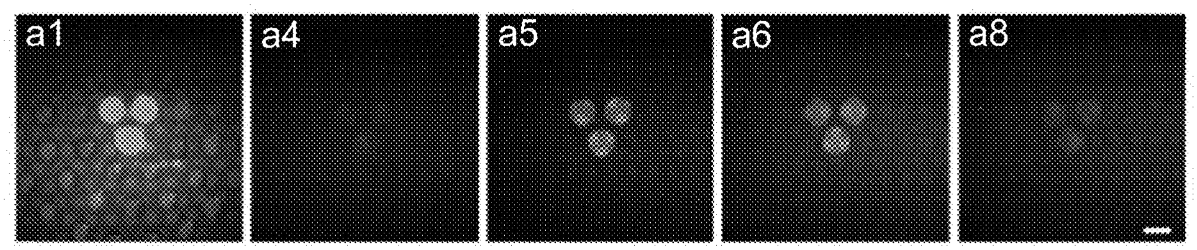
Figure 16C:
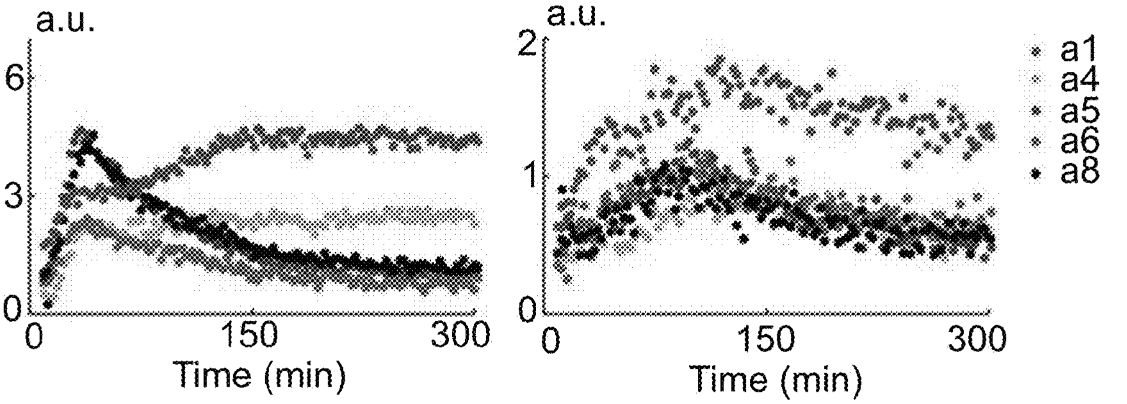
Figure 17A:
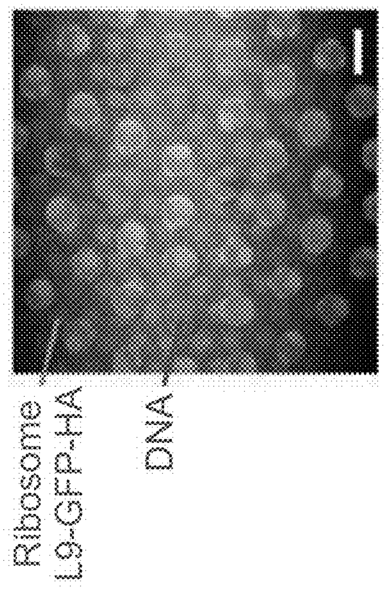
Figure 17B:
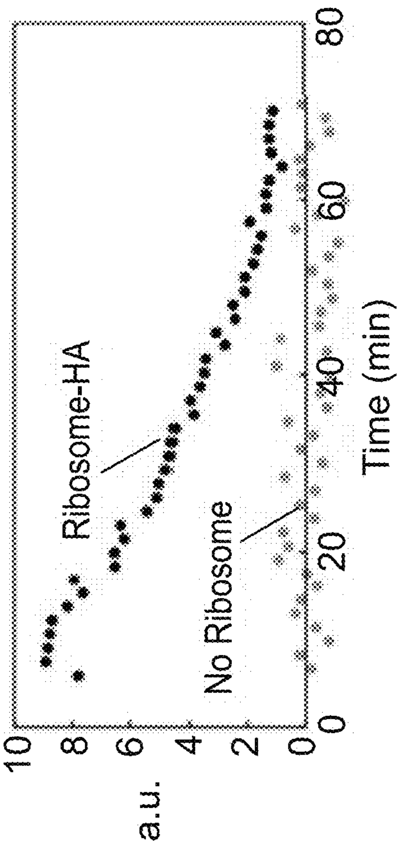
Figure 17C:
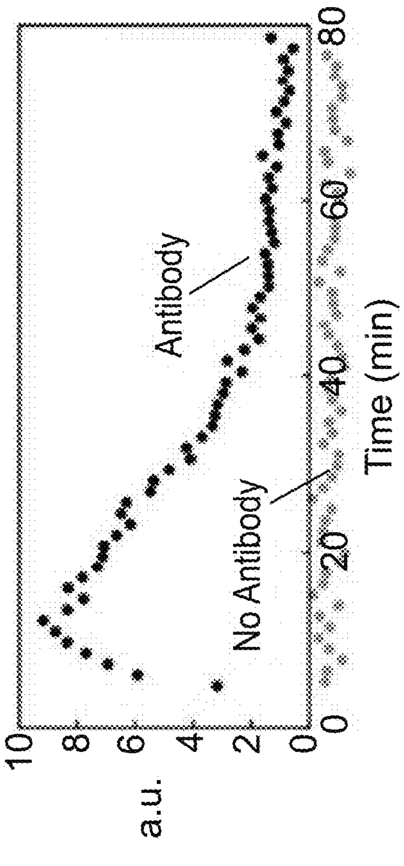
Figure 17D:
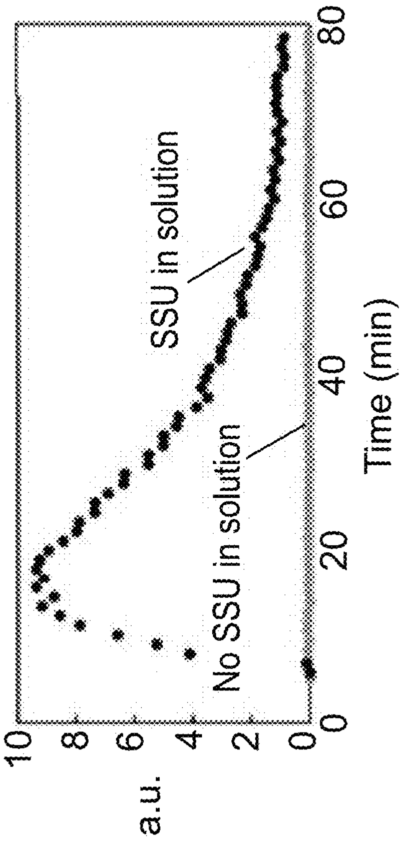

FIGS. 16A-C. rR:S2-HA interaction with 4 cofactors and different domain deletions. (A) Spatial arrangement of the DNA brushes when all the genes involved are present. (B) TIRF images of the configurations at t=350 min. Scale bar: 100 μm. (C) Repeats of the experiment presented FIG. 4C.

FIGS. 17A-D. Activity of surface immobilized ribosomes. (A) Fluorescent image presenting the arrangement of the DNA brushes (red, epifluorescence excitation 647 nm) and surface immobilized ribosomes (green, TIRF excitation 488 nm) for the experiment described in FIGS. 4E, F. Ribosomes modified with a L9-GFP-HA protein were used here when ribosomes modified with a L9-HA protein (no GFP) were used in the experiment described in FIG. 4F. Scale bar: 100 μm. (B, C, D) Fluorescent signals on surface immobilized ribosomes localized next to DNA brushes coding for GFP-SecM (black circles, see FIG. 4D) compared to the following negative controls (gray circles): (B) the ribosomes are not modified with an HA tag (No Ribosome), (C) the antibodies are not added to the chamber (No Antibody) and (D) the reaction was not supplemented with purified SSU (No SSU in solution).

Figure 18A:
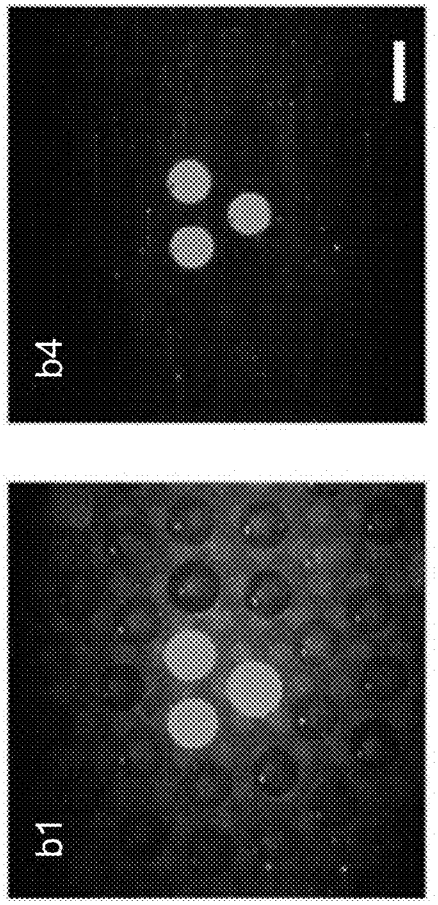
Figure 18B:
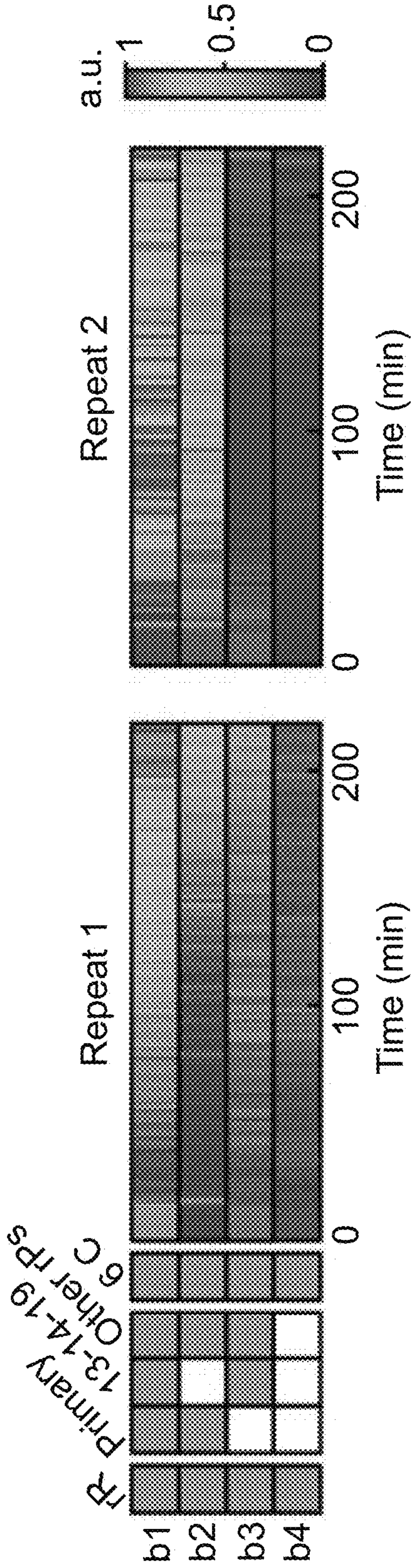

FIGS. 18A-B. interaction with surface immobilized LSU. (A) TIRF images of the configurations b1 and b4 at t=220 min. Scale bar: 100 μm. (B) Repeats of the experiment presented FIG. 4F.

FIGS. 19A-D *S. aureus* SSU biogenesis on a chip. Interactions of *S. aureus* r-RNA with each r-protein-HA in the absence of any other genes (A), in the presence of all r-proteins and 5 assembly factors Era, RsgA, RbfA, RimM, RimP (B), and in the presence of all r-proteins but no assembly factors (C). Signal dynamics for each cluster (top) and $f_{max}$ values (bottom), as defined in FIGS. 1A-F, are arranged according to the *E. coli* assembly map. (D) SSU to timeline without (top) and with (bottom) assembly factors (indicating the onset time of each r-RNA:r-protein-HA interaction. Error bars are standard deviation of three repeats. Time intervals are averages of three repeats.

Figure 19C:
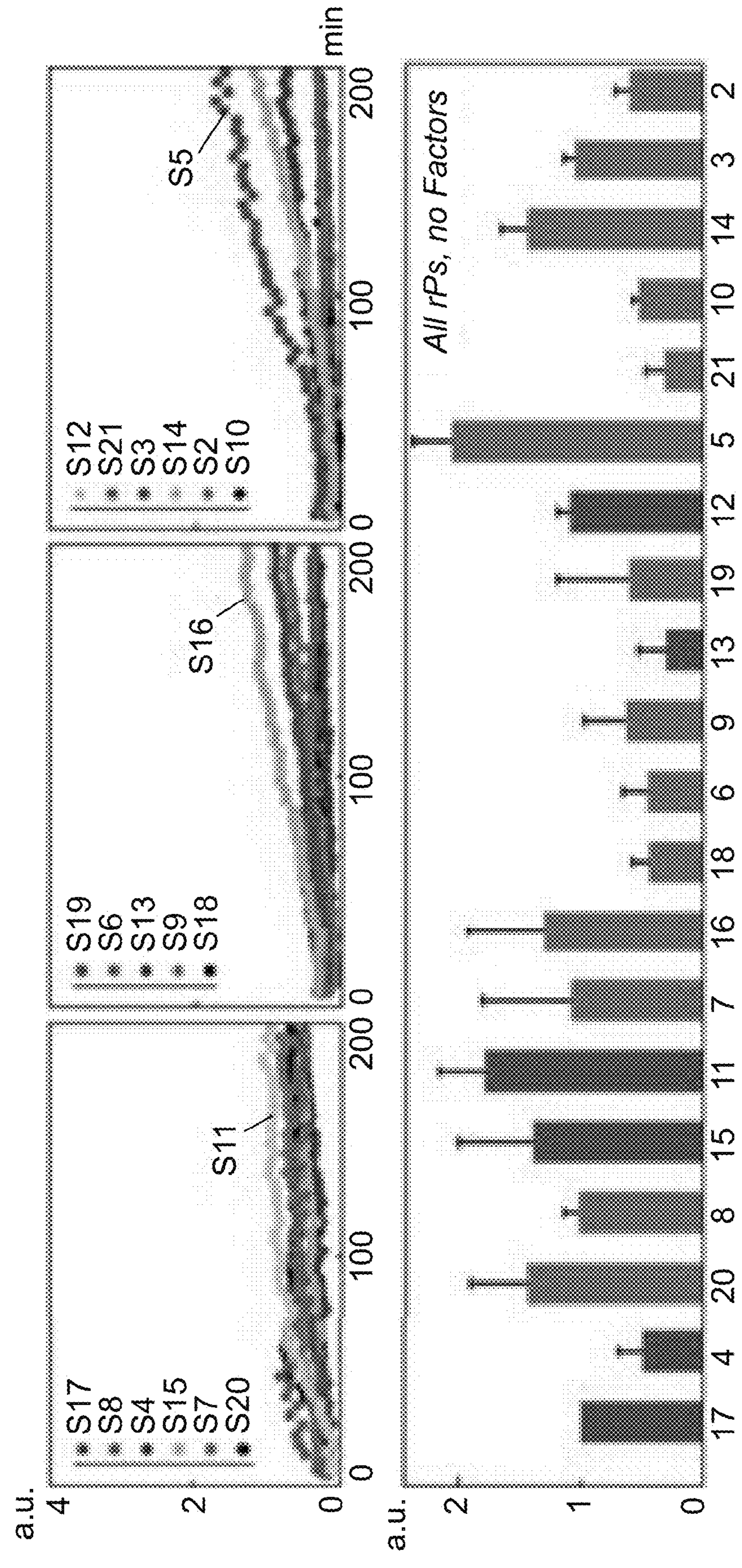
Figure 20:
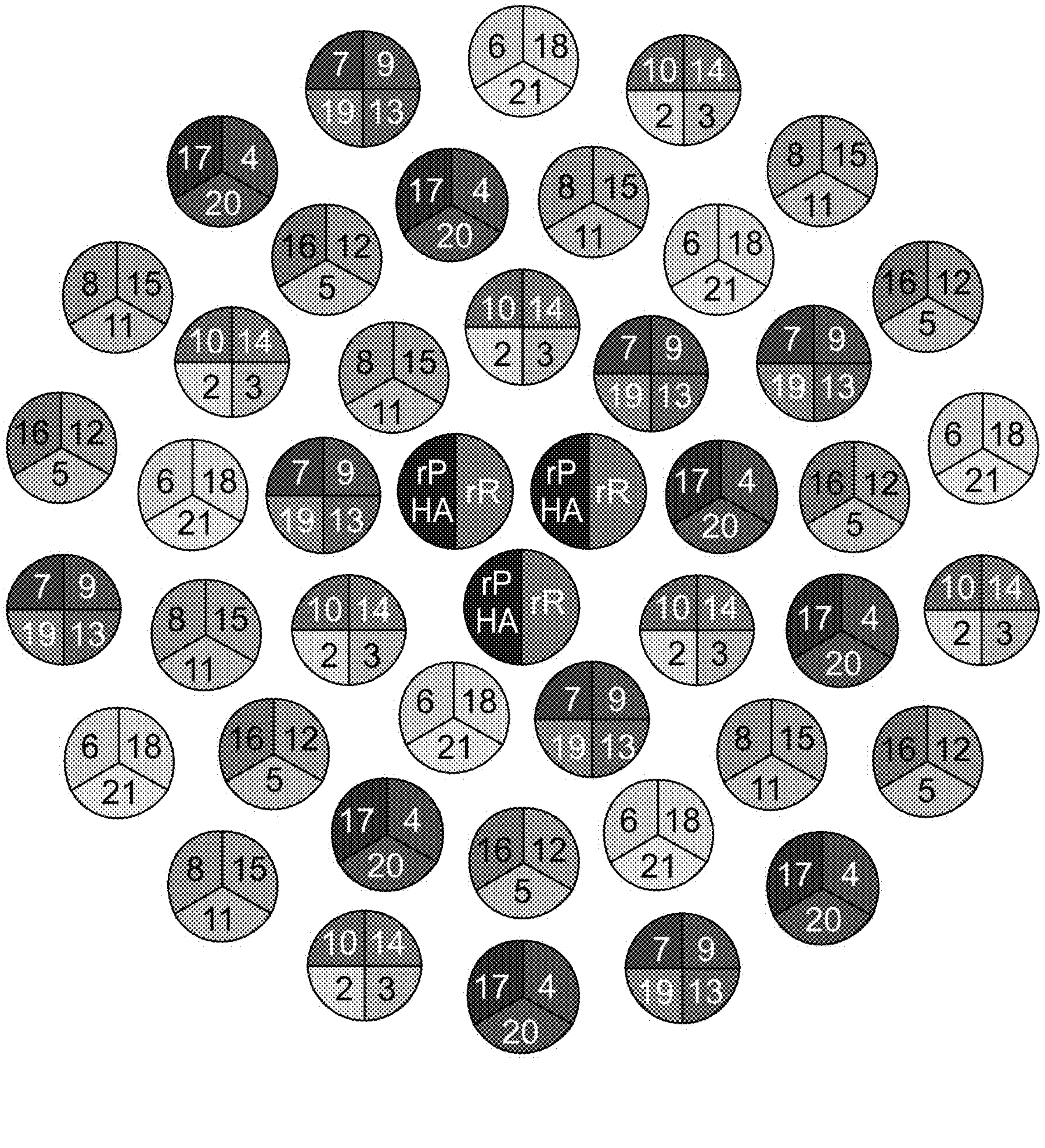

FIG. 20. Spatial organization of the *Staphylococcus Aureus* genes on the chip. Brush layout related to the experiment presented FIG. 19C including all the r-proteins but no assembly factors.

Figure 21:
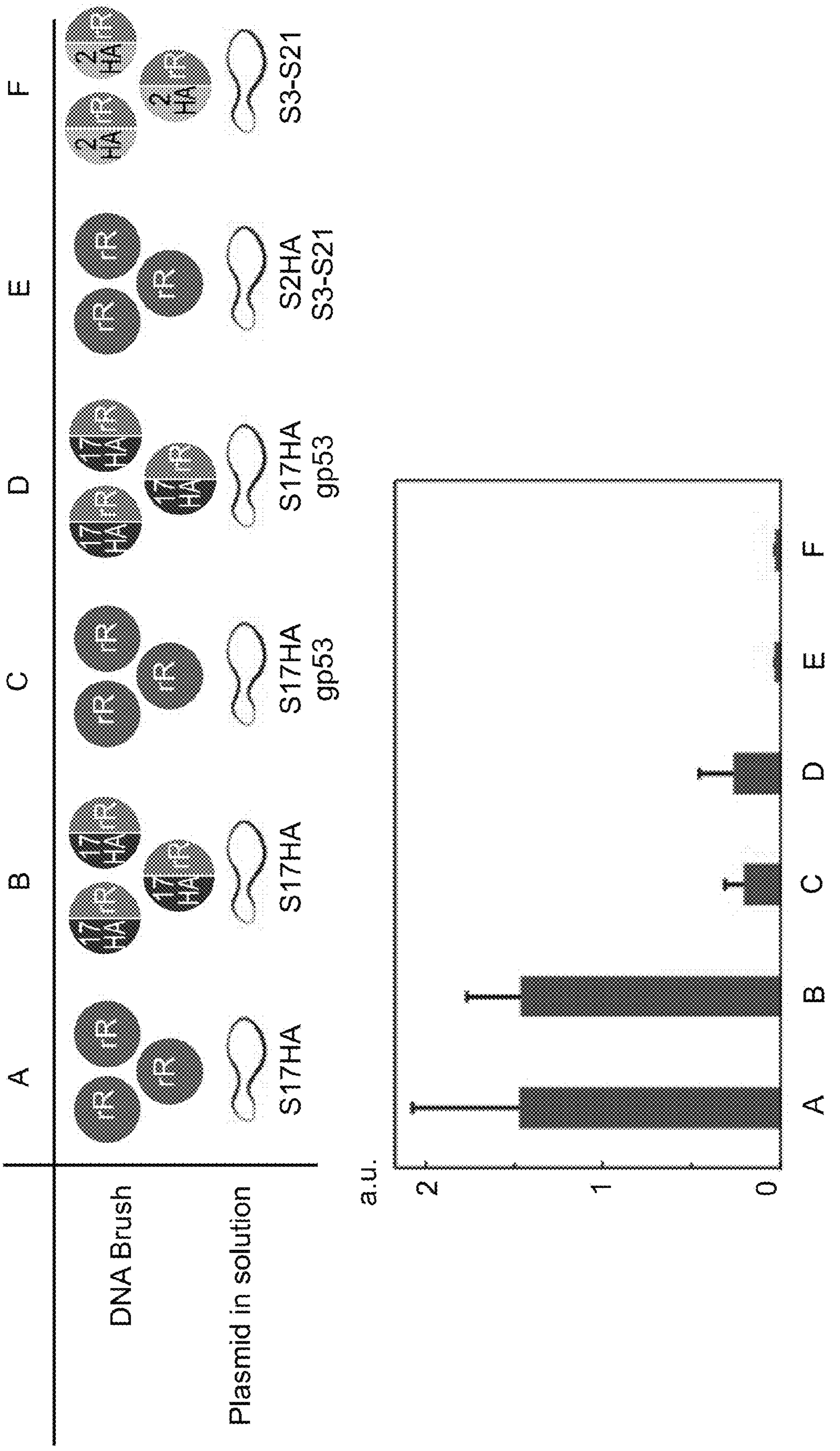
Figure 22A:
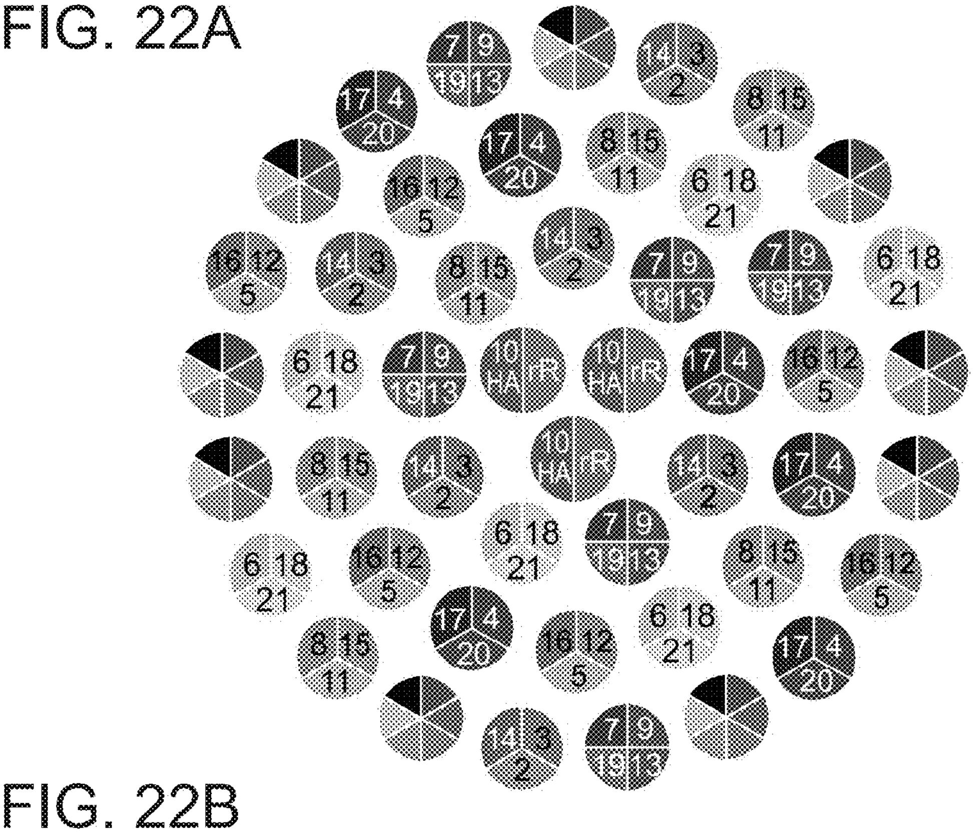
Figure 22B:
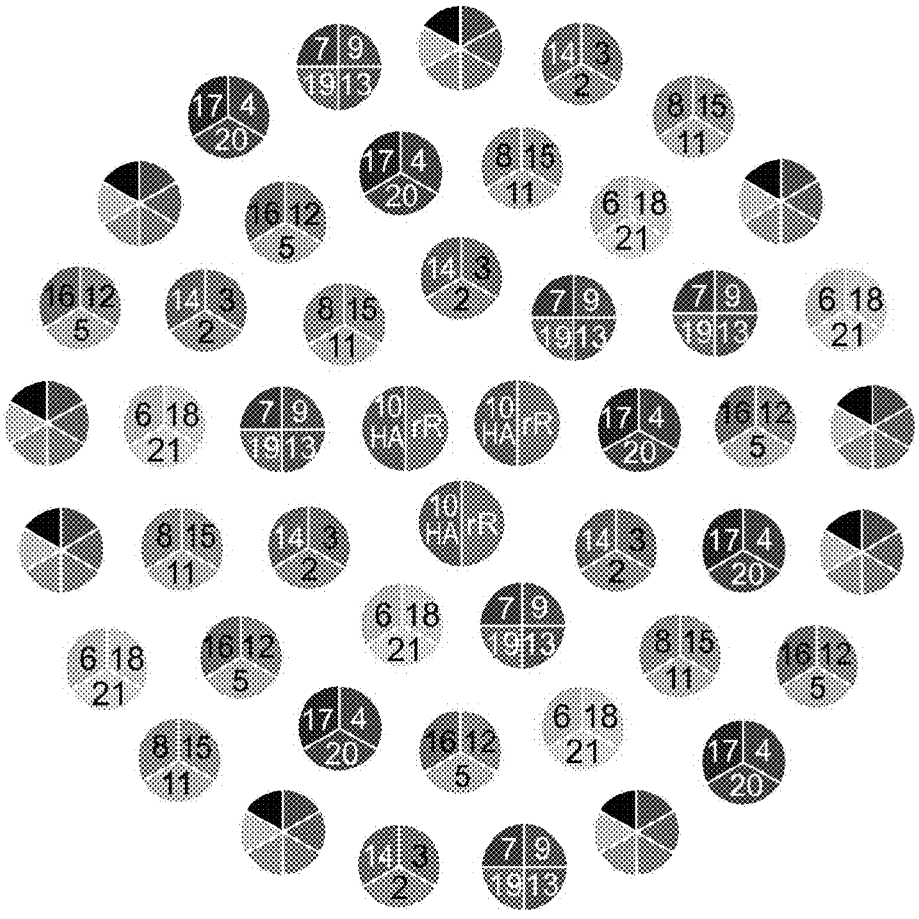
Figure 22C:
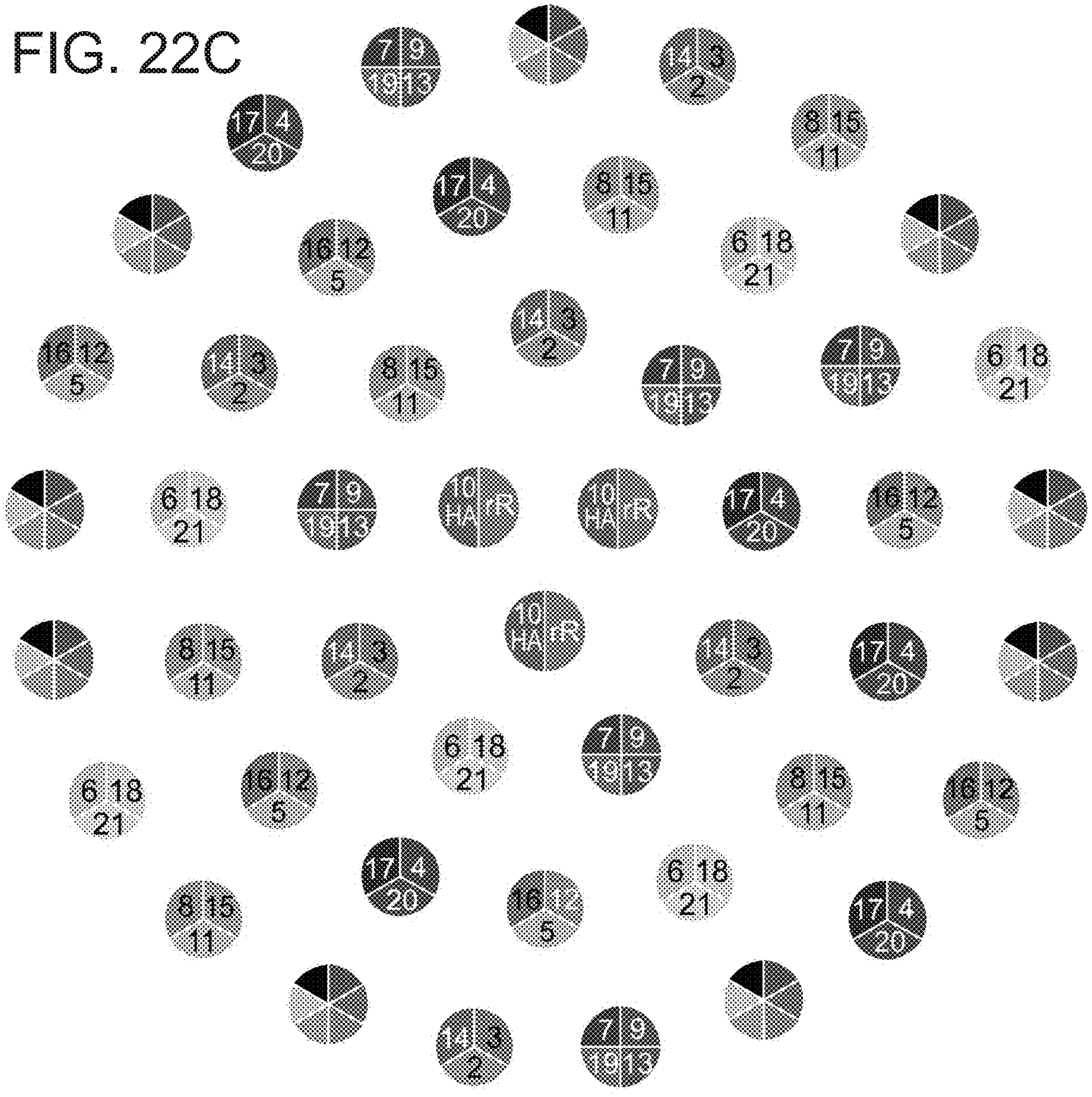
Figure 22D:
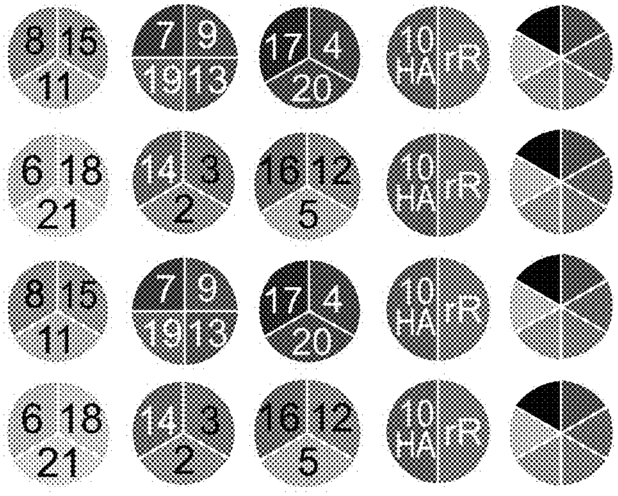
Figure 22E:
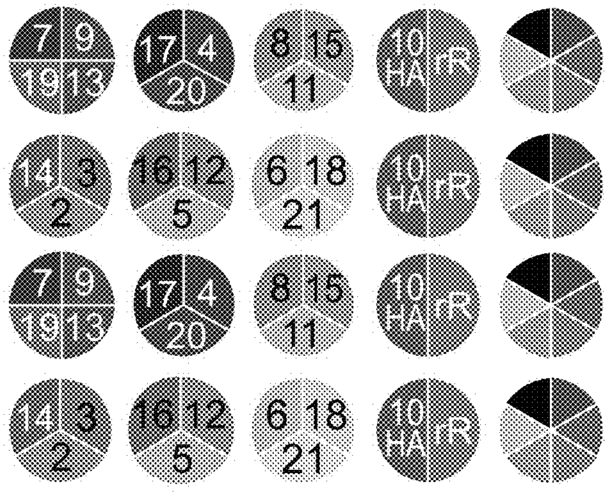
Figure 22F:
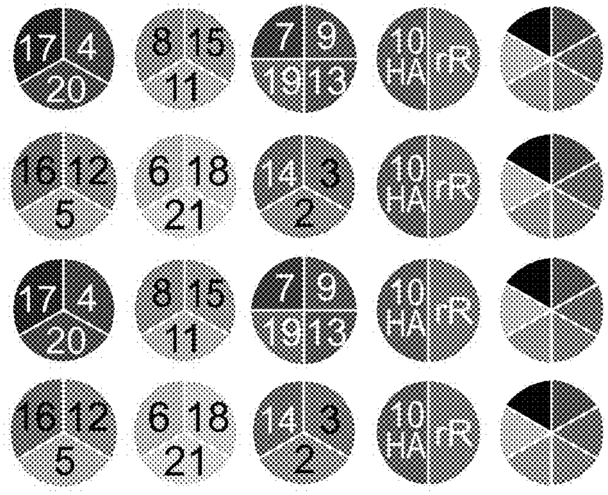
Figure 22H:
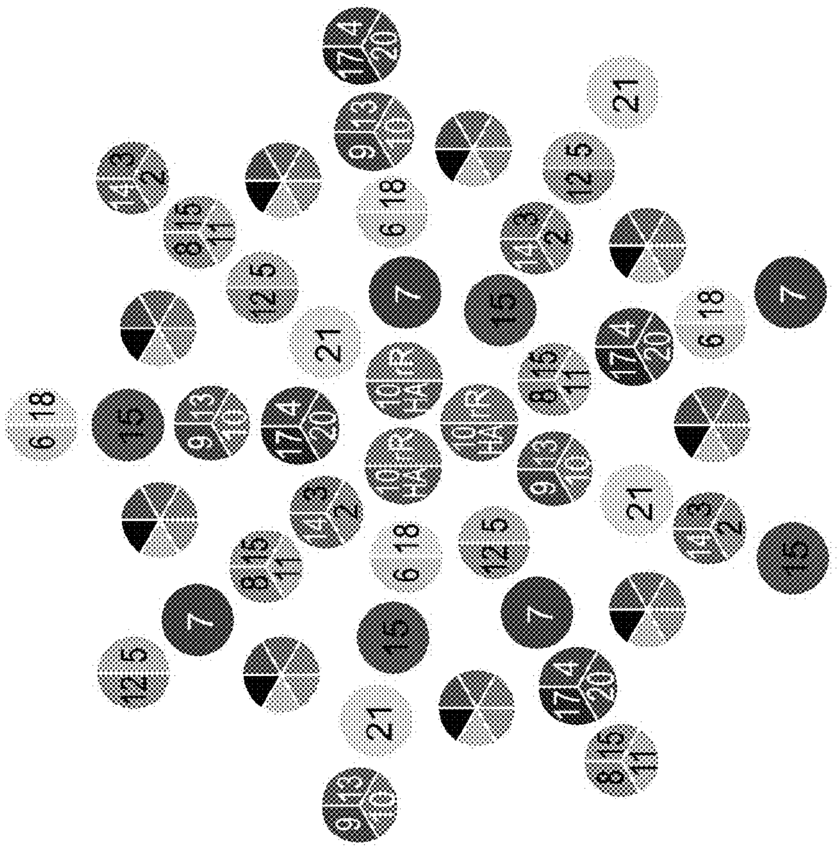
Figure 22G:
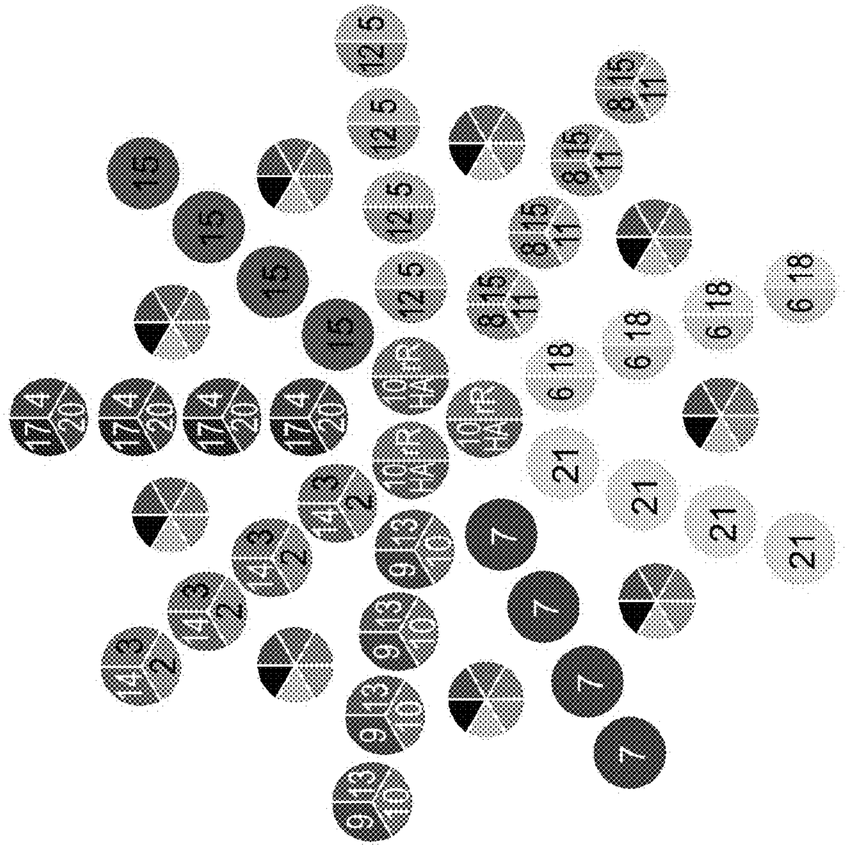
Figure 22J:
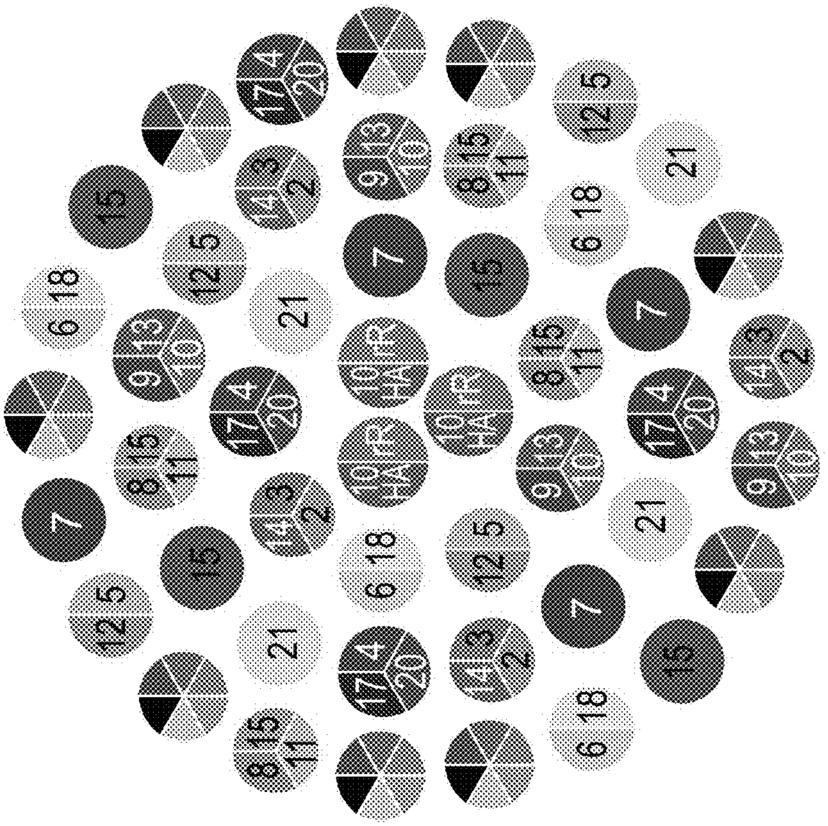
Figure 22I:
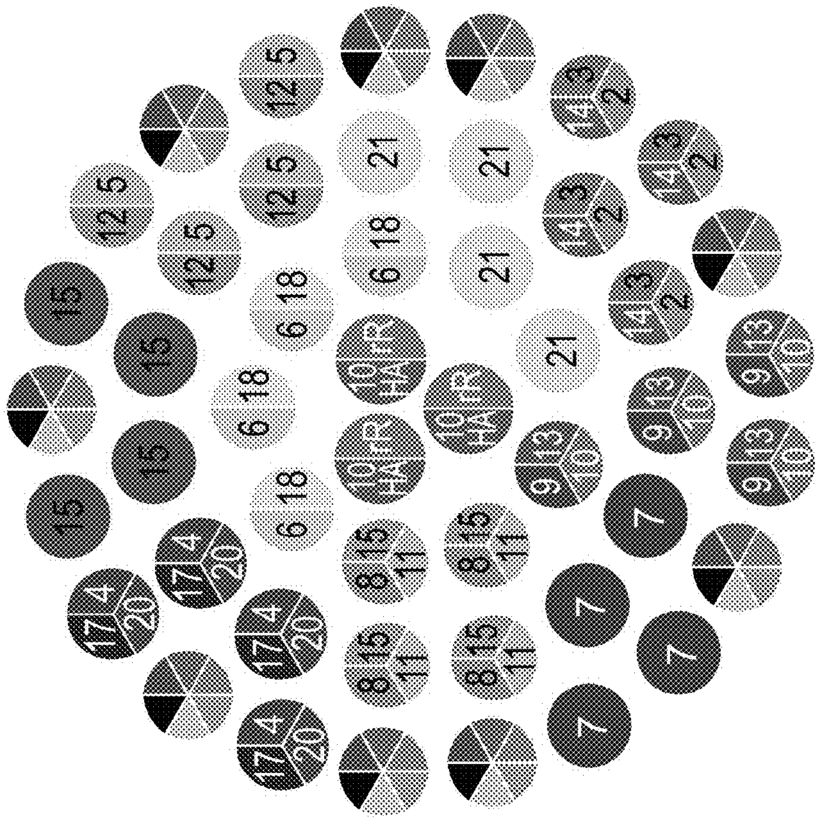
Figure 22K:
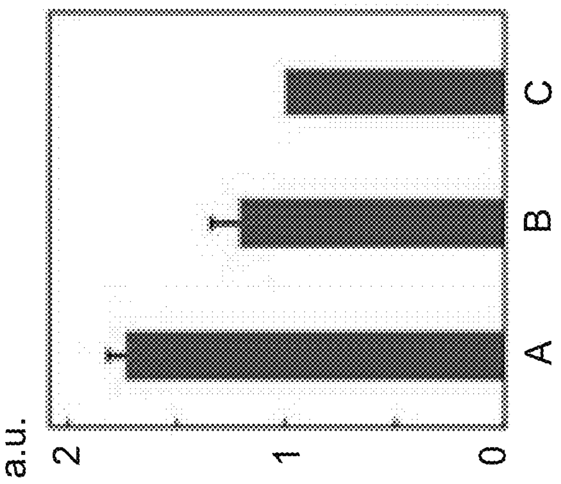
Figure 22L:
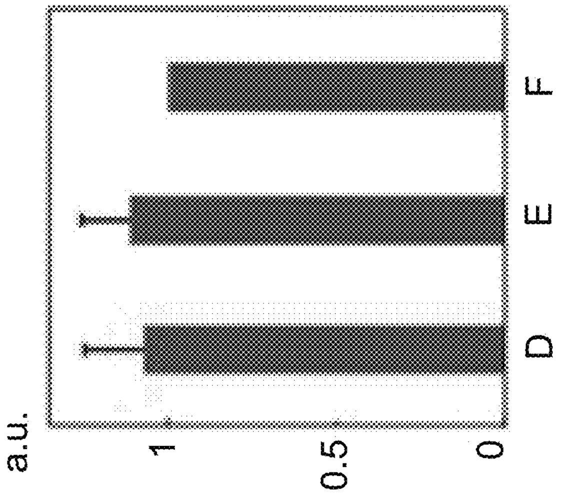
Figure 22M:
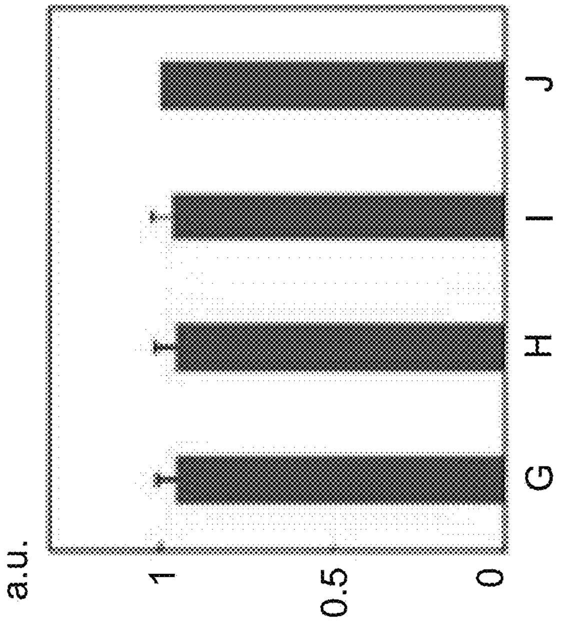

FIG. 21. Expression of r-proteins from plasmids in solution above the surface. Scheme: Each experiment A-F with a different brush cluster: (A, C, E) r-RNA, (B, D) r-RNA: S17-HA, (F) r-RNA:S2-HA; and different plasmids in the solution: (A, B) S17-HA, 2 nM (C, D) S17-HA+bacteriophage T4 gp53, 2 nM and 38 nM, respectively (E) S2-HA+S3-S21, each at 2 nM, total of 40 nM (F) S3-S21, each at 2 nM. Bottom: Histograms $f_{max}$ values of A-F. Error bars are standard deviations of 12 repeats for A, C, E and F (2 chips with 6 repeats each), and 4 repeats for B and D (2 chips with 2 repeats each).

FIGS. 22A-M. Effect of brush spatial organization. Different spatial arrangements of *E. coli* r-protein genes, with S10-HA and r-RNA in all central brushes. Configurations B and C occupy a surface twice and three times larger than A, respectively, thereby changing DNA surface density (Table 3). Configurations D, E and F permute the position of genes from the 5' (red), central (yellow) and 3' (blue) domains relative to the S10-HA:rRNA brushes. Assembly factors (gray-scale) remain on the right of the configurations. In A-F, genes are clustered as in FIGS. 1A-F. In G-J, genes are clustered in the following way: 5' primary, 5' secondary, 5'tertiary, central primary, central secondary, central tertiary, 3'primary, 3'secondary, 3'tertiary, 6 assembly factors, S10-HA:rRNA. The number of brushes was constant but they are reshuffled. In G and I, similar brushes are grouped together while in H and J, brushes are randomly organized. K-M—Histograms are of averaged $f_{max}$ values of each layout. Error bars are standard deviation of three repeats.

FIGS. 23A-F. Cell-free protein synthesis in microscale 2D compartments. A, Images and schemes of DNA brushes (black circles) in silicon compartments, surrounded by on-chip expressed and captured proteins (red circles). Ribosomes and RNA polymerase (grey) bind the DNA, express T4 wedge proteins (brown) that assemble and bind to gp11 on surface antibodies; scale bar 100 μm (left), 1 mm (right). B, Sequential assembly pathway of T4 wedge. C, TEM images and scheme of star assembly (right) from 6 wedges and gp53 (left); scale bar=25 nm. D, scheme of site-directed fluorescent labeling of proteins by CFE and on-chip staining. E, quantitative deletion analysis of on-chip wedge assembly by post-staining with gp53 (red) in 2D compartments scale bar 100 μm. F, Fluorescent detection of GFP and T4 wedges diluted with expressible un-related genes in the DNA brush.

FIGS. 24A-D. Parallel detection of on-chip T4 wedge assembly intermediates. A, Post-staining scheme of on-chip wedges in reverse order to the assembly pathway. B, (top) Five of 64 compartments post-stained and imaged with 3-channels, shown separately, of gene-6 titration. Top left compartment had no gene-10 as control. (bottom) Collage of 3-channel superpositions of all 64 compartments. Scale bar=100 μm. C, Calculated yield of wedge formation from pre-wedges by post-staining with gp6. D, Dose response curves of wedge yield for wedge gene fractions, calculated from data in FIG. 24B, and FIGS. 33A-D, 34A-D, 35A-D and 36A-D.

FIGS. 25A-E. Dynamic protein gradients from programmable 1D geometries of gene brushes. A, an array of wells carved in silicon, each programmed with a different geometric DNA brush layout. Enlarged image, spotting of two DNA brushes along the short 200 μm axis, forms a semi-uniform gene source; scale bar 1 mm. B, scheme of GFP profiles (green) along the long axis of compartments from two DNA brushes (red). C, diffusion and capture of HA-GFP monitored on a patterned surface, from DNA brushes at X=200 μm. Full dynamics in Extended data Movie 1; scale bar 100 μm. D, profiles of bound and freely-diffusing HA-eGFP. E, profiles of bound gp10 to gp11-HA from DNA brushes of 5, 10 and 100% gene-10 diluted with non-coding DNA. The position of DNA brushes is indicated by an arrow.

FIGS. 26A-D. T4 Wedge Assemblograms. A, geometrically programmed DNA brushes of 2, 3, and 4 wedge genes (white circles), arranged by the order of assembly. B. The chip was post stained in reverse order by gp53, gp6, gp8. Shown only channels of the last assembly step for each gene configuration; scale bar=100 μm. C, calculated yield of pre-wedge and wedge assembly as a function of brush distance. Yield was calculated based on staining with gp8 and gp6, respectively. D, nine geometric gene programs (i-ix) produce 27 wedge assemblogrames, each in three channels. Each plot is an average of three repeats on the same biochip.

Figure 27A:
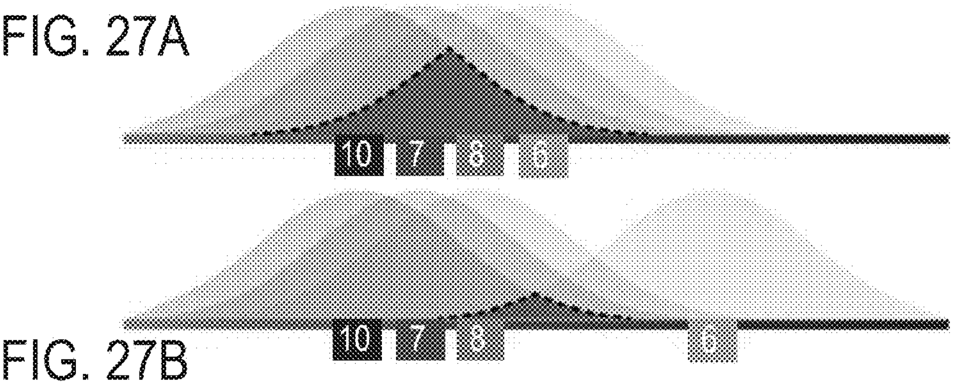
Figure 27B:
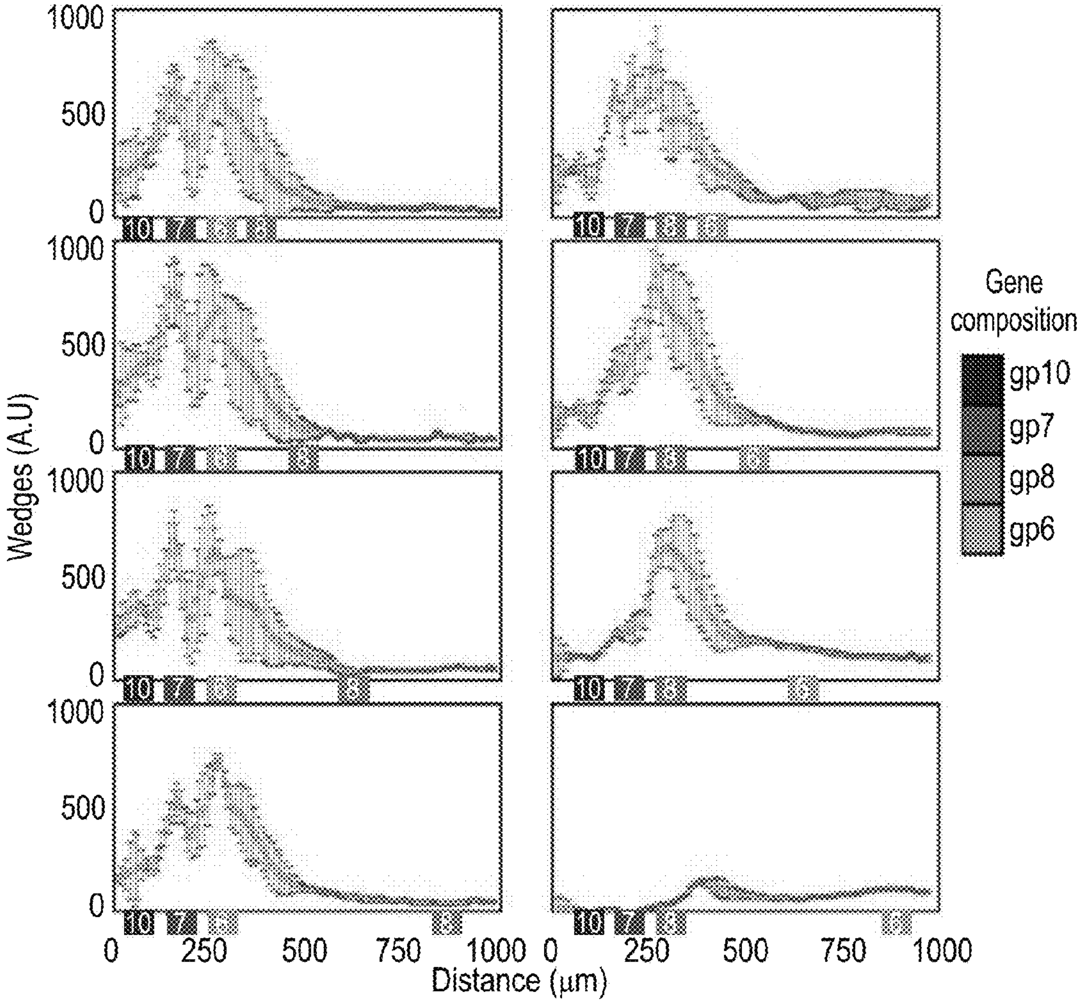
Figure 27C:
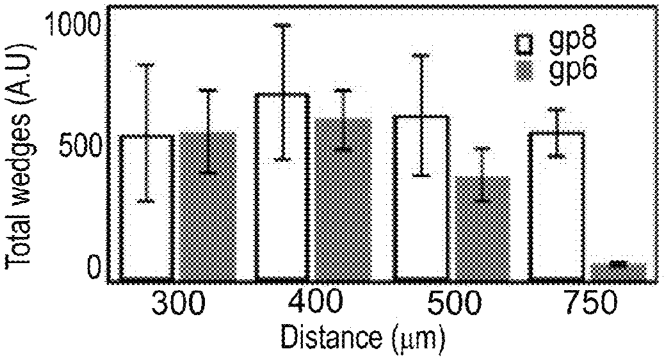

FIGS. 27A-C. Assemblograms as rulers for protein affinity. A, scheme, cross section of protein concentration profiles (red) from localized sources during CFE depend on 1D gene geometry (brown rectangles with gene numbers). B, assemblograms of wedges produced by systematic resolution of gene-8 (left) or gene-6 (right) from the rest of wedge genes, stained with gp53. C, total wedges integrated across the entire compartments in B. Distance is from the gene-8 or 6 brushes to the gene-10 brush.

FIGS. 28A-F. Kinetic competition between solution assembly and scaffolding. A, scheme of two competing assembly pathways in the non-sequential gp11-10-7 assembly. B-C, gp10 pre-bound to gp11 on surface antibodies competes on binding to gp7 with gp10 produced in the brush. Reduction in yield of gp10-7 measured by post-staining with gp8. D-E, assemblograms of gp10-7 in 1D compartments revealed by post-staining with gp8 with increasing distance between gene-10 and gene-7 brushes (green and red rectangles, respectively). Monte-Carlo simulation (Methods) fitted to 2 hours of CFE reveals profiles of complexes formed by solution assembly (grey) or scaffolding mechanism (black). Relative solution assembly of the total gp10-7 (red curve) is noted for each graph. F, Monte-Carlo dynamic simulation of assembly yield at two gene ratios (1:1 and 1:3) in a mixed brush or separated by 500 μm.

Figure 29:
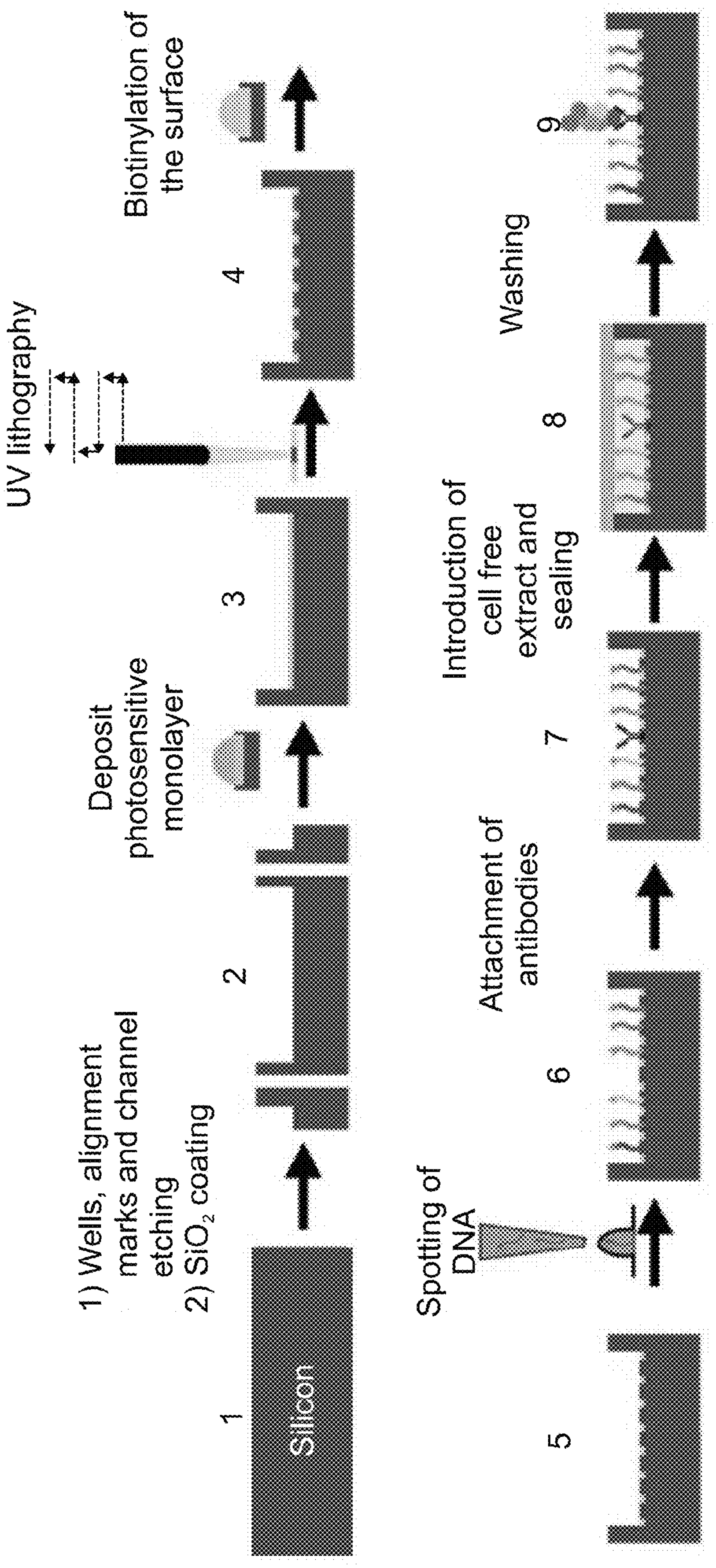

FIG. 29. Experimental outline scheme. A side view of part of a silicon wafer (step 1) that is etched to produce 2 μm deep compartments with 50 μm deep channels on each side (step 2) The surface is covered with $SiO_2$ and with a photosensitive monolayer (yellow, step 3). A desired pattern is written in each compartment using laser UV lithography (red marks, step 4). After biotinylation of the lithographed patterns (blue marks, step 5), fluorescently labeled DNA is applied on the surface as discrete spots, each spot may have a different gene pool (depicted as different colors, step 6). Biotinylated antibodies are then applied and cover the entire surface surrounding the DNA brushes (step 7). Cell-free extract is introduced (step 8). After 1-2 hours of incubation, the chip is washed and assembly on the antibodies is monitored (colored circles on antibodies, step 9).

FIGS. 30A-E. On-chip spotting of DNA-streptavidin conjugates. A solution of fluorescently labeled DNA-streptavidin conjugates (A) is deposited on the surface of a coated chip using a micro capillary connected to piezoelectric element (B) spotting 10-20 pL drops with a diameter of ~60 μm (C). The DNA attaches to patterned biotins (yellow surface) and not to protected regions (green surface) (D). Array of droplets before and after washing, allows immobilization of two different genes (red and green spots) in close proximity with no mixing (E).

Figure 31A:
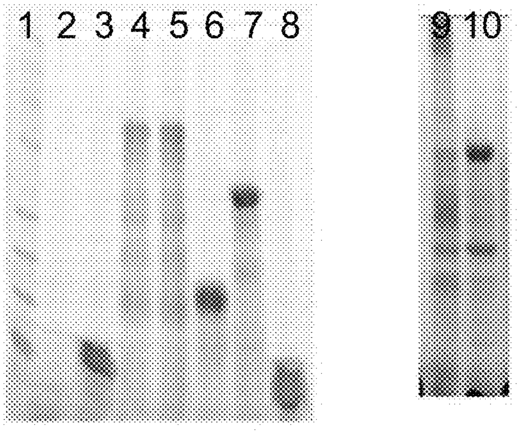
Figure 31B:
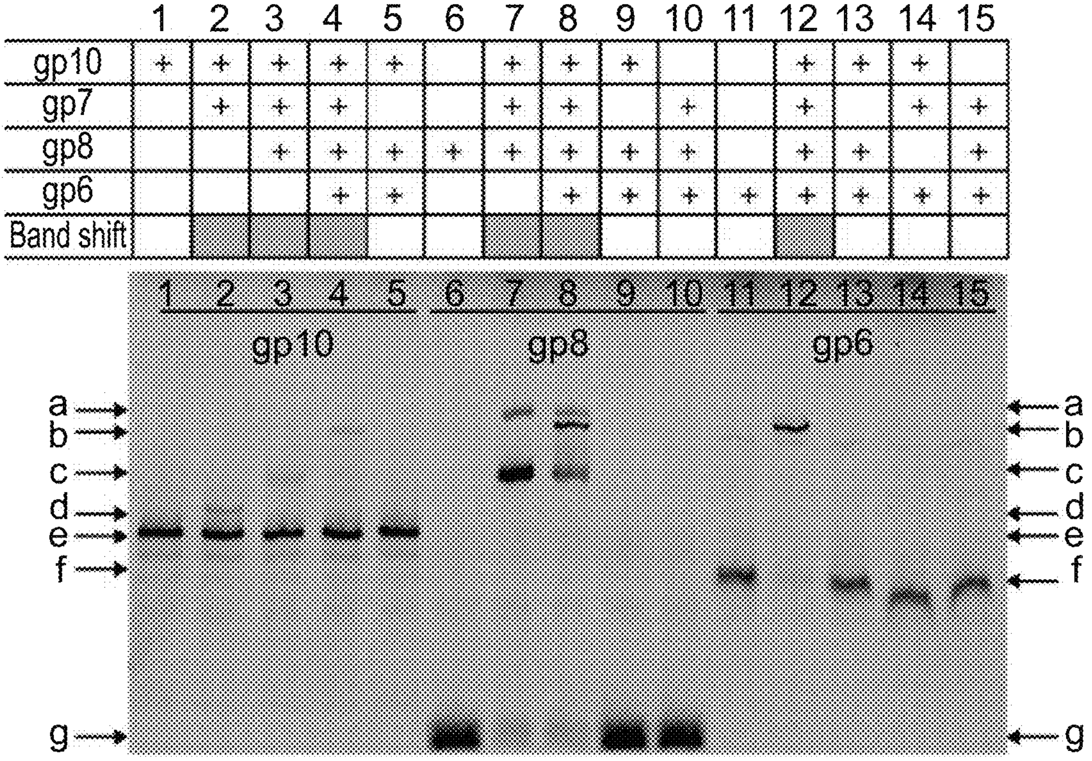

FIGS. 31A-B. In situ labeling and wedge assembly in off-chip cell-free expression reactions. (A) In situ labeled wedge proteins were resolved by 4-20% gradient denaturing PAGE, size markers (1), no gene (2), gp 11 (3), gp 7 (4,5), gp 8, (6), gp6 (7), gp53 (8), gp10 (9), gp10 with reducing agents and boiling (10). (B) deletion analysis of wedge assembly. Each wedge protein was expressed separately, followed by mixing, incubation and loading the mix on a step gradient native PAGE (methods). Gene content in each mix is indicated above each lane. Arrows mark the position of assembly intermediates deduced from gene deletion, a, c—two forms of gp10-7-8 (pre-wedge); b—gp10-7-8-6 (wedges), d-gp10-7; e-gp10; f-gp6; g-gp8.

Figure 32A:
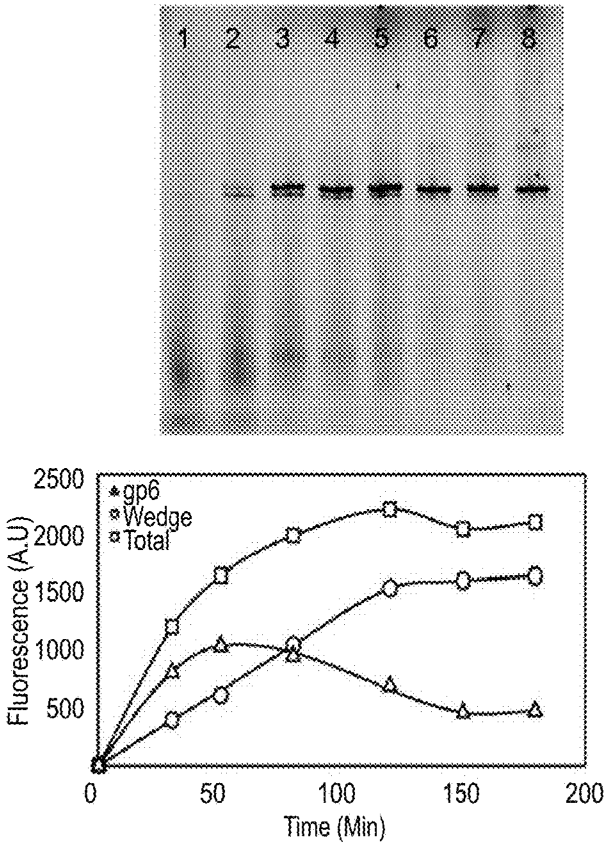
Figure 32B:
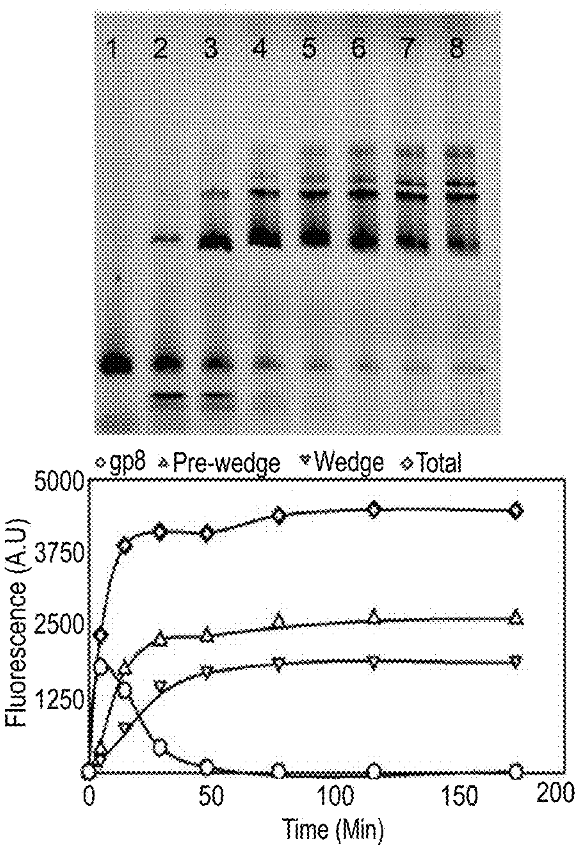

FIGS. 32A-B. Kinetics of off-chip wedge formation. Co-expression of wedge proteins with either in situ labeled gp6 (A) or gp8 (B). Aliquots were removed from the cell-free reactions and resolved by step-gradient native PAGE. The amount of wedges, intermediated and total assembly is shown below each gel. Pre-wedges could not be detected when in situ-labeled gp6 is used.

FIGS. 33A-D. On-chip wedge assembly as a function of gene-10 brush fraction. All other genes were kept at a constant ratio (gp7=10%, gp8=10%, gp6=10%). (A) amount of wedges revealed by post-staining with labeled gp53 (B) amount of occupied gp11-HA, revealed by post-staining with labeled gp10 (Methods) (C) amount of pre-wedges revealed by post-staining with labeled gp6 (D) pre-wedge signal (post-staining with gp6) normalized by the occupied gp11-HA sites (Methods). Error bars are standard deviation of 4 compartments.

FIGS. 34A-D. On-chip wedge assembly as a function of gene-7 brush fraction. All other genes were kept at a constant ratio (gp10=5%, gp8=10%, gp6=10%). Analysis as in FIGS. 33A-D.

FIGS. 35A-D. On-chip wedge assembly as a function of gene-8 brush fraction. All other genes were kept at a constant ratio (gp10=5%, gp7=10%, gp6=10%). Analysis as in FIGS. 33A-D.

FIGS. 36A-D. On-chip wedge assembly as a function of gene-6 brush fraction. All other genes were kept at a constant ratio (gp10=5%, gp7=10%, gp8=10%). Analysis as in FIGS. 33A-D.

Figure 37:
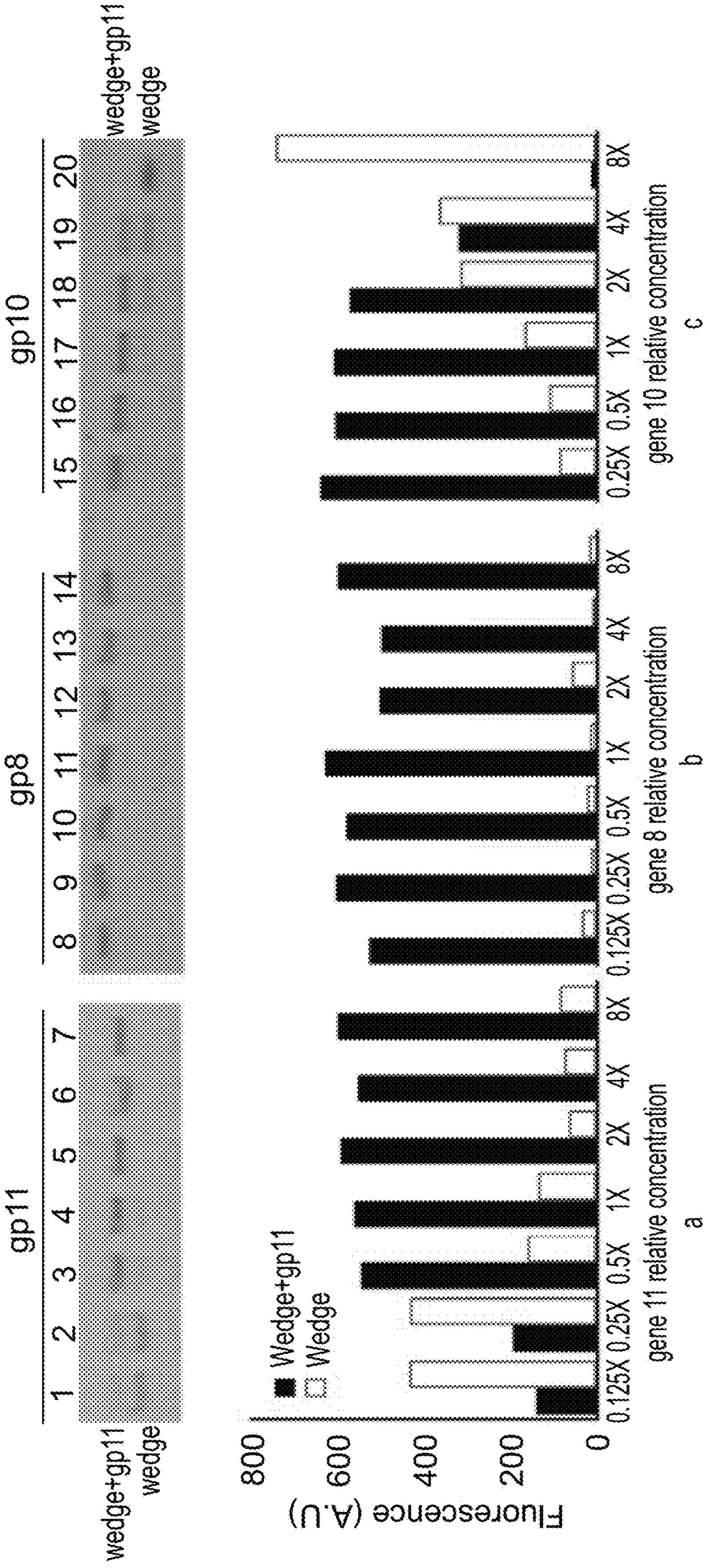

FIG. 37. Protein stoichiometry regulates non-sequential assembly. The formation of bacteriophage T4 wedges in complex with gp11 was monitored using labeled gp6 on native PAGE. The fluorescence of the bands corresponding to the wedge and wedge+gp11 complexes was quantified.

The relative concentration of either gp11 (a), gp10 (b) or gp8 (c) was titrated compared to the rest of the proteins.

Figure 38A:
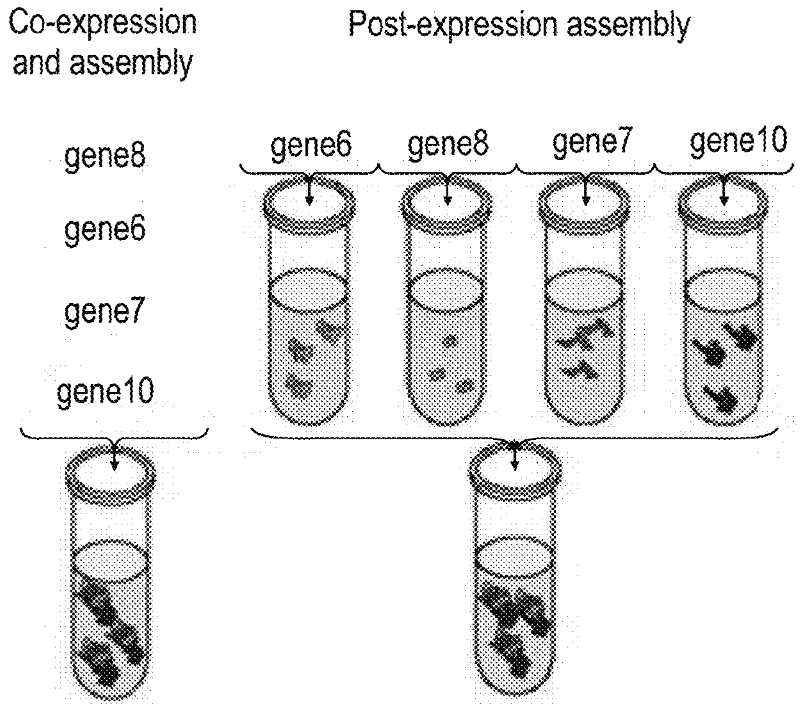
Figure 38B:
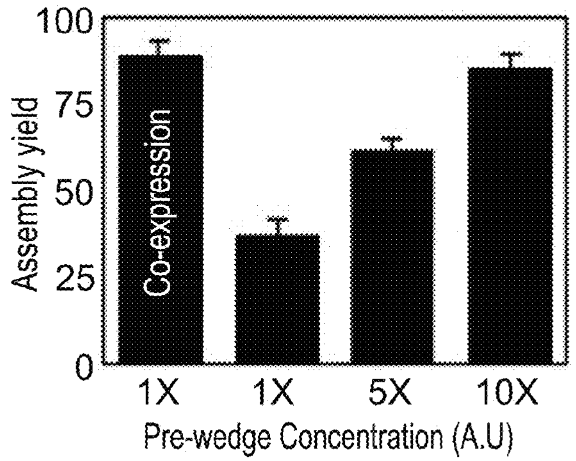
Figure 38C:
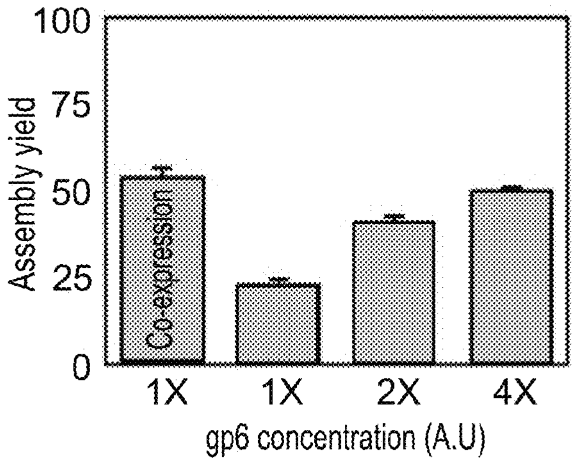

FIGS. 38A-C. Off-chip coupled expression and assembly increases assembly yield. (A) scheme of co-expression and assembly of all wedge genes in one cell-free reactions compared to separate expression of wedge genes and mixing of cell-free reactions. (B) Wedge assembly yield was analyzed by native PAGE with in situ labeled gp6 either during co-expression or with different amounts of pre-expressed gp10, gp7 and gp8 added to gp6. (C) same as in (B) with in situ labeled gp8. Error bar represent measurement error.

Figure 39:
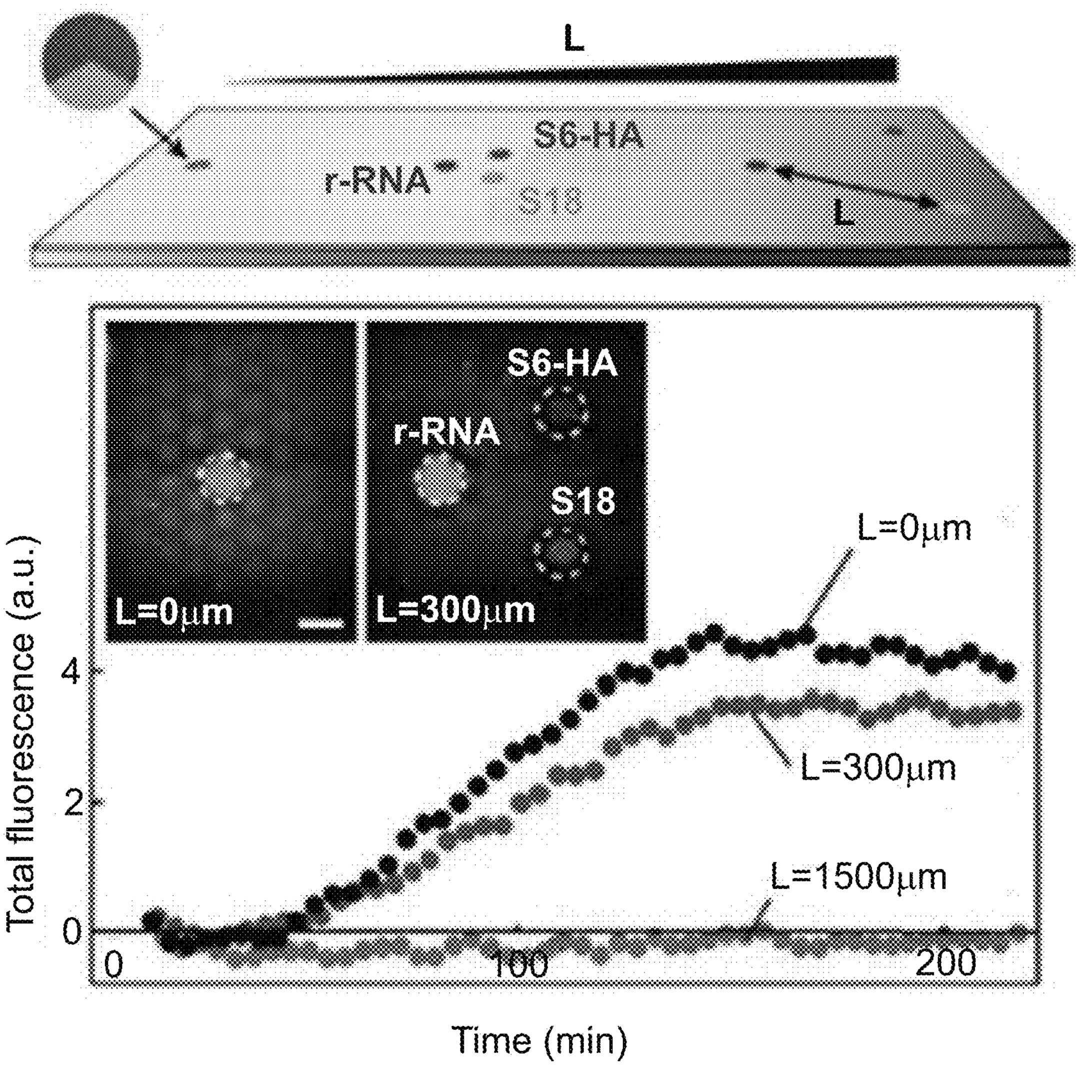

FIG. 39. Efficiency of a three-body interaction dependent on DNA brush distance. Top: scheme of three brushes coding for r-RNA, S6-HA and S18 are separated by length L, with L from 0 (mixed brush) to 1500 μm. Bottom: total r-RNA fluorescent signal as a function of time for the different values of L and the corresponding fluorescent images for L=0 μm and L=300 μm. Scale Bar: 100 μm.

Figure 40A:
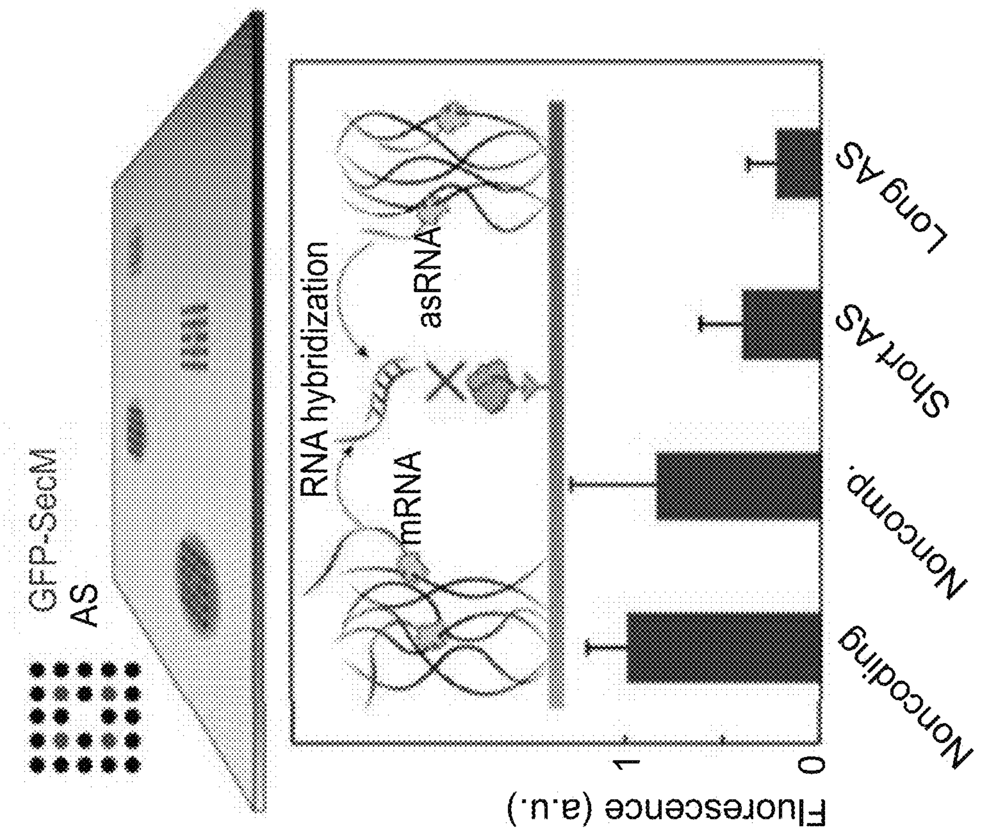
Figure 40B:
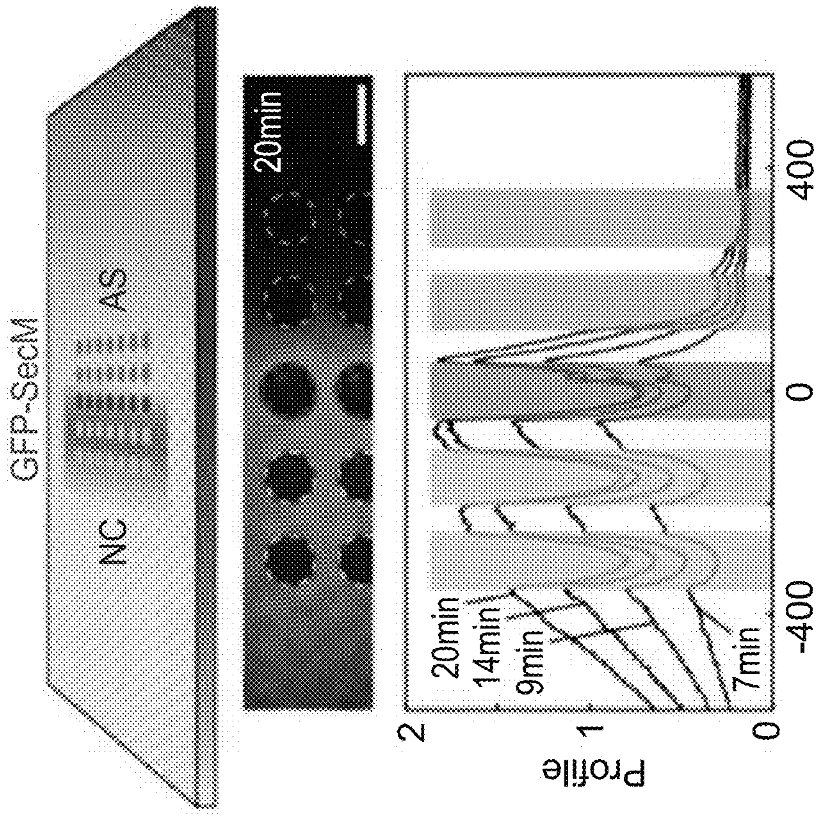

FIGS. 40A-B. Genetically encoded anti-sense RNA (as-RNA). (A) Top scheme of GFP-SecM brushes surrounded by asRNA brushes (AS) or controls on a surface covered with patterned ribosomes. Bottom; Fluorescent signal at t=13 min. Error bars are standard deviation of 4-7 repeats. Scheme: asRNA hybridizes with GFP-SecM mRNA and inhibits its translation on surface bound ribosomes. (B) Top: Scheme of a line of GFP-SecM brushes surrounded by asRNA brushes on one side and noncoding brushes on the other side. Middle: fluorescent image showing asymmetric expression. Bottom: profiles of the signal. Scale Bar: 100 μm.

Figure 41A:
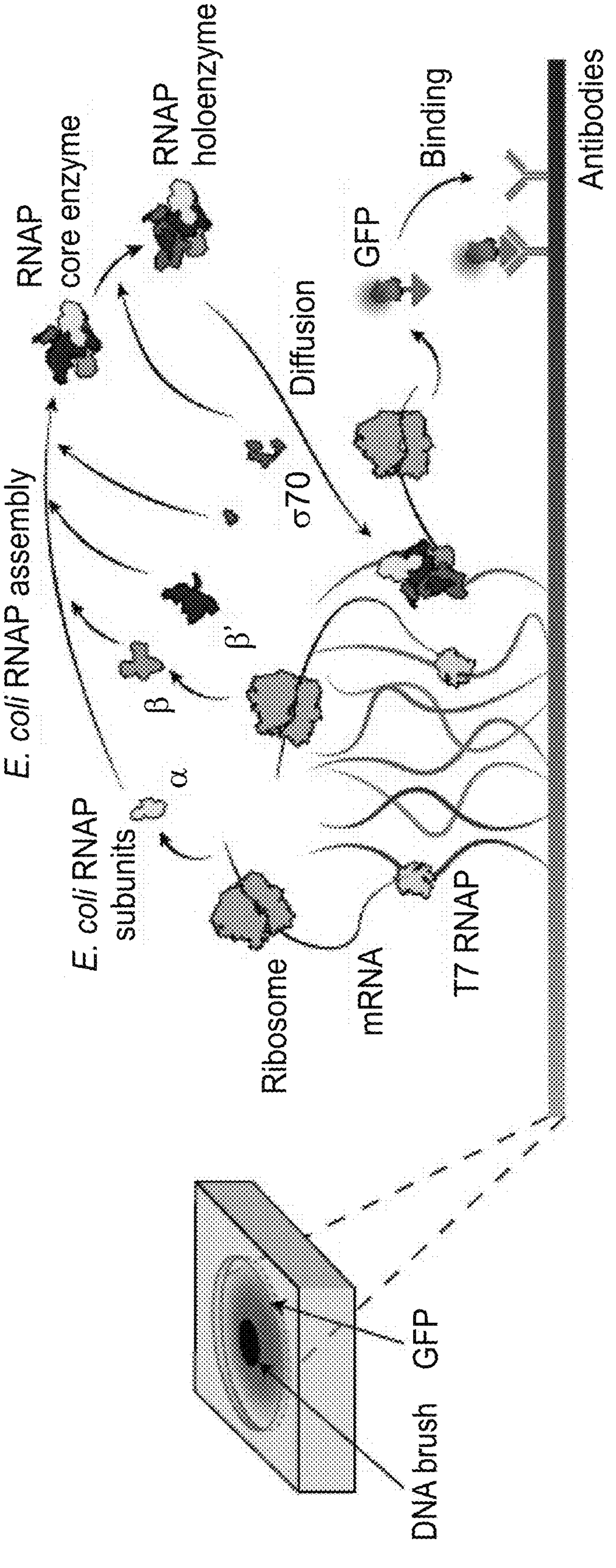
Figure 41B:
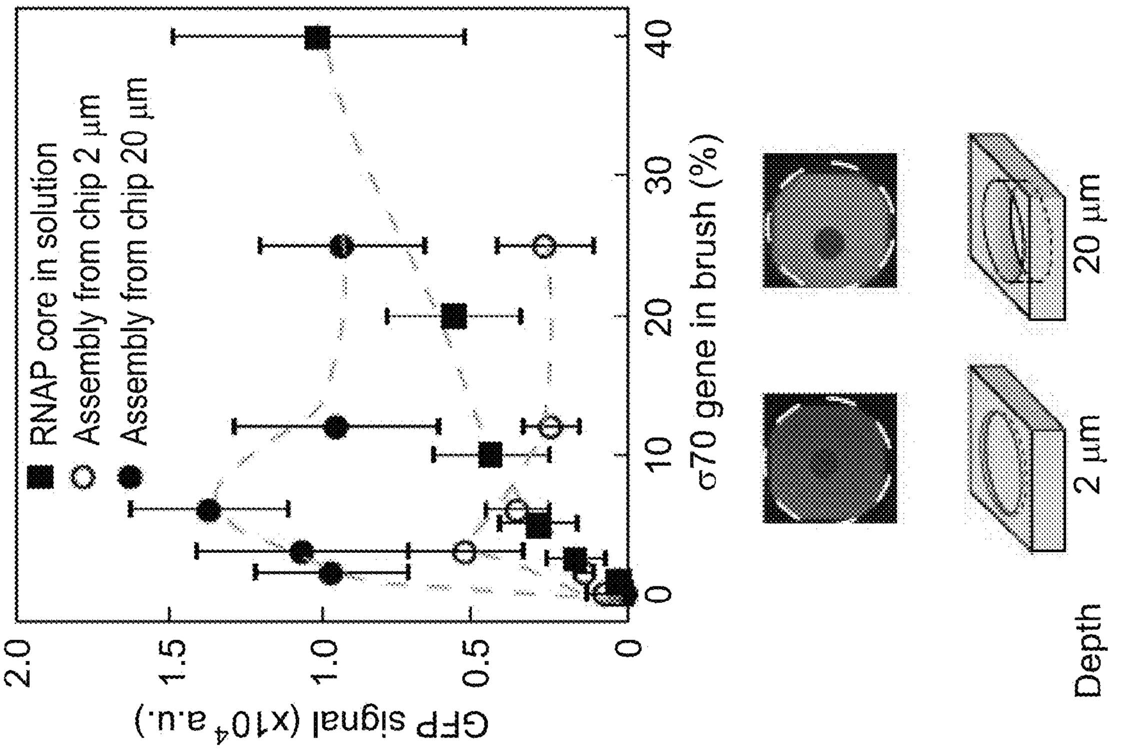
Figure 41C:
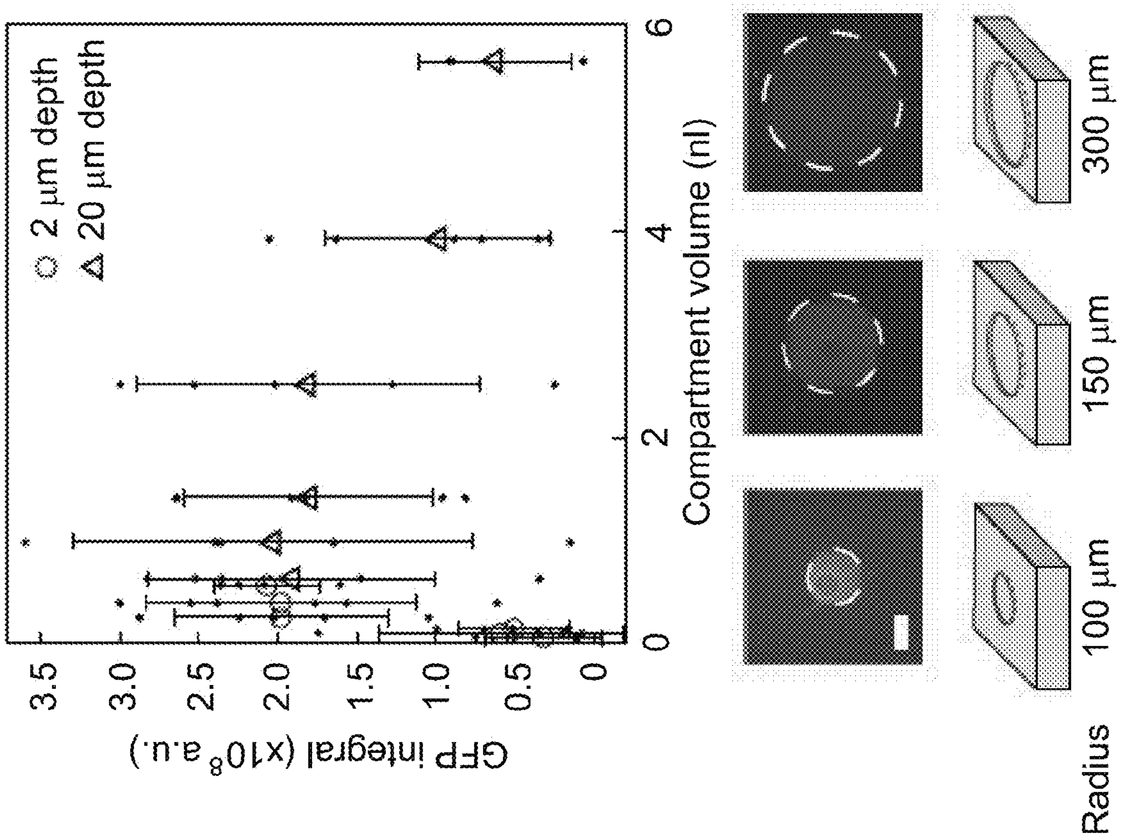

FIGS. 41A-C. Gene composition and compartment geometry impact *E. coli* RNAP assembly. A, Scheme, synthesis of *E. coli* RNAP core enzyme and σ70 subunits from a mixed brush, result in. *E. coli* RNAP genes are under T7 promoter, GFP is under *E. coli* P70 promoter. Color and object scheme as in FIG. 1A. B, GFP signal as a function of σ70 gene fraction in the DNA brush, in 2 μm (hollow circles) and 20 μm (full circles) deep circular compartments. All core genes were present. Purified core enzyme was added to 2 μm compartments with only σ70 gene brushes (squares). Lines are a guide to the eye. Representative images are of compartments with RNAP core genes and σ70 gene at the peak of each graph. C, Integral of HA-GFP signal over entire compartment surface, at variable compartment radii (100 μm-300 μm) and depth (2 μm and 20 μm). DNA brushes contained an identical mix of RNAP and P70-GFP genes. Images are of 2 μm deep compartments with the indicated radii. Data are presented as mean, error bars represent ±s.d. All images are in the same scale. Scale bar 100 μm.

FIGS. 42A-E. Local regulation of gene expression by resource partitioning. A-C. Total GFP signal (a) in compartments with brush layouts [mixed (i), separate (ii), spread-out (iii)], and color coding of genes as defined in the scheme (c, right). Localized GFP signal (b) in 2 and 20 μm deep compartments with brush layout (iii). Bar graph displays the percentage of the GFP signal in each slice out of the total GFP signal in the compartment. Depth and layout for each representative image are marked below and above. Image of the 2 μm compartment presented with an enhanced contrast to demonstrate localization. D, E, GFP signal, integrated around each of five identical brushes (1-5 in the respective representative images in E) and normalized to the signal around brush 1. Brush layout and gene content as in the scheme (right). The position of an additional brush (white circle) containing passive or active DNA is marked (Methods). Data are presented as mean and error bars represent ±s.d. Scale bar 100 μm.

DESCRIPTION OF SPECIFIC EMBODIMENTS OF THE INVENTION

The present invention, in some embodiments thereof, relates to cell-free synthesis, assembly and immobilization of protein complexes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Biological assembly in the cell is governed by gene-expression and is precise, rapid, and robust, representing a diverse spectrum of functional nanostructures. Current approaches for fabrication of nanomachines could benefit from genetically programmable assembly, but techniques and design principles are lacking.

The present inventors used geometric programming of DNA brushes as foci for synthesis and capture of proteins and nucleic acids on a solid surface. Specifically, the present inventors studied gene clusters encoding the wedge of T4 bacteriophage—a part of its cell-puncturing machine, and two bacterial ribosomal subunits (the *E. Coli* ribosomal subunit and the *S. aureus* ribosomal subunit). The present inventors showed that they could capture and identify intermediates and full protein complexes, which self-organize as surface-bound assemblograms.

Thus, according to a first aspect of the present invention there is provided a method of assembling and immobilizing a proteinaceous complex comprising:

(a) providing a chamber having at least one surface, wherein a plurality of nucleic acids encoding at least two components of the proteinaceous complex are immobilized onto said at least one surface and wherein a binding agent which binds specifically to one component of the proteinaceous complex is immobilized onto said at least one surface; and (b) contacting said at least one surface of said chamber with agents for performing expression of the components from said plurality of nucleic acids, under conditions that allow expression and immobilization of the proteinaceous complex to said at least one surface, thereby assembling and immobilizing the proteinaceous complex.

The term "assembling" refers to the ability to generate a proteinaceous complex from its constituent subunits.

As used herein, the phrase "proteinaceous complex" refers to a collection of proteins which are bound together (either directly, or non-directly). In one embodiment, the proteins of the complex are bound to one another in their natural state. In one embodiment, at least some of the proteins of the complex are associated via at least one RNA. In another embodiment, the proteins are associated non-covalently (either directly with one another, or non-directly through additional components of the complex, such as via RNA) to generate a functional complex—for example a functional ribosomal subunit or a functional ribosome.

In the case of a ribosomal subunit, the ribosomal proteins are associated with the ribosomal RNA non-covalently by multiple weak interactions, including electrostatic and Van-der-Waals interaction. The ribosomal RNA is a scaffold for the assembly of the ribosomal subunits. Ribosomal proteins bind to the ribosomal RNA in a hierarchal order, some bind independently of others, some bind contingently on the pre-binding of others.

As used herein, the term "functional ribosome" refers to a ribosome that is capable of linking amino acids together in the order specified by messenger RNA (mRNA) molecules.

The term "functional ribosomal subunit" refers to a subunit, which together with other subunits of the ribosome, is capable of forming a functional ribosome.

Additional examples of proteinaceous complexes include, but are not limited to a bacteriophage, a spliceosome, a proteasome, a replisome, a divisome, a virus and a proteasome subunit.

In one embodiment, the proteinaceous complex is a eukaryotic (e.g. mammalian or yeast) proteinaceous complex.

In still another embodiment, the proteinaceous complex is a human proteinaceous complex.

In another embodiment, the proteinaceous complex is a prokaryotic (e.g. bacterial) proteinaceous complex.

According to a particular embodiment, the proteinaceous complex is a bacterial ribosomal subunit—e.g. an *E. Coli* ribosomal subunit or an S. *Aureus* ribosomal subunit.

According to a more particular embodiment, the proteinaceous complex is an *E. Coli* small ribosomal subunit or an S. *Aureus* small ribosomal subunit.

The proteinaceous complex of this aspect of the present invention comprises at least 2 proteins, at least 3 proteins, at least 4 proteins, at least 5 proteins, at least 6 proteins, at least 7 proteins, at least 8 proteins, at least 9 proteins, at least 10 proteins, at least 11 proteins, at least 12 proteins, at least 13 proteins, at least 14 proteins, at least 15 proteins, at least 16 proteins, at least 17 proteins, at least 18 proteins, at least 19 proteins, at least 20 proteins.

The proteinaceous complex of this aspect of the present invention may comprise between 5-20 proteins, 5-10 proteins, 10-30 proteins, 20-40 proteins or 30-50 proteins.

The proteinaceous complex of this aspect of the present invention may comprise additional components other than proteins including for example polynucleotides (such as DNA or RNA molecules). In a particular embodiment, the proteinaceous complex comprises protein and RNA. In still another embodiment, the proteinaceous complex consists of protein and RNA.

The term "chamber" as used herein, refers to an open or closed compartment in which transcription and translation takes place. The chamber may comprise volumes of between 1 pl-10 ml. Exemplary ranges include 1 pl-100 pl, 1 pl-1000 μl, 1 pl-100 μl, 1 pl-10 μl, 1 pl-1 μl, 1 pl-100 nl, 1 pl-10 nl, 1 μl-1000 μl and 1 μl-100 μl.

The chamber may be any shape—e.g. rectangular, square or circular.

According to a particular embodiment, the area of the surface to which the complex binds is between 100 $\mu m^2$-100 $cm^2$.

Preferably, the dimensions of the chamber are such that at least 1%, at least 10%, at least 20%, at least 30%, at least 40%, at least 50%, at least 60%, at least 70%, at least 80%, at least 90%, at least 95% of the total amount of proteinaceous complex is immobilized to the surface.

Preferably, the dimensions of the chamber are such that at least 50%, of the total amount of proteinaceous complex is immobilized to the surface.

According to a particular embodiment, the height of the chamber is between 1 μm-20 μm or between 1 μm-10 μm.

The aspect ratio of the height of the chamber:lateral dimension of the chamber (e.g. a diameter of a circle or the length of a rectangle/square is preferably 1:10-1:100. The chamber of the present invention is fabricated from a substrate (i.e. a single material or a combination of materials).

Preferably, the substrate material is substantially non-fluorescent or emits light of a wavelength range that does not interfere with the photoactivation.

Examples of such materials include, but are not limited to, silicon-based materials (exemplified hereinbelow) and elastomeric materials.

The term "elastomer" and "elastomeric" as used herein refers to the general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application. Examples of elastomeric materials which can be used to fabricate the devices of the present invention include, but are not limited to, GE RTV 615 (formulation), a vinyl-silane crosslinked (type) silicone elastomer (family e.g., PDMS).

The choice of materials typically depends upon the particular material properties (e.g., solvent resistance, stiffness, gas permeability, and/or temperature stability) required for the application being conducted. Additional details regarding the type of materials that can be used in the manufacture of the chamber are disclosed herein are set forth in Unger et al. (2000) Science 288:113-116, and PCT Publications WO 02/43615, and WO 01/01025. Exemplary low-background substrates include those disclosed by Cassin et al., U.S. Pat. No. 5,910,287 and Pham et al., U.S. Pat. No. 6,063,338.

Preferred elastomers of the instant invention are biocompatible, gas permeable, optically clear elastomers useful in soft lithography including silicone rubbers, most preferably PDMS. Other possible elastomers for use in the devices of the invention include, but are not limited to, polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(l-butene), poly (chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

In a preferred embodiment, the substrate material is substantially non-reactive with nucleic acids, thus preventing non-specific binding between the substrate and the nucleic acids. Methods of coating substrates with materials to prevent non-specific binding are generally known in the art. Exemplary coating agents include, but are not limited to cellulose, bovine serum albumin, and poly(ethyleneglycol). The proper coating agent for a particular application will be apparent to one of skill in the art.

In one embodiment, the chamber is comprised in a microfluidic device.

As mentioned, a plurality of nucleic acids encoding at least two of the components of the proteinaceous complex are immobilized onto a surface of the chamber. Typically each nucleic acid encodes a single component of the proteinaceous complex. Thus, for example if the proteinaceous complex comprises 10 different proteins, the chamber comprises 10 distinct nucleic acids, each nucleic acid encoding a single protein.

The nucleic acid may be single stranded or double stranded. The nucleic acid may be DNA (e.g. cDNA, genomic DNA, synthetic DNA), RNA, a combination of both. Preferably, the nucleic acid is linear DNA. The nucleic acid may be isolated from a cell, or may by synthesized in vitro. Typically, the nucleic acids of this aspect of the present invention comprise at least one promoter and encode each of the proteins of the complex—i.e. each DNA molecule encodes a distinct protein of the complex.

The nucleic acids may be of any length. According to a particular embodiment, the nucleic acids are between 200 bp-500 bp, or between 200 bp-2000 bp, or between 200 bp-3000 bp, or between 200 bp-4000 bp, or between 200-5000 bp.

Nucleic acids of this aspect of the present invention are further described herein below.

According to one embodiment, at least a portion of the surface of the chamber is coated with the nucleic acids.

Preferably, the density of the nucleic acids on the surface of the chamber is between 1-$10^3$ DNA $\mu m^2$, for example in the order of $10^2$ DNA $\mu m^2$.

According to a specific embodiment, each nucleic acid is immobilized to the surface of the chamber such that the space between them is about 30-100 nm.

The nucleic acid of the present invention is typically orientated on the substrate of the chamber such that the regulatory region of the nucleic acid (e.g. promoter) is further from the substrate and the direction of protein synthesis is in the direction towards the substrate.

The nucleic acids encoding the components of the proteinaceous complex may be attached to the substrate of the chamber (or portion thereof) in a wide variety of ways, as will be appreciated by those in the art. The components (e.g. nucleic acids) may either be synthesized first, with subsequent attachment to the substrate, or may be directly synthesized on the substrate of the chamber. The chamber and the nucleic acids may be derivatized with chemical functional groups for subsequent attachment of the two. For example, the chamber may be derivatized with a chemical functional group including, but not limited to, amino groups, carboxyl groups, oxo groups or thiol groups. Using these functional groups, the nucleic acid may be attached using functional groups on the nucleic acid either directly or indirectly using linkers.

The isolated nucleic acid may also be attached to the chamber non-covalently. For example, a biotinylated nucleic acid can be prepared, which may bind to surfaces covalently coated with streptavidin, resulting in attachment. Alternatively, a nucleic acid may be synthesized on the surface using techniques such as photopolymerization and photolithography. Additional methods of attaching nucleic acids to solid surfaces and methods of synthesizing nucleic acids on solid surfaces are well known in the art, i.e. VLSIPS technology from Affymetrix (e.g., see U.S. Pat. No. 6,566,495, and Rockett and Dix, "DNA arrays: technology, options and toxicological applications," Xenobiotica 30(2):155-177, all of which are hereby incorporated by reference in their entirety).

According to a preferred embodiment of this aspect of the present invention, the chamber is coated with a coat composed of a compound which can be represented by the general formula I below:

X-L-Y    Formula I wherein X is the functionalized group capable of binding to a solid surface of the chamber; L is the polymer capable of forming a monolayer on the chamber; and Y is a photoactivatable group capable of generating a reactive group upon exposure to light.

The functionalized group is preferably selected such that it binds to the chamber by reacting with at least one functional group present on a surface of the chamber.

Preferred functionalized groups according to the present invention comprise one or more reactive silyl group(s).

As used herein, the phrase "reactive silyl group" describes a residue of a compound comprising at least one silicon atom and at least one reactive group, such as an alkoxy or halide, such that the silyl group is capable of reacting with a functional group, for example on a surface of a microfluidic device, to form a covalent bond with the surface. For example, the reactive silyl group can react with the surface of a silica substrate comprising surface Si—OH groups to create siloxane bonds between the compound and the silica substrate.

Exemplary reactive silyl groups that are usable in the context of the present invention include, without limitation, trialkoxysilanes, alkyldialkoxysilanes, alkoxydialkylsilanes, trihalosilanes, alkyldihalosilanes and dialkylhalosilanes. Such reactive groups are easily reacted when contacted with free hydroxyl groups on a surface of solid surfaces and particularly with such hydroxyl groups on a silica surface.

Herein, the terms "silica" and "$SiO_2$" are used interchangeably.

In a preferred embodiment of the present invention the reactive silyl group is trialkoxysilane such as, for example trimethoxysilane, triethoxysilane, tripropyloxysilane or trihalosilane such as, for example, trichlorosilane.

The functionalized group according to the present invention may further include a chemical moiety that is terminated with the reactive silyl group. Such a chemical moiety can comprise, for example, alkyl, alkenyl, aryl, cycloalkyl and derivatives thereof, as these terms are defined herein.

Preferably, the functionalized group comprises an alkyl terminating with a trialkoxysilane.

As discussed hereinabove, the polymer is selected so as to form a monolayer on the chamber. Thus, the polymer group in the coat compounds of the present invention may be any hydrophobic, hydrophilic and amphiphilic polymer that has suitable characteristics for forming a monolayer. Such characteristics include, for example, long, relatively inert chains, which may interact therebetween via e.g., hydrogen or Van-der-Waals interactions.

A preferred polymer according to the present invention comprises polyethylene glycol (PEG). As described hereinabove, PEG is characterized by resistance to nonspecific absorptions of biomolecules and is therefore beneficial for use in some contexts of the present invention. In addition, when self-assembled on a substrate, PEG chains typically interact therebetween via hydrogen bonds, so as to produce a well-ordered monolayered film.

The polyethylene glycol residue in the coat compounds described herein can be derived from PEGs having a molecular weight that ranges from about 400 grams/mol and about 10000 grams/mol. Preferred PEGs are those having a molecular weight that ranges from about 2000 grams/mol and about 5000 grams/mol. Such PEGs allow the productions of a monolayered film when deposited on a solid surface in the presence of a functionalized group, as described hereinabove.

The polyethylene glycol residue may be substituted or unsubstituted and can be represented by the general Formula II below:

$$—(CR^1R^2CR^3R^4O)n- \qquad \text{Formula II}$$

wherein n is an integer from 10 to 200; and $R^1$, $R^2$, $R^3$ and $R^4$ are each independently selected from the group consisting of hydrogen, alkyl, cycloalkyl, aryl, alkenyl alkynyl, alkoxy, thioalkoxy, aryloxy and thioaryloxy.

In a preferred embodiment, the PEG is unsubstituted such that $R^1$, $R^2$, $R^3$ and $R^4$ are each hydrogen.

In another preferred embodiment, the PEG residue is a medium-sized residue such that n is an integer from 60 to 100.

The polymer is preferably attached to the functionalized group described above via a linking moiety.

Exemplary linking moieties include, without limitation, oxygen, sulfur, amine, amide, carboxylate, carbamate, sulphonate, sulphonamide, phosphate, hydrazine, hydrazide, as these terms are defined herein and derivatives thereof.

In a representative example the linking moiety is an amide, formed between a carboxylic end group of the polymer and an amine end group of the functionalized moiety, as is detailed herein under.

The compounds of the present invention, by comprising the functionalized group and the polymer described hereinabove, readily form self-assembled monolayers when contacted with the solid surface of the chamber, in a one-step, simple to perform, reaction.

As the polymer residue in the compounds of the present invention further has a photoactivatable group attached thereto, each of the formed monolayers has a photoactivatable group attached thereto.

As used herein, the phrase "photoactivatable group" describes a group that is rendered active when exposed to photoactivation, namely when exposed to light. Photoactivatable groups typically comprise a protected reactive group, which upon exposure to light are de-protected, so as to generate a reactive group.

As used herein, the phrase "reactive group" describes a chemical moiety that is capable of interacting with another moiety. This interaction typically results in a bond formation between these moieties, whereby the bond can be, for example a covalent bond, a hydrogen bond, a coordinative bond, or an ionic bond.

Representative examples of reactive groups include, without limitation, amine, hydroxy, thiohydroxy, halo, alkoxy, thioalkoxy, aryloxy, thioaryloxy, carboxylate, phosphate, phosphonate, sulfate and sulfonate, as these terms are defined herein.

Depending on the intended use of the compound, the photoactivatable group is selected so as to generate a desired reactive group.

Thus, for example, a photoactivatable group that comprises a carbamate can generate upon exposure to light amine as the reactive group.

The photoactivatable groups according to the present invention are preferably derived from photoactivatable compounds and therefore preferably include a residue of, for example, photoactivatable compounds that has light-absorbing characteristics such as 6-nitrovertaryl chloroformate, 6-nitrovertaryl carbonyl, 2-nitrotoluene, 2-nitroaniline, phenacyl, phenoxy, azidoaryl, sulfonic ester, desyl, p-hydroxyphenacyl, 7-methoxy coumarin, o-ethylacetophenone, 3,5-dimethylphenacyl, dimethyl dimethoxybenzyloxy carbonyl, 5-bromo-7-nitroindolinyl, o-hydroxy-α-methyl cinnamoyl and 2-oxymethylene anthraquinone.

When exposed to light such as, for example, UV, IR, or visible light or a monochromatic light of a predetermined wavelength, primary amines are exposed by releasing protecting groups. The exposed amines can react with certain reactive chemical moieties (such as succinimide) thus providing means to conjugate small molecules such as biotin and/or bio molecules (nucleic acids and antibodies).

Electron beams can also be used to activate the surface.

The above-described compounds can be readily prepared using a simple two-step synthesis. A process of preparing the compounds is described in details in PCT Application No. WO2006/064505 to the present inventor.

As discussed hereinabove, the surface of the chamber and the compound of the present invention may be selected such that upon contacting the polymer with the substrate, a self-assembled monolayered film of the polymer forms on the substrate surface, in a one-step reaction.

The contacting procedure is preferably effected by incubating the compound with the selected surface, preferably in the presence of an organic solvent such as, for example, toluene. Once a monolayered film of the polymer is deposited on the surface, the reactive group for binding a screenable moiety can be generated by exposing a pre-selected area of the substrate to light.

Depending on the selected photoactivatable group and the active wavelength in which it is active, the light can be a UV, IR or visible light, or, optionally and preferably, the light can be a monochromatic light of a predetermined wavelength.

Exposure of a limited area of the chamber surface to light is preferably effected using a photo mask to illuminate selected regions the substrate and avoid coating the substrate at the periphery. However, other techniques may also be used. For example, the solid surface may be translated under a modulated laser or diode light source. Such techniques are discussed in, for example, U.S. Pat. No. 4,719,615 (Feyrer et al.), which is incorporated herein by reference. In alternative embodiments a laser galvanometric scanner is utilized. In other embodiments, the synthesis may take place on or in contact with a conventional liquid crystal (referred to herein as a "light valve") or fiber optic light sources. By appropriately modulating liquid crystals, light may be selectively controlled so as to permit light to contact selected regions of the solid surface. Alternatively, synthesis may take place on the end of a series of optical fibers to which light is selectively applied. Other means of controlling the location of light exposure will be apparent to those of skill in the art.

The surface of the chamber may be irradiated either in contact or not in contact with a solution and is, preferably, irradiated in contact with a solution. The solution may contain reagents to prevent the by-products formed by irradiation. Such by-products might include, for example, carbon dioxide, nitrosocarbonyl compounds, styrene derivatives, indole derivatives, and products of their photochemical reactions. Alternatively, the solution may contain reagents used to match the index of refraction of the substrate. Reagents added to the solution may further include, for example, acidic or basic buffers, thiols, substituted hydrazines and hydroxylamines, or reducing agents (e.g., NADH).

In an exemplary embodiment, exposing the chamber surface to light is effected so as to provide a patterned substrate in which reactive groups are generated according to a pre-selected pattern. The pattern can be printed directly onto the substrate or, alternatively, a "lift off" technique can be utilized. In the lift off technique, a patterned resist is laid onto the substrate or onto the light source. Resists are known to those of skill in the art. See, for example, Kleinfield et al., J. Neurosci. 8:4098-120 (1998). In some embodiments, following removal of the resist, a second pattern is printed onto the substrate on those areas initially covered by the resist; a process that can be repeated any selected number of times with different components to produce an array having a desired format.

Binding the nucleic acid can be effected by directly attaching the moiety to the reactive group.

Alternatively, binding the nucleic acid is effected via a mediating moiety. As used herein, the phrase "mediating moiety" describes a mediating agent or a plurality of mediating agents being linked therebetween that may bind to both the reactive group and the component and thus mediate the binding of the component to the reactive group.

The mediating moiety can thus be a bifunctional moiety, having two reactive groups, each independently capable of reacting with the reactive group attached to the chamber or the component. Alternatively, the mediating moiety can comprise two or more moieties, whereby the first moiety can be attached to the reactive group and to a second mediating moiety, whereby the second mediating moiety can bind the component (e.g. nucleic acid).

Optionally and preferably, the mediating moiety comprises an affinity pair, such as, for example, the biotin-avidin affinity pair.

In one embodiment, the mediating moiety can comprise biotin. When attached to the reactive group, biotin can bind a variety of chemical and biological substances that are capable of reacting with the free carboxylic group thereof.

As mentioned herein above, the sequence of the isolated nucleic acids which is attached to the chamber (or portion thereof) encodes a promoter which is operatively linked to a nucleic acid sequence encoding a polypeptide.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter.

A "constitutive" promoter is a promoter that is active under most environmental and developmental conditions. An example of a constitutive promoter is cytomegalovirus (CMV) or Rous sarcoma virus (RSV) promoter.

An "inducible" promoter is a promoter that is active under environmental or developmental regulation.

Examples of inducible promoters include the tetracycline-inducible promoter (Srour, M. A., et al., 2003. Thromb. Haemost. 90: 398-405), an IPTG inducible promoter, P70, P70b, P28, P38 or Plac \arac ($P_{la}$).

In the isolated nucleic acid, the promoter is preferably positioned approximately the same distance from the heterologous transcription start site as it is from the transcription start site in its natural setting. As is known in the art, however, some variation in this distance can be accommodated without loss of promoter function.

A DNA segment such as an expression control sequence is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a pre-protein that participates in the secretion of the polypeptide. Generally, DNA sequences that are operably linked are contiguous, and, in the case of a signal sequence, both contiguous and in reading phase. However, enhancers need not be contiguous with the coding sequences whose transcription they control. Linking is accomplished by ligation at convenient restriction sites or at adapters, linkers, or PCR fragments by means know in the art.

According to one embodiment, the promoter is a eukaryotic promoter.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

According to another embodiment, the promoter is a prokaryotic promoter.

According to yet another embodiment, the promoter is a plant-specific promoter.

According to still another embodiment, the promoter is a tissue specific promoter.

The nucleic acid of this aspect of the present invention may further comprise an enhancer element. Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences may also be present in the nucleic acids in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

The nucleic acid of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

In the context of this invention, the term "translational initiator sequence" is defined as the ten nucleotides immediately upstream of the initiator or start codon of the open reading frame of a DNA sequence coding for a polypeptide. The initiator or start codon encodes for the amino acid methionine. The initiator codon is typically ATG, but may also be any functional start codon such as GTG, TTG or CTG.

It will be appreciated that the individual elements comprised in the nucleic acid can be arranged in a variety of configurations. For example, enhancer elements, promoters and the like, and even the polynucleotide sequence(s) encoding the polypeptide can be arranged in a "head-to-tail" configuration, may be present as an inverted complement, or in a complementary configuration, as an anti-parallel strand. While such variety of configuration is more likely to occur with non-coding elements of the nucleic acid, alternative configurations of the coding sequence within the nucleic acid are also envisioned.

In a particularly preferred embodiment of the invention, the nucleic acid molecule comprises a coding sequence coding for one of the proteins of the ribosomal subunit.

Below is a list of each of the components of the 30S ribosomal subunit of *E. Coli*.

S1—DNA sequence SEQ ID NO: 64, protein sequence SEQ ID NO: 146.

S2—DNA sequence SEQ ID NO: 65, protein sequence SEQ ID NO: 147.

S3—DNA sequence SEQ ID NO: 66, protein sequence SEQ ID NO: 148.

S4—DNA sequence SEQ ID NO: 67, protein sequence SEQ ID NO: 149.

S5—DNA sequence SEQ ID NO: 68, protein sequence SEQ ID NO: 150.

S6—DNA sequence SEQ ID NO: 69, protein sequence SEQ ID NO: 151.

S7—DNA sequence SEQ ID NO: 70, protein sequence SEQ ID NO: 152

S8—DNA sequence SEQ ID NO: 71, protein sequence SEQ ID NO: 153.

S9—DNA sequence SEQ ID NO: 72, protein sequence SEQ ID NO: 154.

S10—DNA sequence SEQ ID NO: 73, protein sequence SEQ ID NO: 155.

S11—DNA sequence SEQ ID NO: 74, protein sequence SEQ ID NO: 156.

S12—DNA sequence SEQ ID NO: 75, protein sequence SEQ ID NO: 157.

S13—DNA sequence SEQ ID NO: 76, protein sequence SEQ ID NO: 158.

S14—DNA sequence SEQ ID NO: 77, protein sequence SEQ ID NO: 159.

S15—DNA sequence SEQ ID NO: 78, protein sequence SEQ ID NO: 160.

S16—DNA sequence SEQ ID NO: 79, protein sequence SEQ ID NO: 161.

S17—DNA sequence SEQ ID NO: 80, protein sequence SEQ ID NO: 162.

S18—DNA sequence SEQ ID NO: 81, protein sequence SEQ ID NO: 163.

S19—DNA sequence SEQ ID NO: 82, protein sequence SEQ ID NO: 164

S20—DNA sequence SEQ ID NO: 83, protein sequence SEQ ID NO: 165

S21—DNA sequence SEQ ID NO: 84, protein sequence SEQ ID NO: 166 rR (16S)—DNA sequence SEQ ID NO: 85.

The immobilized nucleic acids may also encode for additional components that aid in the assembly of the complex (e.g. GTPase).

Thus, for example, the present inventors contemplate immobilized nucleic acids encoding for at least one, two, three, four, five or all of the below disclosed assembly cofactors for assembly of the 30S ribosomal subunit.

Assembly cofactor 1—Era—DNA sequence SEQ ID NO: 86.

Assembly cofactor 2—RsgA—DNA sequence SEQ ID NO: 90.

Assembly cofactor 3—RbfA DNA sequence SEQ ID NO: 89.

Assembly cofactor 4—RimM—DNA sequence SEQ ID NO: 88.

Assembly cofactor 5—RimN—DNA sequence SEQ ID NO: 91.

Assembly cofactor 6—RimP—DNA sequence SEQ ID NO: 87.

Below is a list of each of the components of the 30S ribosomal subunit of S. *Aureus*. Sequences 92, 94, 96, 98, 100, 102, 104, 106, 108, 110, 112, 114, 116, 118, 120, 122, 124, 126, 128, 130, 132, 134, 136, 138, 140, 142 and 144 are the DNA sequences with no codon optimization, whereas sequences 95, 97, 99, 101, 103, 105, 107, 109, 111, 113, 115, 117, 119, 121, 123, 125, 127, 129, 131, 137, 139, 141, 143 and 145 are after codon optimization for *E. coli* usage.

S1—DNA sequence SEQ ID NO: 92.

S2—DNA sequence SEQ ID NO: 94, 95.

S3—DNA sequence SEQ ID NO: 96, 97.

S4—DNA sequence SEQ ID NO: 98, 99.

S5—DNA sequence SEQ ID NO: 100, 101.

S6—DNA sequence SEQ ID NO: 102, 103.

S7—DNA sequence SEQ ID NO: 104, 105.

S8—DNA sequence SEQ ID NO: 106, 107.

S9—DNA sequence SEQ ID NO: 108, 109.

S10—DNA sequence SEQ ID NO: 110, 111.

S11—DNA sequence SEQ ID NO: 112, 113.

S12—DNA sequence SEQ ID NO: 114, 115.

S13—DNA sequence SEQ ID NO: 116, 117.

S14—DNA sequence SEQ ID NO: 118, 119.

S15—DNA sequence SEQ ID NO: 120, 121.

S16—DNA sequence SEQ ID NO: 122, 123.

S17—DNA sequence SEQ ID NO: 124, 125.

S18—DNA sequence SEQ ID NO: 126, 127.

S19—DNA sequence SEQ ID NO: 128, 129.

S20—DNA sequence SEQ ID NO: 130, 131.

S21—DNA sequence SEQ ID NO: 132, 133.

rR (16S)—DNA sequence SEQ ID NO: 134.

The immobilized nucleic acids may also encode for additional components that aid in the assembly of the complex (e.g. GTPase).

Thus, for example, the present inventors contemplate immobilized nucleic acids encoding for at least one, two, three, four, five or all of the below disclosed assembly cofactors for assembly of the 30S ribosomal subunit.

Assembly cofactor 1—Era—DNA sequence SEQ ID NO: 136, 137, protein sequence SEQ ID NO:

Assembly cofactor 2—RsgA—DNA sequence SEQ ID NO: 144, 145, protein sequence SEQ ID NO:

Assembly cofactor 3—RbfA DNA sequence SEQ ID NO: 142, 143, protein sequence SEQ ID NO:

Assembly cofactor 4—RimM—DNA sequence SEQ ID NO: 140, 141, protein sequence SEQ ID NO:

Assembly cofactor 6—RimP—DNA sequence SEQ ID NO: 138, 139, protein sequence SEQ ID NO:

As mentioned, a binding agent which binds specifically to one component of the proteinaceous complex is immobilized onto the surface of the chamber.

In one embodiment, the binding agent is an antibody directed towards the complex.

In one embodiment, the binding agent is an antibody directed towards an affinity tag pair which is expressed with the component of the complex.

The binding agent (e.g. antibody) may comprise an affinity tag itself (e.g biotin) so that it can be immobilized to the chamber.

Affinity tags and affinity tag pairs are further described herein below.

Immobilization of the binding agent can be effected as known in the art. In one embodiment, the binding agent (e.g. antibody) is biotinylated, mixed with streptavidin and attached to the surface of the chamber as described above for biotinylated nucleic acids (see also examples section herein below). Preferably, the binding agent is immobilized onto the surface of the chamber in a predefined continuous pattern surrounding the nucleic acids. The pattern may comprise of any shape—e.g. circle, square, hexagon, pentagon etc.

Preferably, the binding agent is immobilized onto the identical surface of the chamber onto which the nucleic acids are immobilized.

Preferably, the pattern of the immobilized binding agent is surrounding the nucleic acids which are immobilized to the same surface.

According to a particular embodiment, at least 50% of the surface of the chamber is patterned with the binding agent.

According to a particular embodiment, at least 60% of the surface of the chamber is patterned with the binding agent.

According to a particular embodiment, at least 70% of the surface of the chamber is patterned with the binding agent.

According to a particular embodiment, at least 80% of the surface of the chamber is patterned with the binding agent.

According to a particular embodiment, at least 90% of the surface of the chamber is patterned with the binding agent.

As mentioned, in one embodiment at least one of the proteins or RNA molecules encoded by the nucleic acid molecules comprises an affinity tag.

In other embodiments, the antibody is specific to one of the proteins, rendering the tag redundant.

An affinity tag is a sequence that generally permits the expressed protein or RNA to be attached to an affinity tag pair with a known orientation. Several different kinds of affinity tags are known in the art. In particular embodiments, the affinity tag is selected from the group consisting of hemagglutinin (HA), AviTag™, V5, Myc, T7, FLAG, HSV, VSV-G, His, biotin, or streptavidin.

The phrase "affinity tag pair" refers to an agent that binds specifically to the affinity tag. In one embodiment, the affinity tag pair serves as the binding agent. The affinity tag pair is typically immobilized on the surface of the chamber.

According to a particular embodiment, the affinity tag is HA and the affinity tag pair is an anti-HA antibody. Preferably, the anti-HA antibodies comprise an affinity tag (e.g. biotin) so that they can be immobilized on the surface of the chamber (or a portion thereof).

Additional agents may be immobilized on to the surface of the chamber to aid in analyzing the association of the components of the complex. In one embodiment, an agent which binds the proteinaceous complex with at least ten fold higher affinity when it is in an assembled form over a non-assembled form is attached to the surface. In the case where the complex is a ribosomal subunit, for example, the present inventors contemplate attaching the second ribosomal subunit to the surface. Binding of the expressed first ribosomal subunit complex to the second immobilized ribosomal subunit complex could serve as a test to analyze correct association of the complex.

According to another embodiment, at least one of the nucleic acids attached to the chamber encodes a polypeptide/RNA comprising a detectable moiety.

Examples of detectable moieties include, but are not limited to fluorescent moieties, phosphorescent moieties, chemiluminescent moieties and luminescent moieties.

Preferably, the component of the complex which is attached to an affinity tag is not the same component that is attached to the detectable moiety. Thus, in one embodiment, it is envisaged that no single component of the complex comprises both an affinity tag and a detectable moiety.

Examples of such detectable moieties include, but are not limited to green fluorescent protein from *Aequorea victoria* ("GFP"), the yellow fluorescent protein (YFP) and the red fluorescent protein (RFP) and their variants (e.g., Evrogen). Others may include unnatural fluorescent amino acids (as in FIG. 10).

Table 1 provides non-limiting examples of detectable moieties and affinity tags contemplated by the present invention.

TABLE 1

| Identifiable Moiety | Amino Acid sequence (GenBank Accession No.) | Nucleic Acid sequence (GenBank Accession No.) |
|---|---|---|
| Green Fluorescent protein | AAL33912 | AF435427 |
| Alkaline phosphatase | AAK73766 | AY042185 |
| Peroxidase | CAA00083 | A00740 |
| Histidine tag | Amino acids 264-269 of GenBank Accession No. AAK09208 | Nucleotides 790-807 of GenBank Accession No. AF329457 |
| Myc tag | Amino acids 273-283 of GenBank Accession No. AAK09208 | Nucleotides 817-849 of GenBank Accession No. AF329457 |
| Biotin lygase tag | LHHILDAQKMVWNHR (SEQ ID NO: 51) | |

TABLE 1-continued

| Identifiable Moiety | Amino Acid sequence (GenBank Accession No.) | Nucleic Acid sequence (GenBank Accession No.) |
|---|---|---|
| orange fluorescent protein | AAL33917 | AF435432 |
| Beta galactosidase | ACH42114 | EU626139 |
| Streptavidin | AAM49066 | AF283893 |
| HA tag | YPYDVPDYA (SEQ ID NO: 135) | TACCCATACGATGTTCCAG ATTACGCT SEQ ID NO: 93 |

According to a specific embodiment, the nucleic acid which encodes the RNA molecule of a ribosomal subunit is such that the encoded RNA comprises a detectable moiety. This may be effected via aptamers such as green fluorescent aptamers (broccoli aptamer, spinach aptamer), red and orange fluorescent aptamers (mango aptamer) or yellow fluorescent aptamer (corn aptamer).

In order to generate the proteinaceous complex in the chamber, the immobilized nucleic acids are contacted with agents for performing expression therefrom. Such agents are typically not immobilized to the chamber, although it will be appreciated that it is possible to also mobilize certain of these agents to the chamber if desired—see for example FIGS. 3A-E. The contacting is effected under conditions (e.g. temperature and time) that allow expression from the immobilized nucleic acids of the various components and association thereof so as to generate the proteinaceous complex.

Exemplary agents for performing expression include but are not limited to ribonucleotides, RNA polymerase (e.g. RNA polymerase II), transcription factors, ribosomes, tRNA, tRNA amino acyl synthetase, initiation factors, elongation factors, termination factors and amino acids. Preferably, the non-immobilized agents of this aspect of the present invention do not include DNA.

The fluid which carries/contains the non-immobilized components are typically buffered solutions which are physiologically relevant such that they do not interfere with expression of the components or interaction therebetween.

In one embodiment, the chamber is heated to physiological temperatures (e.g. 37° C.) to promote transcription/translation and/or association of the components.

In one embodiment, a cell-free protein expression system is used in the method to provide the non-immobilized agents. Examples of cell-free expression systems include minimal expression systems from purified components: PUREexpress from New England Biolabs; PUREfrex from CosmoBio, Japan; Cell extracts: myTXTL™—Cell-Free Protein Expression from arbor biosciences; Expressway cell-free Expression system, Invitrogen; *E. coli* S30 Extract System, Promega; Remarkable Yield Expression System (RYTS), CosmoBio, Japan.

In another embodiment, a cell-extract is used in the method to provide the non-immobilized agents.

It will be appreciated that the protein complexes described herein may assemble in solution and then immobilize to the chamber, or a single component may be immobilized initially to the chamber and then the other components may assemble thereto.

Once the complex is immobilized, it may be detected according to methods known in the art and according to the nature of the detectable moiety which is expressed on the component.

In one embodiment, the detection is carried out by fluorescent microscopy imaging.

In a particular embodiment, the imaging is carried out using Total Internal Reflection Fluorescence (TIRF) microscopy.

According to a particular embodiment, the chamber is comprised in a microfluidic device comprising, at its minimum, a test chamber and a flow-through channel.

As used herein the phrase "microfluidic device" refers to a synthetic device in which minute volumes of fluids are flowed. The flow-through channel of the device is generally fabricated at the micron to sub-micron scale, e.g., the flow-through channel typically has at least one cross-sectional dimension in the range of less than about 1 mm. Microfluidic devices of the present invention can be incorporated in complicated systems such as those described herein below.

The test chamber of a microfluidic device is connected to the flow-through channel such that components (i.e. non-immobilized components) which flow there-through can reach the test chamber and take part in the biological process (e.g. by diffusion or by fluid flow). In one embodiment, the flow-through channel is connected directly to the test chamber. In another embodiment, the flow-through channel is connected via a microchannel to the test chamber.

According to one embodiment, the test chamber of a microfluidic device is circular and has a diameter of about 10-400 microns. In a microfluidic device, the test chambers typically have a volume of less than 100 pl, in other instances less than 50 pl; in other instances less than 40 pl, 30 pl, 20 pl or 10 pl.

The term "flow-through channel" as used herein, refers to a low resistance flow channel, about 25 microns to about 150 microns deep, preferably about 25 microns to about 100 microns deep and more preferably about 30 microns to about 100 microns deep. Flow-through channels are sufficiently wide so as to not inhibit the flow of fluid through the channel, and not excessively wide to inhibit the function of valves. Such considerations are well understood by those of ordinary skill in the art. Exemplary widths of the flow-through channel are between 100 microns-1 mm wide. The flow-through channel has at least one inlet port and at least one outlet port, at least one of which being in fluid communication with a reservoir such as by tubing. Fluids may be passively or actively infused into the flow channels such as by capillary forces or pumps (e.g., external pumps, e.g., peristaltic pumps or electro-osmotically pumps).

Flow through the flow-through channel may be regulated using a valve.

A "valve" is a component of the device that regulates flow through a fluid channel of the device by substantially inhibiting flow through the fluid channel upon closure. Substantially inhibiting the flow means that flow is inhibited at least 80%, preferably at least 90%, more preferably at least 95%, even more preferably at least 99%, most preferably flow is completely (i.e., 100%) inhibited. The size of the valve is dependent on the size and shape of the fluid channel and the amount of pressure required to close the valve. In a preferred method, the fluid channel is about 250 microns wide and the valve is about 300 microns wide. The channel and control valve cross perpendicularly. Upon actuation of the valve, preferably by hydrostatic pressure, the channel closes and opens.

The term "microchannel" as used herein, refers to a high resistance channel, about 1 micron to about 20 microns deep, more preferably about 1 micron to about 10 microns deep. The length of the microchannel can vary between 20 microns to about 1 mm or between 20 microns to about 500 microns. The width of the microchannel is typically between 2-50 microns. According to embodiments of the present invention the ratio of the width of microchannel:width of the flow-through channel is greater than 1:5. Exemplary ratios include 1:5, 1:6, 1:7, 1:8, 1:9, 1:10 and 1:20.

According to a particular embodiment, the hydrodynamic resistance of the microchannel is at least 5 or 6 orders of magnitude higher than in the flow-through channel. This reduces the flow in the microchannel by 5 or 6 orders of magnitude compared with the flow in the flow chamber.

Resistance of fluid flow through the microchannel may be higher than the resistance in the flow-through channel. This resistance is typically established by having microchannels that are substantially and sufficiently shallower and/or narrower than the adjacent flow-through channels to create resistance. In one embodiment, the relative dimensions of the microchannel: flow-through channel is such that there is essentially no flow in the microchannel. Such parameters can be readily determined by one of ordinary skill in the art using mathematical or empirical modeling. According to a particular embodiment, the depth ratio of the reaction unit: flow-through channel is greater than 1:5. Exemplary ratios include 1:5, 1:6, 1:7, 1:8, 1:9, 1:10 and 1:20.

The device of the present invention can be used for a myriad of purposes. In one embodiment, the device can be used to analyze whether a candidate agent disrupts the assembly of a complex. According to this embodiment, the device is contacted with the candidate agent under conditions that allow expression of each of the components which are immobilized on the device, wherein a downregulation in the amount of the assembled complex as compared to the amount of the assembled complex in the absence of the candidate agent, is indicative that the candidate agent disrupts the assembly of the complex. When the complex is a ribosome or ribosomal subunit, the candidate agent can be an antibiotic. When the complex is a virus or part of a virus, the candidate agent can be an anti-viral drug. If the candidate agent is confirmed as being able to disrupt association of the complex it can be screened in other assays to confirm its antibiotic properties—e.g. it may be contacted with bacterial populations and the amount of bacteria that are present in the presence and absence of the agent can be counted. The device may be used to screen for potential genetically-encoded peptides and RNA aptamers as potential drugs that inhibit assembly (see for example FIGS. 40A-B). The genetically encoded materials can be encoded in the DNA immobilized in the same compartment as the genes encoding the complex. Every DNA brush can test the effect of a different peptide or RNA aptamer within the same device.

The device may be used to determine whether a candidate agent disrupts ribosome assembly, and/or ribosome function, and/or RNA polymerase function.

It will be appreciated that the device may be used to understand the biology/relevance of the different components of the complex. For example, a device may be generated on which nucleic acids are immobilized which encode for a subset of the components of the complex. The device may be used to understand the relevance of the missing component.

The device may be used to evaluate the binding affinity between two or several proteins based on the distance between their two respective genes and the position of their complex on the surface (see for example FIG. 39).

The device may be used to decipher the order of an assembly line of a megacomplex by a gene deletion analysis.

The device may be used for accelerated evolution of the mega complex. For example, mutations can be introduced in one nucleic acid coding for one component of the mega complex, and the effect on activity of the mega complex that is spatially linked to the site of this nucleic acid is determined.

The device may be used to construct unnatural complexes by design. For example, the architecture of a viral capsid can be modified to serve as a gene delivery vehicle. Likewise, the deice may be used to create hybrid megacomplexes, for example, a mix of *E. coli* and *S. aureus* ribosomal proteins that would create a superior ribosome (highly stable ribosome) for a particular task by merely mixing their genes on the surface.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Autonomous Synthesis and Assembly of a Ribosomal Subunit on a Chip

Materials and Methods

DNA Preparation

Cloning rR and rPs genes in cell-free expression plasmids: Genes of rR and rPs were amplified from the genome of *E. coli* K12 JM109 using KAPA HiFi HotStart ReadyMix (KAPA BIOSYSTEMS) and the appropriate primers (IDT, Table 2).

TABLE 2

| Name | Sequence |
|---|---|
| F16S rRNA | GCGAAATTAATACGACTCACTATAGGGTAAATTGAAGAGTTT GATCATGGCTC (SEQ ID NO: 1) |
| R16S rRNA | AAAGGCCTCCTGCAGGTTAACCTTACTCGAGTAAGGAGGTGA TCCAACCGCAG (SEQ ID NO: 2) |
| F16S HDV | TGGCGGCTAGTGGGCAACATGCTTCGGCATGGCGAATGGGAC GTAACTAGCATAACCCCTTGGGGCC (SEQ ID NO: 3) |
| R16S HDV | GCGAGGAGGCTGGGACCATGGCTAGCTAAGGAGGTGATCCAA CCGCAGGTTCCCCTAC (SEQ ID NO: 4) |

TABLE 2-continued

| Name | Sequence |
|---|---|
| F16S Broccoli | GTATCTGTCGAGTAGAGTGTGGGCTCCGCTGCTTCTTTGCTGA CGAGTGGCGGAC (SEQ ID NO: 5) |
| R16S Broccoli | GAATATCTGGACCCGACCGTCTCCGCAGCTTCTTCCTGTTACC GTTCGAC (SEQ ID NO: 6) |
| FS2 | F-Cons.seq-ATGGCAACTGTTTCCATGCGCG (SEQ ID NO: 7) |
| RS2 | R-Cons.seq-CTCAGCTTCTACGAAGCTTTC (SEQ ID NO: 8) |
| FS3 | F-Cons.seq-ATGGGTCAGAAAGTACATCCTAATG (SEQ ID NO: 9) |
| RS3 | R-Cons.seq-TTTACGGCCTTTACGCTGC (SEQ ID NO: 10) |
| FS4 | F-Cons.seq-ATGGCAAGATATTTGGGTCCTAAG (SEQ ID NO: 11) |
| RS4 | R-Cons.seq-CTTGGAGTAAAGCTCGACGATC (SEQ lD NO: 12) |
| FS5 | F-Cons.seq-ATGGCTCACATCGAAAAACAAGC (SEQ ID NO: 13) |
| RS5 | R-Cons.seq-TTTCCCCAGAATTTCTTCAACGG (SEQ ID NO: 14) |
| FS6 | F-Cons.seq-ATGCGTCATTACGAAATCGTTTTTATGG (SEQ ID NO: 15) |
| RS6 | R-Cons.seq-CTCTTCAGAATCCCCAGCATC (SEQ lD NO: 16) |
| FS7 | F-Cons.seq-ATGCCACGTCGTCGCGTCATT (SEQ ID NO: 17) |
| RS7 | R-Cons.seq-CCAACGGTAGTGTGCGAACG (SEQ ID NO: 18) |
| FS8 | F-Cons.seq-ATGAGCATGCAAGATCCGATCGC (SEQ ID NO: 19) |
| RS8 | R-Cons.seq-GGCTACGTAGCAGATAATTTCGCC (SEQ ID NO: 20) |
| FS9 | F-Cons.seq-ATGGCTGAAAATCAATACTACGGC (SEQ ID NO: 21) |
| RS9 | R-Cons.seq-ACGTTTGGAGAACTGCGGACG (SEQ ID NO: 22) |
| FS10 | F-Cons.seq-ATGCAGAACCAAAGAATCCGTATCC (SEQ ID NO: 23) |
| RS10 | R-Cons.seq-ACCCAGGCTGATCTGCACGTC (SEQ lD NO: 24) |
| FS11 | F-Cons.seq-ATGGCAAAGGCACCAATTCGTGC (SEQ ID NO: 25) |
| RS11 | R-Cons.seq-TACGCGACGTTTTTTCGGCGG (SEQ lD NO: 26) |
| FS12 | F-Cons.seq-ATGGCAACAGTTAACCAGCTGGTAC (SEQ ID NO: 27) |
| RS12 | R-Cons.seq-AGCCTTAGGACGCTTCACGCC (SEQ ID NO: 28) |
| FS13 | F-Cons.seq-ATGGCCCGTATAGCAGGCATTAAC (SEQ ID NO: 29) |
| RS13 | R-Cons.seq-TTTCTTGATCGGTTTGCGCGG (SEQ ID NO: 30) |
| FS14 | F-Cons.seq-ATGGCTAAGCAATCAATGAAAGC (SEQ ID NO: 31) |
| RS14 | R-Cons.seq-CCAGCTAGCCTTTTTCAGACCC (SEQ ID NO: 32) |
| FS15 | F-Cons.seq-ATGTCTCTAAGTACTGAAGCAACAG (SEQ ID NO: 33) |
| RS15 | R-Cons.seq-GCGACGCAGACCCAGG (SEQ ID NO: 34) |
| FS16 | F-Cons.seq-ATGGTAACTATTCGTTTAGCACGTC (SEQ ID NO: 35) |
| RS16 | R-Cons.seq-AGCTGCTTTGTTTACTTCTTTGATC (SEQ ID NO: 36) |
| FS17 | F-Cons.seq-ATGACCGATAAAATCCGTACTCTGC (SEQ ID NO: 37) |
| RS17 | R-Cons.seq-CAGAACCGCTTTCTCTACAACG (SEQ ID NO: 38) |
| FS18 | F-Cons.seq-ATGGCACGTTATTTCCGTCGTCGC (SEQ ID NO: 39) |
| RS18 | R-Cons.seq-CTGATGGCGATCAGTGTACGGC (SEQ lD NO: 40) |
| FS19 | F-Cons.seq-ATGCCACGTTCTCTCAAGAAAGG (SEQ ID NO: 41) |

TABLE 2-continued

| Name | Sequence |
| --- | --- |
| RS19 | R-Cons.seq-TTTCTTCTTCGCTTTTTTATCAGCAG (SEQ ID NO: 42) |
| FS20 | F-Cons.seq-ATGGCTAATATCAAATCAGCTAAGAAGCG (SEQ ID NO: 43) |
| RS20 | R-Cons.seq-AGCCAGTTTGTTGATCTGTGC (SEQ ID NO: 44) |
| FS21 | F-Cons.seq-ATGCCGGTAATTAAAGTACGTGAAAAC (SEQ ID NO: 45) |
| RS21 | R-Cons.seq-GTACAGACGAGTGCGGCGTG (SEQ ID NO: 46) |
| F-Cons.seq-PUREfrex control plasmid | GTTTAACTTTAAGAAGGAGATATACAT (SEQ ID NO: 47) |
| R-Cons.seq-PUREfrex control plasmid | AAAGGCCTCCTGCAGGTTAACCTTACTTA (SEQ ID NO: 48) |
| F-Cons.seq pIVEX2.5 | GTTTAACTTTAAGAAGGAGATATACATATGTAG (SEQ ID NO: 49) |
| R-Cons.seq pIVEX2.5 | GGGTAGCTGGTCCCGGGAGCTCGCTT (SEQ ID NO: 50) |

Each primer was composed of a variable sequence specific to the cloned gene and a constant sequence of the target plasmid. Enzyme-free cloning was performed using Gibson assembly cloning kit (NEB) by replacing the DHFR gene under the T7 promoter in the PURE system control vector (CosmoBio, Japan). For HA-tagged rPs, cloning was into pIVEX 2.5 (Roche) in frame with the C terminal HA tag using primers with the same variable sequence but a different constant sequence (Table 1). For rP fluorescent in situ labeling (UAG-rP), the TAG codon was introduced into the pIVEX clones using forward primers with a similar variable sequence as in Table 1 but with the TAG codon inserted between the ATG codon and the second codon of each gene. The rR gene, without its leader sequence, was cloned into the PURE control vector immediately after the promoter sequence using appropriate primers (Table 1).

Broccoli aptamer and HDV ribozyme genetic insertions into the 16S rR gene: The broccoli aptamer sequence (19) was inserted into helix 6 (H6) of the rR, that has been shown to tolerate sequence insertions while maintaining ribosome function (M. Wieland, B. Berschneider, M. D. Erlacher, J. S. Hartig, Aptazyme-mediated regulation of 16S ribosomal RNA. Chem. Biol. 17, 236-42 (2010)). Hepatitis delta virus (HDV) ribozyme sequence was inserted at the 3' end of the 16S rR to ensure formation of an exact 3' end (C. Walker, J. M. Avis, G. L. Conn, General plasmids for producing RNA in vitro transcripts with homogeneous ends. *Nucleic Acids Res.* 31, e82 (2003)). For both Broccoli and HDV insertions, the PURE plasmid containing the rR gene was amplified by inverse PCR using phosphorylated F and R primers (Table 1), followed by ligation and transformation into competent *E. coli* DH5α.

In vitro synthesis of rR and rPs in test-tube reactions: Plasmids coding for UAG-rPs with or without the HA tag were added to a 5 μl cell-free in vitro transcription translation reaction (PUREfrex2.0, CosmoBio, Japan) at a 3 nM final concentration. The in vitro reactions were supplemented with tRNA with an amber codon charged with an unnatural fluorescent amino acid (CloverDirect 5-CR110-X amber (498), CosmoBio, Japan) according to the manufacturer instructions. Reactions were incubated for 2 hrs at 37° C., and quenched by a 4-fold dilution with SDS loading buffer (at a final concentration of 2% SDS, 10% glycerol, 5% 2-mercaptoethanol, 0.002% bromphenol blue and 62.5 mM Tris HCl, pH 6.8). 3 μl of each reaction were loaded on an 18% bis:acrylamide gel and resolved with 25 mM Tris-192 mM Glycine-2% SDS running buffer (FIG. 7). Gels were scanned using FLA-5100 scanner (FUJIFILM).

Linear PCR fragments coding for rR with or without aptamer and ribozyme sequences, under T7 promoter but with no terminator sequence were incubated at a final concentration of 3 nM in transcription buffer (80 mM Tris-HCl pH7.8, 1 mM Spermidine, 2 mM DTT, 15 mM $MgCl_2$). The reaction was supplemented with rATP, rCTP, rGTP, rUTP each at 5 mM and 5 U/μl T7 RNA polymerase (NEB). Transcription reactions with rR-HDV or rR-Broccoli were supplemented with Aminoallyl-UTP-ATTO-488 or Aminoallyl-UTP-ATTO-647N, respectively (Jena Bioscience) to a final concentration of 16.6 μM. After 1 hr incubation at 37° C., reactions were quenched with SDS loading buffer and 5 μl were loaded on a 4-20% polyacrylamide gel (GeBa). Gels were run in 25 mM Tris-192 mM Glycine buffer and scanned using FLA-5100 scanner (FUJIFILM) (FIG. 7). For in-gel visualization, prior to scanning, the gel was washed 3×5 min with water and then stained for 10-30 min in 10 μM DFHBI-1T (Lucerna) in 40 mM HEPES pH 7.4, 100 mM KCl, 1 mM $MgCl_2$ (G. S. Filonovet al. Chem. Biol. 22, 649-60 (2015)).

Preparation of linear DNA fragments for DNA brushes: Linear double stranded DNA (dsDNA) fragments were synthesized and conjugated to streptavidin (SA, 50677, Sigma Aldrich) essentially as described in D. Bracha, et al., Acc. Chem. Res. 47, 1912-1921 (2014) and references therein. Briefly, a 5'-AlexaFluor647 F-primer (IDT) positioned ~200 bp upstream to the T7 promoter and 5'-biotin R-primer (IDT) positioned downstream to the T7 terminator were used to amplify genes by PCR with KAPA HiFi HotStart ReadyMix (KAPA BIOSYSTEMS). The distance of 5'-Biotin primer from the T7 terminator was variable, depending on gene length, to obtain similar overall length of ~1700 bp for all DNA fragments, except for rR, which was 2400 bp long. Non-coding DNA was prepared similarly to coding DNA but without the T7 promoter. Biotinylated DNA was conjugated to SA at a 1:1.4 ratio at a final concentration of 150 nM in 0.01 M phosphate buffered saline (NaCl 0.138 M; KCl—0.0027 M); pH 7.4 (1×PBS), supplemented with 7% glycerol to reduce evaporation at the following DNA surface deposition. Linear DNA fragments coding for GFP-uv3 under a T7 promoter, with a SecM arrest sequence were amplified from the plasmid pETC1 (S. Uemura et al., Nucleic Acids Res. 36, e70 (2008).

Ribosome preparation: The rP L9 of the LSU was cloned into plasmid pRSFduet under control of T7 promoter/lac operator. An HA peptide sequence was cloned at its C-terminus. L9-HA was overexpressed in BL21 (DE3) grown in LB by induction with 1 mM IPTG at OD600 of 0.25-0.35 for 3 hours. Cell lysis and ribosome purification were performed similarly to the method described in A. Trauner, et al., PLoS One. 6, e16273 (2011). Frozen cells were resuspended in Ribosome Buffer (10 mM Tris-HCl, 70 mM KCl, 10 mM $MgCl_2$, pH ~7.8), disrupted by short sonication on ice (Sonics VCX750 Vibra Cell, tapered microtip, 40% amplitude, 5-15 second pulses, 60 second total sonication) and further lysed by passing through a French Press at 15 kPSI and 4° C. The lysate was filtered and loaded on a quaternary amine monolith column (CIMmultus™ QA-8 ml, BIA separations). After washing with Ribosome Buffer (RB)+0.35 M $NH_4Cl$, ribosomes were eluted by a gradient of 0.35-0.45 M $NH_4Cl$ in RB. Ribosome fractions were collected and concentrated on a VivaSpin 20 10 kDa MWCO concentration membrane (Sartorius), with buffer exchange to RB. Batches were brought to a final concentration of 20-25 μM, measured by UV absorption at 260 nm with an extinction coefficient of 4.2-107 M-1, in RB+30% glycerol, frozen in liquid $N_2$ and stored at −80° C.

Biochip Preparation

Photosensitive biocompatible monolayer coating: The protocol to form a photosensitive and biocompatible monolayer coating on fused-silica slides was described elsewhere (D. Bracha, et al., Acc. Chem. Res. 47, 1912-1921 (2014). Briefly, fused-silica slides (24×24×1 mm, UQG Optics) were cleaned in boiling ethanol (10 min) followed by sonication (10 min) and base piranha cleaning ($H_2O_2$:$NH_3$:$H_2O$; 1:1:4, heated to 70° C. for 10 min). The slides were then coated with a polymer composed of a polyethylene glycol backbone with a protected amine at one end, and a triethoxysilyl group at the other end. The slides were incubated with the polymer, dissolved in toluene (0.2 mg/mL), for 20 min, rinsed with toluene and dried.

UV patterning: The coated slides were exposed to 365 nm UV light (2.5 J/$cm^2$) through a custom photomask with an array of 40 μm hexagons (CAD/Art Services) using UV-KUB (Kloe) (FIGS. 5A-E). The saturating UV dose fully deprotected surface amines inside hexagons. Surface amines located between hexagons were 53% deprotected due to leakiness of the mask (FIGS. 5A-E). Biotin N-hydroxysuccinimidyl ester (biotin-NHS, Pierce) dissolved in borate buffer to a final concentration of 0.5 mg/mL, was applied to the surface for 40 min and reacted with exposed amines. The slides were then washed with water and dried.

Biochip prism mounting and Chamber preparation: The slides were fixed on custom fused silica prisms (Zell Quarzglas and Technische Keramik) with adhesive cut out of Frame-Seal Slide Chambers (Bio-Rad). The slit between prism and slide was filled with index-matching liquid (Cargille) before experiments. Rectangular chambers were cut in thin PDMS sheets (100±30 μm) or in adhesive tape (50±5 μm) depending on the desired height. The surface area of the chamber was of the order of 1 $cm^2$ depending on the specifics of each experiment.

DNA brush layout and deposition: Equimolar solutions of SA-conjugated linear DNA constructs were mixed at equal amounts according to the gene content, e.g. a mixed DNA solution of genes coding for S17, S4 and S20 had 33% of each. The exception was the central brushes with a mix of rP-HA and rR genes. An optimal ratio to obtain the highest rR signal was found empirically to be 1:9 rR:rP-HA (FIGS. 9A-C). Nano-liter droplets of these mixes were deposited in an automated way onto the biotin-patterned surface within the PDMS chamber using GIX Microplotter II (Sonoplot Inc., Middleton, Wis.) and 60 μm diameter micropipettes (FIGS. 6A-C). Every DNA mixture was deposited between 5-7 times in each brush configuration to increase the concentration of expressed rPs. Droplets were incubated overnight in a humidity-controlled chamber to allow formation of dense DNA brushes. The spatial arrangement of the different brush configurations in the chamber was usually randomized and modified between experimental repeats.

Antibodies and ribosome deposition: Biotinylated Anti-HA-Biotin antibodies (50 mg/ml, High Affinity, 3F10 clone, Roche) were mixed with SA at a molar ratio of 1:1.5 in 1×PBS and incubated 30 minutes on ice, followed by dilution to 50 nM in 1×PBS. SA-anti-HA conjugates were applied to the chamber without prior rinsing of the DNA droplets to prevent smearing of SA-DNA on the surface. The chamber was washed several times with 1×PBS followed by rinsing with 50 mM Potassium-HEPES buffer pH 7, never drying the surface.

For experiments with surface-bound ribosomes, the chip was washed with RB after antibodies deposition and incubation, and then replaced by a 2 μM solution of purified ribosomes in RB, of which ~100-200 nM were estimated to be modified with L9-HA. After further 2-hour incubation at 4° C., the chamber was washed intensively with RB to remove non-specifically adsorbed ribosomes.

On-chip cell-free gene expression reactions: The chip was positioned on a temperature-controlled holder set at 17° C. placed on an upright microscope (Olympus BX51WI). Humidity in the room was reduced to avoid condensation on the prism. The Potassium-HEPES buffer in the chamber was exchanged with PUREfrex® 2.0 (rinsing four times with 40 μL of PUREfrex), supplemented with Polyethylene glycol (PEG) 8000 and DFHBI-1T (Lucerna, NY) at final concentrations of 4% and 60 μM, respectively. For direct in situ labeling of rPs using unnatural fluorescent amino acids, the reaction was supplemented with Clover Direct ATT0655-X-AF amber (CosmoBio, Japan). On-chip expression reactions with some genes in the solution were supplemented with plasmids at a final concentration of 2 nM each, up to a total of 42 nM depending on the number of different plasmids added. Expression reactions with immobilized ribosomes were supplemented with 1 μM of purified SSU by sucrose gradient. The chamber was sealed with a glass coverslip and the temperature was then switched to 37° C. to initiate gene expression.

Imaging: The microscope was positioned on a motorized stage (Scientifica). It was equipped with optical filter sets for excitation at 488 and 647 nm and a fluorescent light source (EXFO X-Cite 120Q) to allow epifluorescence microscopy. Two-color Total Internal Reflection Fluorescence (TIRF) microscopy was performed by coupling two lasers (OBIS 488-150 LS and OBIS 647 LX, Coherent) into a single-mode optical fiber (Oz optics). The beam was then collimated and directed on the prism using a goniometer (Thorlabs) (FIGS. 5A-E). Epifluorescence and TIRF images were taken with Andor iXon Ultra camera (Andor Technology plc., Belfast, UK) and 10× Olympus objective. The stage, the microscope, the lasers and the camera were controlled by LabVIEW (National Instruments).

Data Analysis: Images were analyzed with ImageJ and Mathematica 11 (Wolfram Research). The fluorescent time traces were evaluated as described in FIG. 5D. When presented as color maps (FIGS. 3A-E, 4A-F, 12A-C, 15A-B, 18A-B), fluorescent signals were normalized by the maximal signal obtained in each experiment. The time of initial signal detection to was determined for each gene configuration as presented in FIG. 5E. The maximal fluorescent signal $f_{max}$ of each dynamic trace was normalized by the highest $f_{max}$ that was obtained in each particular experiment. For example, in FIG. 1E and FIG. 2C, $f_{max}$ of each rP-HA was normalized by the $f_{max}$ of the S17-HA configuration. In FIG. 4A, each $f_{max}$ was normalized by the $f_{max}$ of the 2C/a1 configuration. For the Venn diagrams presented in FIGS. 3A-E and 4A-F, $f_{max}$ was normalized similarly to the color maps according to the maximal signal in each experiment. All values represent averages of 3 different experiments.

Results

The present inventors established an experimental scheme for autonomous self-synthesis of the *E. coli* small ribosomal subunit (SSU) in a minimal gene expression reaction on a chip, allowing for its observation in real-time and recreation of its assembly pathway (FIGS. 1A, 1B). This self-orchestrated pathway displays two signatures. One is the classification of rPs according to their binding dependence on the presence of other rPs, with the binding of secondary and tertiary rPs contingent on the pre-binding of primary and secondary binders (FIG. 1C); the other is the kinetic order by which rPs join the complex (13) (Table 3). They inferred on-chip SSU assembly in their cell-free system by identifying these signatures, allowing them to unravel features unique to SSU assembly coupled to synthesis.

TABLE 3

| On-chip self-synthesis rates, this study | | In vitro assembly rates with purified rPs (4, 13) | |
|---|---|---|---|
| Group | rPs | Group | rPs |
| 1 | S4, S17, S20, S8 | B1 | S4, S17, S20, S8, S16 |
| A2 | S7, S15, S9, S18, S13 | B2 | S6, S15, S18 |
| | S10, S19, S6, S16, S11 | B3 | S7, S9, S10, S11, S19 |
| A3 | S21, S5, S3, S14 | B4 | S3, S5, S12, S13, S14 |
| A4 | S12, S2 | B5 | S2, S21 |

Groups of rPs Based on rR Binding Dynamics.

The SSU rPs are organized in 4 groups (A1-A4) based on the on-chip assembly timeline presented in FIG. 1F, and compared to 5 groups (B1-B5) of binding kinetics with purified rPs (4, 13). Groups A1, B1 are of early binders, A2, B2, B3 intermediate, A3 and B4 early-late, and A4 B5 late binders. Underlined are rPs that were found to be in groups that do not correspond kinetically.

Figure 5A:
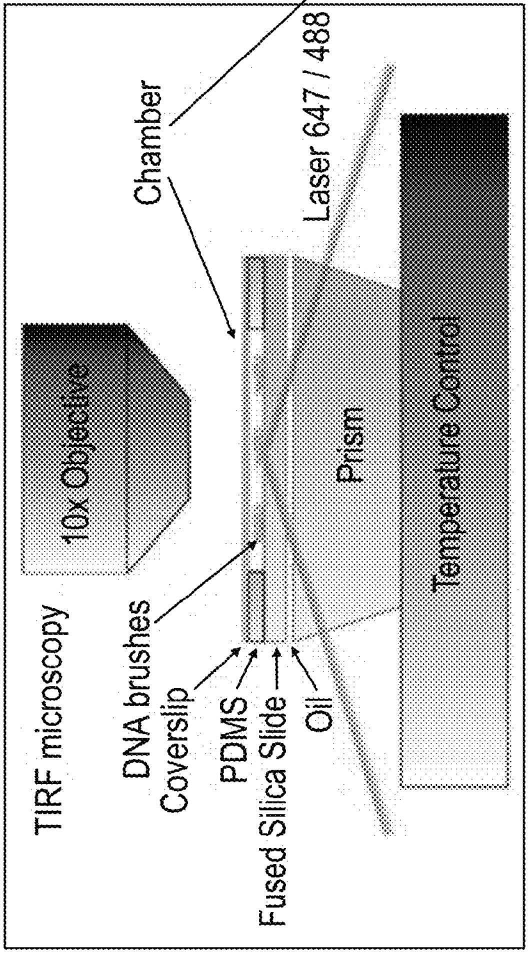
Figure 5B:
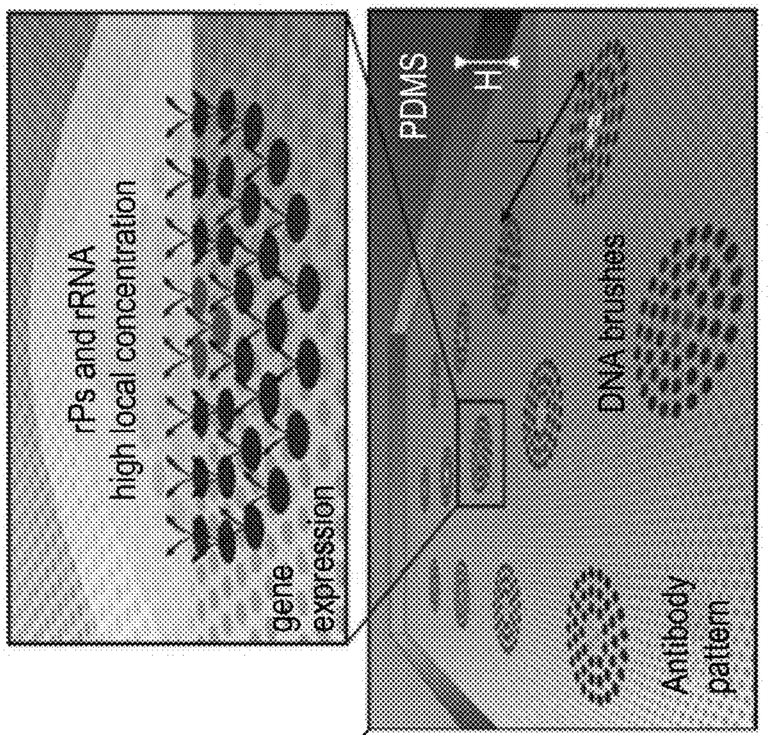
Figure 5C:
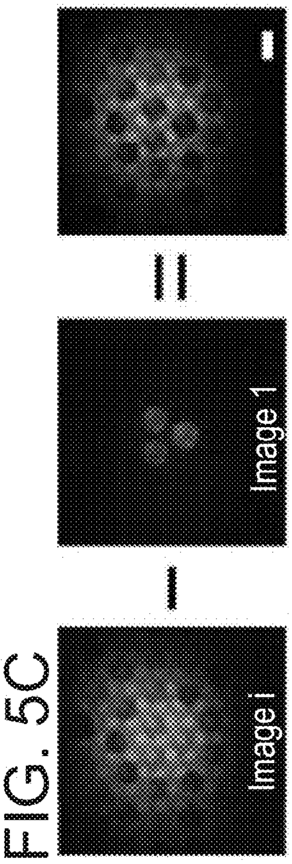
Figure 5D:
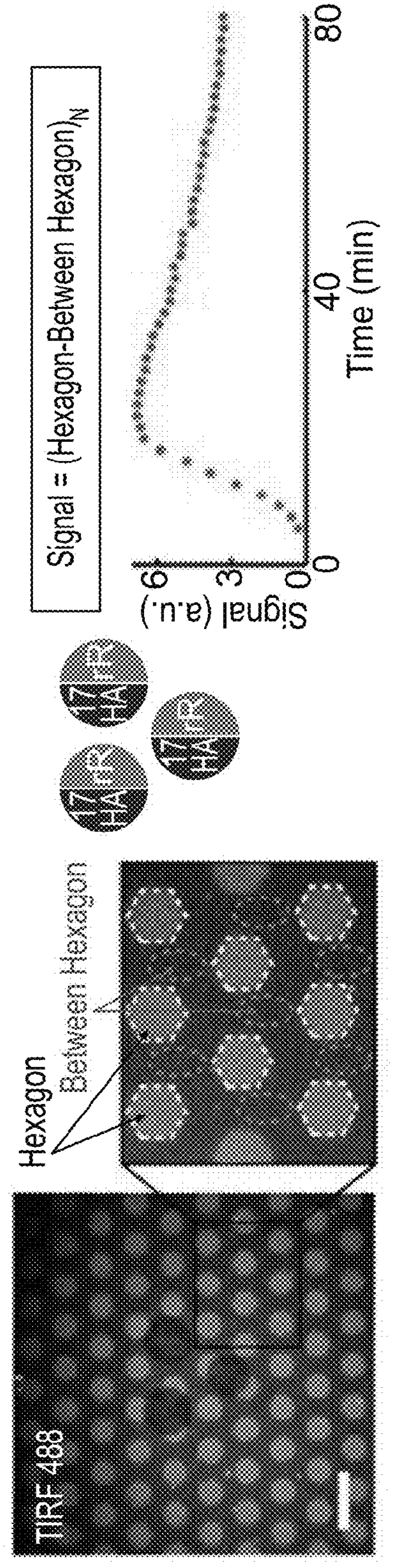
Figure 5E:
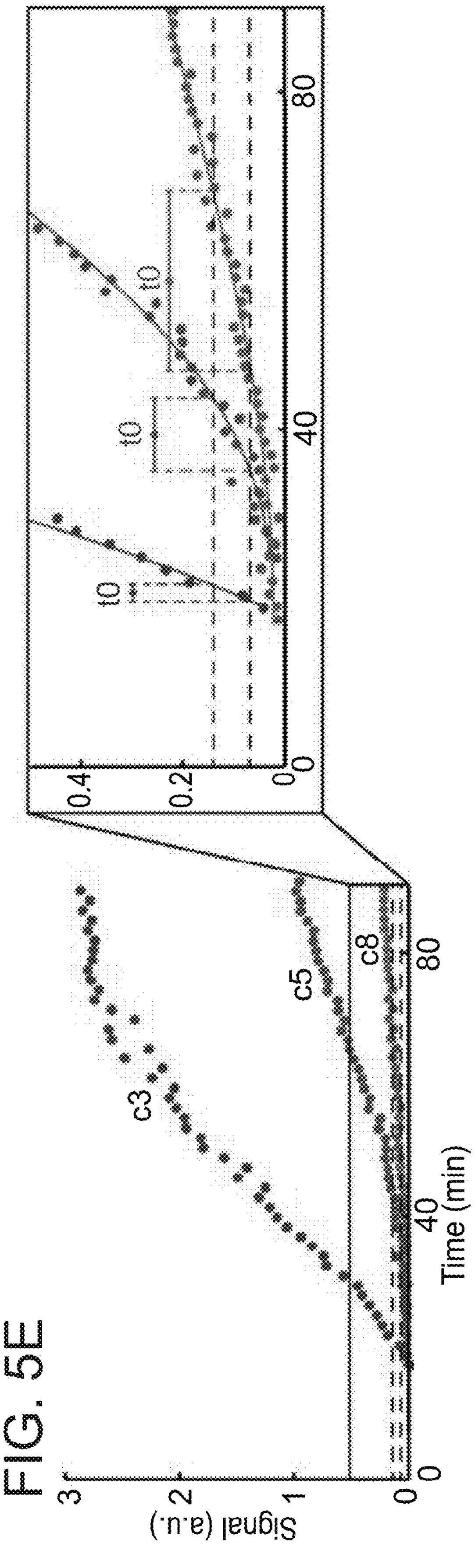

The key factor to successful assembly was the surface immobilization of highly dense DNA brushes(14) coding for all SSU components: 20 rPs (S2-S21), one rR (16S) and 6 assembly cofactors, that have been shown to promote in vitro SSU assembly(10, 15) (FIGS. 5A-E and 6A-C). DNA brushes localize the transcription-translation machineries (RNA polymerase and ribosome, respectively), becoming a local source for rPs and rR products(16, 17). Thus, despite the minute amount of DNA in the bulk reaction, on the order of 1 pM, gene expression products are localized at sufficiently high concentrations to drive interactions. All the genes were grouped in discrete DNA brushes according to the SSU assembly map (FIG. 1C) with one of the rPs tagged with an HA peptide (rP-HA, FIG. 7, Table 2), targeting it to surface-immobilized anti-HA antibodies for further localization and sensitive detection by Total Internal Reflection Fluorescence (TIRF) imaging (SM). The rP-HA gene was mixed in the 3 central brushes with rR genes, modified at Helix 6 with a Broccoli-aptamer for its in situ labeling (18, 19), and a ribozyme sequence for synthetic processing by self-cleavage(20) (FIGS. 8A-C). They added a minimal expression reaction mix made from purified components (21), supplemented with a molecular crowding reagent found to enhance multi-component interactions(22) (FIGS. 9A-C), and heated the chamber to 37° C. A rR fluorescent signal appeared, propagating radially from the 3 central brushes and accumulating on surface antibodies in a hexagonal pattern that help identifying specific signals with high sensitivity (FIG. 1D, FIG. 5D). The signal signified rR binding to the rP-HA on the surface since it was sensitive to the rP-HA:rR genes ratio within the central brushes, reducing to background levels in the absence of rP-HA genes (FIG. 9B, C). Thus, binding of fluorescent rR to surface antibodies was mediated by the rP-HA.

This brush layout was repeated 20 times on the same surface (FIG. 1B), each layout containing a different central rP-HA, with the central rP not included in the surrounding brushes. For each rP-HA layout, the present inventors plotted the kinetics of the emerging hexagonal patterns (FIG. 1E, FIG. 5D) and recorded both the onset time ($t_0$) of initial detection (FIG. 5E), and the maximal fluorescent signal ($f_{max}$) (FIG. 1E). The $f_{max}$ values were broadly consistent with the well-established binding dependencies of rPs (FIG. 1C, E) implying that each of the rPs was synthesized in the minimal cell-free reaction in a competent form to bind the rR, and that binding of secondary and tertiary rP-HAs was mediated by the non-HA tagged rPs. Aligning all $t_0$ from fast to slow outlined a kinetic timeline for SSU cell-free self-synthesis (FIG. 1F), unraveling 4 kinetic binding groups, with $t_0$'s highly overlapping within a group, which is consistent with previously observed multiple assembly pathways due to competition of rPs binding to rR (4, 13, 23). For the most part, the $t_0$'s timeline was consistent with in vitro assembly rates measured with purified rPs(4, 13), with a few deviations (Table 2). For example, in the present system, S16 was found to bind slower than the rest of the 5' domain rPs, while S13 assembled much faster than the rest of the secondary 3' domain rPs. These differences may stem from the presence of assembly cofactors and the coupling of SSU assembly to rP and rR synthesis in the present system.

Next, the present inventors verified that surface confinement was an essential pre-requisite for successful assembly by repeating the experiment with only r-RNA genes immobilized on the surface, while r-proteins genes were added to the cell-free reaction bathing the surface (FIG. 21). Despite the addition of high DNA concentrations to the cell-free reaction, on the order of 40 nM, appreciable signals of r-RNA around its brushes were detected only when primary r-protein (S17-HA) but not tertiary genes (S2-HA) were used, as the latter requires the interaction of 20 different r-proteins with the r-RNA. Mixing S17-HA genes with genes coding for a non-ribosomal protein decreased the r-RNA signal, most likely due to saturation of the gene expression machinery. On the other hand, synthesis of ribosomal parts from brush layouts, that are at 70 pM, could reach sufficiently high local concentrations without saturating the expression machinery, suggesting that even more genes could potentially be added. In addition, the effect of brush arrangements was tested within a layout on r-RNA binding to S10-HA (FIGS. 22A-M), always keeping the number of brushes constant. A drop in the signal was observed when the radius of layout was increased, but was not affected by reshuffling brushes, suggesting that assembly yield was determined by the local concentration of r-proteins and r-RNA above each layout, dictated by the DNA density on the surface.

The present inventors also performed rP gene deletion experiments to reveal which rPs mediated the binding of rR to rP-HA. They did so in the absence of assembly cofactors, and in a bulk reaction chamber twice as thick, to reduce overall concentrations (Table 4), allowing them to observe rR:rP-HA that are exclusively contingent on the presence of rPs.

TABLE 4

Figures 3A, 3B:
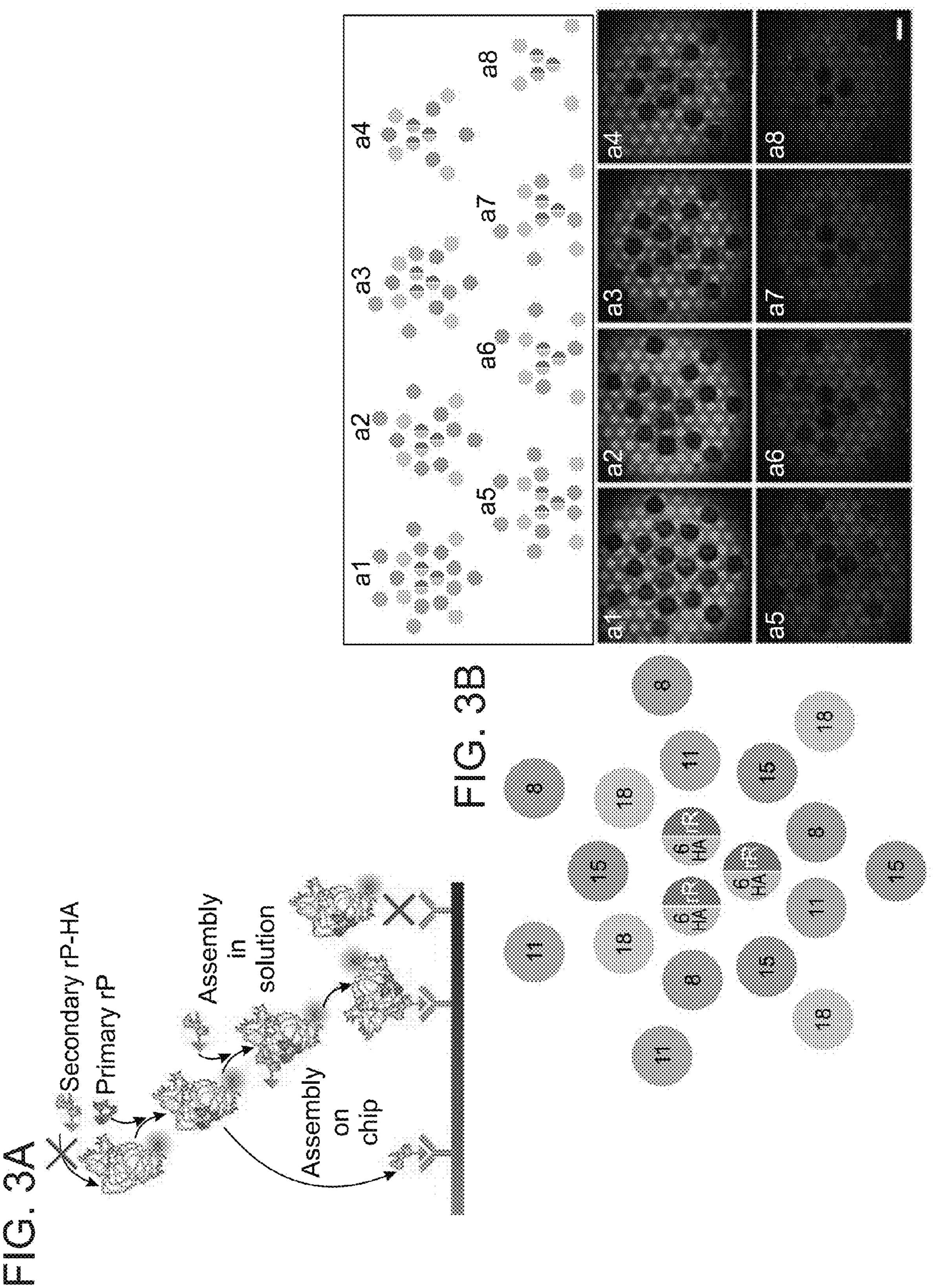
Figure 3C:
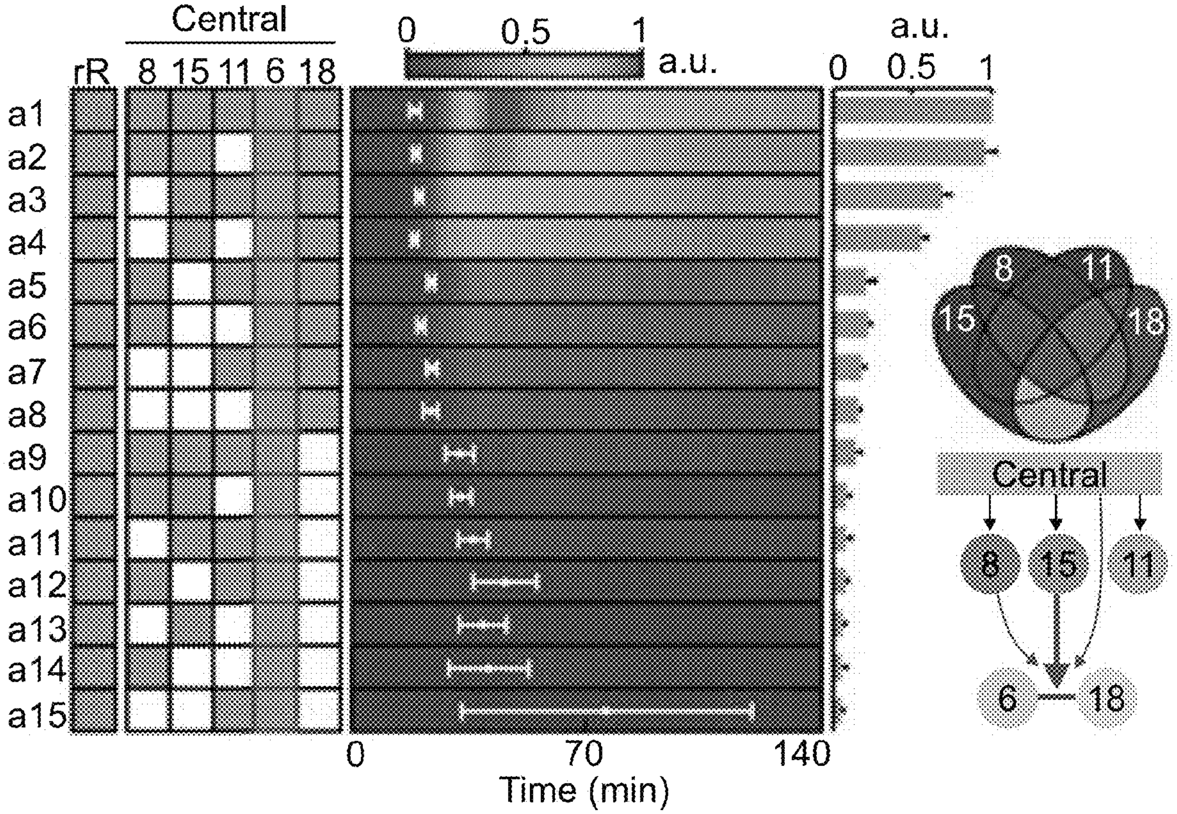
Figure 3D:
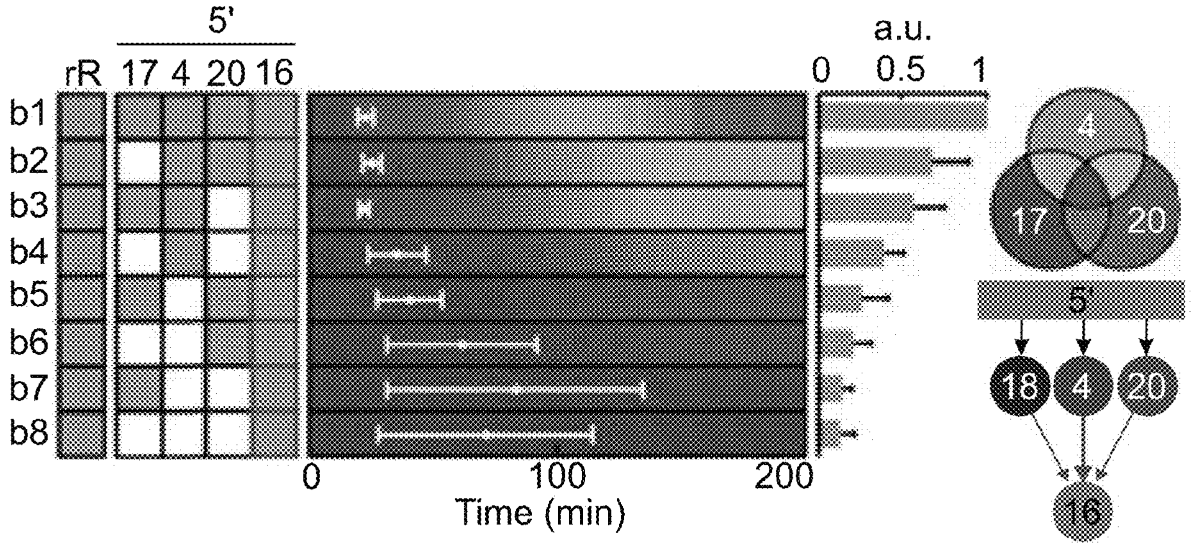
Figure 3E:
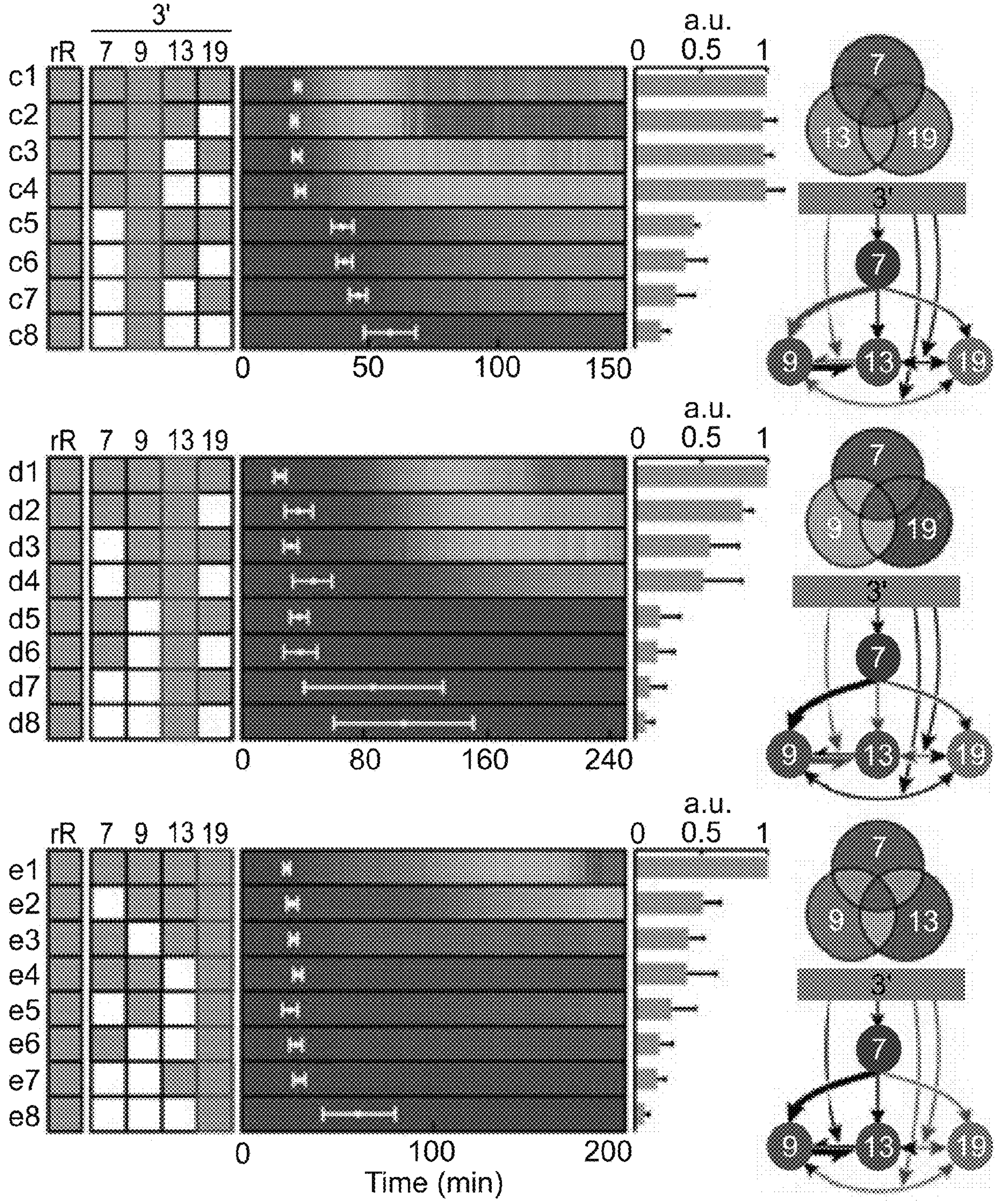
Figure 4A:
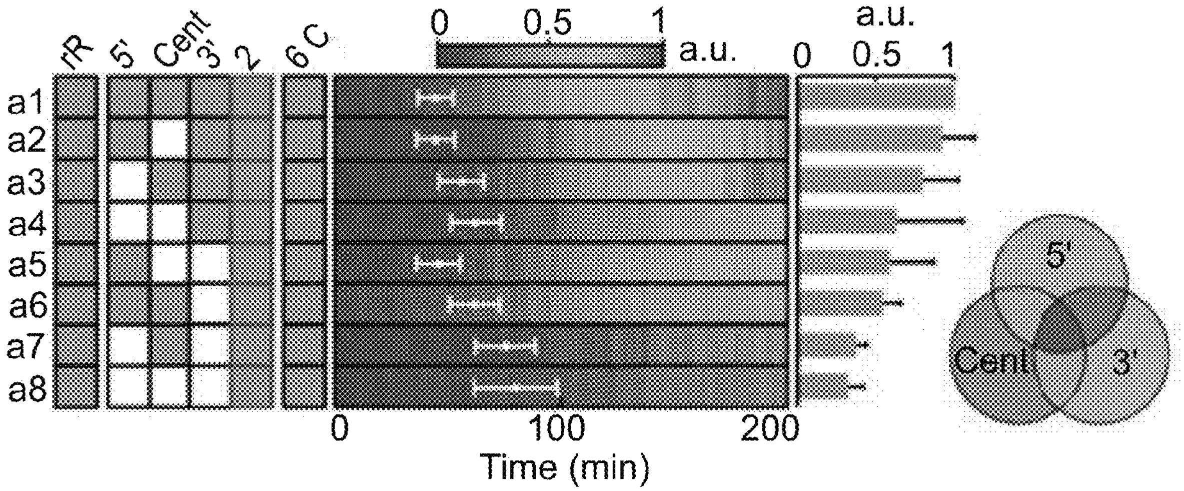
Figure 4B:
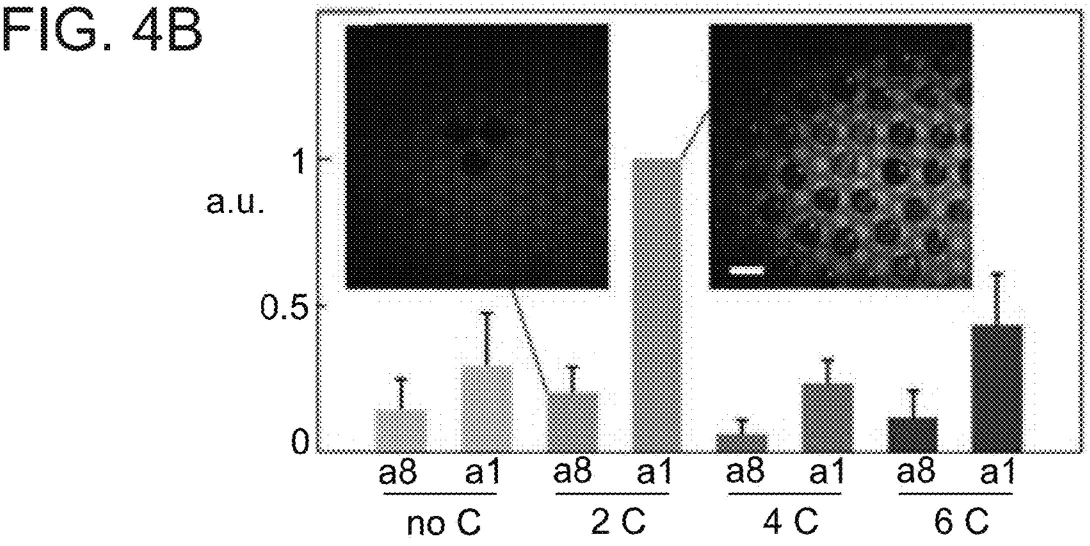
Figure 4C:
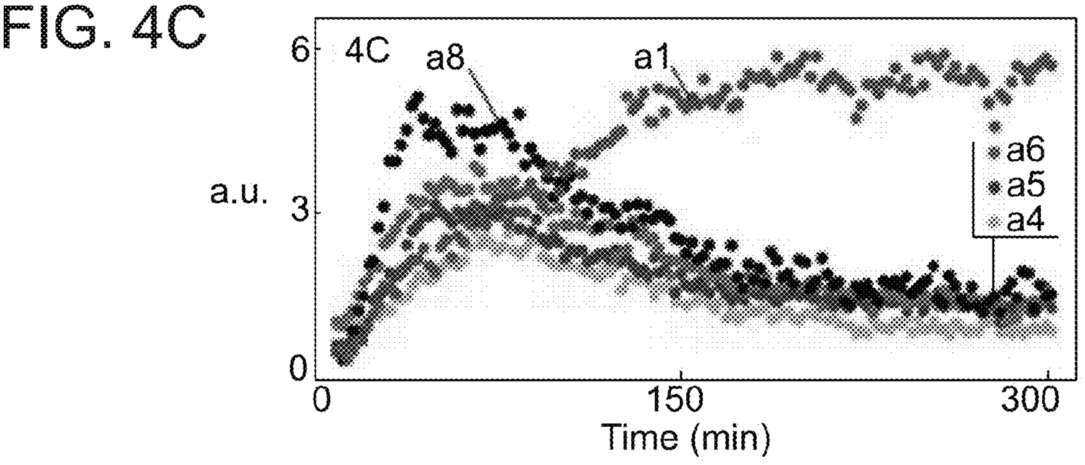
Figure 4D:
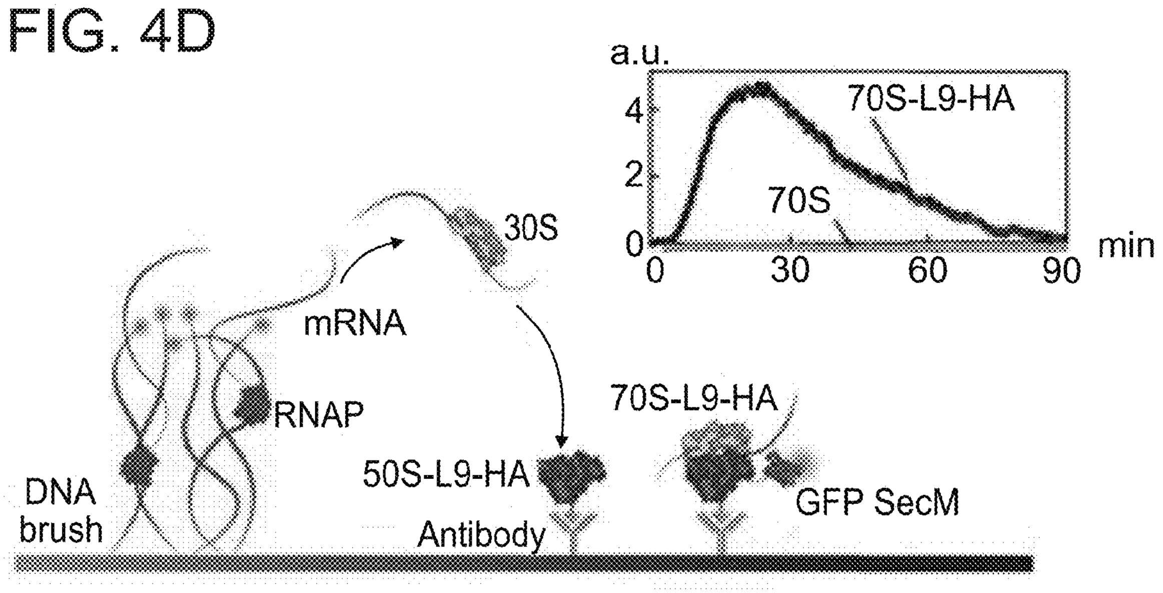

| Experiment | Number of genes | Configuration diameter D (μm) | Center-to-center distance between nearest configurations ($L_X$, $L_Y$) (mm) | Chamber height H (μm) | Estimated time of diffusion between configurations* $t_{max} = L^2/4D_0$ (min) |
|---|---|---|---|---|---|
| FIG. 1E | 2 | 120 | (2, 2) | 100 | 330 |
| FIG. 1F | 27 | 840 | (2.5, 3) | 50 | 520 |
| FIG. 2 | 2 to 6 | 540 | (2.5, 2.5) | 100 | 520 |
| FIG. 3A | 8 to 27 | 840 | (4, 4) | 50 | 1330 |
| FIG. 3B | 2 to 27 | 840 | (2.7, 6) | 50 | 600 |
| FIG. 3C | 6 to 25 | 840 | (4.3, 4.3) | 50 | 1540 |
| FIG. 3E | 7 to 28 | 1080 | (3.5, 3.5) | 50 | 1020 |
| FIG. 4A | 2 | 120 | (2.5, 2.5) | 50 | 520 |
| FIG. 4B | 26 | 840 | (2.5, 3) | 50 | 520 |
| FIG. 4C | 21 | 840 | (2.5, 3) | 50 | 520 |

*To avoid crosstalk between brush configurations in the same chamber due to diffusion of molecules, we calculated the time $t_{max} = L^2/4D_0$ for a typical rP to diffuse a distance L separating two configurations (center-to-center), with $D_0 = 50\ \mu m^2/s$, an estimated diffusion coefficient of a typical rP. The experimental analysis was always performed for $t < t_{max}/2$.

Although the use of fluorescently labeled rPs could directly demonstrate their participation in the assembly reaction (FIG. 10), the present inventors continued to use the rR to quantitatively compare between different brush layouts (FIG. 1B). They first deleted all rP genes and monitored the intrinsic interaction of each rP-HA with the rR in a minimal two-body interaction (FIG. 2A,B). In complete agreement with the assembly map (FIG. 1C), the highest signals were obtained for the primary rP-HAs, and much lower yet measurable signals for the secondary and tertiary rPs, (FIG. 2C, FIG. 11), suggesting that each of the rPs has an intrinsic affinity to the rR, that is enhanced by the rest of rPs (FIG. 1E).

The on-chip expression reactions, programmed by genes, allowed the present inventors to investigate interdependencies of rPs binding to rR in a simple parallel high-throughput fashion (FIGS. 3A-B). They scanned all possible primary and secondary rP combinations within the 5', central, and 3' domains for mediating rR binding above the basal level of the two-body interactions (FIGS. 3C-E, FIGS. 12A-C, FIGS. 13A-D, FIGS. 14A-I). Each of these domains has been previously shown to assemble in vitro in the absence of others(24-26). In general, the present data demonstrated that the 5' and 3' domains were formed stably onto their respective rPs (S6-HA for 5'; S9-HA, S13-HA, and S19-HA for 3'), while the signal of the central domain (S6-HA) was unstable and decreased after an initial accumulation (FIG. 3C).

Comparison of the kinetic profiles within each domain revealed interdependencies of binding, which for the most part adequately matched those previously documented, with some new features uncovered. For example, the present analysis revealed that the binding of rR to S6-HA is highly dependent on the presence of S18, which has been shown to form a dimer with S6(27), and that as a dimer, S18:S6-HA were able to bind the rR in the absence of other rPs (FIG. 3C). Consistent with the assembly map, rR binding to S18:S6-HA was highly dependent on the presence of S15 and increased non-additively with the addition of S8, suggesting a cooperative binding mode(1, 28). It was further found, consistent with previous work(29) that addition of S4, or to a lesser extent S20, facilitated the rR binding to S16-HA, and their combinations increased the signal additively (FIG. 3D). Interestingly, the presence of the 3' secondary rPs may replace S7 in stabilizing the subdomain (FIG. 3E) as evident by a strong signal of rR binding to S13-HA or S19-HA in the absence of the primary S7. Some of the stable combinations that were detected in the absence of S7 have been previously observed (30). From the analysis of binding dependencies among primary and secondary rPs, it was inferred that three-body (e.g. S9-HA:S7:rR) and four-body (e.g. S6-HA:S18:S15:rR) complexes were formed on the chip.

S2-HA was one of the two slowest binders in the present on-chip reaction (FIG. 1F), signifying late stages of SSU assembly, and therefore its binding dependencies were analyzed by deletions of groups of rPs and assembly cofactors (FIGS. 4A-C, FIGS. 15A-B and 16A-C). In the presence of the 6 cofactors, the strongest signal was obtained with all rPs present, and to a lesser extent with the 5' or 3' only, but not the central rPs (FIG. 4A). The assembly of S2-HA with rPs of the 3' domain is consistent with previous observations (26).

The cofactors were separated into 2 groups, GTPases (Era, RsgA, 2C), and non-GTPases (RbfA, RimM, RimN, RimP, 4C) (FIG. 4B), and observed that inclusion of rPs always enhanced the stability of the rR:S2-HA interaction. Interestingly, the 4C group exhibited an inhibitory effect on the rR:S2HA interaction, with a much higher signal obtained for the 2C compared to the 6C combination (FIG. 4B). In addition, the signal obtained with 2C but no rPs was similar to that obtained with rPs but no cofactors, and was double in the presence of both, suggesting that their mutual effect is cooperative. The 2 GTPases were removed from the domain deletion analysis in order to reveal the intrinsic stabilizing effect of the rPs (FIG. 4C, FIGS. 16A-C) and found that only in the presence of all rPs, a stable interaction was observed. In all other deletion combinations, the interaction onset time appeared at early time points but decreased with time, clearly demonstrating that participation of rPs from all domains was essential to obtain a stable SSU assembly. The unstable binding mode of rR:S2-HA that was observed in the absence of some rPs may represent an unstable intermediate, reminiscent of an interesting in vivo observation of early S2 binding to nascent rR co-transcriptionally(31). Taken together, these results imply that rPs and assembly cofactors may be considered as rR stabilization factors, with rPs having lower dissociation rates than assembly cofactors.

Figure 4E:
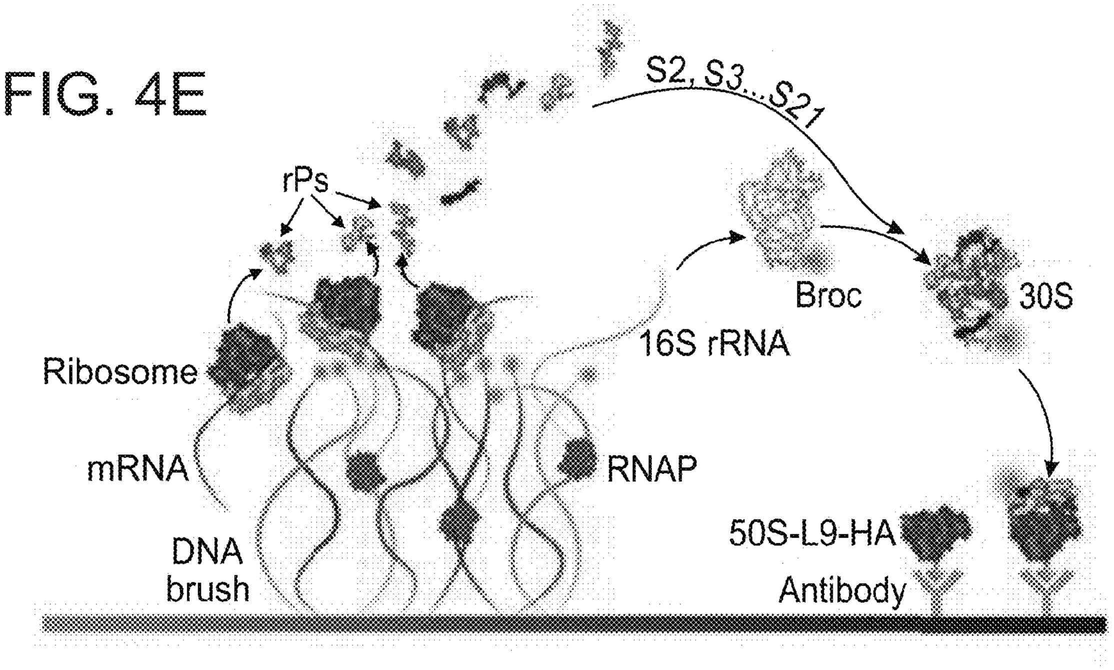
Figure 4F:
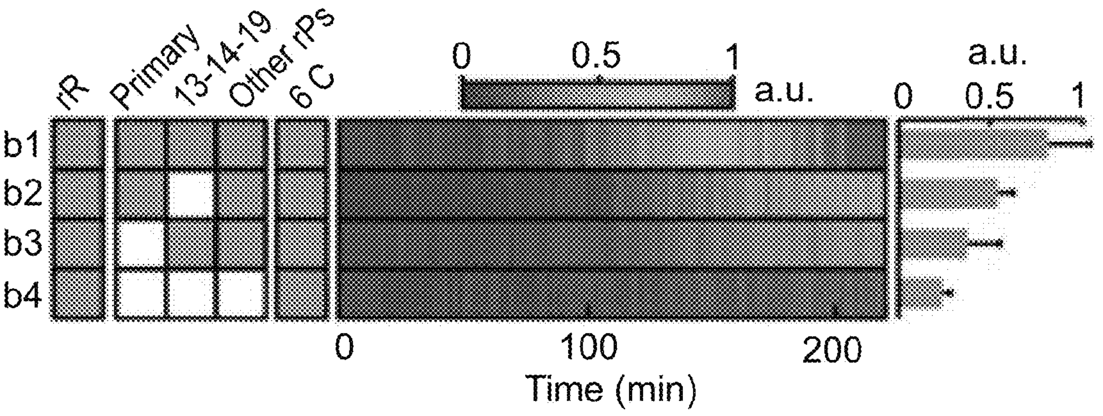

As one of the hallmarks for correct SSU assembly, the present inventors looked for the ability of de novo synthesized SSU to interact specifically with the LSU(3). To that end, purified ribosomes(32) modified with an HA tag on LSU's rP L9 (L9-HA, SM), were bound to surface antibodies in patterned hexagons (SM, FIGS. 17A-D). In a preliminary experiment (FIG. 4D), these surface ribosomes surrounded DNA brushes coding for GFP with a SecM translation pause sequence (GFP-SecM) (33). Addition of a cell-free gene expression reaction lacking ribosomes resulted in a fluorescent signal appearing on the hexagonal pattern (FIG. 4D, inset, FIGS. 17A-D), suggesting that mRNA produced in DNA brushes diffused and bound to surface ribosomes, leading to GFP synthesis. More control experiments (FIGS. 17A-D) confirmed the conclusion that surface-bound ribosomes maintained their activity. Replacing the GFP-secM gene brushes with those coding for rR and all rP genes, including S1, but no rP-HA, resulted in a clear rR signal on the immobilized ribosomes pattern (FIG. 4E, F, FIGS. 18A-B). A two-fold decrease in signal was observed when either primary rPs or the inter-subunit bridge-forming rPs(34) were deleted, suggesting that an inter-subunit bridge was formed between the nascent SSU and the immobilized LSU.

Finally, the robustness of the methodology to study SSU assembly of the pathogenic bacterium *S. aureus* was challenged. With no prior knowledge of the assembly pathway and in a completely bio-safe procedure independent of purified r-proteins, using only synthetic genes, the analysis revealed a pattern of primary r-proteins different than the *E. coli* signature (FIG. 19A), with S20, S7 and S8 displaying very low signals and S12 and S13 appearing as clear primary binders. Addition of all other r-protein genes and 5 genes of putative *S. aureus* assembly factors changed the binding pattern to resemble more of the *E. coli* one, with some differences. For example, *E. coli* SSU assembly was dominated by the signal of several primary 5' and central domain r-proteins, while that of *S. aureus* was dominated only by S17 (compare FIG. 19B and FIG. 1E). Despite the great resemblance of final structure of the two SSUs(38), the assembly pathways seem to differ.

Figure 19A:
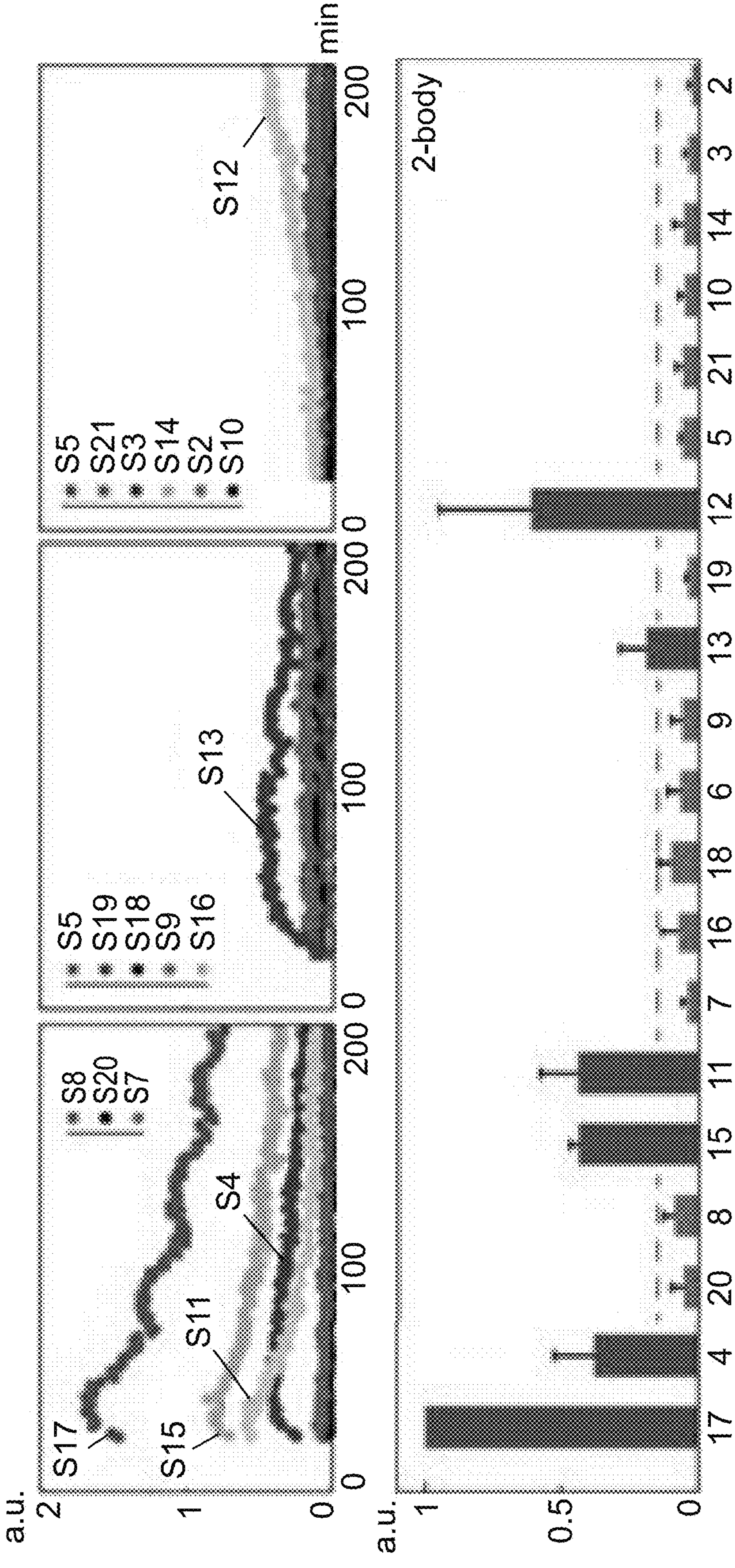
Figure 19B:
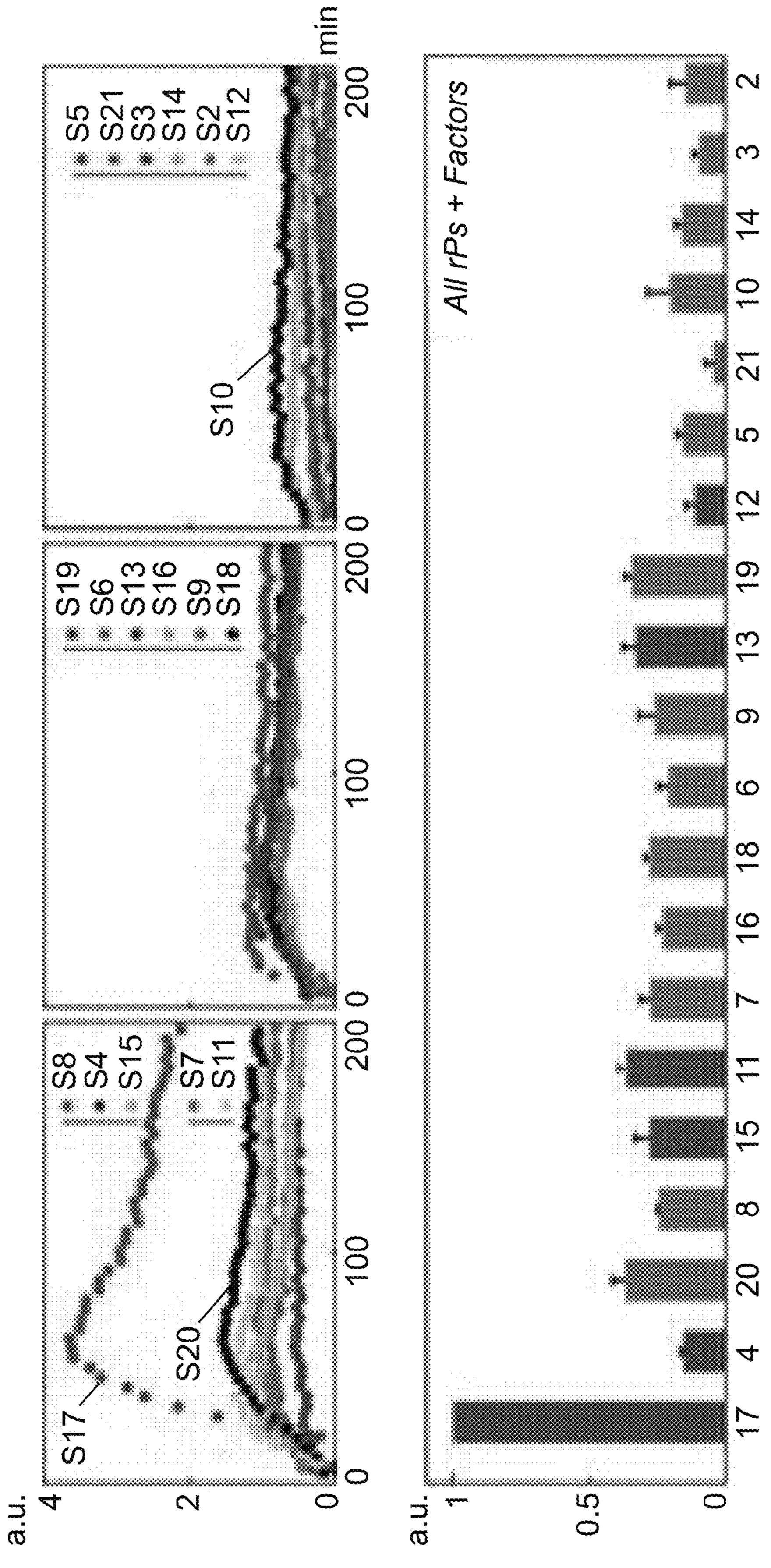
Figure 19D:
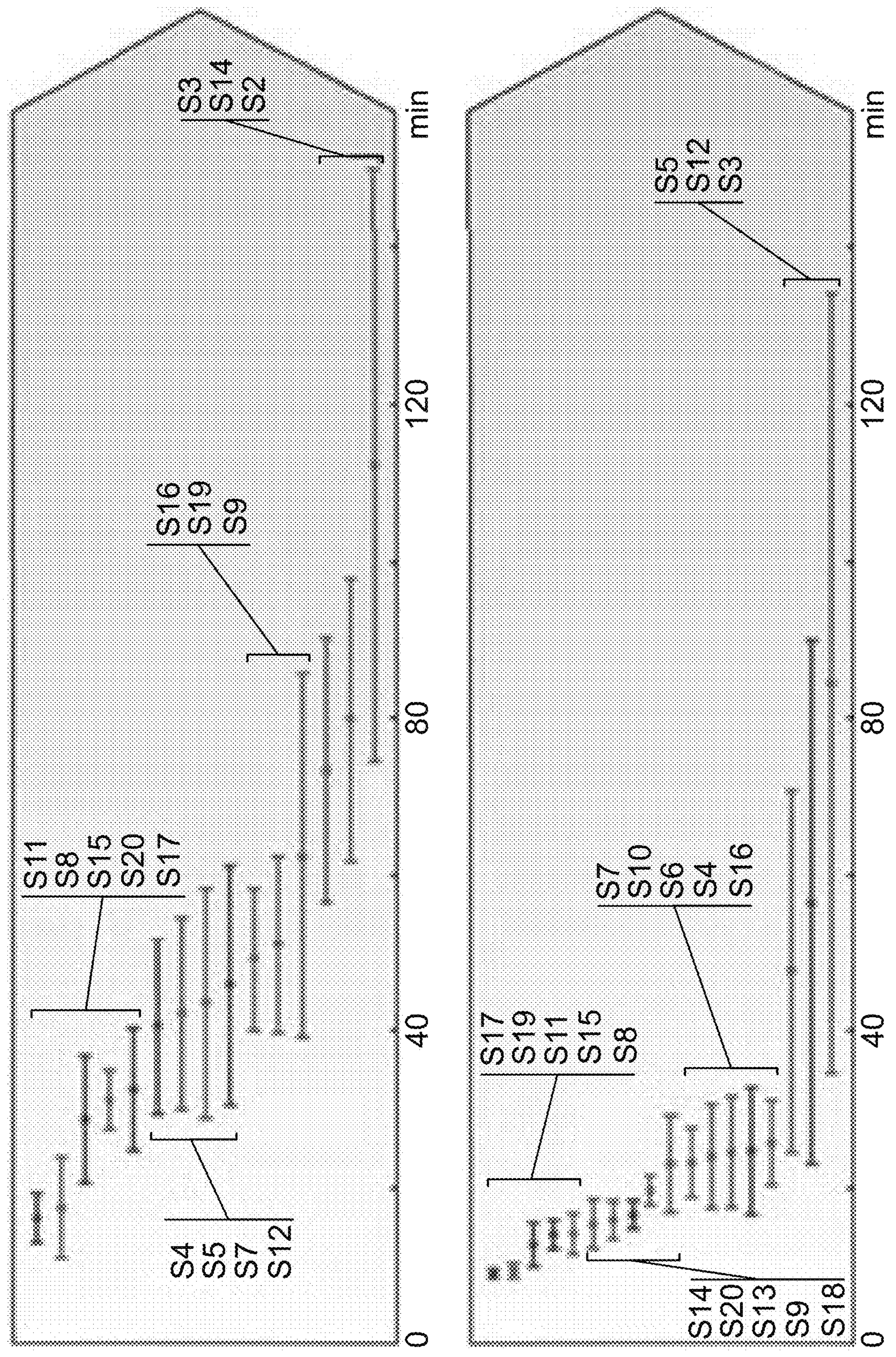

In order to find out whether the putative *S. aureus* assembly factors were participating in the assembly process, the experiment was repeated in their absence. It was found that the S17's $f_{max}$ was no longer dominating (FIGS. 19C, 20). Several other r-proteins, even non-primary such as S5 and S14, displayed higher $f_{max}$ signals than S17. The emergent notion that assembly factors were shaping the assembly pathway was also evident in the assembly dynamics. In the absence of factors, the kinetic traces of r-RNA binding did not reach $f_{max}$ values even after 100 minutes, except for very few r-proteins such as S8 and S11, while almost all reached saturation in less than 100 minutes in their presence (FIGS. 19B, C). The $t_0$'s analysis of *S. aureus* assembly revealed a compact timeline in the presence of the factors. By 20 minutes after the initial binding of S17, r-RNA binding of 15 of the 20 r-proteins initiated, while in their absence, initial binding spanned over 80 mins (FIG. 19D).

Taken together, the timelines of SSU assembly of both *E. coli* and *S. aureus* led the present inventors to conclude that the SSU was assembled on the chip in about 80 minutes (FIG. 1F, FIG. 19D), comparable to in vivo SSU re-assembly from disassembled r-proteins after a thermal shock or in previous in vitro SSU assembly systems. Additional assembly factors, absent from the current system, could be tested for stimulation of assembly rate. It can be speculated that further miniaturization of the reaction chamber dimensions may increase the overall assembly rate by further increasing the local concentration of reaction components.

As a future outlook, the genotype/phenotype linkage of brush layouts allows to screen for mutations in r-proteins and r-RNA, genetically encoded activities or small molecule drugs that could modulate ribosome assembly. Comparative dynamics of SSU assembly from different organisms are feasible, as well as attempting to assemble hybrid ribosomes. The assembly process of other multicomponent complexes such as proteasomes, replisomes, divisomes, and viruses could be studied. Symmetry breaking, inherent to the present setup, with newly assembled SSUs anchored to the surface spatially resolved from original ribosomes, may prove an advantage in attempting to assess the full functionality of de novo assembled subunits. The present approach should be able to support the synthesis of ribosomal parts of both the SSU and LSU, leading to the autonomous assembly of a full ribosome, a cornerstone for protein-based self-replicating artificial cells.

REFERENCES

1. W. A. Held, B. Ballou, S. Mizushima, M. Nomura, Assembly mapping of 30 S ribosomal proteins from *Escherichia coli*. Further studies. *J. Biol. Chem.* 249, 3103-11 (1974).
2. M. Herold, K. H. Nierhaus, Incorporation of six additional proteins to complete the assembly map of the 50 S subunit from *Escherichia coli* ribosomes. *J. Biol. Chem.* 262, 8826-33 (1987).
3. G. M. Culver, H. F. Noller, Efficient reconstitution of functional *Escherichia coli* 30S ribosomal subunits from a complete set of recombinant small subunit ribosomal proteins. *RNA*. 5, 832-43 (1999).
4. A. M. Mulder et al., Visualizing ribosome biogenesis: parallel assembly pathways for the 30S subunit. *Science*. 330, 673-7 (2010).
5. H. Kim et al., Protein-guided RNA dynamics during early ribosome assembly. *Nature*. 506, 334-338 (2014).
6. P. L. Luisi, F. Ferri, P. Stano, Approaches to semi-synthetic minimal cells: a review. *Naturwissenschaften*. 93, 1-13 (2006).
7. A. C. Forster, G. M. Church, Towards synthesis of a minimal cell. *Mol. Syst. Biol.* 2, 45 (2006).
8. V. Noireaux, Y. T. Maeda, A. Libchaber, Development of an artificial cell, from self-organization to computation and self-reproduction. *Proc. Natl. Acad. Sci. U.S.A* 108, 3473-80 (2011).
9. M. C. Jewett, B. R. Fritz, L. E. Timmerman, G. M. Church, In vitro integration of ribosomal RNA synthesis, ribosome assembly, and translation. *Mol. Syst. Biol.* 9, 678 (2013).
10. D. Tamaru, K. Amikura, Y. Shimizu, K. H. Nierhaus, T. Ueda, Reconstitution of 30S ribosomal subunits in vitro using ribosome biogenesis factors. RNA. 24, 1512-1519 (2018).
11. J. Li et al., Cogenerating Synthetic Parts toward a Self-Replicating System. *ACS Synth. Biol.* 6, 1327-1336 (2017).
12. S. A. Woodson, RNA folding and ribosome assembly. *Curr. Opin. Chem. Biol.* 12, 667-673 (2008).
13. M. W. T. Talkington, G. Siuzdak, J. R. Williamson, An assembly landscape for the 30S ribosomal subunit. *Nature*. 438, 628-632 (2005).
14. D. Bracha, E. Karzbrun, S. S. Daube, R. H. Bar-Ziv, Emergent Properties of Dense DNA Phases toward Artificial Biosystems on a Surface. *Acc. Chem. Res.* 47, 1912-1921 (2014).
15. B. Thurlow et al., Binding properties of YjeQ (RsgA), RbfA, RimM and Era to assembly intermediates of the 30S subunit. *Nucleic Acids Res.* 44, 9918-9932 (2016).

16. Y. Heyman, A. Buxboim, S. G. Wolf, S. S. Daube, R. H. Bar-Ziv, Cell-free protein synthesis and assembly on a biochip. *Nat. Nanotechnol.* 7, 374-8 (2012).
17. Y. Efrat, A. M. Tayar, S. S. Daube, M. Levy, R. H. Bar-Ziv, Electric-Field Manipulation of a Compartmentalized Cell-Free Gene Expression Reaction. *ACS Synth. Biol.* 7, 1829-1833 (2018).
18. M. Wieland, B. Berschneider, M. D. Erlacher, J. S. Hartig, Aptazyme-mediated regulation of 16S ribosomal RNA. *Chem. Biol.* 17, 236-42 (2010).
19. G. S. Filonov, C. W. Kam, W. Song, S. R. Jaffrey, In-gel imaging of RNA processing using broccoli reveals optimal aptamer expression strategies. *Chem. Biol.* 22, 649-60 (2015).
20. S. C. Walker, J. M. Avis, G. L. Conn, General plasmids for producing RNA in vitro transcripts with homogeneous ends. *Nucleic Acids Res.* 31, e82 (2003).
21. Y. Shimizu et al., Cell-free translation reconstituted with purified components. *Nat. Biotechnol.* 19, 751-5 (2001).
22. J. Garamella, R. Marshall, M. Rustad, V. Noireaux, The All *E. coli* TX-TL Toolbox 2.0: A Platform for Cell-Free Synthetic Biology. *ACS Synth. Biol.* 5, 344-355 (2016).
23. T. M. Earnest et al., Toward a Whole-Cell Model of Ribosome Biogenesis: Kinetic Modeling of SSU Assembly. *Biophys. J.* 109, 1117-1135 (2015).
24. C. J. Weitzmann, P. R. Cunningham, K. Nurse, J. Ofengand, Chemical evidence for domain assembly of the *Escherichia coli* 30S ribosome. *FASEB J.* 7, 177-80 (1993).
25. S. C. Agalarov et al., Structure of the S15,S6,S18-rRNA complex: assembly of the 30S ribosome central domain. *Science.* 288, 107-13 (2000).
26. R. R. Samaha, B. O. Brien, T. W. O. Brient, H. F. Noller, Independent in vitro assembly of a ribonucleoprotein particle containing the 3' domain of 16S rRNA. 91, 7884-7888 (1994).
27. M. I. Recht, J. R. Williamson, Central domain assembly: thermodynamics and kinetics of S6 and S18 binding to an S15-RNA complex. *J. Mol. Biol.* 313, 35-48 (2001).
28. R. J. Gregory et al., Interaction of ribosomal proteins S6, S8, S15 and S18 with the central domain of 16 S ribosomal RNA from *Escherichia coli. J. Mol. Biol.* 178, 287-302 (1984).
29. S. C. Abeysirigunawardena et al., Evolution of protein-coupled RNA dynamics during hierarchical assembly of ribosomal complexes. *Nat. Commun.* 8,492 (2017).
30. W. K. Ridgeway, D. P. Millar, J. R. Williamson, Quantitation of ten 30S ribosomal assembly intermediates using fluorescence triple correlation spectroscopy. *Proc. Natl. Acad. Sci. U.S.A* 109, 13614-9 (2012).
31. C. C. de Narvaez, H. W. Schaup, In vivo transcriptionally coupled assembly of *Escherichia coli* ribosomal subunits. *J. Mol. Biol.* 134, 1-22 (1979).
32. A. Trauner, M. H. Bennett, H. D. Williams, Isolation of Bacterial Ribosomes with Monolith Chromatography. *PLoS One.* 6, e16273 (2011).
33. S. Uemura et al., Single-molecule imaging of full protein synthesis by immobilized ribosomes. *Nucleic Acids Res.* 36, e70 (2008).
34. Q. Liu, K. Fredrick, Intersubunit Bridges of the Bacterial Ribosome. *J. Mol. Biol.* 428, 2146-64 (2016).
35. M. Tal, A. Silberstein, K. Møyner, In vivo reassembly of 30-S ribosomal subunits following their specific destruction by thermal shock. *Biochim. Biophys. Acta—Nucleic Acids Protein Synth.* 479, 479-496 (1977).

Example 2

Genetically Encoded Assembly-Lines in 2D Compartments Programmed by Geometry DNA Preparation Cloning of genes: Bacteriophage T4 wedge genes were amplified from the T4 GT7 genome (Nippon Gene, Japan) using appropriate primers (Table 5) and standard Polymerase Chain Reaction (PCR) with KAPA HotStart ready mix (Kapa Biosystems).

TABLE 5

| Gene | Forward | Reverse |
|---|---|---|
| Gp11 | ATGAGTTTACTTAATAATAAAGCG (SEQ ID NO: 52) | TGCTGTTCTCTCAAAATGATAAAATACTGTAGG (SEQ ID NO: 53) |
| Gp10 | ATGAAACAAAATATTAATATCGGTAATGTTG (SEQ ID NO: 54) | TGCAATCCTTATCCAACGATAAAC (SEQ ID NO: 55) |
| Gp7 | ATGACAGTAAAAGCACCTTCAGTCAC (SEQ ID NO: 56) | TTCATCTATTTTAACCTGTGTTGGATTTTCAGG (SEQ ID NO: 57) |
| Gp8 | ATGAATGATTCAAGTGTTATCTATCG (SEQ ID NO: 58) | AAATGTAAACAGAATATTGATTTCTTCTG (SEQ ID NO: 59) |
| Gp6 | ATGGCAAATACCCCTGTAAATTATC (SEQ ID NO: 60) | TTGTGATATAGGCTCCAAATCGATAG (SEQ ID NO: 61) |
| Gp53 | ATGCTCTTTACATTTTTTGATCCGATTG (SEQ ID NO: 62) | CTTATCATTTCCATAAGATTTCTCC (SEQ ID NO: 63) |

Primers were designed Using SnapGene software (GSL Biotech LLC). The Enhanced green fluorescent protein (eGFP) F64L/S65T mutant sequence was used in all experiments containing eGFP. The genes were cloned into plasmids pIVEX 2.6 and pIVEX 2.5 (5 prime) under control of the T7 promoter for N or C terminus HA-tagging, respectively using published restriction-free cloning protocols[22]. For T4 gene-6 containing a C terminus 6×His tag for protein purification, primers containing the tag (Table 5) were used in a PCR amplification followed by blunt end ligation.

For protein fluorescent labeling, a UAG amber stop codon was introduced into all T4 wedge genes as the second codon after the initiation AUG, using PCR amplification with mutated primers.

Plasmids were transformed into *E. coli* DH5α and purified using Wizard® SV-Gel (Promega) either at the miniprep or midiprep scale. Plasmid concentrations were determined using NanoDrop ND-1000 (NanoDrop Technologies, Inc./ThermoFisher Scientific).

Preparation of linear DNA fragments for DNA brush formation: Linear double strand DNA fragments were amplified by PCR, as above, with 0.1 ng/μl plasmid template and 300 nM of 5' modified forward and reverse primers (IDT), one conjugated to biotin (IDT), the other to a fluorescent marker (either ATTO 488\ATTO 647\ Alexa Fluor™ 647, IDT), respectively, following a published protocol[23]. Amplified fragments were purified by Wizard™ SV-Gel and PCR Clean-Up (Promega) and mixed with streptavidin (Sigma Aldrich) at a 1.5:1 ratio in 1× Phosphate buffer, saline (PBS), forming a DNA-streptavidin conjugate. DNA concentration was adjusted to 150-300 nM and glycerol (J.T.

Baker) was added to 5% final concentration to minimize evaporation during surface deposition. DNA-streptavidin conjugations were evaluated by 1% agarose gel electrophoresis.

Off-Chip Cell-Free Gene Expression

All proteins were expressed in an *E. coli* extract prepared according to published protocols[15]. Each reaction was supplemented with 5 μM $His_6$-GamS protein and 0.2 μM $His_6$-T7 RNA polymerase, that have been purified using published protocols[16,24]. Template DNA was added either as plasmids or linear fragments at a final concentration of 0.01-5 nM and 0.5-5 nM, respectively. Reactions were incubated at 30° C. and were either stopped by the addition of SDS loading buffer prior to resolution on denaturing protein gels, or by the addition of spectinomycin to a final concentration of 5 μg/ml and incubated for 30 min prior to resolution by native gels.

Fluorescent In Situ Labeling

Unnatural fluorescent amino acids were incorporated as the second amino acid in each T4 wedge gene by supplementing each 30 μl CFE reaction with 5 nM of plasmid DNA and 0.5 μl CloverDirect tRNA reagent with one of the following fluorophores HiLyte Fluor 488 AF, TAMRA-C6 AF, ATTO 633 and ATTO 655-X-AF (Cosmo Bio, Japan). Reactions were incubated at 30° C. for 2 hours and were used for post-staining (below) or for gel analysis (above).

Purification and Pull Down of Proteins gp6-His and un-tagged gp7, 8, 10, 11 were co-expressed in a 100 μl CFE reaction. After 2 hours at 30° C., the reaction was diluted 1:1 v/v with binding buffer (50 mM NaCl 50 mM Tris and 20 mM imidazole pH 8) and mixed with $Ni^{2+}$ beads (Ni-NTA His•Bind® Resin, Milipore/Merk) pre-equilibrated in binding buffer. After 30 minutes incubation, beads were separated by centrifugation at 1200 rcf. Excess solution was removed by pipetting and the beads were washed with 30 volumes of binding buffer in repeated centrifugation steps. Wedges were eluted with a 1:1 bead volume of elution buffer (50 mM NaCl 20 mM Tris and 500 mM imidazole). Washing efficiency and elution were evaluate Transmission electron microscopy analysis: T4 wedges expressed in CFE reaction and purified by $Ni^{2+}$ affinity beads were concentrated to ~0.1 mg/ml using a 100 kDa MWCO Vivaspin 500 (Sartorius). 10 μl of the sample were applied to a glow-discharged, carbon-coated copper TEM grid (300 mesh, EMS) for 10-20 sec. Excess liquid was then blotted, and after a wash with distilled water, the grids were stained with a 2% uranyl acetate solution. Samples were visualized with Tecnai T12 transmission electron microscope (FEI), equipped with a ES500W Erlangshen camera (Gatan).

Polyacrylamide gel electrophoresis: Tris-Glycine (TG) Linear gradient gels were purchased from GeBa at 4-20%. Gels pre-equilibrated with Sodium dodecyl sulfate (SDS) by pre-run (160 V for 12 minutes) with TG-SDS buffer (Bio-Lab, Israel) for denaturation conditions.

Native step gradient (bottom 12% 1 cm, middle 5.5% 2.5 cm, top 4%) gels and uniform SDS-PAGE were made using Mini-PROTEAN (Bio-Rad) using 1:29 bis-acrylamide\acrylamide (Bio-Lab, Israel).

Gels containing fluorescent proteins were imaged using FLA5100\FLA9500 scanner (FUJI Typon/GE Typhoon). Imaged were analyzed using FIJI software[25].

Chip Preparation

Multi-well array fabrication by deep silicone etching: A two-step silicon etching was preformed using an induced coupled plasma (ICP) machine (Multiplex ICP, SPTS Technologies) on a 5" <100> Si wafer (University Wafer, USA). The chambers were formed using a single 25-30 sec etching process (30 mTor 130 sccm SF6, Bias voltage 500 W applied to the 13.56 MHz RF coil and 100 W to the platen) applied on a S1805 photoresist patterned wafer, resulting in a 2-3 μm deep etch. The separation channels were etched using 50 cycles of SF6 etch alternating with C4F8 polymer deposition (Bosch process[26]) (etching: 12 sec, 30 mTor, 130 sccm SF6, 13 sccm 02, Bias voltage 500 W applied to the RF coil and 100 W to the platen: passivation: 10 sec, 30 mTor, 30 sccm C4F8, Bias voltage 500 W applied to RF coil) on a AZ4562 patterned wafer, resulting in a 40-50 μm deep etch. All heights were measured using a stylus profiler (DektakXT, Dektak/Bruker, MA, USA).

$SiO_2$ deposition: The etched wafer was divided by hand into separate chips. Each chip was coated with 50 nm $SiO_2$ layer using plasma enhanced chemical vapor deposition (PECVD) by a VERSALINE PECVD machine (Plasma-Therm, Saint Petersburg, Fla., USA) under the following conditions; 21 sec: pressure of 1200 mTorr, 5% SiH4 in He, flow rate of 750 sccm, N2O flow rate of 1250 sccm, $N_2$ flow rate of 400 sccm, RF power of 110 W, upper electrode temperature of 200° C. and lower electrode temperature of 300° C.

Photosensitive biocompatible monolayer coating: The protocol to form a photosensitive and biocompatible monolayer coating on silicon chips was described previously[27]. Briefly, the chips were coated with a polymer composed of a polyethylene glycol backbone with a protected amine at one end, and a triethoxysilyl group at the other end. The slides were incubated with a toluene solution of the polymer (0.2 mg/mL), for 20 minutes, rinsed with toluene and dried.

Photosensitive biocompatible monolayer UV photo-lithography: De-protection of surface amines was performed using the μPG101 Laser writer (Heidelberg Instruments) and a pattern created in dxf format on AutoCAD software (AutoDesk). The coated surfaces were exposed alternatively to 35 mW 50% with write head 4 mm, or to 70 mW 100% with 20 mm write head. Exposed amines were immediately coupled to biotin by incubating the surfaces with 0.5 mg/ml biotin 3-sulfo-N-hydroxysuccinimide ester (EZ-link, Pierce) in 0.2 M borate-buffered solution pH 8.6 (ThermoFisher Scientific) for 15 minutes, followed by rinsing and drying.

DNA deposition: DNA-streptavidin conjugates were deposited on biotin-patterned surfaces using a GIX II microplotter (Sonoplot). A 60 μm diameter tip apparatus was used for all DNA deposition experiments. Minimum spacing between micro droplets of DNA-streptavidin conjugates was 100 μm. Pattern for the GIX II were made by the SonoGuide software (Sonoplot). Micro droplets were incubated for at least 2 hours.

Immobilization of antibodies and tagged proteins: 50 mg/ml (~500 nM) Anti-HA-Biotin, High Affinity (3F10) (Roche, Sigma-Aldrich) were mixed at 2:1 ratio of streptavidin (Sigma Aldrich) in 1× PBS. After 30 minutes incubation at 4° C. the mix was diluted to 25-50 nM in 1×PBS supplemented with 0.2 mg/ml BSA, applied to the surface and incubated for at least 1 hour. After washing with 1× PBS, the surface was either directly covered with cell-free extract or first covered with a tagged protein (gp11-HA), freshly synthesized in CFE reaction. The crude reaction (30-90 μl, depending on chip size) was applied to the biochip without drying the antibodies, and incubated for 1 hour followed by washing in 1× PBS. For reactions with pre-adsorbed gp10, the process was identically repeated.

On-chip cell-free protein expression: The chip was rinsed in 1×PBS and excess solution was carefully blotted using paper (Whatman™ #1) while keeping the chambers wet. Fresh CFE solution (30-90 μl, depending on chip size, prepared as for the off-chip reactions) was applied on the chip and spread uniformly to cover all chambers. After excess solution was removed, the chip was covered with 1-2 mm Polydimethylsiloxane (PDMS) slabs (SYLGARD™ 184 silicone elastomer kit, Dow Corning). Expression was carried out for 2 hours in a PCR machine (Mastercycler gradient (EPPENDORF™, Hamburg, Germany) or Labcycler 48, SensQuest) fitted with a slide hybridization adapter at 30° C. and lid at 32° C. After expression the PDMS slab was removed and the chip was washed with 1× PBS. For visualization of on-chip dynamic expression, the chip was placed in an incubator chamber (Bold-line stage top incubator, Okolab) installed on the microscope stage.

Post-staining: The crude protein-labeling reaction was applied on the washed chip either directly (for gp10 and gp8); diluted 1:4 in PBS (for gp53); or centrifuged for 5 min in 16K rcf at 4° C. to remove unspecific background (for gp6). The chip was incubated for 1 hour and washed with 1× PBS. For multiple post-staining steps, the labeled proteins were introduced one by one, with 1× PBS washing between steps, in the reverse assembly order to ensure that a labeled protein would not bind to labeled complexes.

Fluorescent microscopy imaging: Fluorescent images were obtained using an AxioObserver Z1 inverted microscope with a motorized stage (Zeiss) and Plan-Apochromat 20×/0.8 M27, EC Plan-Neofluar 40×/0.9 Pol M27 (Zeiss) and 10×/0.3 MPlanFL N (Olympus) Objectives. Illumination was preformed using Colibri2 LED illumination system equipped with 470 nm and 625 nm LED module (Zeiss) and filter sets 38 HE and 50 (Zeiss), (excitation 470/40 nm, dichroic mirror 495 nm, emission 525/50; excitation 640/30 nm, dichroic mirror 660 nm, emission 690/50, respectively). Images were captured using iXon Ultra CCD camera (Andor Technology, Belfast, UK). Chip alignment and multi-image acquisition was preformed using the Zeiss ZEN 2012 software.

Data analysis: For circular 400 μm diameter compartments (FIGS. 23A-F and 24A-D), the total fluorescent signal was measured in the entire compartments patterned area excluding the center area of the DNA brush. For 1D compartments (FIGS. 25A-E, 26A-D, 27A-C and 28A-F), five or six images (with 5-10% overlap) were acquired in order to cover an individual compartment, followed by stitching. Inhomogeneous lightening of image area was corrected by normalizing to a reference image. Integrated total fluorescence was taken as the entire compartment. The 1D profile was generated from an average along a 100 μm strip in the center of the Y-axis. The profile was smoothed using a moving average of 15-20 μm window. The area of the DNA brush was not included in the signal averaging.

The yield of a given assembly step, facilitated by gene i, was calculated by $(N_{i=0}-N)/N_{i=0}$, with $N_{i=0}$ the signal in a compartment with no gene-i stained with labeled gp-i, and N the total signal in a compartment with all genes.

A normalized wedge signal (FIG. 24D) was calculated relative to the amount of occupied gp11-HA within each compartment (gp10 staining, $N_{occupied}$). Wedge signal (gp53 staining, $N_{wedge}$) was divided by the occupied gp11-HA ($N_{occupied}$) signal for each compartment. An average of 4 repetitions and their standard deviation was calculated. To fit all gene titrations to the same graph, values were normalized between 1 and 0, by normalizing each to its highest signal. Original data appears is in FIGS. 33A-D until 36A-D.

Simulation

The assembly yield (FIG. 28F) was calculated at each time point as the fraction of complexes captured on the surface out of the total possible complexes that could have formed. The expression rate of gp7 was identical in all 4 scenarios and was the limiting factor for the yield calculation.

RESULTS

On-Chip 2D Compartments for Synthesis and Assembly of Proteins

The inventors etched into a silicon wafer compartments of radius 200 μm and 2 height embedded in a relief structure of height 50 μm above the surface. In the center of each compartment, they immobilized linear DNA polymers, 1-3 kbps long, packed in a dense brush coding for clusters of interacting proteins synthesized by cell-free expression (CFE) using T7 RNA polymerase in *E. coli* cell-free extracts[14-16]. Antibodies immobilized on the entire surface surrounding the DNA brush capture specific proteins diffusing away from the brush (Methods, FIG. 23A, FIG. 29 and FIGS. 30A-E). The gene concentration within the 0.25 nL volume of the compartment could reach ~0.2 μM, some 1-2 orders of magnitude beyond typical bulk solution CFE reactions. With ~2 μM proteins synthesized in 2 hr and antibody density of 500-2000 $\mu m^{-2}$, all newly synthesized proteins could be captured.

Figures 23A, 23B:
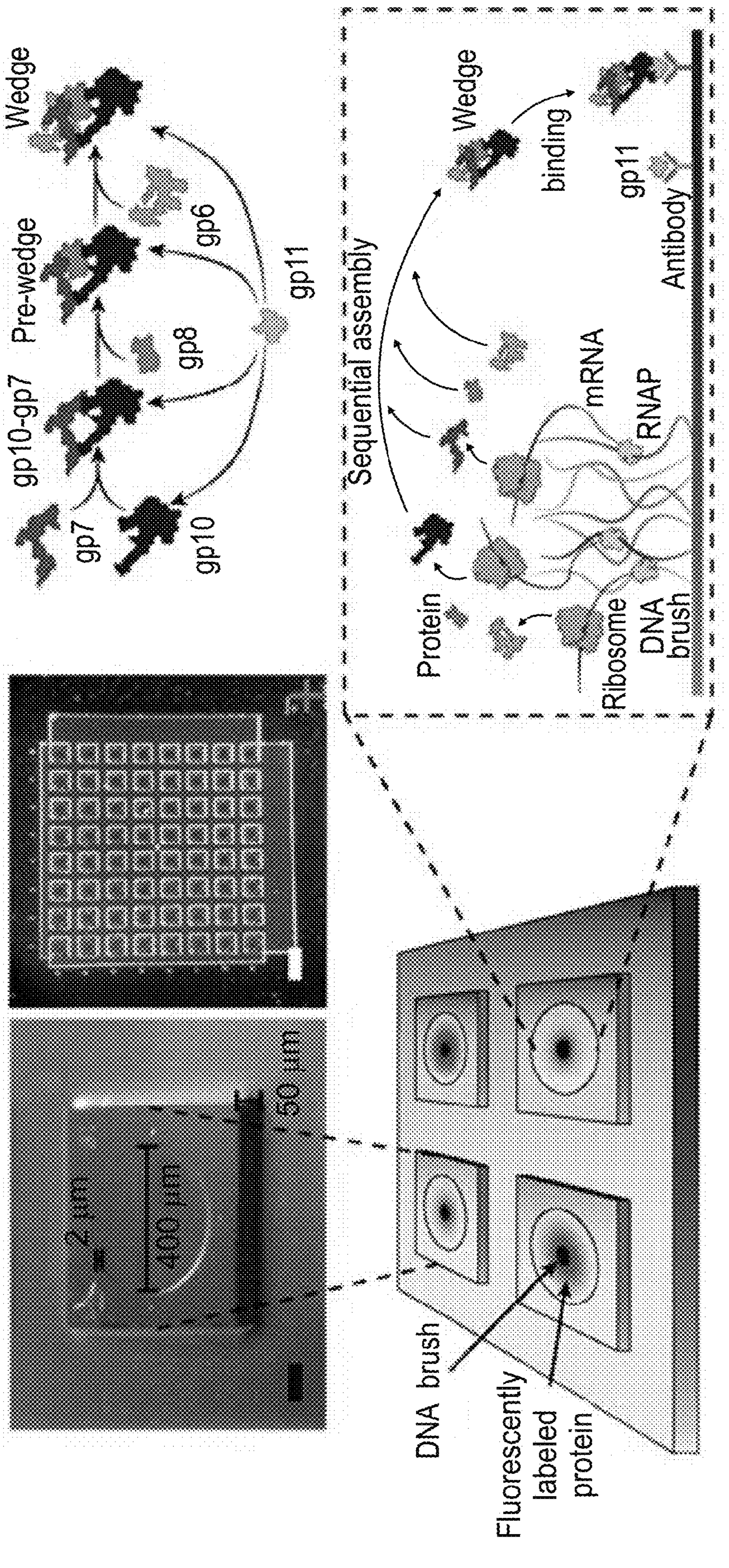

The T4 wedge, a part of the bacteriophage cell puncturing machine, is coded by T4 genes 6, 7, 8, 10, and 11, that self-assemble with 2:1:2:3:3 protein stoichiometry, respectively[17] (FIG. 23B). Except for gene product 11 (gp11), all other wedge proteins bind sequentially in a stepwise contingent mode, with gp8 forming pre-wedge structures by binding only to gp10-7 complexes, and gp6 joining pre-wedges to complete the wedge structure with no apparent binding to any other intermediate[18]. Sequential binding of one copy of gp53 to each wedge drives the self-assembly of six wedges into a star-shaped complex[19] (FIG. 23B, C).

Figure 23C:
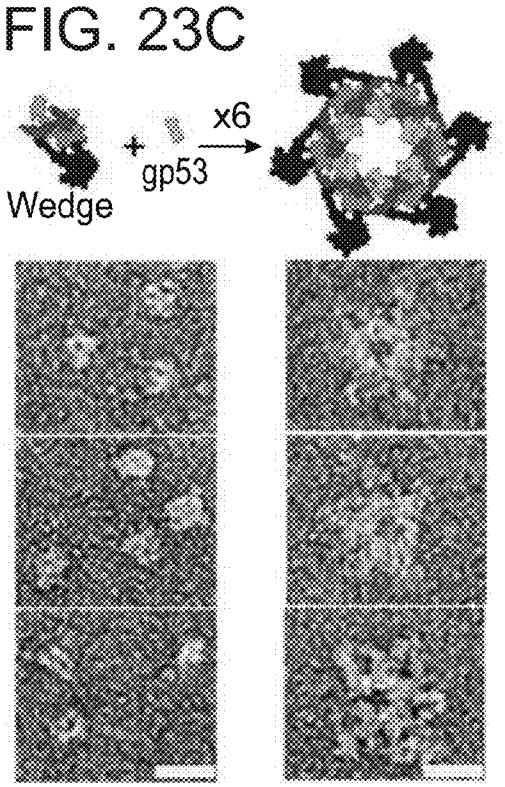
Figure 23D:
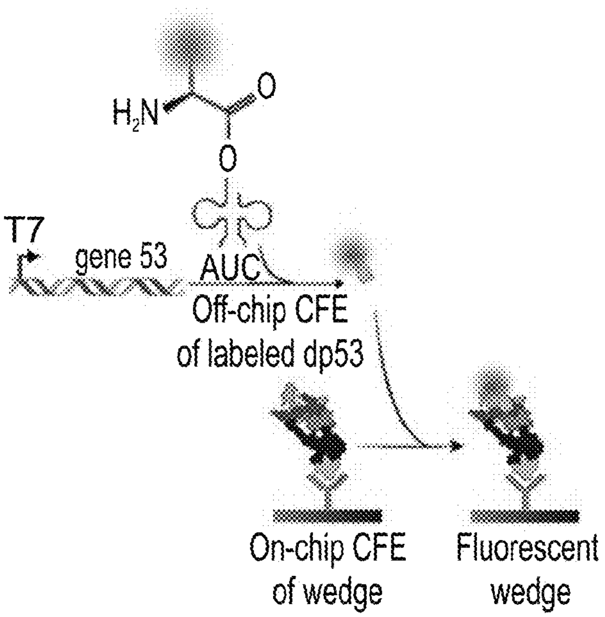

Gel electrophoresis analysis was used in order to verify that wedge proteins could be fluorescently-labeled in situ while maintaining assembly competency FIGS. 31A-B and 32A-B). Native gel analysis allowed verification of the assembly order by a simple gene deletion assay (FIGS. 31A-B), as well as by a kinetic assay of coupled synthesis and assembly (FIGS. 32A-B). Finally, Transmission Electron Microscopy (TEM) imaging structurally verified that off-chip CFE of wedge proteins led to wedge and star formation (FIG. 23C).

Figure 23E:
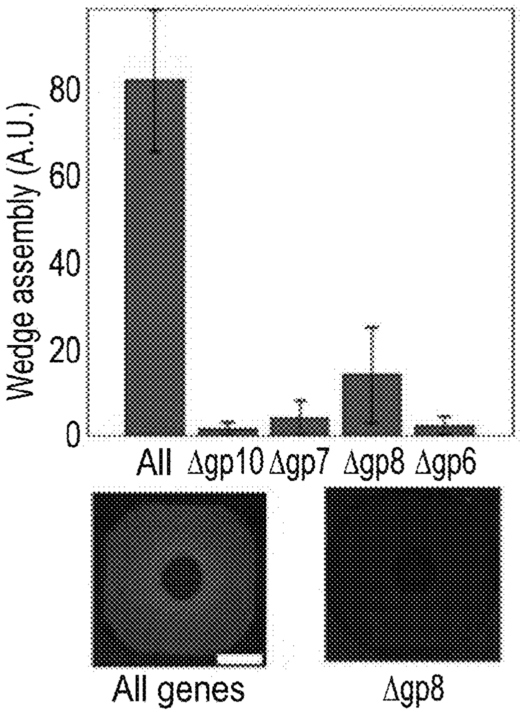

The present inventors then tested whether wedge proteins synthesized from gene brushes in the compartments properly assembled on the surface. For this, off-chip gp11 fused to an HA peptide (gp11-HA) was pre-synthesized and bound to anti-HA antibodies covering the surface surrounding a brush of wedge genes (Methods). Once the proteins were synthesized and captured the bound complexes were stained by fluorescently-labeled gp53 pre-synthesized off-chip (Methods, FIG. 23D), and specific assembly of T4 wedges was confirmed by deleting each one of the wedge genes, observing no signal accumulation above background level when any one of the genes was missing (FIG. 23E). This methodology could be used in the future to deduce unknown assembly pathways with no limitation of size and charge of the proteins involved that are limiting factors in gel electrophoresis analysis, and avoiding tedious structural characterization by TEM.

Sensitive Detection of Surface-Captured Protein Assemblies

Figure 23F:
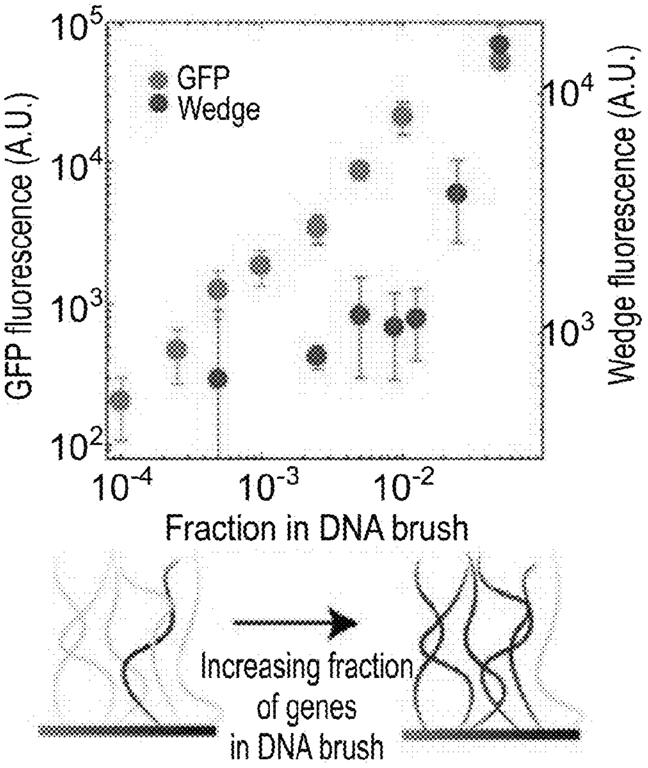

With a brush diameter of ~60 μm and a typical density of gene templates of ~1000 $\mu M^{-2}$, the brush can potentially encode an unlimited number of different genes. To assess the capacity of protein synthesis and assembly in the compartment, the wedge genes in the brush were diluted by a gene coding for a non-related protein, thereby maintaining a fixed load on the transcription-translation machinery. By surface capture and staining wedge formation was detected even when diluting wedge genes by 2 orders of magnitude (Methods, FIG. 23F). Similarly, in situ synthesis and capture of HA-tagged Green Fluorescent Protein (HA-GFP) could be detected even at ~4 orders of magnitude dilution of its gene (FIG. 23F). Interestingly, whereas the GFP dilution exhibited linear response, the dose response curve of the wedge genes was nonlinear, which may reflect multi-component assembly interactions with variable binding affinities. These gene dilution results demonstrate the capacity of 2D confined compartments to potentially provide conditions for synthesis, localization and highly sensitive detection of hundreds of protein complexes and thousands of independent proteins.

High-Yield Protein Assembly in the Compartments

Figure 24B:
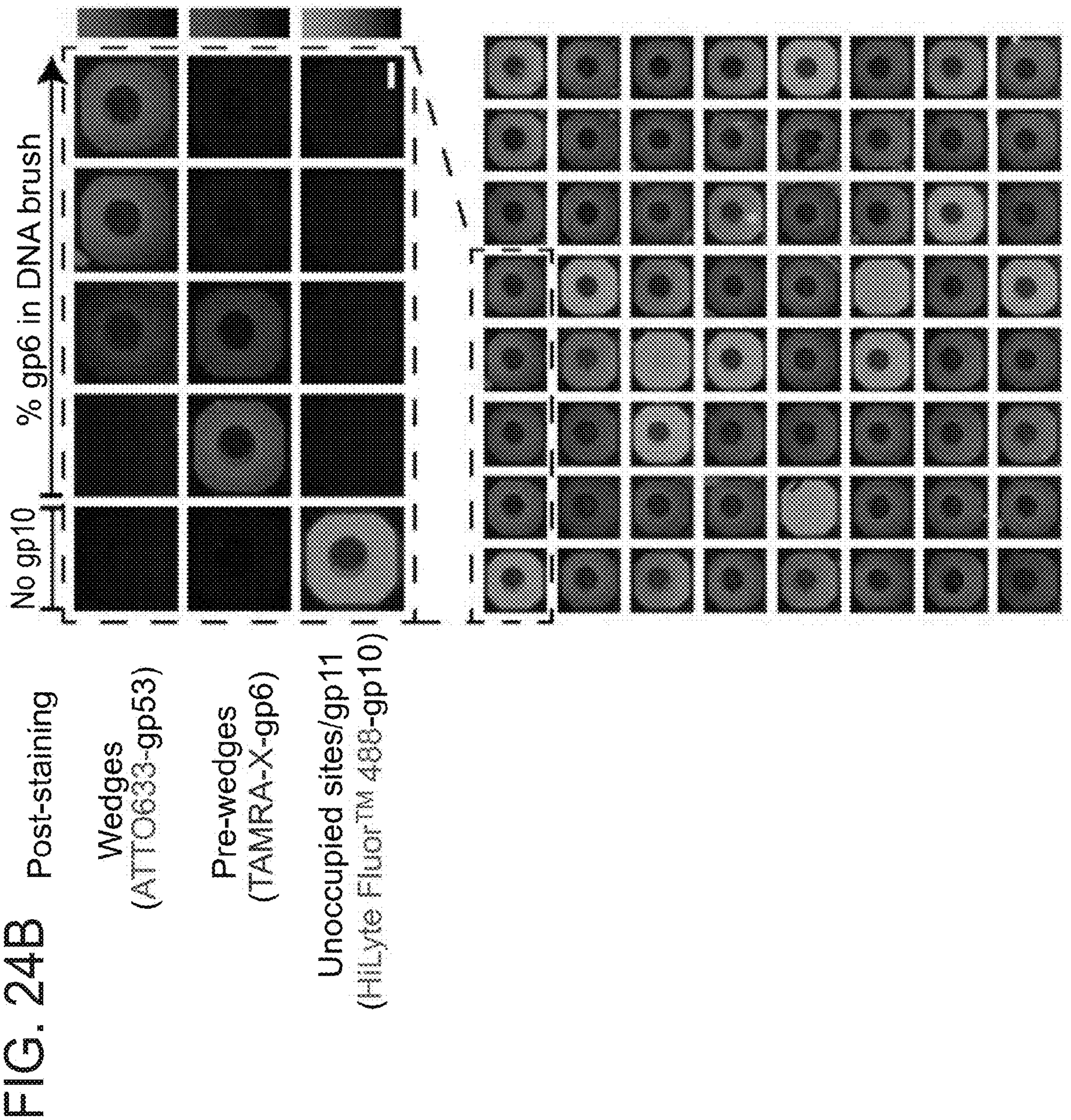
Figure 24A:
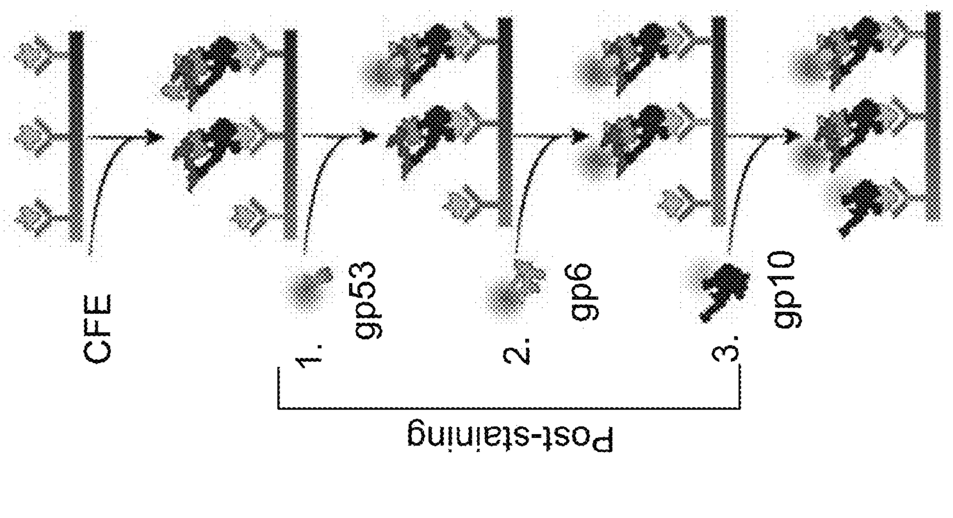
Figure 24D:
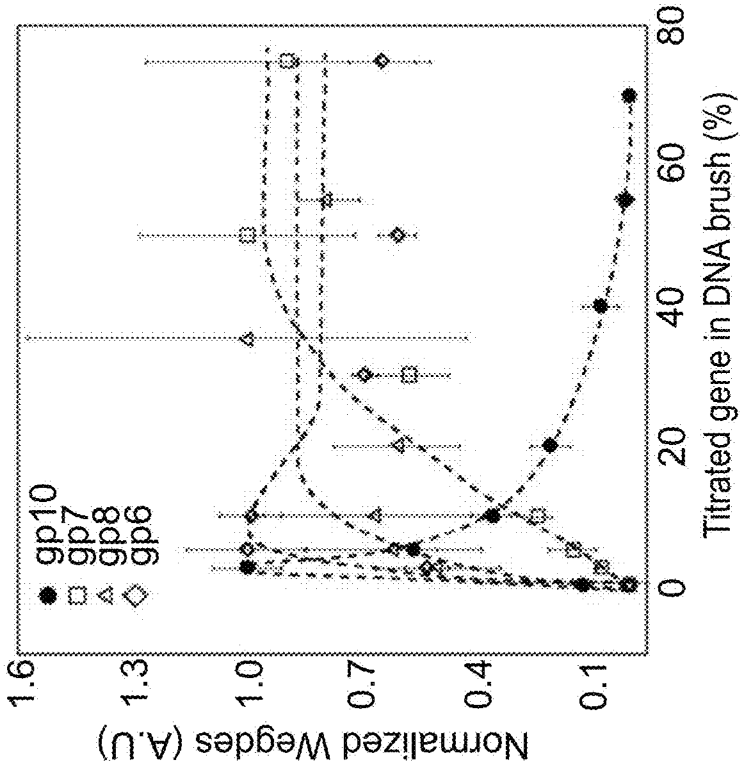
Figure 24C:
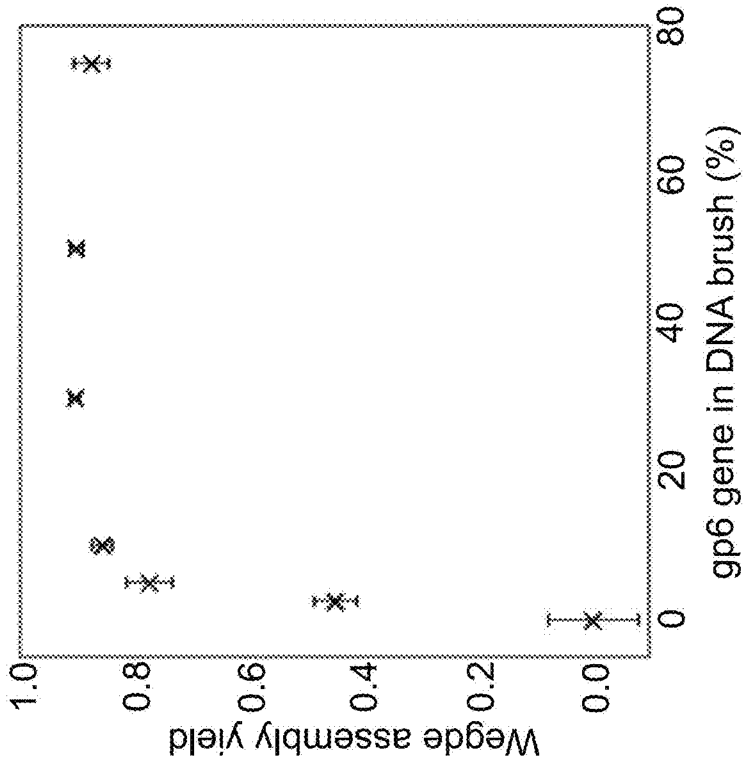
Figures 30A, 30B, 30C, 30D, 30E:
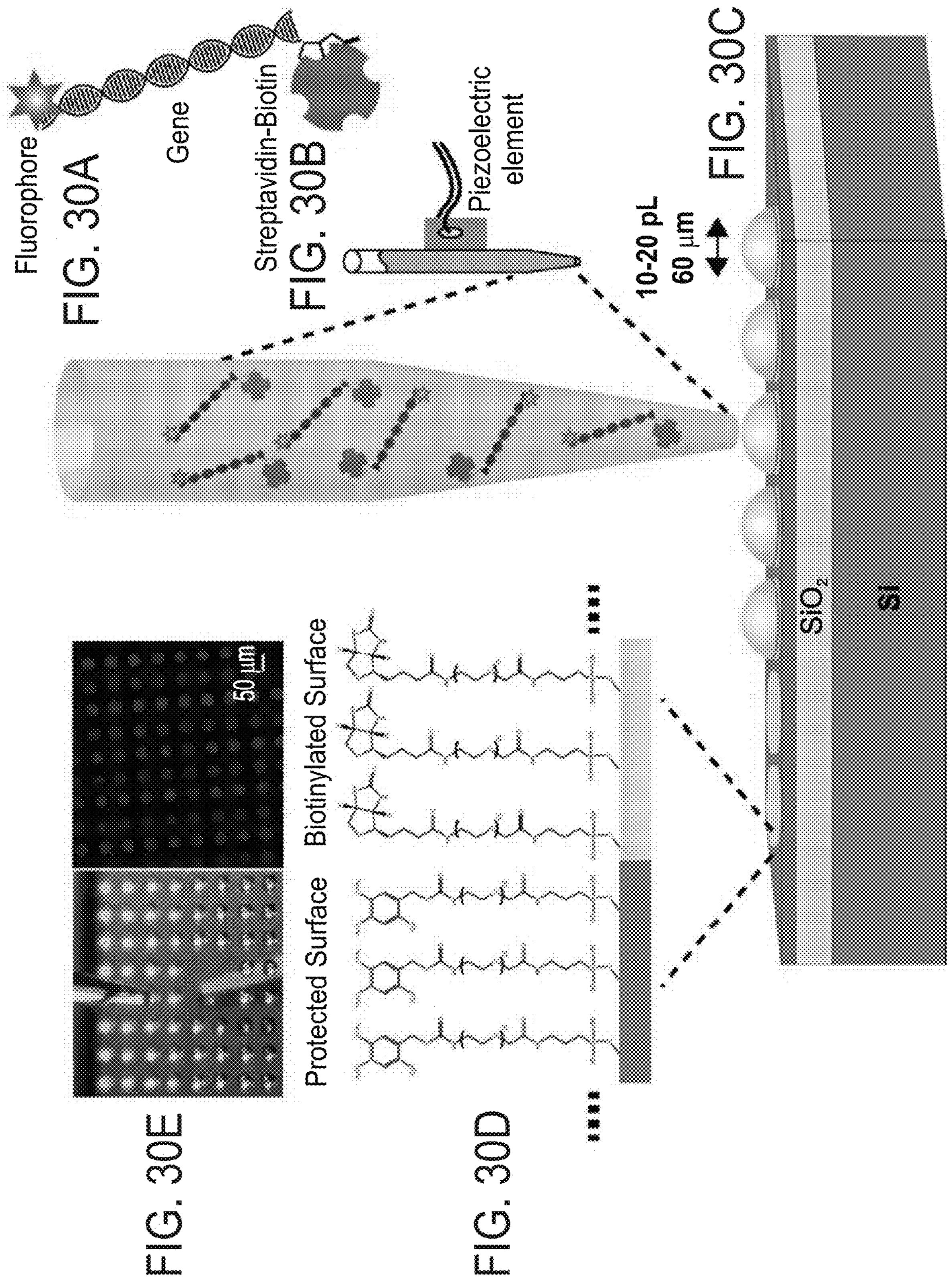

Next, the present inventors demonstrated how expressing genes in an array of 2D compartments can reveal inherent properties of biological assembly pathways. They expressed the wedge genes by titrating the copy number of each gene in the brush from zero to maximal value (FIGS. 24A-D, FIGS. 33A-D, 34A-D, 35A-D and 36A-D). They stained the array in a three-step procedure adding fluorescently labeled gp53, gp6 and gp10, in reverse order to the assembly pathway, to quantitatively detect wedges, pre-wedges and gp11 available for binding on the surface, respectively (FIG. 30A). With this procedure, they could calculate the on-chip yield of pre-wedge and wedge formation observing that almost all pre-wedges were converted to wedges (Methods, FIG. 24C). In addition, the dose response curves exhibited increased wedge formation up to saturation values of high efficiency, except for gene-10, which exhibited a narrow peak (FIG. 24D). This peak may stem from the fact that gp11-10 interaction, unlike the rest of wedge assembly pathway, is non-sequential, as gp7 can bind gp10 either prior to or after the latter has bound to gp11 (FIG. 23B). Therefore, excess gp10 most likely saturated gp11 on the surface and sequestered surface binding of wedges pre-assembled in solution, a notion corroborated by off-chip experiments (FIG. 37).

These gene titration experiments suggest a general biological design principle in which sequential steps in a pathway are robust to variations in stoichiometry because advancing from one step to the next can occur by only one mechanism, whereas non-sequential steps proceed by competing mechanisms, and are hence susceptible to variations in stoichiometry[20]. Specific to gene brushes, these experiments implied that when genes are mixed in a single brush, interaction of nascent proteins can occur either in solution close to the brush, or by scaffolding on the surface, as reflected in the observed sequestration by gp10. It was hypothesized that immobilizing the genes in separated brushes could expose this interesting competition, and provide a dial to experimentally separate solution-dominated assembly from assembly by surface scaffolding.

Programmable Assemblograms in a 1D Geometry

Figures 25A, 25B, 25C, 25D, 25E:
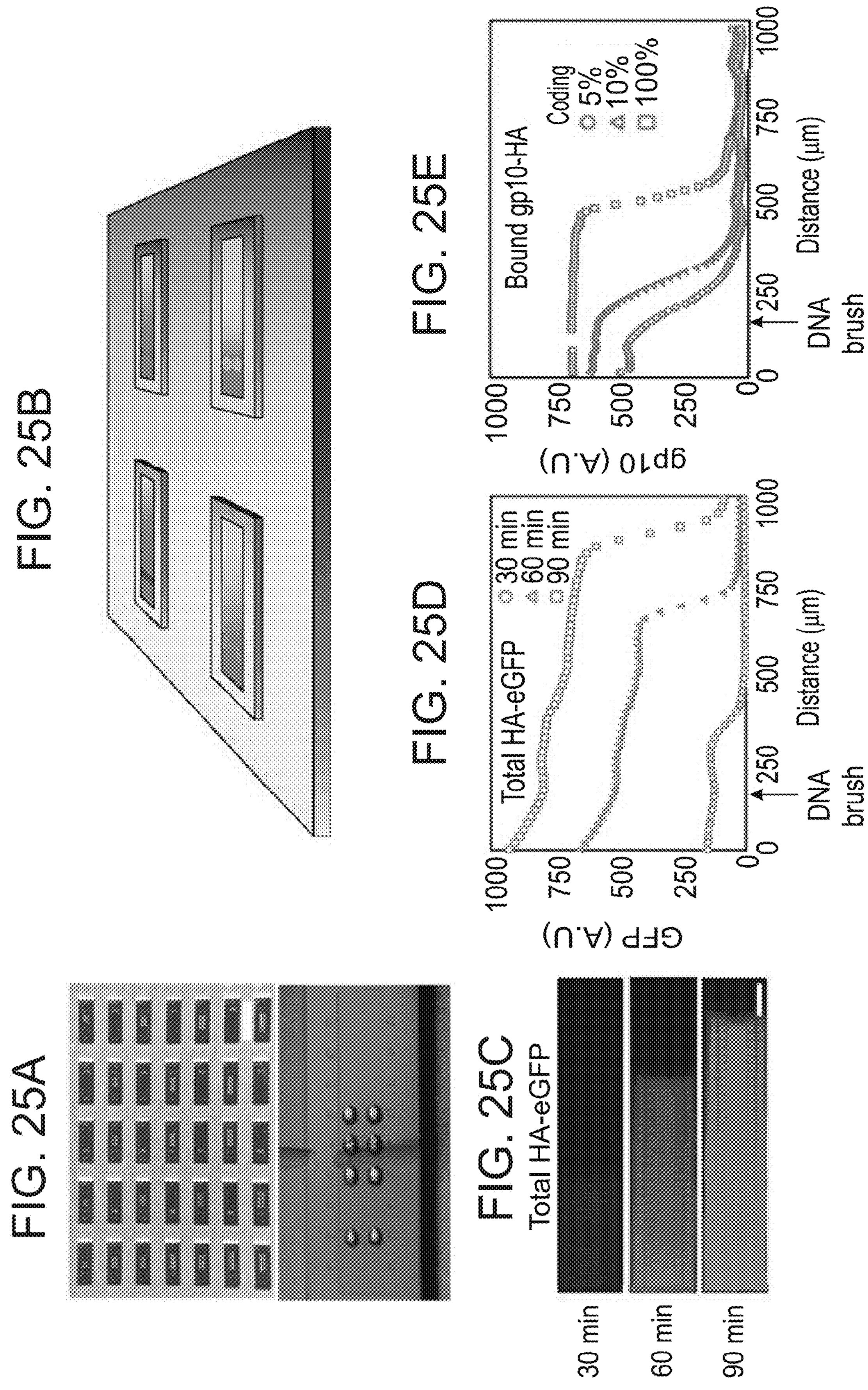

To expose the interplay between competing assembly modes, the present inventors designed rectangular compartments of dimensions 200×1000 $\mu m^2$ (FIG. 25A), which enable positioning of genes along a 1D geometry. They first characterized the expression and capture profile of a single protein by immobilizing two gene brushes coding for HA-GFP close to one compartment edge, with anti-HA antibodies covering the entire surface, and measured the signal in time and space from both GFP bound to the surface traps and in solution (FIGS. 25B-D). They also immobilized a brush of gene-10, at variable gene doses, with pre-synthesized gp11-HA as traps, and stained the resulting profile after 2 h of synthesis by labeled gp10 (FIG. 25E). The data were consistent with localized protein synthesis, followed by diffusion to the next available site, and saturation of surface traps in time and at high gene copy number. The resulting step-function profiles suggested that the majority of proteins produced in the compartment were captured.

Next, the wedge genes were immobilized along the axis according to their binding order in the sequential pathway, and in three types of layouts (with gp11-HA pre-immobilized): genes mixed in a single brush, separated genes in packed brushes 100 μm apart, and spread out brushes 250 μm apart (FIGS. 26A-D). gp10-7, gp10-7-8, and gp10-7-8-6 were expressed in separate compartments, in order to reveal the position of assembly intermediates, and all the compartments in the array were post-stained, resulting in 27 assemblograms. The assemblograms of the mixed layout were centered on the gene brush and overlapped with the profile of the gp10-7 complex, but the assemblograms of the separated and spread out brush layouts had an apparent peak shift in response to the position and separation of gene-7 from gene-10. That is, the position of gp10-7 seemed to have dictated assembly of pre-wedges and wedges, which most likely occurred in a scaffolded step-wise assembly of gp8 and gp6 onto surface-bound gp10-7. Therefore, the geometrical arrangement of the genetic program dictated assembly mode.

Figure 26A:
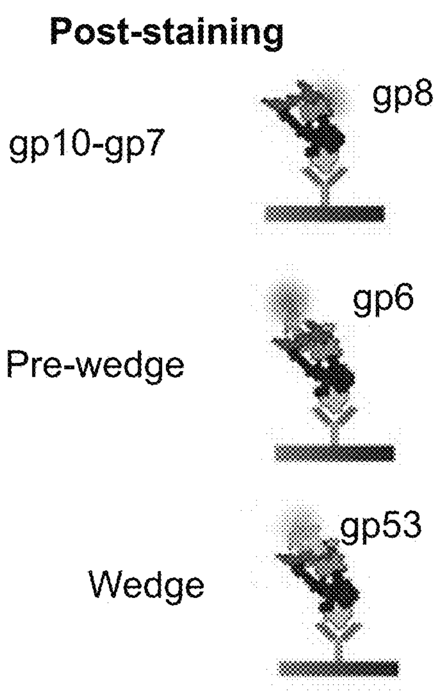
Figure 26B:
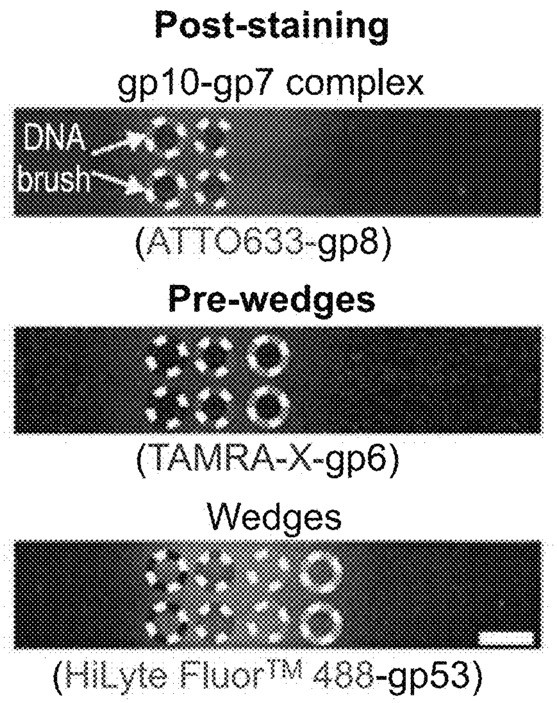
Figure 26C:
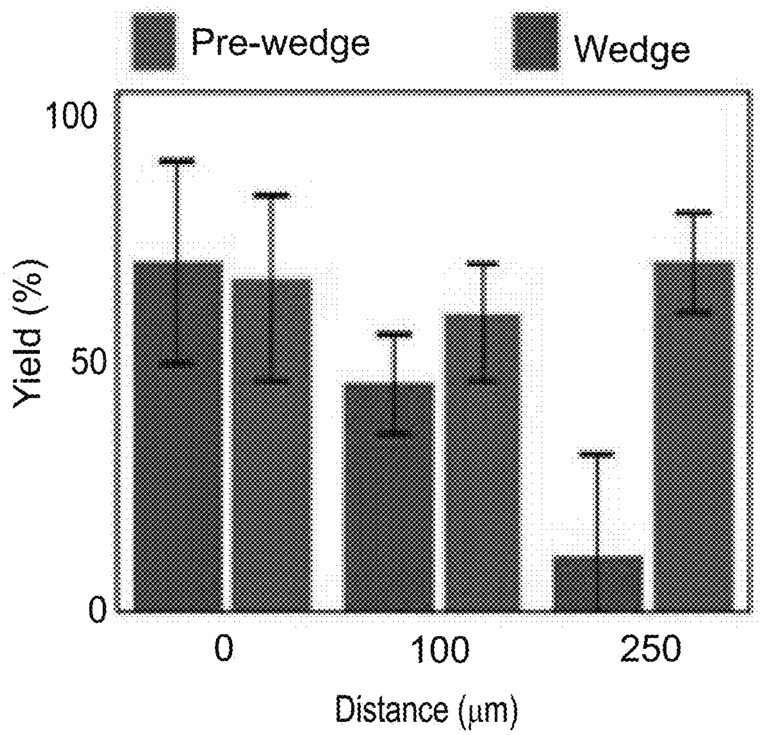
Figure 26D:
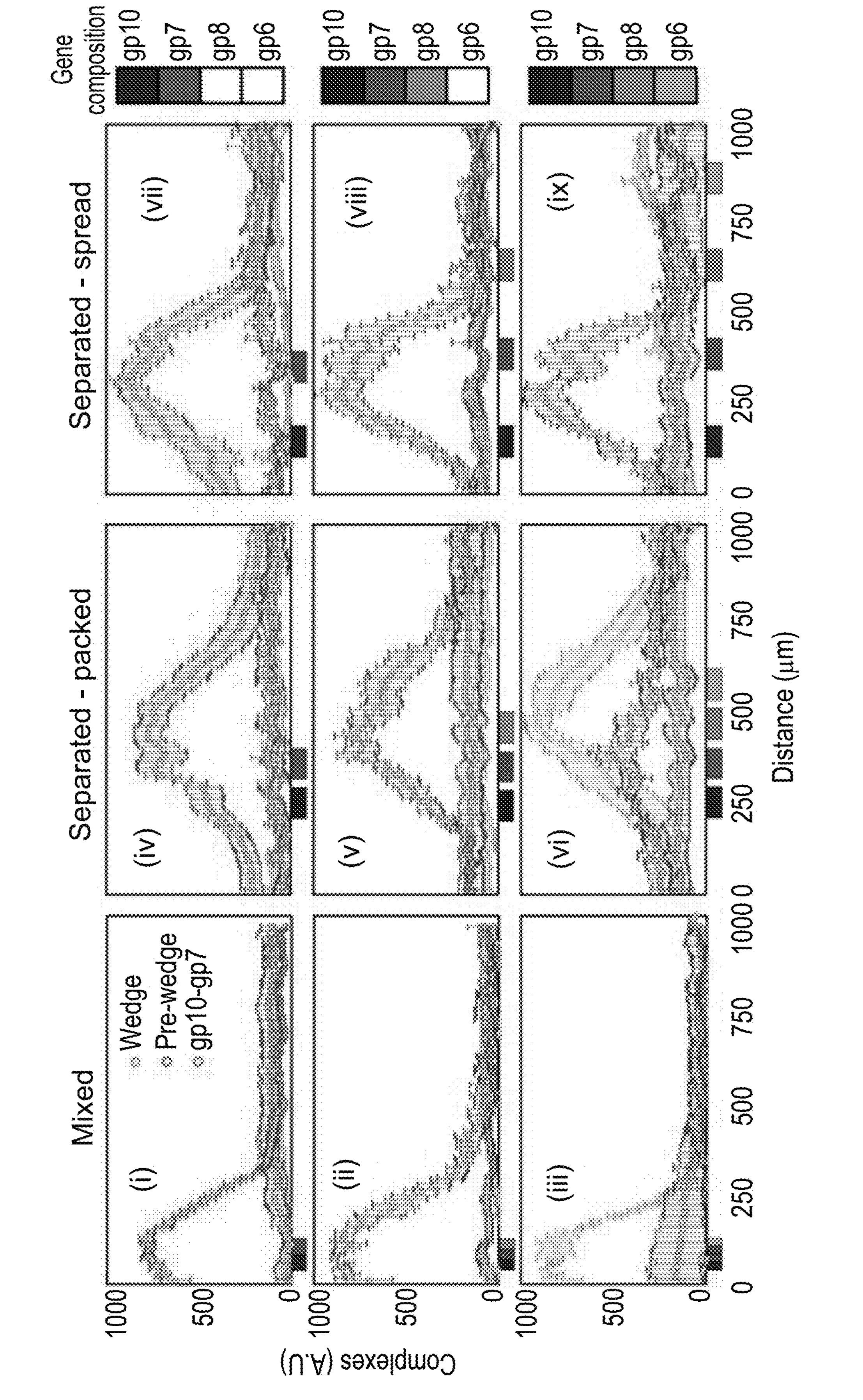

In addition, the geometrical arrangement reduced assembly yield in some layouts (FIG. 26C). High yield was obtained for the mixed brush at every step of the pathway: all the gp10-7 complexes converted to pre-wedges when adding gene-8 to genes-10-7, and nearly all pre-wedges converted to wedges when adding gene-6 to genes-10-7-8 (FIG. 26D(i-iii)). Similarly, high-yield formation of pre-wedges was observed in the packed and separated configurations (FIG. 26D(iv-v),(vii-viii), except for a small fraction of the pre-wedges that remained free and did not convert into wedges (FIG. 26D(vi)), indicating that separating the genes reduced wedge yield (FIG. 26D(vi)). Remarkably, in the spread configuration no wedges assembled, despite the high yield of pre-wedges. Based on this latter result, the possibility that the scaffolded assembly mode was responsible for the reduced yields could be ruled out, as the two assembly steps were not equally affected. Rather, it seems that reduced yield was directly related to the binding strength of gp6 to pre-wedges.

It was reasoned that the spread layout required gp6 to diffuse over ~500 μm to reach the site of bound gp10-7-8, resulting in reduced concentration of gp6 at the assembly site, too low to drive wedge formation if its binding affinity is much lower than that of gp8. To directly test this model, three wedge genes were packed in brushes 100 μm apart and either a brush of gene-6 or gene-8 was positioned at increasing distances up to 750 μm (FIGS. 27A-C). Interestingly, all the gene-8 configurations resulted in wedge assembly with no dramatic effect on yield, yet almost no wedges formed for the farthest gene-6 brush, which suggests that gp6 binds weaker to pre-wedges than gp8 to gp10-7 complexes. This was validated by off-chip experiments showing that significantly more wedges were formed with all the genes expressed simultaneously in comparison to mixing the proteins after they were synthesized separately, and that adding increasing amounts of gp6 expressed separately boosted the wedge assembly yield (FIGS. 38A-C). Therefore, 1D arrangements of gene brushes in the compartment can serve as a ruler for binding affinity of proteins and a filter of weak complexes.

Kinetic Competition Between Assembly Modes in the Compartment

Figure 28A:
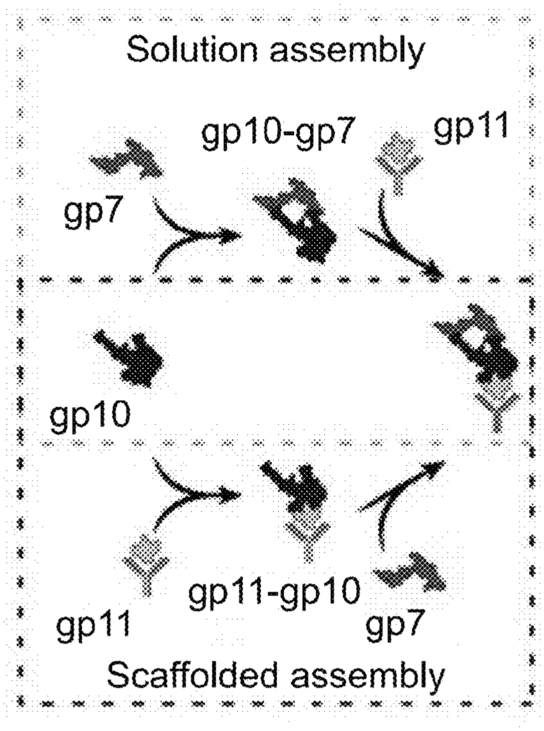
Figure 28B:
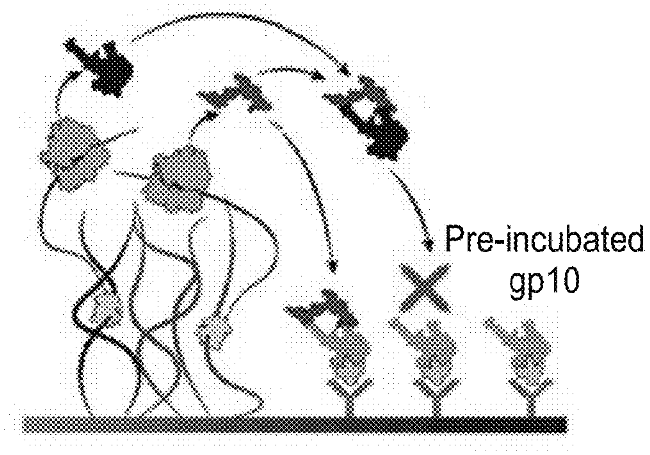
Figure 28C:
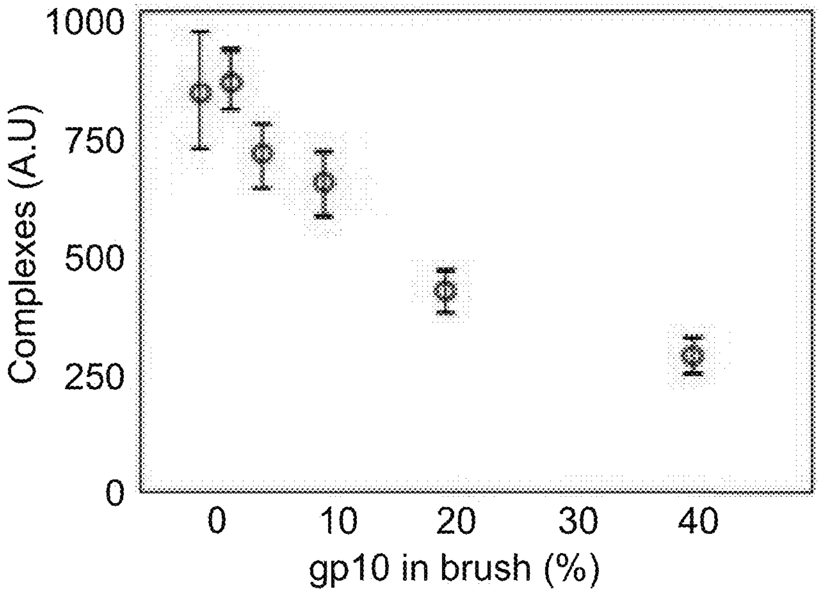
Figure 34A:
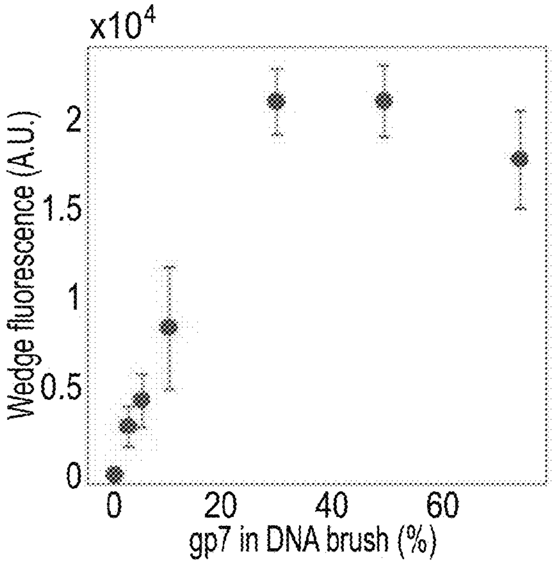
Figure 34B:
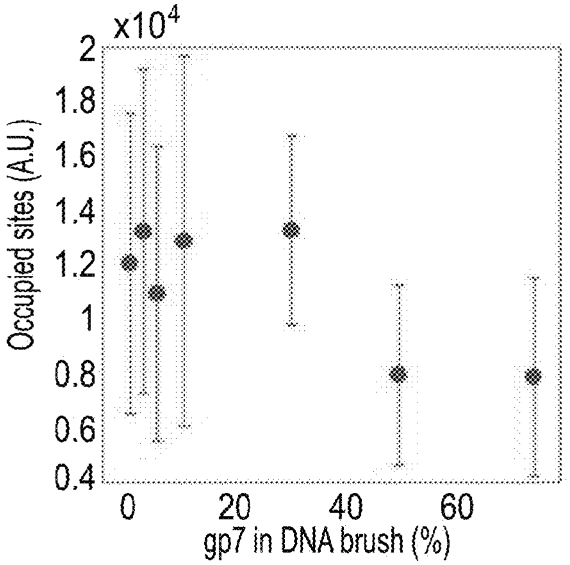
Figure 34C:
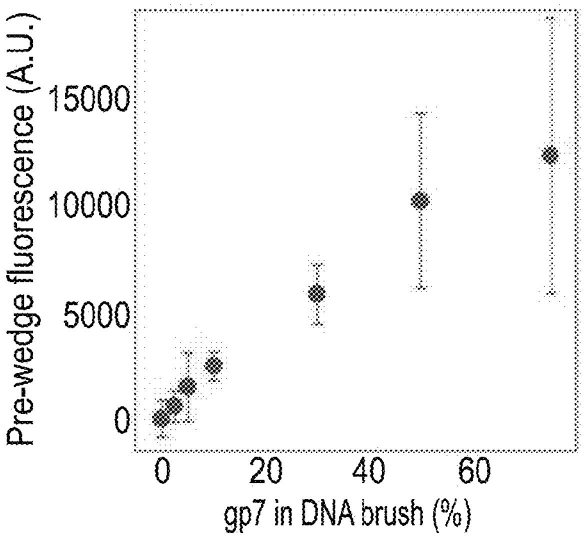
Figure 34D:
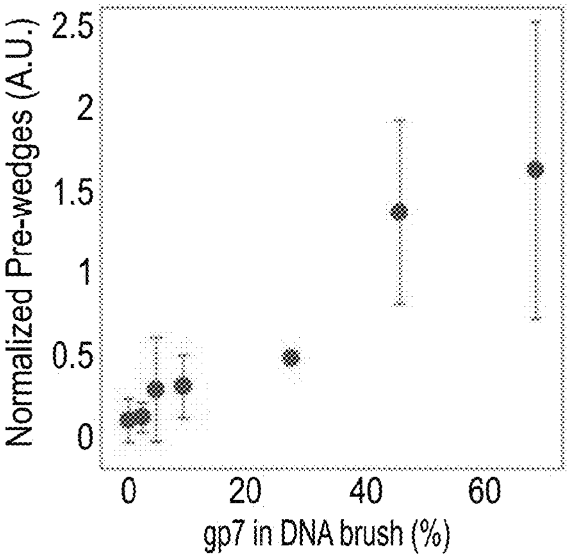
Figures 35A, 35B, 35C, 35D:
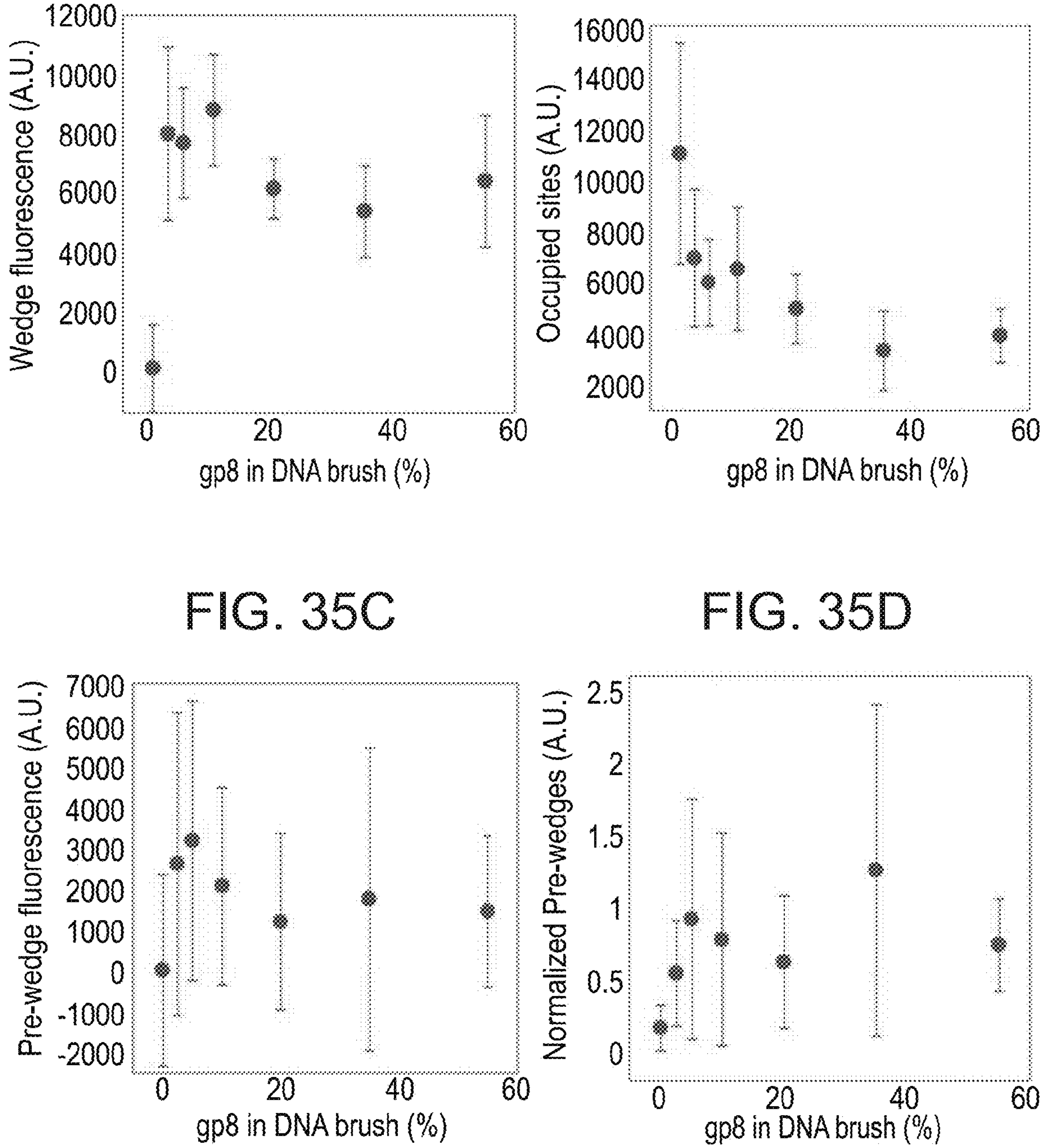
Figure 36A:
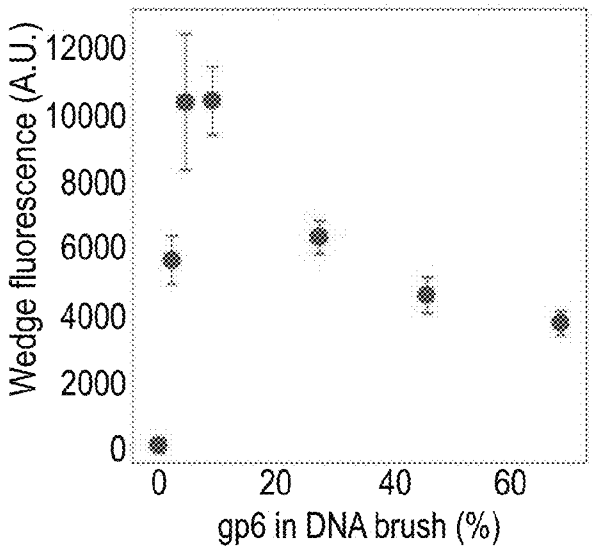
Figure 36B:
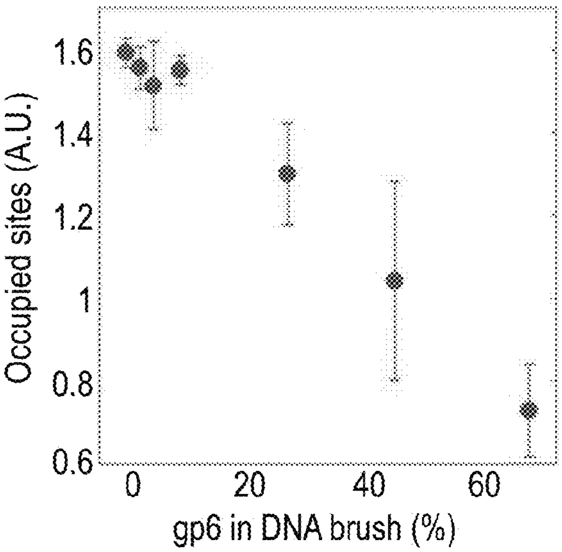
Figure 36C:
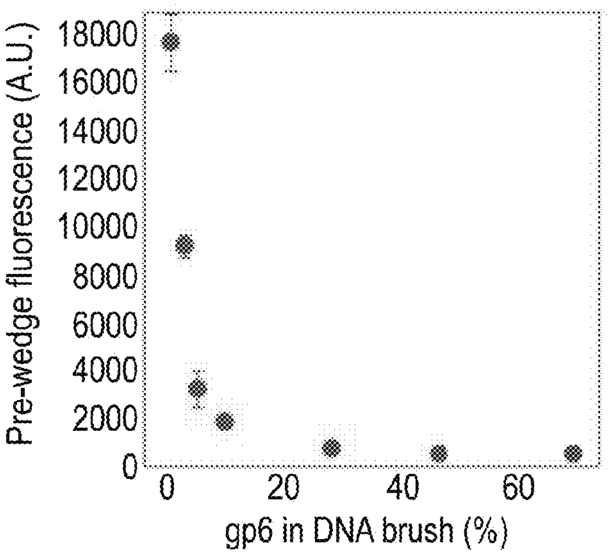
Figure 36D:
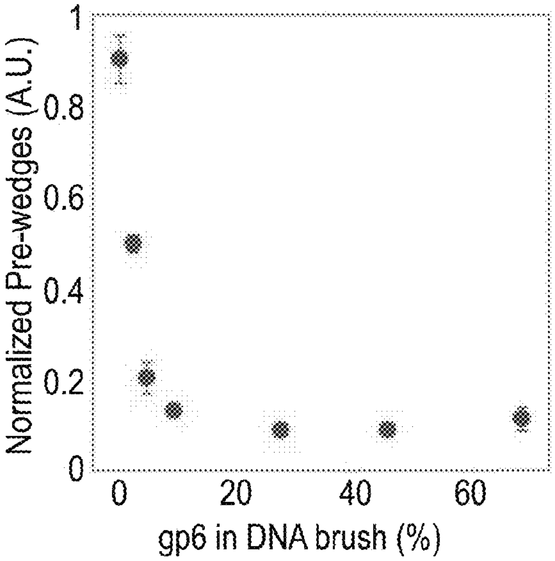

Taken together, the results in FIGS. 26A-D and 27A-C suggested that the two assembly modes could lead to similar assembly yields for thermodynamically stable interactions, but weak interactions could be compensated for only in the coupled synthesis and assembly scenario (mixed gene brushes) and not in the scaffolded assembly (separated brushes). In order to assess just how efficient is the interaction in solution between proteins synthesized in the same brush, a scenario was created that generated kinetic competition between solution assembly and scaffolding (FIGS. 28A, B). A mixed brush of genes-10-7 was assembled in the circular compartments, but with gp10 already pre-incubated on gp11-HA bound surface, so that gp7 can either bind nascent gp10 in the brush or on the surface. It was found that synthesis of additional gp10 always lowered formation of gp10-7 complexes on the surface, thereby indicating that coupled protein synthesis and interaction in the brush vicinity outcompetes interaction by scaffolding (FIG. 34C).

Figures 28D, 28E, 28F:
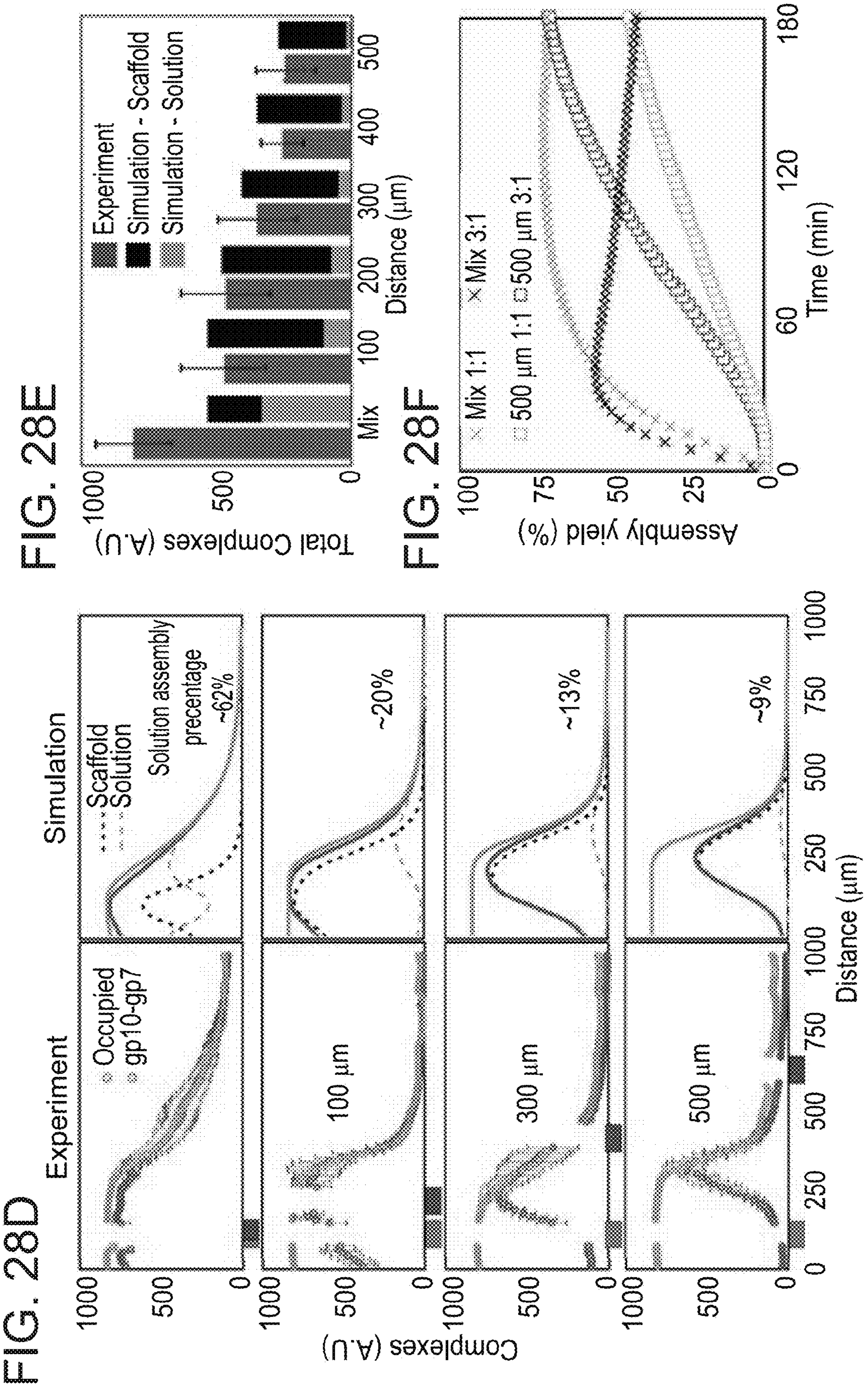

To address the question whether there is a transition from coupled synthesis and interaction in a single brush to stepwise scaffolding in a multi-brush scenario, the inventors pre-immobilized gp11-HA only, and determined the yield of gp10-7 complex formation for a mixed brush and systematic separation of brushes in a 100-500 μm range (FIGS. 28D, E). Notably, for the mixed brush, the gp10-7 complex exactly followed the gp10 profile, but decayed much slower in space than the single-gene profile (FIG. 25E). Separating the two genes by 100 μm reverted to sharply decaying profiles of both gp10 and gp10-7. As the two brushes separated further, the gp10 profile remained unchanged, whereas the gp10-7 profile gradually became narrower, concomitantly with a three-fold reduction in yield of gp10-7 complexes from the mixed to the 500 μm separated configuration.

Assembly Mode Determined by Geometry

To explain the data, the present inventors simulated synthesis, interaction, diffusion, and surface capture of gp10 and gp7 in a quasi-1D compartment (Methods). They reproduced the main features of the observations using a set of experimentally relevant parameters for all configurations, including the adjustment that capture of gp10-7 is 10-fold weaker than gp10 binding to gp 11 already captured on the surface, likely due to steric hindrance. Notably, fitting the high-yield and shallow profile of gp10-7 for the mixed brush required to increase the probability of nascent gp10 and gp7 synthesized in the same brush bind by at least 10-fold than by diffusion-limited interaction for separate brushes. The simulation showed that in the mixed brush, 62% of the gp10-7 complexes form in solution and the rest by scaffolding. Near the brush the gp10-7 profile is dominated by diffusion of free gp10 proteins that sequester capture of gp10-7 complexes, whereas far from the brush, solution assembly and diffusion of gp10-7 to the next available site dominates the profile. In contrast, and consistent with the results presented in FIGS. 24D, 26A-D and 27A-C for the separate brushes, the majority of gp10-7 complexes formed by scaffolding, as for example, only 9% form in solution for the 500 μm configuration. It can be concluded that a mixed brush induces high-yield complexes but the competition between solution and scaffolding assembly modes comes at a price of sensitivity to variations in stoichiometry for non-sequential assembly steps. In contrast, separating the brushes reduces the overall yield due to lower local protein concentrations, but eliminates the competition between the two modes and restores robustness. This notion was corroborated by simulating 4 situations of 2 genes (gene-10 and gene-7) at two different gene ratios (1:1 and 3:1, respectively) and at two distances (mixed brush and 500 μm). At short times, up to 30 minutes, there was a significant higher assembly yield in mixed than separated brushes. At longer times, a clear decrease is observed at the 3:1 imbalanced stoichiometry. With time, the yield of scaffolded assembly increased, enhanced by excess of gene-10 (FIG. 28F).

Conclusions

Overall, the present results signify a paradigm shift from bulk cell-free reactions, where the number of expressible genes is limited by the volumetric dilution when adding DNA templates, and assembly yield is limited by diffusion-limited interactions, to confined surface-localized reactions with a capacity for genome-scale, high-yield synthesis and assembly of protein clusters. The spatial organization of genes coding for interacting proteins in quasi-1D compartments produced assemblograms on the surface that could potentially be imaged by higher resolutions methods and help identify assembly intermediates in the assembly pathway. These assemblograms revealed that close proximity between genes is essential for overcoming weak interactions and that gene spreading creates a ruler for binding affinities. The use of unnatural amino-acid fluorescent labeling of proteins allowed the present inventors to gain mechanistic insight on assembly of T4 wedges as a model gene cluster, such as the importance of sequential assembly to maximize yield against imbalanced protein stoichiometry. Thus, sequential assembly may be a natural mechanism to ensure robust and efficient assembly even when gene-expression regulation fails to produce equal amounts of proteins. Indeed, gene-10 and 11 are organized on a single operon in the T4 genome[21], suggesting that stoichiometry must be closely regulated at the level of gene expression for this non-sequential assembly step. Importantly, the present inventors could regulate the binding mode of wedges from a coupled synthesis and assembly to a scaffolded surface assembly by packing genes in a mixed brush as a synthetic operon, or as separate gene brushes, respectively.

For T4 wedges, the synthetic operon mode resulted in higher assembly yields. Finally, with some modifications, the present methodology could be used to decipher unknown assembly pathways at high throughput.

REFERENCES

1. Rustad, M., Eastlund, A., Jardine, P. & Noireaux, V. Cell-free TXTL synthesis of infectious bacteriophage T4 in a single test tube reaction. doi:10.1093/synbio/ysy002
2. Matthies, D. et al. Cell-Free Expression and Assembly of ATP Synthase. *J. Mol. Biol.* 413, 593-603 (2011).
3. Asahara, H. & Chong, S. In vitro genetic reconstruction of bacterial transcription initiation by coupled synthesis and detection of RNA polymerase holoenzyme. *Nucleic Acids Res.* 38, 1-10 (2010).
4. Shieh, Y.-W. et al. Operon structure and cotranslational subunit association direct protein assembly in bacteria. aac8171 (2015).
5. Wells, J. N., Bergendahl, L. T. & Marsh, J. A. Operon Gene Order Is Optimized for Ordered Protein Complex Assembly. Cell Rep. 14, 679-685 (2016).
6. Nevo-Dinur, K., Nussbaum-Shochat, A., Ben-Yehuda, S. & Amster-Choder, O. *Translation-Independent Localization of mRNA in E. coli.*
7. Holt, C. E., Martin, K. C. & Schuman, E. M. Local translation in neurons: visualization and function. *Nat. Struct. Mol. Biol.* 26, 557-566 (2019).
8. McGuffee, S. R. & Elcock, A. H. Diffusion, crowding & protein stability in a dynamic molecular model of the bacterial cytoplasm. *Plos Comput. Biol.* 6, e1000694 (2010).
9. Minton, A. P. Implications of macromolecular crowding for protein assembly. *Curr. Opin. Struct. Biol.* 10, 34-39 (2000).
10. Daube, S. S., Bracha, D., Buxboim, A. & Bar-Ziv, R. H. Compartmentalization by directional gene expression. Eur. Cells Mater. 20, (2010).
11. Bracha, D., Karzbrun, E., Daube, S. S. & Bar-Ziv, R. H. Emergent properties of dense DNA phases toward artificial biosystems on a surface. *Acc. Chem. Res.* 47, (2014).
12. Efrat, Y., Tayar, A. M., Daube, S. S., Levy, M. & Bar-Ziv, R. H. Electric-Field Manipulation of a Compartmentalized Cell-Free Gene Expression Reaction. *ACS Synth. Biol.* 7, 1829-1833 (2018).
13. Noren, C. J., Anthony-Cahill, S. J., GRIFFITH, M. C. & Schultz, P. G. A general method for site-specific incorporation of unnatural amino acids into proteins. 244, 182-188 (1989).
14. Shin, J., Jardine, P. & Noireaux, V. Genome replication, synthesis, and assembly of the bacteriophage T7 in a single cell-free reaction. *ACS Synth. Biol.* 1, 408-413 (2012).
15. Caschera, F. & Noireaux, V. Synthesis of 2.3 mg/ml of protein with an all *Escherichia coli* cell-free transcription-translation system. Biochimie 99, 162-8 (2014).
16. Garamella, J., Marshall, R., Rustad, M. & Noireaux, V. The All *E. coli* TX-TL Toolbox 2.0: A Platform for Cell-Free Synthetic Biology. *ACS Synth. Biol.* 5, 344-355 (2016).
17. Yap, M. L. et al. Role of bacteriophage T4 baseplate in regulating assembly and infection. *Proc. Natl. Acad. Sci.* 113, 2654-2659 (2016).
18. Yap, M. L. et al. Sequential assembly of the wedge of the baseplate of phage T4 in the presence and absence of gp11 as monitored by analytical ultracentrifugation. *Macromol. Biosci.* 10, 808-813 (2010).
19. Yap, M. L., Mio, K., Leiman, P. G., Kanamaru, S. & Arisaka, F. The baseplate wedges of bacteriophage T4 spontaneously assemble into hubless baseplate-like structure in vitro. *J. Mol. Biol.* 395, 349-360 (2010).
20. Murugan, A., Zou, J. & Brenner, M. P. Undesired usage and the robust self-assembly of heterogeneous structures. *Nat. Commun.* 6, 6203 (2015).
21. Luke, K. et al. Microarray analysis of gene expression during bacteriophage T4 infection. *Virology* (2002). doi:10.1006/viro.2002.1409
22. Erijman, A., Dantes, A., Bernheim, R., Shifman, J. M. & Peleg, Y. Transfer-PCR (TPCR): A highway for DNA cloning and protein engineering. 175, 171-177 (2011).
23. Buxboim, A., Daube, S. S. & Bar-Ziv, R. Ultradense synthetic gene brushes on a chip. *Nano Lett.* 9, 909-913 (2009).
24. He, B. et al. Rapid Mutagenesis and Purification of Phage RNA Polymerases. *PROTEIN Expr. Purif.* 9, 142-151 (1997).
25. Schindelin, J. et al. Fiji: an open-source platform for biological-image analysis. *Nat. Methods* 9, 676-682 (2012).
26. Laermer, F. & Schilp, A. Method for anisotropic etching of silicon.
27. Buxboim, A. et al. A single-step photolithographic interface for cell-free gene expression and active biochips. *Small* 3, 500-510 (2007).

Example 3

Machine Assembly and Gene Silencing Impacted by Geometry

On-chip synthesis and assembly of *E. coli* RNAP, a five-protein molecular machine responsible for the transcription of every gene in *E. coli* was studied. The genes coding for the core RNAP (α, β, β', ω subunits) and the promoter-specific σ70 subunit were immobilized, together forming the holoenzyme, packed as a mixed brush in the center of compartments with radius of 200 μm, the *E. coli* extract was replaced with a minimal gene-expression system devoid of *E. coli* RNAP. The synthetic operon thus coded for a cascaded reaction initiated by T7 transcription of *E. coli* RNAP genes, that once expressed and assembled led to synthesis of GFP under control of a σ70-specific promoter[14] (P70-GFP) (FIG. 41A). In contrast to the T4 wedge, RNAP assembly was programmed to assemble in solution since it needs to bind immobilized P70-GFP genes.

In the presence of all RNAP subunit genes, GFP expression originated from the central brush with a ~50 minutes delay compared to the expression of the *E. coli* RNAP subunits. The GFP profile was consistent with diffusion from the brush source and capture on the next available site. Deletion of each of the RNAP genes, except for those coding for the ω subunit, a non-essential subunit for RNAP functionality, abolished GFP signal, proving that nascent *E. coli* RNAP machines were assembled in a functional form. It was further shown that σ70 subunits expressed from a gene brush could complement the activity of purified core enzyme added to the minimal gene expression reaction. The GFP signal increased with σ70 genes, unlimited by the excess of core enzyme in solution but peaked when all subunits were expressed from brushes with a fixed amount of core genes (FIG. 41B. Since both steps of the cascaded reaction consume the same resources, which are limited in the minimal gene expression system, protein synthesis in the initial step of the reaction may consume resources for the expression of GFP in the second step.

The present inventors attempted to increase available resources by expanding the depth of the compartments from 2 to 20 μm (FIG. 41B). Indeed, a three-fold higher GFP signal was observed, possibly due to localization of the reactions to the vicinity of the brush creating a sink for resources that are more abundant at the large-volume compartments. Consistently, addition of increasing amounts of active genes to the DNA brush dramatically reduced GFP expression. Thus, at maximal GFP production (FIG. 41B) highest local concentrations of RNAP subunits were synthesized to drive efficient assembly leaving enough resources for GFP expression. Any further increase in protein synthesis would increase resources consumption, but to a lesser extent at the large volume compartments.

The compartment volume was varied from ~60 pL to ~6 nL by systematically changing the diameter of the 2 and 20 μm compartments, (FIG. 41C). Indeed, the total amount of GFP produced in each compartment increased with the diameter, and hence compartment volume. The diameter series of both types of compartments merged into a continuous trend, which reached a constant GFP yield, that reduced only at high volumes beyond 3 nL. The reduction may stem from lower local concentrations of resources diffusing over large distances.

Figure 42B:
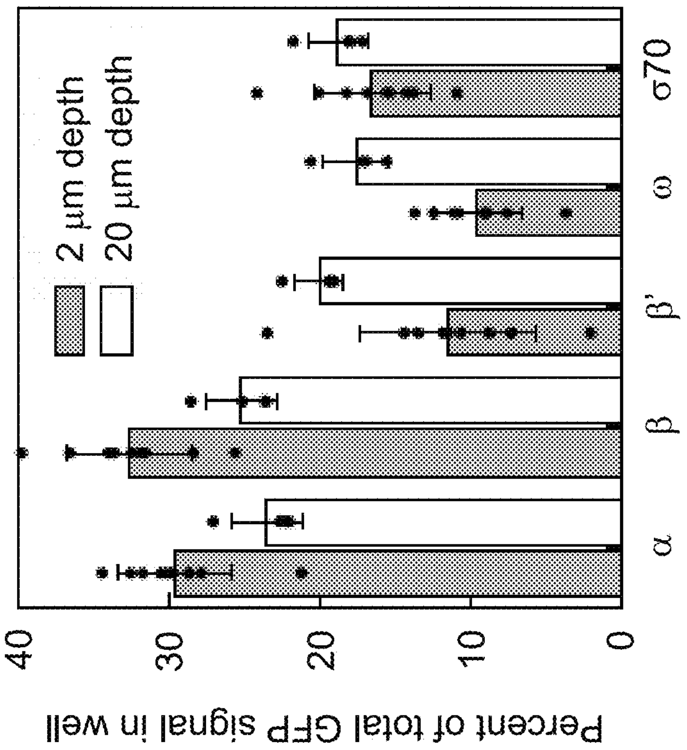
Figure 42A:
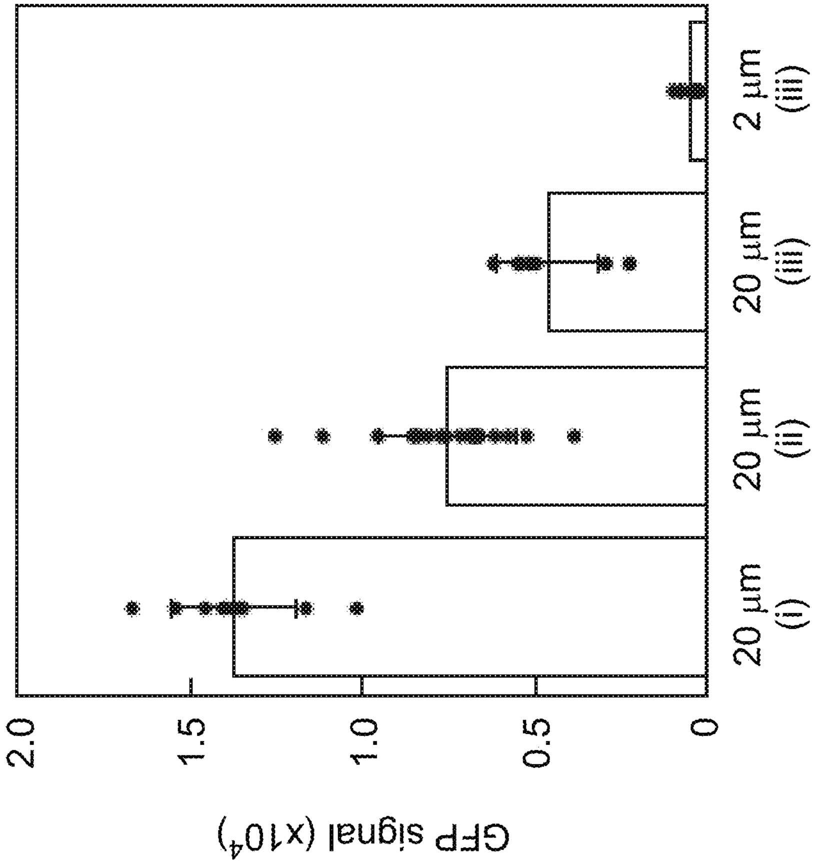
Figure 42C:
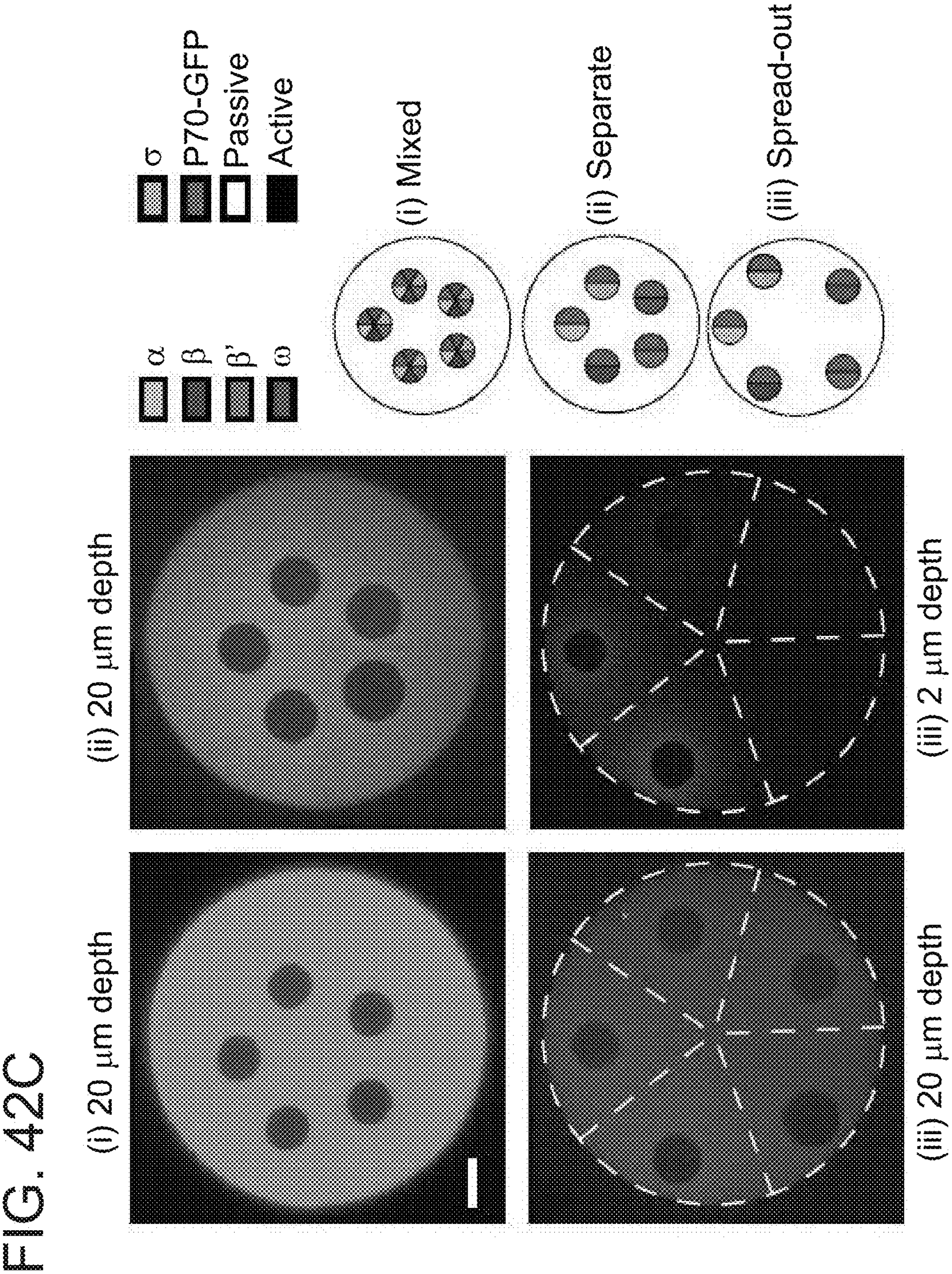

The large diameter compartments provided an opportunity to immobilize several brushes in a circular pattern within a compartment. 5 brushes were immobilized, each coding for one of the RNAP subunits, with the P70-GFP genes added to each brush (FIG. 42A, ii, iii), and compared to GFP expression from the same number of mixed brushes (FIG. 42A, i). GFP expression levels were higher in compartments with mixed RNAP gene brushes (FIG. 42B), consistent with T4 wedge assembly in compartments. The reduced GFP expression due to brush separation could be overcome by placing brushes closely at the compartment centre or by increasing compartment volume (FIG. 42B). At the 2 μm compartments GFP expression was localized to the α and β subunit brushes (FIG. 42C), even when the P70-GFP gene brush was patterned separately, but was almost homogenous at the 20 μm deep compartment, as in FIG. 41C.

Figure 42D:
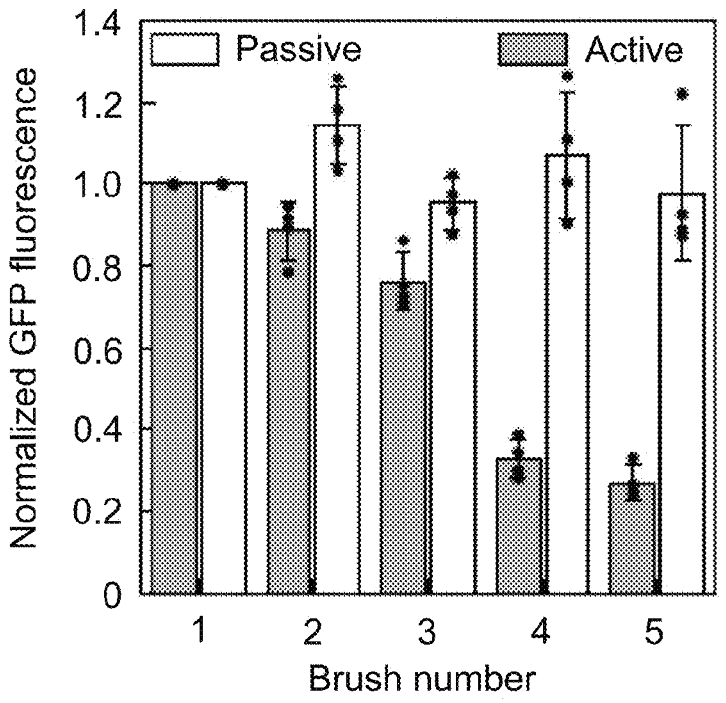
Figure 42E:
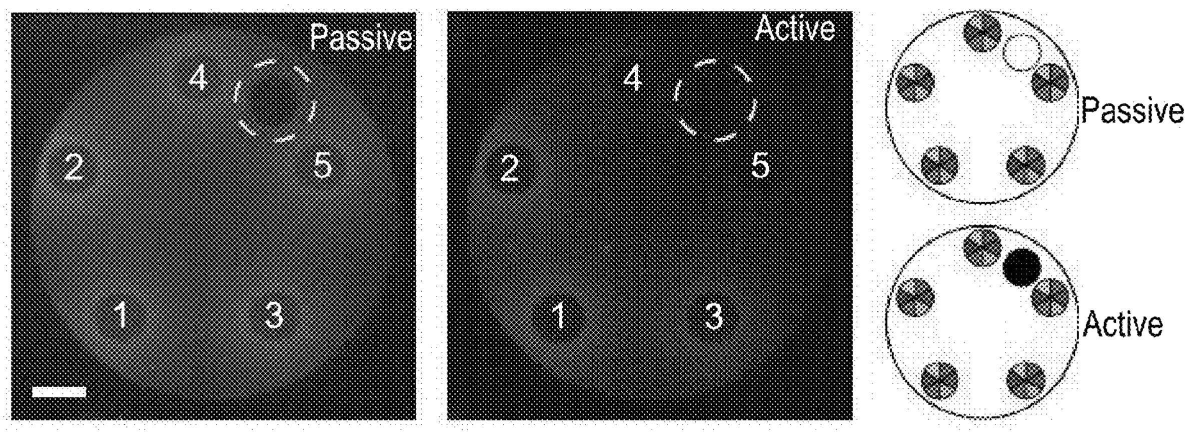

Finally, it is demonstrated how resource partitioning could be used to spatially regulate gene expression. 5 identical brushes composed of P70-GFP and RNAP subunits genes were patterned and an additional non-related yet active brush was immobilized (FIG. 42D). GFP expression was suppressed by competing expression from this brush only in nearby brushes. Consistently, a passive DNA brush with no coding sequences had no effect on GFP expression. This mode of gene-expression silencing regulated by spatial positioning cannot be realized in any off-chip cell-free reaction.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of assembling and immobilizing a proteinaceous complex comprising:

(a) providing a chamber having at least one surface and having a volume between 1 pl-10 ml, wherein a plurality of nucleic acids, each encoding different components of the proteinaceous complex, are immobilized onto said at least one surface and wherein a binding agent which binds specifically to one component of the proteinaceous complex is immobilized onto said at least one surface; and (b) contacting said at least one surface of said chamber with agents for performing expression of the components from said plurality of nucleic acids, under conditions that allow expression and immobilization of the proteinaceous complex to said at least one surface, thereby assembling and immobilizing the proteinaceous complex, wherein said components are expressed as separate polypeptides that associate with one another non-covalently to form the proteinaceous complex.

2. The method of claim 1, wherein said proteinaceous complex comprises at least ten different proteins.

3. The method of claim 1, wherein said complex is functional.

4. The method of claim 1, wherein a plurality of nucleic acids encoding each of the components of the proteinaceous complex are immobilized onto said at least one surface.

5. The method of claim 4, wherein said components are selected from the group consisting of proteins and RNA.

6. The method of claim 1, wherein said proteinaceous complex is selected from the group consisting of a ribosomal subunit, a ribosome, a bacteriophage, a spliceosome, a proteasome, a proteasome subunit, a replisome, a divisome and a virus.

7. The method of claim 1, wherein said proteinaceous complex is a ribosomal subunit.

8. The method of claim 1, wherein said binding agent is an antibody.

9. The method of claim 8, wherein said antibody is directed to an affinity tag which is tagged to one component of the proteinaceous complex.

10. The method of claim 1, wherein said binding agent is immobilized over the entire area of said at least one surface.

11. The method of claim 1, wherein at least one component of the proteinaceous complex comprises a detectable moiety, said at least one component being different to said component which binds to said binding agent.

12. The method of claim 1, wherein said agents for performing expression comprise RNA polymerase, ribosomes and aminoacyl tRNA synthetase.

13. The method of claim 1, further comprising detecting said immobilized proteinaceous complex.

14. A method of analyzing whether a candidate agent disrupts the assembly of a complex comprising:

(a) assembling and immobilizing a complex on a solid surface of a chamber according to the method of claim 1 in the presence of said candidate agent:

(b) analyzing an amount of said assembled complex which is attached to said solid surface, wherein a downregulation in the amount of the assembled complex as compared to the amount of the assembled complex in the absence of said candidate agent, is indicative that the candidate agent disrupts the assembly of the complex.

15. The method of claim 1, wherein a height of the chamber is between 1-10 μm.

* * * * *